(12) United States Patent
Kawashima et al.

(10) Patent No.: US 7,798,966 B2
(45) Date of Patent: Sep. 21, 2010

(54) ULTRASONIC DIAGNOSTIC APPARATUS

(75) Inventors: Tomonao Kawashima, Tokyo (JP);
Shun Yokoi, Tokyo (JP)

(73) Assignee: Olympus Corporation, Tokyo (JP)

( * ) Notice: Subject to any disclaimer, the term of this patent is extended or adjusted under 35 U.S.C. 154(b) by 1742 days.

(21) Appl. No.: 10/965,063

(22) Filed: Oct. 14, 2004

(65) Prior Publication Data

US 2005/0090743 A1 Apr. 28, 2005

(30) Foreign Application Priority Data

Oct. 14, 2003 (JP) .............................. 2003-354316
Dec. 1, 2003 (JP) .............................. 2003-401434

(51) Int. Cl.
*A61B 8/00* (2006.01)
(52) U.S. Cl. ...................... 600/443; 600/437; 600/462; 600/463; 600/466; 600/467
(58) Field of Classification Search ................. 600/437, 600/462, 463, 466, 467, 443
See application file for complete search history.

(56) References Cited

U.S. PATENT DOCUMENTS

| 5,295,486 | A | | 3/1994 | Wollschlager et al. | |
|---|---|---|---|---|---|
| 5,891,030 | A | * | 4/1999 | Johnson et al. | 600/407 |
| 5,920,319 | A | * | 7/1999 | Vining et al. | 345/420 |
| 6,248,074 | B1 | | 6/2001 | Ohno et al. | |
| 2002/0049375 | A1 | | 4/2002 | Strommer et al. | |

FOREIGN PATENT DOCUMENTS

| EP | 1 181 893 A1 | | 2/2002 |
|---|---|---|---|
| JP | 05-052074 | * | 3/1993 |
| JP | 06-261900 | | 9/1994 |
| JP | 7-500506 | | 1/1995 |
| JP | 07-057113 | | 3/1995 |
| JP | 7-155328 | | 6/1995 |
| JP | HEI 8-024260 A | | 1/1996 |
| JP | 10-262964 | | 10/1998 |
| JP | HEI 11-113913 A | | 4/1999 |
| JP | 2001-198125 | | 7/2001 |
| JP | 2002-113004 | | 4/2002 |
| JP | 3325224 | | 7/2002 |
| JP | 2003-520062 | | 7/2003 |
| JP | 2003-325511 A | | 11/2003 |

OTHER PUBLICATIONS

English language abstract only of International Publication No. WO 00/69335 dated Nov. 23, 2000.
English language abstract only of International Publication No. WO 90/13259 dated Nov. 15, 1990.
Patent Abstracts of Japan for Japanese Publication No. 11-299787, published Nov. 2, 1999.
Japanese Office Action dated Oct. 19, 2009 with translation.

* cited by examiner

*Primary Examiner*—Brian Casler
*Assistant Examiner*—James Kish
(74) *Attorney, Agent, or Firm*—Scully, Scott, Murphy & Presser, P.C.

(57) ABSTRACT

An ultrasonic diagnostic apparatus including: an ultrasonic observation device that transmits and receives an ultrasonic wave by an ultrasonic transducer arranged on a tip end of a probe, and that acquires a plurality of two-dimensional ultrasonic tomographic images for a subject in a living body; a position data calculator that detects information indicating a reference position of each of the two-dimensional ultrasonic tomographic images and an orientation of a tomographic plane of the each two-dimensional ultrasonic tomographic image; and an image processor is provided. The image processor generates a band-shaped longitudinal image including a curved plane along a moving path of the ultrasonic transducer.

35 Claims, 78 Drawing Sheets

FIG.76
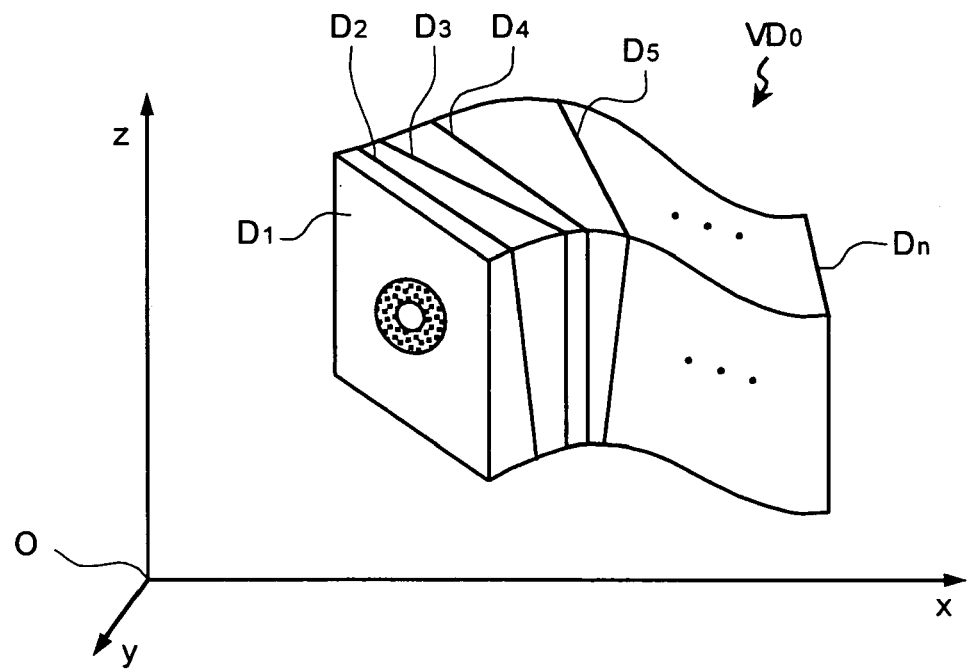
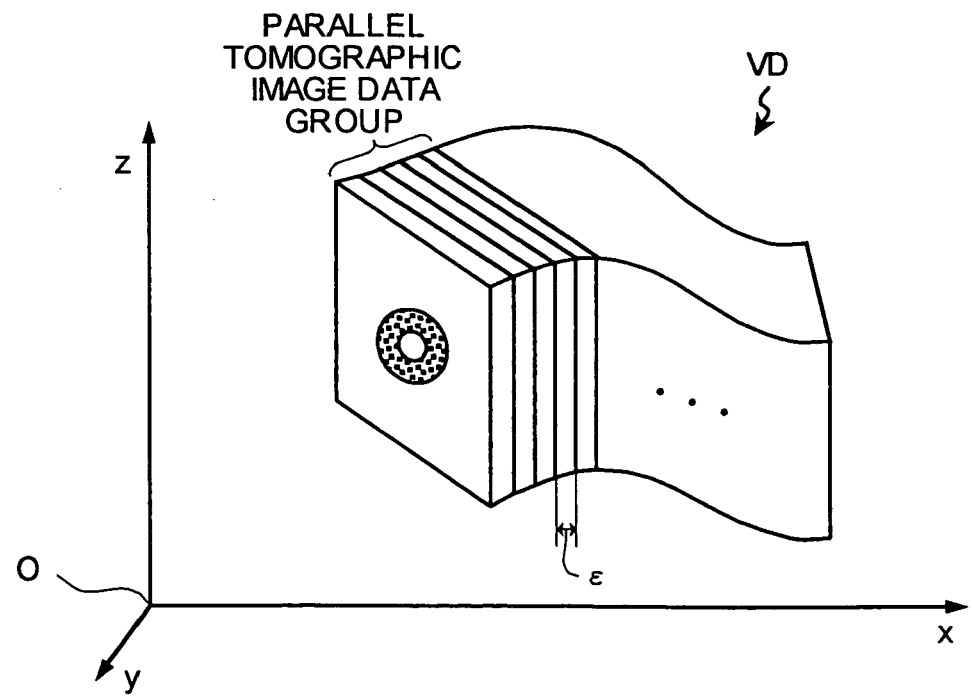

ULTRASONIC DIAGNOSTIC APPARATUS

CROSS-REFERENCE TO RELATED APPLICATIONS

This application claims the benefit of priority of Japanese Patent Applications No. 2003-354316 filed on Oct. 14, 2003 and No. 2003-401434 filed on Dec. 1, 2003, the entire contents of which are incorporated herein by reference.

BACKGROUND OF THE INVENTION

1) Field of the Invention

The present invention relates to an ultrasonic diagnostic apparatus which irradiates a subject, such as a living body, with an ultrasonic wave, receives an echo of the ultrasonic wave, performs three-dimensional (hereinafter, "3D") scan, and which displays a desired tomographic image of the subject on a monitor screen using 3D region image data obtained by the 3D scan.

2) Description of the Related Art

Conventionally, an ultrasonic diagnostic apparatus which irradiates a subject, such as a living body, with an ultrasonic wave, spatially receives an echo of the ultrasonic wave, performs 3D scan on the subject, generates 3D image data on this subject using a plurality of pieces of two-dimensional (hereinafter, "2D") image data obtained by the 3D scan, and which displays a desired tomographic image of the subject on a monitor screen based on the generated 3D image data has been developed. An operator such as a medical doctor or an apparatus operator operates the ultrasonic diagnostic apparatus to display the desired tomographic image of the subject on the monitor screen, which searches or observes a region of interest of the subject such as an affected site, e.g., a tumor or a characteristic site in a body cavity, which grasp a shape, a size or the like of this region of interest, and which performs medical treatments such as ultrasonic diagnosis on the patient.

As related techniques to such a conventional technique, there is known the following technique. According to Japanese Patent Application Laid-Open No. 7-155328 for example, if a plurality of pieces of 2D image data obtained as a result of a 3D scan on a subject are arranged three-dimensionally, then an imaginary cut plane is set on each of the 2D image data thus arranged, the pieces of 2D image data are interpolated, and a tomographic image of the subject on the cut plane is displayed on the screen. According to Japanese Patent No. 3325224 for example, an ultrasonic diagnostic apparatus includes a small-diameter probe inserted into a forceps channel of an endoscope, performs a 3D scan on a subject by moving forward or backward the probe inserted into a hollow portion of the subject using a dedicated drive, generates a longitudinal image of this subject or a tomographic image thereof in various directions based on a plurality of pieces of 2D image data obtained by the 3D scan, and displays the generated image on a monitor screen. In addition, if a plurality of measurement points are set on the tomographic image, then the ultrasonic diagnostic apparatus measures a geometric value of a measurement target region by the measurement points, e.g., a diameter, a perimeter, an area, or the like of an affected site or the like on a plane of an organ displayed on this tomographic image.

However, the conventional ultrasonic diagnostic apparatuses disclosed in Japanese Patent Application Laid-Open No. 7-155328 and Japanese Patent No. 3325224 have the following disadvantages. When each of these conventional ultrasonic diagnostic apparatuses interpolates the 2D image data obtained by the 3D scan, it is assumed that the respective pieces of 2D image data are arranged in parallel. Therefore, irrespective of a scan path of this 3D scan, the apparatus displays the longitudinal image or the tomographic image of the subject almost linearly on the monitor screen. As a result, the longitudinal image or the tomographic image of the subject displayed by the apparatus is often strained, as compared with an actual shape of the subject. If the operator uses this apparatus, it is difficult to obtain the longitudinal image or the tomographic image of the subject which accurately represents the actual shape of the subject, and properly grasp the shape, size, or the like of the region of interest of the subject such as the characteristic site or the affected site.

Furthermore, the ultrasonic diagnostic apparatus disclosed in Japanese Patent No. 3325224 operates and outputs the geometric value of the measurement target region by the measurement points designated by the operator on the tomographic image using the tomographic image generated based on a plurality of pieces of 2D image data arranged in parallel. Therefore, the apparatus often operates and outputs the desired geometric value of the designated measurement target region on the strained longitudinal image or tomographic image, as compared with the actual shape of the subject. As a result, when the operator uses this ultrasonic diagnostic apparatus, it is often difficult to accurately measure the geometric value such as the length, the area, or the volume of the region of interest such as the characteristic site or the affected site present in the actual subject. Consequently, even if using the geometric value, the operator often finds it difficult to properly grasp the shape, the size, or the like of this region of interest.

SUMMARY OF THE INVENTION

It is an object of the present invention to at least solve the problems in the conventional technology.

An ultrasonic diagnostic apparatus according to one aspect of the present invention includes a tomographic image acquisition unit, a detection unit, and an image generation unit. The tomographic image acquisition unit transmits and receives an ultrasonic wave by an ultrasonic transducer arranged on a tip end of a probe, and acquires a plurality of two-dimensional ultrasonic tomographic images for a subject in a living body. The detection unit detects information indicating a reference position of each of the two-dimensional ultrasonic tomographic images and an orientation of a tomographic plane of the each two-dimensional ultrasonic tomographic image. The image generation unit generates a band-shaped longitudinal image including a curved plane along a moving path of the ultrasonic transducer, based on the reference position, the orientation of the tomographic plane, and the each two-dimensional ultrasonic tomographic image.

An ultrasonic diagnostic apparatus according to another aspect of the present invention includes a tomographic image acquisition unit, a detection unit, and an operation unit. The tomographic image acquisition unit transmits and receives an ultrasonic wave by an ultrasonic transducer arranged on a tip end of a probe, and acquires a plurality of two-dimensional ultrasonic tomographic images for a subject in a living body. The detection unit detects arrangement information indicating a reference position of each of the two-dimensional ultrasonic tomographic images and an orientation of a tomographic plane of the each two-dimensional ultrasonic tomographic image. The operation unit operates a geometric value of the subject based on the arrangement information and the each two-dimensional ultrasonic tomographic image.

The other objects, features, and advantages of the present invention are specifically set forth in or will become apparent from the following detailed description of the invention when read in conjunction with the accompanying drawings.

BRIEF DESCRIPTION OF THE DRAWINGS

FIG. 76 is an explanatory view of a processing until a parallel tomographic image data group is set to the 3D image data;

DETAILED DESCRIPTION

Exemplary embodiments of an ultrasonic diagnostic apparatus according to the present invention is explained hereinafter in detail with reference to the accompanying drawings. It should be noted, however, that the present invention is not limited to the embodiment.

Figure 1:
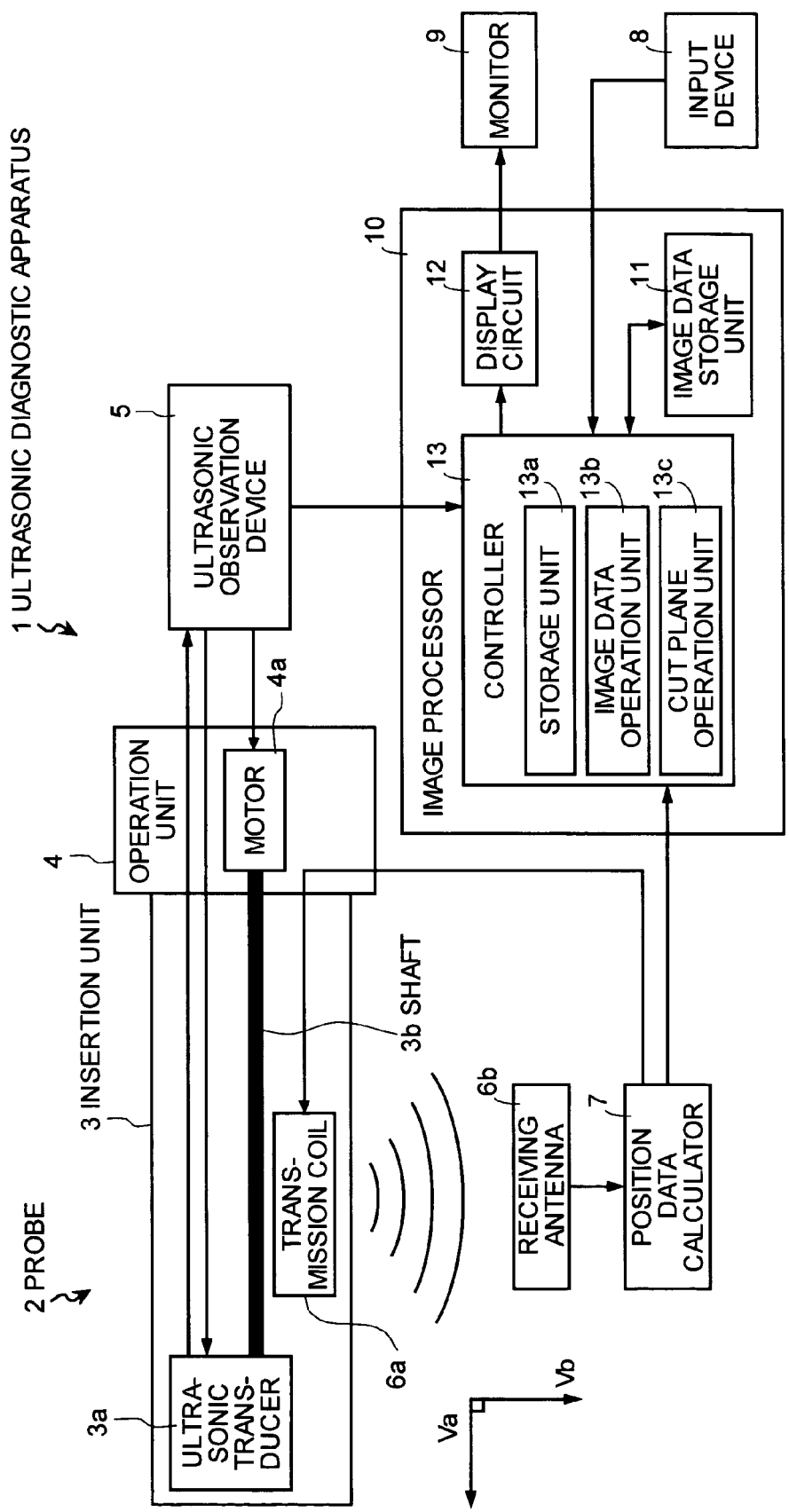
FIG. 1 is a block diagram that depicts schematic configuration of an ultrasonic diagnostic apparatus according to a first embodiment of the present invention.

FIG. 1 is a block diagram that depicts schematic configuration of an ultrasonic diagnostic apparatus according to a first embodiment of the present invention. In FIG. 1, the ultrasonic diagnostic apparatus 1 includes a probe 2 that includes an insertion unit 3 inserted into a living body and an operation unit 4 that operates the insertion unit 3, an ultrasonic observation device 5, a receiving antenna 6b, a position data calculator 7, an input device 8, a monitor 9, and an image processor 10. An ultrasonic transducer 3a is rotatably incorporated into a tip end of the insertion unit 3, and the operation unit 4 is arranged on a rear end of the insertion unit 3. A transmission coil 6a is detachably arranged near the ultrasonic transducer 3a. The operation unit 4 includes a motor 4a. The motor 4a is connected to the ultrasonic transducer 3a through a shaft 3b. The ultrasonic observation device 5 is electrically connected to the ultrasonic transducer 3a and the motor 4a through a power switch (not shown) provided on the operation unit 4 and a cable or the like. The position data calculator 7 is electrically connected to the transmission coil 6a and the receiving antenna 6b through a cable or the like. The image processor 10 is electrically connected to the ultrasonic observation device 5, the position data calculator 7, the input device 8, and the monitor 9 through a cable or the like.

As explained, the probe 2 is composed by the insertion unit 3 having the ultrasonic transducer 3a arranged on its tip end and the operation unit 4 incorporating therein the motor 4a. The probe 2 functions to radially scan an interior of the living body. Alternatively, the probe 2 may include an optical system such as an endoscope. In this alternative, the probe 2 transmits data on an optical image of the interior of the living body acquired by the optical system to the image processor 10. The image processor 10 displays an optical image corresponding to the received data on the optical image on the monitor 9. The insertion unit 3 is realized by a flexible member, and includes a thin cylindrical portion suited to be inserted into the living body. The ultrasonic transducer 3a is realized by piezoelectric ceramic such as barium titanate or lead zirconate titanate (PZT). The ultrasonic transducer 3a includes a function of converting an applied pulsed voltage into an ultrasonic wave by an inverse piezoelectric effect, and a function of converting a reflected wave (an echo) of this ultrasonic wave into an electric echo signal by a piezoelectric effect. The shaft 3b, which is a flexible shaft, functions as a flexible drive shaft which transmits rotational driving generated by the motor 4a to the ultrasonic transducer 3a.

The operation unit 4 functions to curve the tip end of the insertion unit 3 including a region in which the ultrasonic transducer 3a and the transmission coil 6a, in response to an operator's operation. If the operator turns on the power switch of the operation unit 4, the operation unit 4 electrically connects the ultrasonic transducer 3a, the motor 4a, and the ultrasonic observation device 5 to one another. The ultrasonic observation device 5 applies a pulsed voltage (pulse voltage) of, for example, about 100 volts to the ultrasonic transducer 3a, and applies a DC drive voltage of, for example, 12 volts to the motor 4a. The ultrasonic transducer 3a outputs an ultrasonic wave using the pulse voltage applied from the ultrasonic observation device 5, receives an echo of the ultrasonic wave, and transmits an echo signal corresponding to the received echo to the ultrasonic observation device 5. At the same time, the motor 4a makes rotation driving using the drive voltage applied from the ultrasonic observation device 5, and transmits the rotation driving to the ultrasonic transducer 3a through the shaft 3b. Accordingly, the motor 4a rotates the ultrasonic transducer 3a with the shat 3b used as a drive shaft.

When the operator turns on the power switch of the operation unit 4 while the insertion unit 3 is inserted into the living body, the ultrasonic transducer 3a is driven to rotate with the shaft 3b used as the drive shaft, and repeatedly outputs the ultrasonic wave to and receives the echo of the ultrasonic wave from the interior of the living body. In this case, the ultrasonic transducer 3a performs a radial scan on a plane perpendicular to an insertion axis direction of the insertion unit 3. The probe 2 thus completes one radial scan. The ultrasonic transducer 3a repeatedly performs this radial scan until the operator turns off the power switch of the operation unit 4. In addition, the ultrasonic transducer 3a sequentially transmits the echo signals obtained for respective radial scans to the ultrasonic observation device 5. Further, if the operator guides the probe 2 that is executing the radial scan, the ultrasonic transducer 3a performs this radial scan three-dimensionally along a moving path generated by the operator's guide to thereby scan the interior of the living body three-dimensionally (execute a 3D scan on the interior of the living body).

The ultrasonic observation device 5 includes a detector circuit (not shown), an amplifier circuit (not shown), an analog-to-digital (A/D) converter circuit (not shown), a coordinate converter circuit (not shown), and the like. The ultrasonic observation device 5 performs well-known processings such as an envelope detection processing, a logarithmic amplification processing, an A/D conversion processing, and a coordinate transform processing from a polar coordinate system to an orthogonal coordinate system, on the echo signals sequentially received from the ultrasonic transducer 3a, and generates one 2D image data for each of the sequentially received echo signals. The ultrasonic observation device 5 then sequentially transmits a plurality of pieces of generated 2D image data to the image processor 10. Further, when the operator turns on the power switch of the operation unit 4, the ultrasonic observation device 5 applies the pulse voltage of about 100 volts to the ultrasonic transducer 3a and applies the drive voltage of about 12 volts to the motor 4a.

The transmission coil 6a is realized by a first coil related to the insertion axis direction of the insertion unit 3 relative to the interior of the living body, and a second coil related to a direction perpendicular to the insertion axis direction. As explained, the transmission coil 6a is detachably arranged near the ultrasonic transducer 3a, e.g., about 0.5 to 1 centimeter away from the ultrasonic transducer 3a, and also electrically connected to the position data calculator 7 through the cable (not shown) or the like. In this case, the transmission coil 6a is fixedly arranged so that a distance and a direction of the transmission coil 6a relative to the ultrasonic transducer 3a are substantially constant. Therefore, positions and directions of the first and the second coils are set substantially constant relative to the ultrasonic transducer 3a, respectively. Further, if the position data calculator 7 supplies currents to the first and the second coils, the transmission coil 6a generates a magnetic field in a surrounding space of the transmission coil 6a. If the transmission coil 6a is arranged near the ultrasonic transducer 3a, the coil 6a may be detachably arranged on an outer wall of the insertion unit 3. It is, however, preferable to detachably insert the transmission coil 6a into the insertion unit 3.

The receiving antenna 6b is realized by a plurality of coils. The receiving antenna 6b detects the magnetic field generated by the transmission coil 6a, and converts the magnetic field into a current. Thereafter, the receiving antenna 6b transmits an electric signal (a magnetic field signal) corresponding to this current to the position data calculator 7.

When the operator turns on a power switch (not shown) provided on the position data calculator 7, the position data calculator 7 supplies a current to the transmission coil 6a through the cable or the like and receives the magnetic field signal transmitted from the receiving antenna 6b. Further, the position data calculator 7 calculates a position vector r, an axial vector $V_a$ having a unit length, and a plane parallel vector $V_b$ having a unit length of the transmission coil 6a. In addition, the position data calculator 7 sequentially transmits the position vector r, the axial vector $V_a$, and the plane parallel vector $V_b$ thus calculated to the image processor 10 as position data on the transmission coil 6a.

A spatial coordinate system xyz composed by an x axis, a y axis, and a z axis with a predetermined position, e.g., a central position of the receiving antenna 6b set as an origin is set to the position data calculator 7 in advance. The position vector r is a vector that determines a position of the transmission coil 6a on the spatial coordinate system xyz. The position vector r can be approximated as a vector that determines a central position of the rotation driving of the ultrasonic transducer 3a based on the fact that the transmission coil 6a is located near the ultrasonic transducer 3a. The axial vector $V_a$ is calculated based on the magnetic field signal corresponding to the magnetic field and output from the first coil of the transmission coil 6a. Namely, the axial vector $V_a$ is a vector on the spatial coordinate system xyz and a direction vector which has the unit length and which indicates the insertion axis direction of the insertion unit 3 into the living body. Accordingly, the axial vector $V_a$ indicates a direction perpendicular to a plane within the living body on which the ultrasonic transducer 3a performs the radial scan. Further, the plane parallel vector $V_b$ is calculated based on the magnetic field signal corresponding to the magnetic field output from the second coil of the transmission coil 6a. Namely, the plane parallel vector $V_b$ is a vector on the spatial coordinate system xyz and a direction vector which has the unit length and which indicates a predetermined direction perpendicular to the insertion axis direction. Accordingly, the plane parallel vector $V_b$ indicates the predetermined direction in parallel to the plane in the living body on which the ultrasonic transducer 3a performs the radial scan. It is noted that the predetermined direction indicated by the plane parallel vector $V_b$ is set at a constant position relative to the perpendicular direction indicated by the axial vector $V_a$. This results from the fact that the positions and directions of the first and the second coils are set substantially constant relative to the ultrasonic transducer 3a, respectively, as already explained.

The input device 8 is realized by a keyboard, a touch panel, a track ball, a mouse, a joystick, or the like, or a combination thereof. The input device 8 inputs cut point information on coordinate information on a cut point related to a sectional position designated on the 2D image data generated by the ultrasonic observation device 5, angle information for designating a rotation angle of each of the various displayed tomographic images, or indication information on an image display processing on the monitor 9, to the image processor 10. If the input device 8 is, for example, the keyboard or the touch panel, then the operator inputs or selects a numeric value corresponding to the cut point information or the angle information or directly inputs a coordinate position displayed on the screen of the monitor 9 or the touch panel in a state in which the input device 8 accepts input of each information, thereby inputting the cut point information or the angle information in the image processor 10. If the input device 8 is, for example, the track ball, the mouse, or the joystick, then the operator selects a numeric value corresponding to the cut point information or directly inputs the coordinate position displayed on the screen of the monitor 9 in a state in which the input device 8 accepts input of each information, thereby inputting the cut point information in the image processor 10. Alternatively, the operator may select a numeric value corresponding to the angle information and perform an operation for moving a cursor or the like displayed on the screen of the monitor 9 in a predetermined direction while depressing a mouse button (which operation is referred to as "drag operation" hereinafter), thereby inputting the angle information in the image processor 10. For example, if the operator causes the input device 8 to execute this drag operation and the cursor is moved upward on the monitor screen, the input device 8 inputs the angle information indicating that the tomographic image is rotated in a positive direction in the image processor 10. If the operator causes the input device 8 to execute the drag operation and the cursor is moved downward on the monitor screen, the input device 8 inputs the angle information indicating that the tomographic image is rotated in a negative direction in the image processor 10. If the cursor is moved rightward on the monitor screen, the input device 8 inputs the angle information indicating that the tomographic image is rotated in the positive direction in the image processor 10. When the cursor is moved leftward on the monitor screen, the input device 8 inputs the angle information indicating that the tomographic image is rotated in the negative direction in the image processor 10.

The image processor 10 is realized by a well-known computer that includes various recording mediums such as a random access memory (RAM), a read only memory (ROM), and a hard disk, and a central processing unit (CPU). The image processor 10 includes an image data storage unit 11, a display circuit 12, and a controller 13. The image data storage unit 11 is realized by various storage device which can write and read data such as an IC memory such as a RAM, an electrically erasable programmable ROM (EEPROM), and a flash memory, and a hard disk drive or a magneto-optic disk drive. The image data storage unit 11 stores various pieces of image data input from the controller 13 under control of the controller 13. In addition, when the controller 13 generates various pieces of tomographic image data, the image data storage unit 11 stores the tomographic image data under control of the controller 13.

The controller 13 is realized by a ROM that stores various types of data such as a processing program, a RAM that stores each operation parameter, a CPU that executes the processing program stored in the ROM, and the like. The controller 13 includes a storage unit 13a, an image data operation unit 13b, and a cut plane operation unit 13c. The storage unit 13a is composed by the ROM and the RAM, and stores not only the processing program and operation parameters but also the position data which the controller 13 sequentially receives from the position data calculator 7. The spatial coordinate system xyz is set to the controller 13 in advance, and the storage unit 13a stores data on this spatial coordinate system xyz as reference setting data.

Further, when the ultrasonic transducer 3a sequentially transmits n echo signals obtained by n radial scans (where n=1, 2, 3, . . . ) to the ultrasonic observation device 5, then the controller 13 grasps timings at which the ultrasonic observation device 5 generates n pieces of 2D image data based on the n echo signals, respectively, and grasps pieces of position data sequentially received from the position data calculator 7 for the respective timings. Thereafter, the controller 13 sequentially receives the n pieces of 2D image data from the ultrasonic observation device 5, and associates the 2D image data generated at each timing with the position data received at the same timing for each 2D image data. By doing so, the controller 13 ensures associating the position data corresponding to the position at which each radial scan is performed, with the 2D image data generated base on the echo signal generated by this radial scan.

Figure 2:
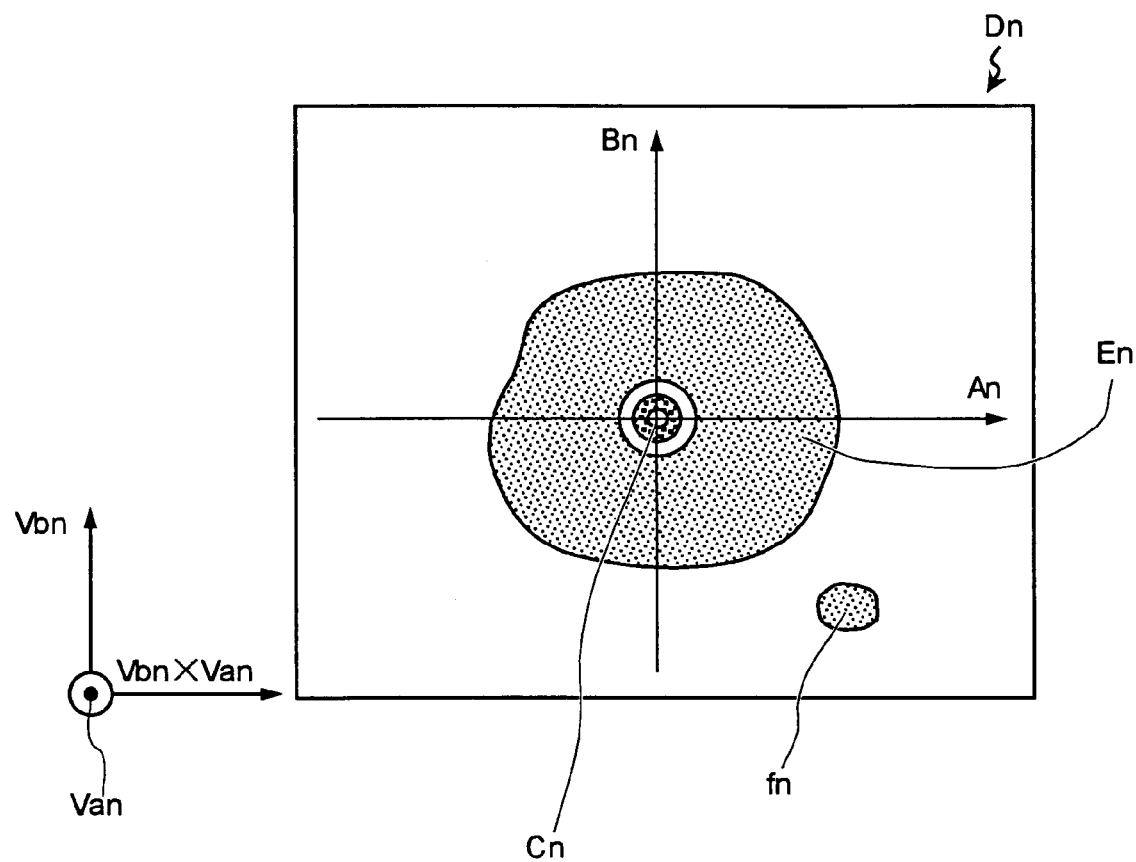
FIG. 2 depicts an example of 2D image data associated with position data.

FIG. 2 depicts an example of $n^{th}$ 2D image data associated with the position data by the controller 13 when the controller 13 sequentially receives the n pieces of 2D image data from the ultrasonic observation device 5. An instance in which the operator inserts the insertion unit 3 into a duodenum of the subject, a radial scan is performed by the ultrasonic transducer 3a, the insertion unit 3 is gradually guided in the insertion axis direction, and this subject is thereby scanned three-dimensionally is explained hereafter. However, this is not intended to limit the present invention.

As shown in FIG. 2, the $n^{th}$ 2D image data $D_n$ includes a duodenum image En that shows a cross section of the duodenum and a pancreatic duct image fn that shows a cross section of the pancreatic duct. As already explained, the controller 13 associates the 2D image data $D_n$ with the position data received at the timing at which the 2D image data $D_n$ is generated. In this case, the controller 13 sets an axial vector $V_{an}$ as a normal vector of the plane corresponding to the 2D image data $D_n$. In addition, the controller 13 sets a plane parallel vector $V_{bn}$ as a direction vector that is parallel to this plane and which indicates a predetermined direction relative to the axial vector $V_{an}$, e.g., a direction of 12 o'clock on this plane. Further, the controller 13 sets a position vector $r_n$ which indicates an image center $C_n$ of the 2D image data $D_n$. Thus, the controller 13 can set an orthogonal coordinate system composed by an axis parallel to the plane parallel vector $V_{bn}$ and an axis parallel to an outer product vector $(V_{bn} \times V_{an})$ with the image center $C_n$ set as an origin. The outer product vector $(V_{bn} \times V_{an})$ can be calculated by an outer product between the plane parallel vector $V_{bn}$ and the axial vector $V_{an}$.

Likewise, the controller 13 associates (n−1) pieces of 2D image data $D_1, D_2, \ldots,$ and $D_{n-1}$, received sequentially from the ultrasonic observation device 5, with the position data, respectively. Thus, the axial vectors $V_{a1}, V_{a2}, \ldots,$ and $V_{an}$, the plane parallel vector $V_{b1}, V_{b2}, \ldots, V_{bn}$, and the position vectors $r_1, r_2, \ldots,$ and $r_n$ are set to the n pieces of 2D image data $D_1, D_2, \ldots,$ and $D_n$, respectively.

Figure 3:
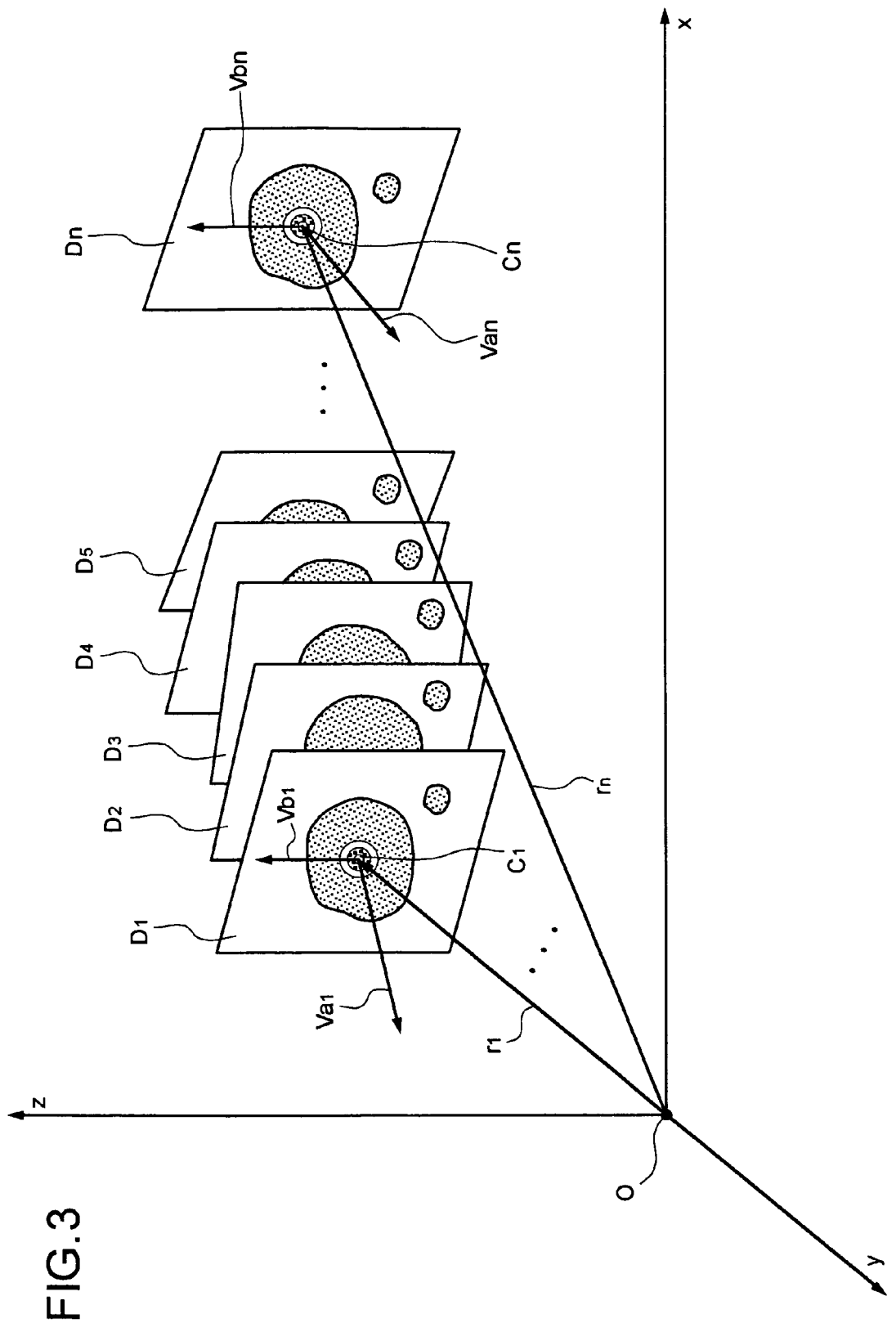
FIG. 3 is an explanatory view illustrating an operation for arranging pieces of 2D image data associated with respective pieces of position data on a spatial coordinate system.

FIG. 3 is an explanatory view of an operation for arranging the n pieces of 2D image data associated with the respective pieces of position data by the controller 13 on the spatial coordinate system xyz. As shown in FIG. 3, if the controller 13 associates the n pieces of 2D image data $D_1, D_2, \ldots,$ and $D_n$ with the respective pieces of position data, the controller 13 arranges the n pieces of 2D image data $D_1, D_2, \ldots$ and $D_n$ on the spatial coordinate system xyz based on the spatial coordinate system xyz and the position data associated with the respective pieces of 2D image data, both of which are read from the storage unit 13a. The axial vectors $V_{a1}, V_{a2}, \ldots,$ and $V_{an}$, the plane parallel vectors $V_{b1}, V_{b2}, \ldots,$ and $V_{bn}$, and the position vectors $r_1, r_2,$ and $r_3$ determine the respective positions and direction of the 2D image data $D_1, D_2, \ldots,$ and $D_n$ arranged on the spatial coordinate system xyz. Therefore, the controller 13 can arrange the n pieces of 2D image data $D_1, D_2, \ldots,$ and $D_n$ on the spatial coordinate system xyz so that a positional relationship of the 2D image data is substantially equal to an actual positional relationship when the ultrasonic transducer 3a performs a radial scan three-dimensionally. Thereafter, the controller 13 stores the n pieces of 2D image data $D_1, D_2, \ldots,$ and $D_n$, the arrangement relationship on the spatial coordinate system xyz of which is set, in the image storage unit 11.

Figure 4:
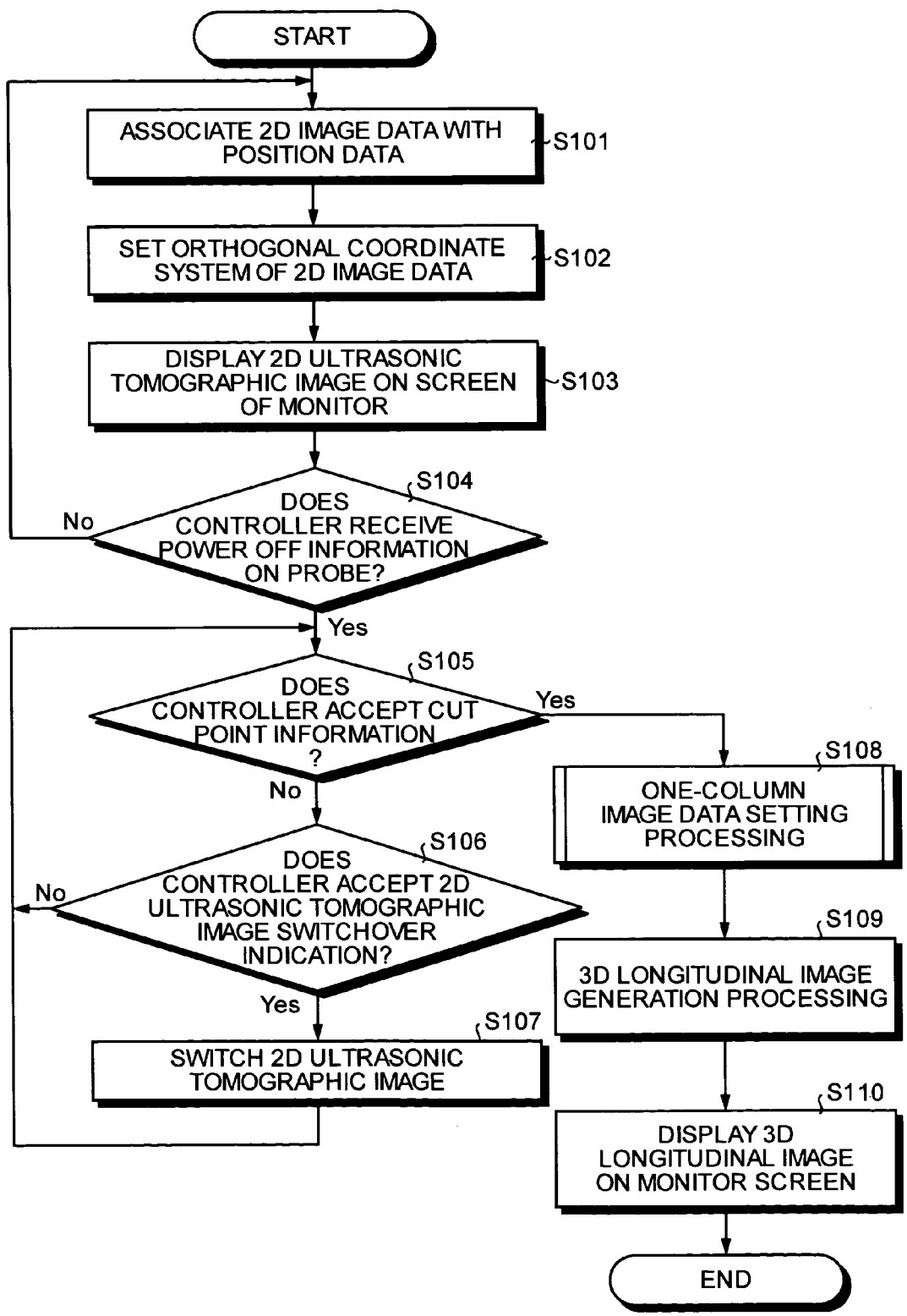
FIG. 4 is a flowchart that depicts processing steps executed until the ultrasonic diagnostic apparatus according to the first embodiment displays a 3D longitudinal image on a screen of a monitor screen.

FIG. 4 is a flowchart showing processing steps since the controller 13 acquires n pieces of 2D image data and n pieces of position data until setting a cut plane including respective cut points, and then displaying a band-shaped 3D longitudinal image which indicates a tomographic image of each cut plane on the monitor 9. Referring to FIG. 4, if the ultrasonic observation device 5 generates 2D image data based on the echo signal, and the position data calculator 7 calculates position data on the position at which this echo signal is obtained, then the controller 13 acquires the 2D image data output from the ultrasonic observation device 5 and the position data output from the position data calculator 7. In addition, the controller 13 associates the acquired 2D image data with the position data, as explained (at step S101).

The controller 13 arranges the 2D image data associated with this position data on the spatial coordinate system xyz, and sets an orthogonal coordinate system based on the axial vector and the plane parallel vector made to correspond for the 2D image data (at step S102). Specifically, as shown in FIG. 2, the controller 13 sets an orthogonal coordinate system $A_n B_n$ composed by the axis ($B_n$ axis) in parallel to the plane parallel vector $V_{bn}$ and the axis ($A_n$ axis) in parallel to the outer product vector $(V_{bn} \times V_{an})$, with the image center $C_n$ set as the origin, for the 2D image data $D_n$ (where n=1, 2, 3, . . . ).

Thereafter, the controller 13 stores the 2D image data for which the orthogonal coordinate system is set, in the image data storage unit 11 while arranging the 2D image data on the spatial coordinate system xyz, transmits the 2D image data to the monitor 9, through the display circuit 12 and displays a 2D ultrasonic tomographic image corresponding to the 2D image data on the monitor 9 (at step S103). If the probe 2 is executing a radial scan, that is, the power switch of the operation unit 4 is turned on, the controller 13 does not receive power-OFF information corresponding to a power-OFF state of the probe 2 ("No" at step S104). If so, the controller 13 repeatedly executes the processing step S101 and the following. Namely, if n radial scans are performed before the probe 2 is turned off, the controller 13 repeatedly executes the processing step S101 and the following n times. The controller 13 thereby acquires n pieces of 2D image data $D_1, D_2, \ldots,$ and $D_n$ associated with the respective pieces of position data, associates the orthogonal coordinate systems with the respective pieces of 2D image data $D_1, D_2, \ldots,$ and $D_n$. Further, as shown in FIG. 3, the controller 13 stores the n pieces of 2D image data $D_1, D_2, \ldots,$ and $D_n$ thus acquired, in the image data storage unit 11 while arranging the 2D image data $D_1, D_2, \ldots,$ and $D_n$ on the spatial coordinate system xyz.

If the operator turns off the power switch of the operation unit 4 after the n radial scans, the controller 13 receives the power-OFF information on the probe 2 ("Yes" at step S104). Thereafter, if the operator inputs indication information for indicating that the 2D ultrasonic tomographic image displayed on the monitor screen is switched over to another 2D ultrasonic tomographic image (switchover indication information) without performing the cut point information input operation using the input device 8, then the controller 13 does not accept the cut point information ("No" at step S105) but accepts a switchover indication corresponding to the switchover indication information ("Yes" at step S106). If so, the controller 13 reads the 2D image data stored in the image data storage unit 11 based on the switchover indication corresponding to the switchover indication information the input of which the controller 13 accepts. In addition, the controller 13 transmits this 2D image data to the monitor 9 through the display circuit 12. The display circuit 12 performs various processings such as digital-to-analog (D/A) conversion on the 2D image data. The monitor 9 switches display of the 2D ultrasonic tomographic image over to display of a 2D ultrasonic tomographic image corresponding to this 2D image data (at step S107). The controller 13 repeatedly executes the processing step S105 and the following. Further, if neither the cut point information nor the switchover indication information are input to the controller 13, then the controller 13 does not accept the cut point information ("No" at step S105) and does not accept the switchover indication based on the switchover indication information ("No" at step S106). If so, the controller 13 repeatedly executes the processing step S105 and the following.

On the other hand, if the operator inputs cut point information on two cut points designated as respective desired positions on a desired 2D ultrasonic tomographic image using the input device 8, the controller 13 accepts the input cut point information ("Yes" at step S105). In addition, the controller 13 sets the two cut points corresponding to the cut point information the input of which the controller 13 accepts, on the orthogonal coordinate system of the 2D image data corresponding to this 2D ultrasonic tomographic image. The two cut points are set on the orthogonal coordinate system of one of the n piece of 2D image data. The controller 13 sets two cut points and a straight line that passes through the two cut points on each of the orthogonal coordinate systems of the n pieces of 2D image data based on the coordinate information on the two cut points. In addition, the controller 13 sets the straight line as a longitudinal plane position of each of the n pieces of 2D image data arranged on the spatial coordinate system xyz. Namely, curved planes that passes through the straight lines correspond to cut planes forming the longitudinal planes of the respective n pieces of 2D image data arranged on the spatial coordinate system xyz. The controller 13 calculates all pixels on each straight line thus obtained and luminances of the pixels for each of the n pieces of 2D image data, generates one-column image data in one column and j row (where j=1, 2, 3, . . . ), and sets position vectors on the spatial coordinate system xyz ("pixel position vectors") for the pixels in each row of each one-column image data obtained. Thus, the controller 13 sets one-column image data, for which the pixel positions in the rows correspond to the coordinates of pixels on the spatial coordinate system xyz, for the n pieces of 2D image data, respectively (at step S108).

If the controller 13 sets the one-column image data for respective pieces of 2D image data, the image data operation unit 13b linearly interpolates adjacent pieces of one-column image data using the n pieces of 2D image data for which pieces of the one-column image data are set, respectively. In addition, the image data operation unit 13b generates 3D longitudinal image data corresponding to the tomographic images of the respective cut planes, i.e., corresponding to a band-shaped 3D longitudinal image (at step S109). Details of the processing for generating the 3D longitudinal image data (3D longitudinal image generation processing) performed by the image data operation unit 13b is explained later.

Figure 5:
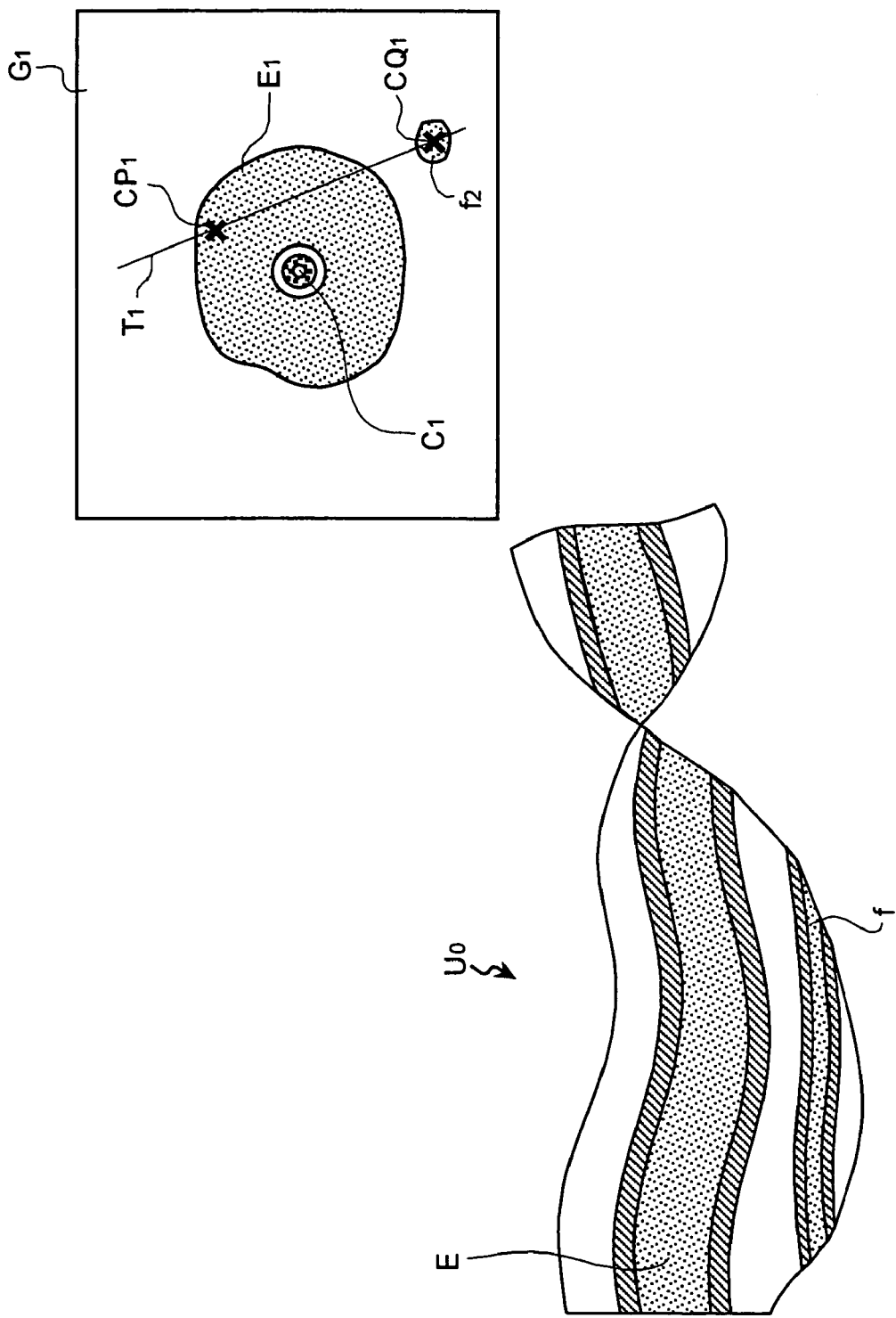
FIG. 5 depicts an example of the 3D longitudinal image displayed on the screen of the monitor screen.

If the image data operation unit 13b generates the 3D longitudinal image data, then the controller 13 transmits this 3D longitudinal image data to the monitor 9 through the display circuit 12 to display a 3D longitudinal image corresponding to the 3D longitudinal image data on the monitor 9 (at step S110). FIG. 5 depicts an example of the 3D longitudinal image displayed on the screen of the monitor 9. As explained, the image data operation unit 13b generates the 3D longitudinal image data on the cut planes defined as the curved plane that includes straight lines on the n pieces of 2D image data, respectively. Therefore, a 3D longitudinal image $U_0$ corresponding to the 3D longitudinal image data is a band-shaped longitudinal image having a curved plane, a twist or the like according to an actual moving path, moving direction, or the like of the probe 2 that is moved into the living body when the 3D scan is performed, as shown in FIG. 5. Namely, this 3D longitudinal image $U_0$ can represents a tomographic image that is less strained as compared with the subject in the living body on which the probe 2 performs the 3D scan, and which is substantially equal in shape to the actual subject. For example, when the operator designates the cut points on a duodenum image and a pancreatic duct image captured in the 2D ultrasonic tomographic image, respectively, then the 3D longitudinal image $U_0$ can ensure representing a duodenum image E substantially equal in shape to the actual duodenum and a pancreatic duct image f substantially equal in shape to the actual pancreatic duct.

When the operator inputs angle information using the input device 8, the band-shaped 3D longitudinal image $U_0$ that is displayed is rotated in a predetermined direction according to an angle corresponding to the angle information. Therefore, even if the 3D longitudinal image $U_0$ has twists or the like, the operator can easily observe all tomographic images, including hidden portions, captured in the 3D longitudinal image $U_0$. Further, when the operator inputs indication information on image magnification or image reduction using the input device 8, the controller 13 magnifies or reduces the 3D longitudinal image $U_0$ in accordance with an input amount input to the input device 8. When the operator inputs indication information on image display using the input device 8, the controller 13 may display the 3D longitudinal image $U_0$ and a 2D ultrasonic tomographic image $G_1$ corresponding to the 2D image data $D_1$ as shown in FIG. 5.

If the operator causes the ultrasonic transducer 3a to perform a radial scan and guides the probe 2 following step S110, the 3D scan using the ultrasonic transducer 3a resumes. In addition, the controller 13 generates the 3D longitudinal data based on the cut points already set at step S108 and the pieces of 2D image data obtained successively by the 3D scan, and displays the 3D longitudinal image corresponding to the 3D longitudinal data on the monitor 9. In this case, the controller 13 adds the 3D longitudinal image generated by operator's guiding the probe 2 to the 3D longitudinal image $U_0$ already displayed on the screen of the monitor 9 and displays the resultant 3D longitudinal image. The controller 13 thus extends the 3D longitudinal image $U_0$ successively with the operator's operation for guiding the probe 2 during the 3D scan.

Figure 6:
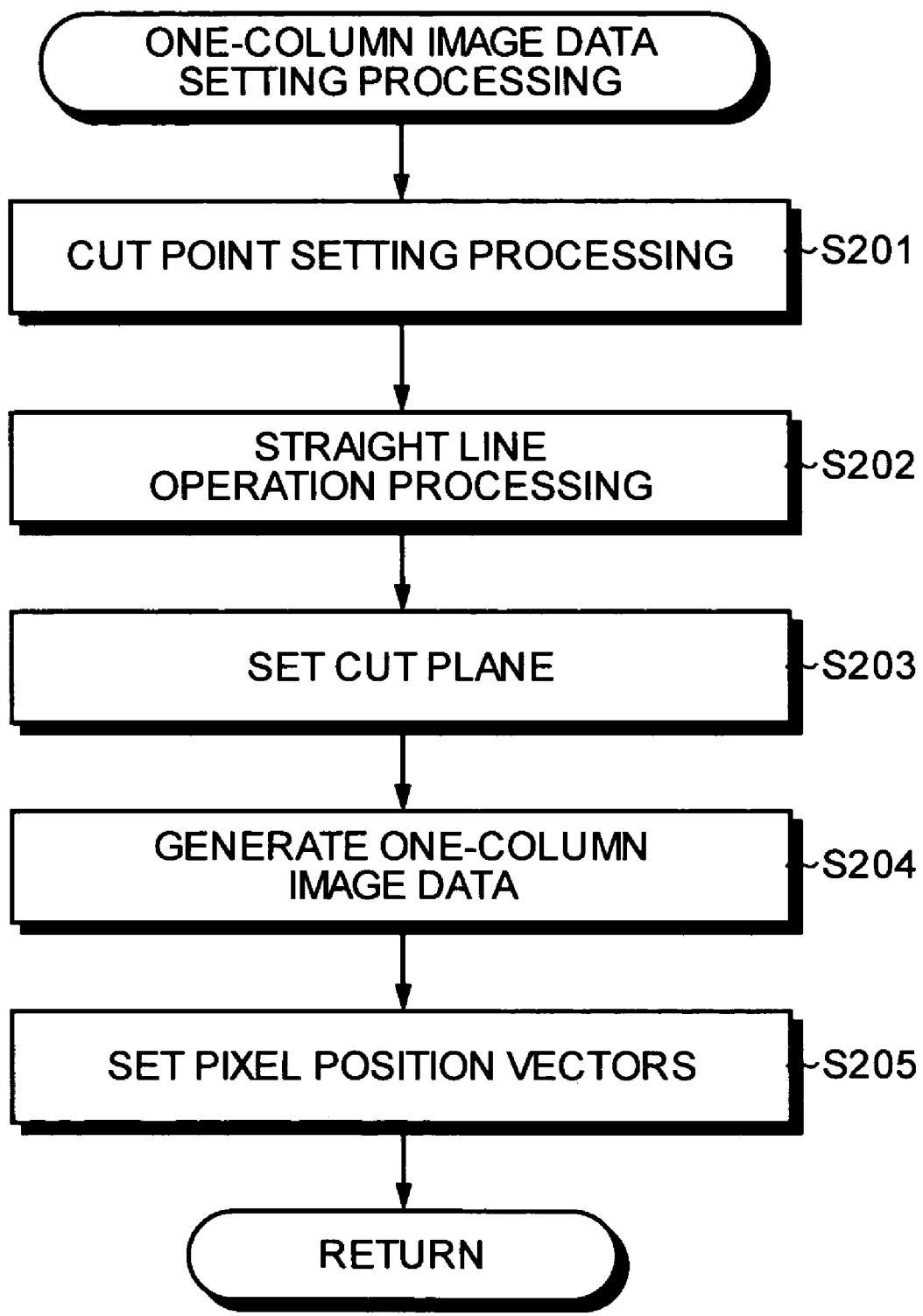
FIG. 6 is a flowchart showing processing steps executed until the ultrasonic diagnostic apparatus according to the first embodiment completes a one-column image data setting processing.
Figure 7:
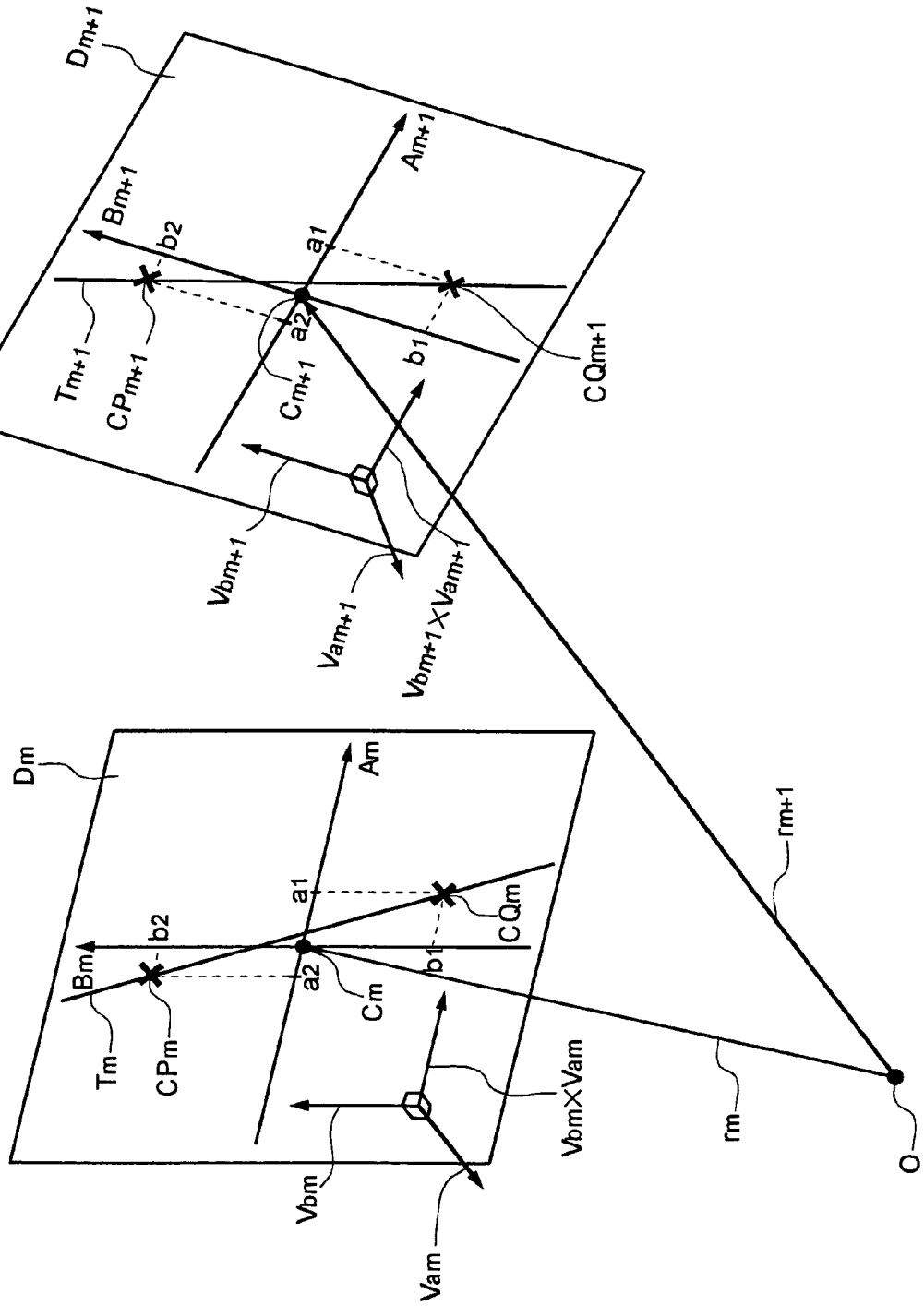
FIG. 7 is an explanatory view of a processing performed by the ultrasonic diagnostic apparatus according to the first embodiment for setting two cut points and a straight line that passes through the two cut points for each 2D image data.

Respective processing steps executed until the controller 13 completes the processing for setting pieces of one-column image data for the n pieces 2D image data, respectively, (one-column image data setting processing) at step S108 will next be explained in detail. FIG. 6 is a flowchart showing the processing steps executed until the controller 13 completes the one-column image data setting processing. FIG. 7 is an explanatory view of a processing performed by the controller 13 for setting two cut points and a straight line that passes through the two cut points for each 2D image data.

Referring to FIGS. 6 and 7, if the operator inputs cut point information on the two cut points designated as the respective desired positions on a desired 2D ultrasonic tomographic image using the input device 8, the controller 13 sets cut points $CP_m$ and $CQ_m$ corresponding to the cut point information on the orthogonal coordinate system $A_m B_m$ of the 2D image data $D_m$ corresponding to this 2D ultrasonic tomographic image. For example, as shown in FIG. 7, the controller 13 sets the cut point $CP_m$ at a coordinate $(a_2, b_2)$ on the orthogonal coordinate system $A_m B_m$, and sets the cut point $CQ_m$ at a coordinate $(a_1, b_1)$ on the orthogonal coordinate system $A_m B_m$. It is noted that the integer m is the integer which satisfies $1 \leq m \leq (n-1)$. In addition, the orthogonal coordinate system $A_m B_m$ is the orthogonal coordinate system that is composed by the $B_m$ axis in parallel to the plane parallel vector $V_{bm}$ and the $A_m$ axis in parallel to the outer product vector $(V_{bm} \times V_{am})$, with the image center $C_m$ set as the origin, as already explained.

If the cut points $CP_m$ and $CQ_m$ have been set on the orthogonal coordinate system $A_m B_m$ of the 2D image data $D_m$, the controller 13 sets cut points $CP_{m+1}$ and $CQ_{m+1}$ on an orthogonal coordinate system $A_{m+1} B_{m+1}$ of 2D image data $D_{m+1}$ adjacent to the 2D image data $D_m$. Specifically, as shown in FIG. 7, the controller 13 sets the cut point $CP_{m+1}$ at a coordinate $(a_2, b_2)$ on the orthogonal coordinate system $A_{m+1} B_{m+1}$, and sets cut points $CQ_{m+1}$ at a coordinate $(a_1, b_1)$ on the orthogonal coordinate system $A_{m+1}B_{m+1}$. Based on this cut point setting method, the controller 13 sets cut points $CP_1$, $CP_2$, ..., and $CP_n$ at respective coordinates $(a_2, b_2)$ on the orthogonal coordinate systems, and sets cut points $CQ_1$, $CQ_2$, ..., and $CQ_n$ at respective coordinates $(a_1, b_1)$ on the orthogonal coordinate systems for the n pieces 2D image data $D_1, D_2, \ldots$, and $D_n$. The controller 13 thereby completes the processing for setting the two cut points for every 2D image data (the cut point setting processing) (at step S201).

The cut plane operation unit 13c then operates and outputs a straight line $T_n$ (where n=1, 2, 3, ...) that passes through the two cut points $CP_n$ and $CQ_n$ (where n=1, 2, 3, ...) which are set for every 2D image data, using coordinate information on the cut points $CP_1, CP_2, \ldots$, and $CP_n$ and coordinate information on the cut points $CQ_1, CQ_2, \ldots$, and $CQ_n$ set for the n pieces of 2D image data $D_1, D_2, \ldots$, and $D_n$, respectively (at step S202). Specifically, the controller 13 sets a straight line $T_m$ that passes through the cut points $CP_m$ and $CQ_m$ on the orthogonal coordinate system $A_m B_m$ of the 2D image data $D_m$, and sets a straight line $T_{m+1}$ that passes through the cut points $CP_{m+1}$ and $CQ_{m+1}$ on the orthogonal coordinate system $A_{m+1}B_{m+1}$ of the 2D image data $D_{m+1}$. If the controller 13 sets straight lines $T_1, T_2, \ldots$, and $T_n$ for the n pieces of 2D image data $D_1, D_2, \ldots$, and $D_n$, respectively, the cut plane operation unit 13c operates and outputs a curved plane including the straight lines $T_1, T_2, \ldots$, and $T_n$. In this case, the controller 13 sets the straight lines $T_1, T_2, \ldots$, and $T_n$ as longitudinal plane positions of the n pieces of 2D image data arranged on the spatial coordinate system xyz, and sets the curved plane operated and output by the cut plane operation unit 13c as a cut plane on which the band-shaped 3D longitudinal image is formed (at step S203).

If the controller 13 sets the $T_1, T_2, \ldots$, and $T_n$ for the n pieces of 2D image data, the image data operation unit 13b sets pixel groups in one column and j row for the straight lines $T_1, T_2, \ldots$, and $T_n$, respectively. In addition, the image data operation unit 13b calculates the luminances of pixels in the respective pixel groups, and generates n pieces of one-column image data $d_1, d_2, \ldots$, and $d_n$ in one column and j row for the n pieces of 2D image data $D_1, D_2, \ldots$, and $D_n$, respectively (at step S204). The one-column image data $d_1, d_2, \ldots$, and $d_n$ correspond to the respective straight lines $T_1, T_2, \ldots$, and $T_n$. Therefore, the image data operation unit 13b can calculate positions of the respective pixels of the one-column image data $d_1, d_2, \ldots$, and $d_n$ as pixel position vectors on the spatial coordinate system xyz.

For example, since the image center $C_m$ and the orthogonal coordinate system $A_m B_m$ are present on the spatial coordinate system xyz, a position vector $O(CP_m)$ of the cut point $CP_m$ set at the coordinate $(a_2, b_2)$ on the orthogonal coordinate system $A_m B_m$ of the 2D image data $D_m$ can be, therefore, calculated using the coordinate $(a_2, b_2)$ of this cut point $CP_m$ and a position vector $r_m$ of the image center $C_m$, as represented by the following Equation (1).

$$O(CP_m) = r_m + a_2(V_{bm} \times V_{am}) + b_2 V_{bm} \qquad (1)$$

Likewise, a position vector $O(CQ_m)$ of the cut point $CQ_m$ set at the coordinate $(a_1, b_1)$ on the orthogonal coordinate system $A_m B_m$ of the 2D image data $D_m$ can be calculated using the coordinate $(a_1, b_1)$ of this cut point $CQ_m$ and the position vector $r_m$ of the image center $C_m$, as represented by the following Equation (2).

$$O(CQ_m) = r_m + a_2(V_{bm} \times V_{am}) + b_1 V_{bm} \qquad (2)$$

In this calculation, each point on the straight line $T_m$ is operated and output by linearly interpolating or exterpolating the point to the straight line $T_m$ using a distance of the point to the cut point $CP_m$, a distance of the point to the cut point $CQ_m$, and Equations (1) and (2). Namely, the image data operation unit 13b can calculate the position of each pixel of the one-column image data $d_m$ as a position vector on the spatial coordinate system xyz by using the distance of the pixel position to the cut point $CP_m$, the distance of the pixel position to the cut point $CQ_m$, and Equations (1) and (2). The image data operation unit 13b can set the pixel position vectors of the respective pixels of the one-column image data $d_1, d_2, \ldots$, and $d_n$ by performing the same operation processings for the n pieces of one-column image data $d_1, d_2, \ldots$, and $d_n$ (at step S205).

Figure 8:
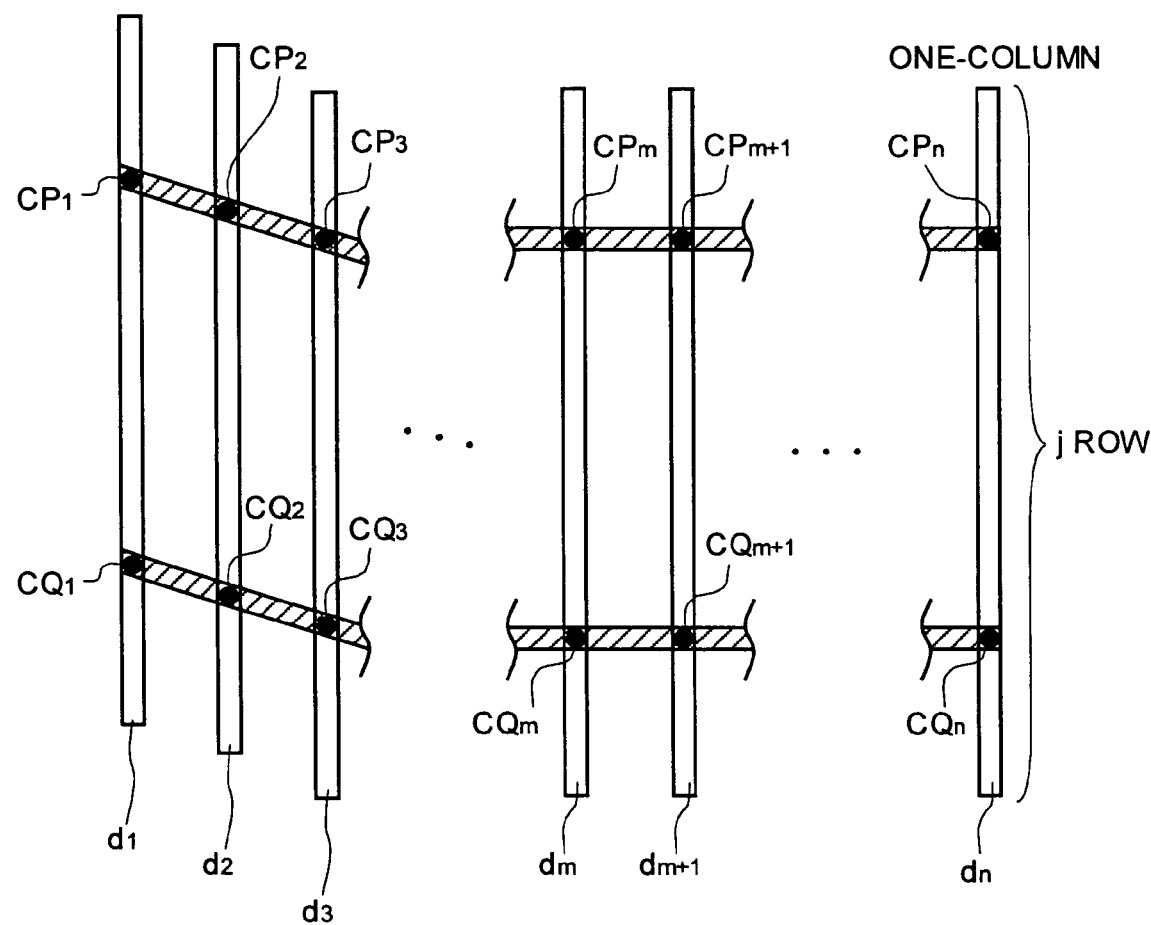
FIG. 8 is an explanatory view of a processing for interpolating respective adjacent pieces of one-column image data.

The 3D longitudinal image generation processing performed by the image data operation unit 13b at step S109 will next be explained in detail. FIG. 8 is an explanatory view of the processing for interpolating the respective adjacent pieces of one-column image data of the n pieces of one-column image data $d_1, d_2, \ldots$, and $d_n$ set for the n pieces of 2D image data $D_1, D_2, \ldots$, and $D_n$. As shown in FIG. 8, the n pieces of one-column image data $d_1, d_2, \ldots$, and $d_n$ are arranged on the spatial coordinate system xyz based on the axial vectors and the plane parallel vectors of the n pieces of 2D image data $D_1$, $D_2, \ldots$, and $D_n$, respectively. The cut points $CP_1, CP_2, \ldots$, and $CP_n$ include the same coordinate components on the respective orthogonal coordinate systems of the 2D image data $D_1, D_2, \ldots$, and $D_n$. The cut points $CQ_1, CQ_2, \ldots$, and $CQ_n$ include the same coordinate components on the respective orthogonal coordinate systems of the 2D image data $D_1$, $D_2, \ldots$, and $D_n$. In FIG. 8, for convenience of explanation with reference to the drawing, the one-column image data $d_1$, $d_2, \ldots$, and $d_n$ are drawn to be on the same plane and parallel to one another. Actually, they are not always present on the same plane and not always parallel to one another.

If the image data operation unit 13b is to interpolate the respective adjacent pieces one-column image data of the n pieces of one-column image data $d_1, d_2, \ldots$, and $d_n$, the image data operation unit 13b sets the cut points $CP_1, CP_2, \ldots$, and $CP_n$ and the cut points $CQ_1, CQ_2, \ldots$, and $CQ_n$ as reference points, and linearly interpolates the respective adjacent pixels equal in pixel position to the reference points and determined by the number of rows from the reference points. For example, as shown in FIG. 8, the image data operation unit 13b linearly interpolates the respective adjacent pixels equal in pixel position to the cut points $CP_1, CP_2, \ldots$, and $CP_n$ and interpolates the respective adjacent pixels equal in pixel position to the cut points $CQ_1, CQ_2$, and $CQ_n$. In addition, the image data operation unit 13b linearly interpolates a pixel located in an $\alpha^{th}$ row (where $\alpha=1, 2, \ldots, j$) from the cut point $CP_m$ and in a $\beta^{th}$ row (where $\beta=1, 2, \ldots, j$) from the cut point $CQ_m$, and the pixel located in the $\alpha^{th}$ row (where $\alpha=1$, $2, \ldots, j$) from the cut point $CP_{m+1}$ and in the $\beta^{th}$ row (where $\beta=1, 2, \ldots, j$) from the cut point $CQ_{m+1}$. The image data operation unit 13b performs the same processings for all the pixels set on the respective pieces of one-column image data $d_1, d_2, \ldots$, and $d_n$. The image data operation unit 13b can thereby interpolate all the adjacent pieces of one-column image data of the n pieces of one-column image data $d_1$, $d_2, \ldots$, and $d_n$. Accordingly, the image data operation unit 13b can generate the 3D longitudinal image data on the cut planes including the respective straight lines $T_1, T_2, \ldots$, and $T_n$. If the image data operation unit 13b is to linearly interpolate the respective adjacent pixels of the adjacent one-column image data $d_m$ and $d_{m+1}$, the image data operation unit 13b interpolates luminances of the respective adjacent pixels equal in pixel position on the one-column image data $d_m$ and $d_{m+1}$, thereby determining luminances between the respective adjacent pixels.

According to the first embodiment, the transmission coil is arranged near the ultrasonic transducer incorporated into the tip end of the probe. In addition, the position data calculator calculates the position data on the radial scan using this ultrasonic transducer, based on the magnetic field output from the transmission coil. However, the present invention is not limited to this method. The position data calculator may calculate the position data on the radial scan using the ultrasonic transducer by detecting a movement acceleration of the ultrasonic transducer when the operator guides this probe 2, and by performing an integral processing or the like on the movement acceleration.

According to the first embodiment, the transmission coil 6a which generates the magnetic field is arranged near the ultrasonic transducer within the probe. If the magnetic field generated by the transmission coil is to be detected by the receiver, the position of this transmission coil is detected. However, the present invention is not limited to this method. The transmission coil may be arranged at the position of the receiving antenna in place of the receiving antenna, and a reception coil having directivities of an ultrasonic vibration insertion direction and a direction perpendicular to the insertion direction may be arranged near the ultrasonic transducer within the probe. In addition, a position of this reception coil may be detected.

According to the first embodiment, a plurality of pieces of 2D image data obtained by the 3D scan are associated with the respective pieces of position data related to the positions and the directions relative to which the 3D can is performed. These pieces of 2D image data thus associated with the respective pieces of position data are arranged on the predetermined spatial coordinate system. The curved plane corresponding to the moving path or moving direction of the probe during the 3D scan is set as the cut planes on which the longitudinal images of the pieces of 2D image data are formed. In addition, the longitudinal image of the subject is displayed on each cut plane. Therefore, even if the probe performs the 3D scan while being curved along the shape of the living body, or even if the probe performs the 3D scan while being twisted dependently on the operator's operation such as the insertion or the guiding, the tomographic image of the subject can be generated on the cut plane obtained by accurately tracing the moving path or moving direction of the probe 2 during the 3D scan based on the pieces of the 2D image data associated with the respective pieces of position data. Therefore, the ultrasonic diagnostic apparatus which can easily display and output the tomographic image substantially equal in shape to the actual subject can be realized. If the operator uses this ultrasonic diagnostic apparatus, then the tomographic image substantially equal in shape to the subject can be easily obtained by artificially inserting or guiding the probe 2 that is executing the radial scan in the living body without using a drive or the like which inserts or draws out the probe into or from the interior of the living body. Accordingly, an in vivo ultrasonic diagnosis can be carried out efficiently using the tomographic image.

Moreover, according to the first embodiment, the tomographic image substantially equal in shape to the actual subject can be easily generated. Therefore, it is possible to highly accurately grasp the size of the desired region of interest such as the characteristic site or the affected side, e.g., a tumor in the living body such as the distance, the area, or the volume of the desired region of interest. Further, when the image rotation indication information is input, the apparatus rotates the tomographic image displayed on the screen of the monitor 9 in a predetermined direction using the rotation angle according to the input amount of this indication information. Therefore, the display direction of the tomographic image can be changed to a desired direction, and the direction of the tomographic image suited for observation of the region of interest or the in vivo ultrasonic diagnosis can be easily set. Besides, if the indication information for magnifying or reducing the image is input, the tomographic image displayed on the monitor is magnified or reduced at a magnification or reduction factor according to the input amount of this indication information. Therefore, the direction of the tomographic image suited for the observation of the region of interest or the in vivo ultrasonic diagnosis can be easily set.

A second embodiment of the present invention is explained in detail. In the first embodiment, the ultrasonic diagnostic apparatus is constituted to display the band-shaped 3D longitudinal image of the cut plane set based on the cut point information after the input of the cut point information is accepted. In the second embodiment, an ultrasonic diagnostic apparatus is constituted to set a default cut plane based on preset default point data, display a 3D longitudinal image of this default cut plane on a monitor screen, accept input of cut point information, and then update this 3D longitudinal image to a 3D longitudinal image of a cut plane based on this cut point information.

Figure 9:
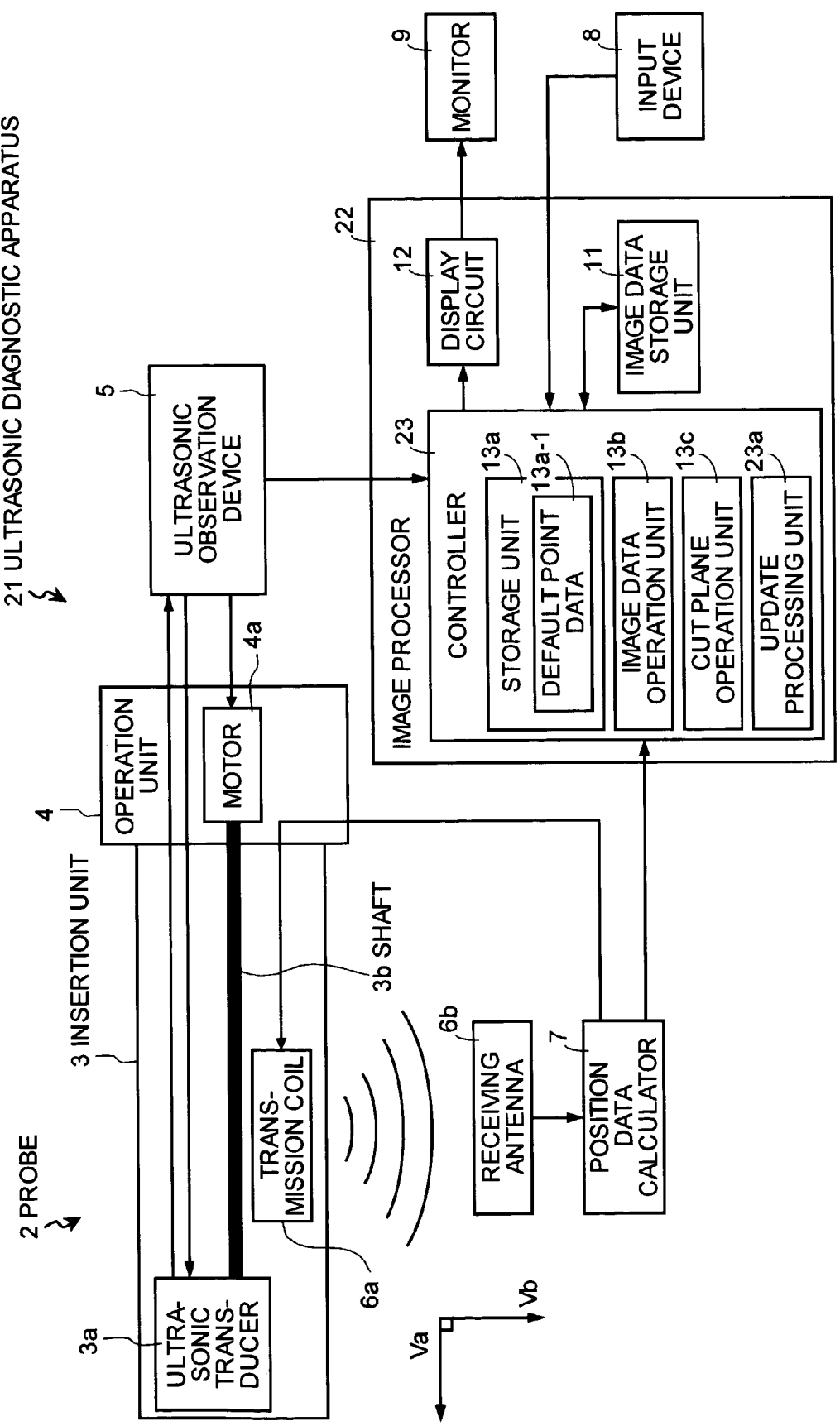
FIG. 9 is a block diagram that depicts schematic configuration of an ultrasonic diagnostic apparatus according to a second embodiment of the present invention.

FIG. 9 is a block diagram that depicts schematic configuration of an ultrasonic diagnostic apparatus according to the second embodiment. An ultrasonic diagnostic apparatus 21 shown in FIG. 9 is constituted so that an image processor 22 is provided instead of the image processor 10, and so that a controller 23 that includes an update processing unit 23a is provided instead of the controller 13. In addition, the storage unit 13a stores default point data 13-1 in advance. The controller 23 is realized, substantially similarly to the controller 13, by a ROM that stores various types of data such as a processing program, a RAM that stores each operation parameter, a CPU that executes the processing program stored in the ROM, and the like. The other constituent elements of the ultrasonic diagnostic apparatus 21 are equal to those of the ultrasonic diagnostic apparatus 1 according to the first embodiment. Like constituent elements as those according to the first embodiment are denoted by like reference symbol, respectively.

Figure 10:
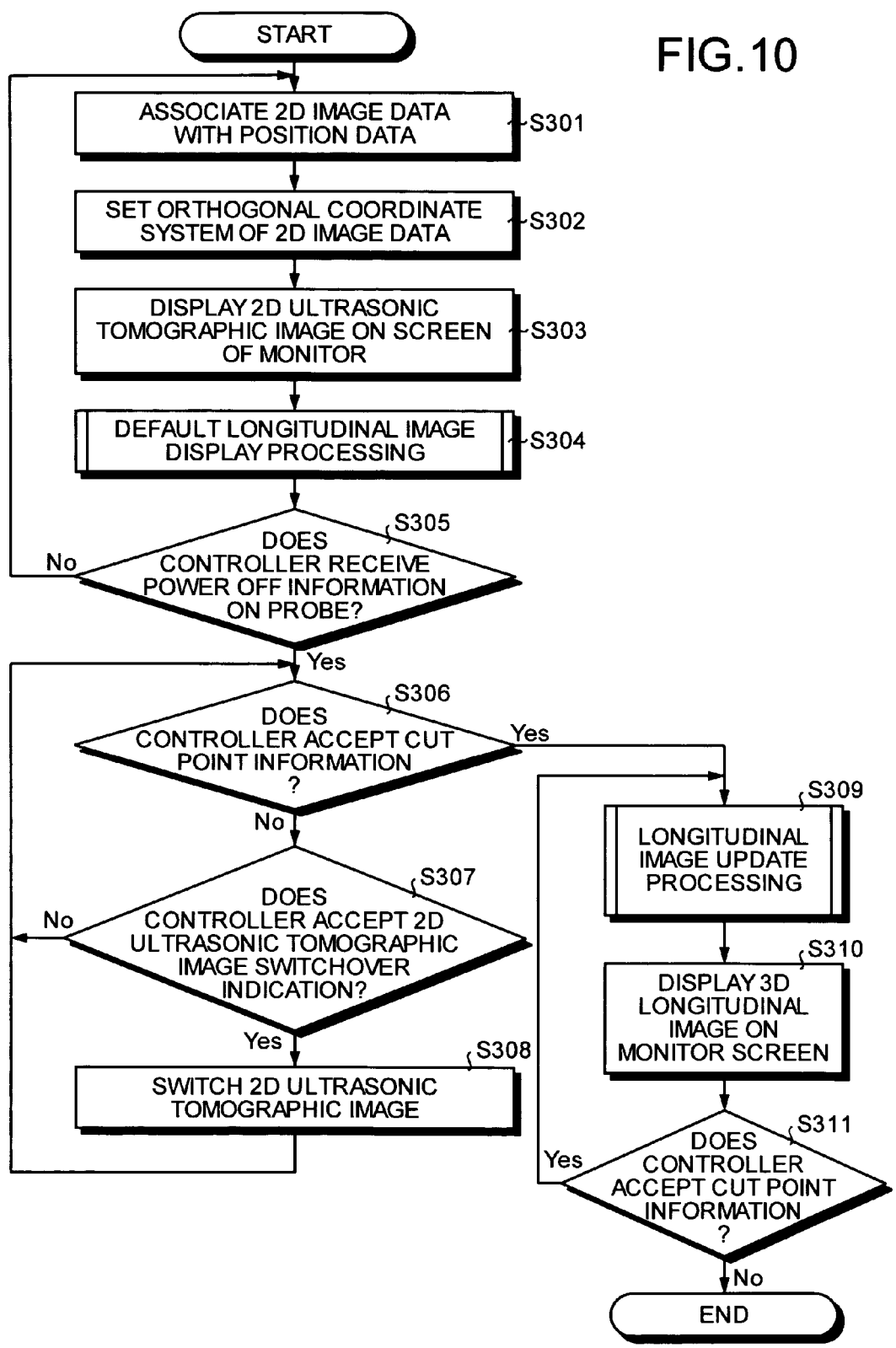
FIG. 10 is a flowchart showing respective processing steps executed until the ultrasonic diagnostic apparatus according to the second embodiment displays a 3D longitudinal image on the monitor screen.

FIG. 10 is a flowchart showing respective processing steps since the controller 23 acquires n pieces of 2D image data and n pieces of position data, displays a 3D longitudinal image of default cut planes based on the preset default point data on a monitor screen, and updates this 3D longitudinal image to a 3D longitudinal image of cut planes based on cut point information until displaying this updated 3D longitudinal image on the monitor 9. Referring to FIG. 10, if the ultrasonic observation device 5 generates 2D image data based on an echo signal, and the position data calculator 7 calculates position data on the position at which this echo signal is obtained, then the controller 23 acquires the 2D image data output from the ultrasonic observation device 5 and the position data output from the position data calculator 7. In addition, the controller 23 associates the acquired 2D image data received from the ultrasonic observation device 5, with the position data received from the position data calculator 7, as explained, similarly to step S101 (at step S301).

If the 2D image data is associated with the position data, then the controller 23 arranges the 2D image data associated with this position data on the spatial coordinate system xyz, and sets an orthogonal coordinate system for the 2D image data similarly to step S102 (at step S302). Thereafter, the controller 23 stores the 2D image data for which the orthogonal coordinate system is set, in the image data storage unit 11 while arranging the 2D image data on the spatial coordinate system xyz, and displays a 2D ultrasonic tomographic image corresponding to the 2D image data on the monitor 9 similarly to the step 103 (at step S303).

The controller 23 sets two default points and a default straight line that passes through the two default line on the orthogonal coordinate system of the 2D image data based on the preset default point data. In addition, using the 2D image data for which the default straight line is set, the controller 23 sets a default cut plane including the default straight line. Thereafter, the controller 23 performs a processing for generating one-column image data on this default straight line, generating 3D longitudinal image data on the default cut planes based on this one-column image data, and displaying a band-shaped 3D longitudinal image corresponding to this 3D longitudinal image data on the monitor 9 (a default longitudinal image display processing) (at step S304).

If the probe 2 is executing a radial scan, that is, the power switch of the operation unit 4 is turned on, the controller 23 does not receive power-off information corresponding to a power-OFF state of the probe 2 ("No" at step S305). If so, the controller 23 repeatedly executes the processing step S301 and the following. Namely, if n radial scans are performed before the probe 2 is turned off, the controller 23 repeatedly executes the processing step S301 and the following n times. The controller 23 thereby acquires n pieces of 2D image data $D_1, D_2, \ldots,$ and $D_n$ associated with the respective pieces of position data, and associates the orthogonal coordinate systems with the respective pieces of 2D image data $D_1, D_2, \ldots, $ and $D_n$. Further, as shown in FIG. 3, the controller 23 stores the n pieces of 2D image data $D_1, D_2, \ldots,$ and $D_n$ thus acquired, in the image data storage unit 11 while arranging the 2D image data $D_1, D_2, \ldots,$ and $D_n$ on the spatial coordinate system xyz. Furthermore, the controller 23 sets default straight lines and default cut planes on the n pieces of 2D image data $D_1, D_2, \ldots,$ and $D_n$, and sets one-column image data on the default straight lines, respectively. In addition, using the n piece of one-column image data, the controller 23 displays a band-shaped 3D longitudinal image on the default cut planes of the n pieces of 2D image data $D_1, D_2, \ldots,$ and $D_n$ on the monitor 9.

If the operator turns off the power switch of the operation unit 4 after the n radial scans, the controller 23 receives the power-OFF information on the probe 2 ("Yes" at step S305). Thereafter, if the operator inputs indication information for switching the 2D ultrasonic tomographic image displayed on the monitor screen over to another 2D ultrasonic tomographic image without performing an operation for inputting cut point information for changing the default point using the input device 8, then the controller 23 does not accept the cut point information ("No" at step S306) but accepts a switchover indication corresponding to the switchover indication information ("Yes" at step S307). If so, similarly to step S107, the controller 23 switches the 2D ultrasonic tomographic image displayed on the screen of the monitor 9 to another 2D ultrasonic tomographic image based on the switchover indication corresponding to the switchover indication information the input of which the controller 23 accepts. Thereafter, the controller 23 repeatedly executes the processing step S306 and the following (at step S308).

Further, if neither the cut point information nor the switchover indication information are input to the controller 23, then the controller 23 does not accept the cut point information ("No" at step S306) and does not accept the switchover indication based on the switchover indication information ("No" at step S307). If so, the controller 23 repeatedly executes the processing step S306 and the following.

On the other hand, if the operator inputs cut point information for changing at least one default point using the input device 8, the controller 23 accepts the input cut point information ("Yes" at step S306). The controller 23 updates the default point that is designated to be changed by the input of the cut point information, out of the default points already set on the orthogonal coordinate system of the 2D image data, to a cut point corresponding to the cut point information. In addition, the controller 23 updates the default straight line and the default cut plane related to the change-designated default point to a straight line and a cut plane including this cut point. Further, the controller 23 updates the one-column image data set at step S304, generates 3D longitudinal image data on the updated cut planes using the updated one-column image data, and updates the 3D longitudinal image data on the default cut planes generated at step S304 to 3D longitudinal image data on the updated cut planes (at step S309).

The controller 23 then displays a band-shaped 3D longitudinal image corresponding to the updated 3D longitudinal image data on the cut planes generated at step S309 on the monitor 9, similarly to step S110 (at step S310). The operator observes the 3D longitudinal image displayed on the screen of the monitor 9, and checks whether a desired region of interest is displayed on the screen of the monitor 9. If the desired region of interest is not displayed on the screen of the monitor 9, the operator inputs cut point information for changing the already set cut point using the input device 8. In this case, the controller 23 accepts this cut point information ("Yes" at step S311), and repeatedly executes step S309 and the following using this cut point information. On the other hand, if the operator observes the 3D longitudinal image displayed on the screen of the monitor 9, and checks that the desired region of interest is displayed on the monitor, the operator does not perform the operation for inputting the cut point information for changing the already set cut point. If so, the controller 23 does not accept this cut point information ("No" at step S311) and does not update the information on the already set cut point. Therefore, the monitor 9 maintains a state in which this 3D longitudinal image is displayed. The operator can thereby observe the desired region of interest displayed on the screen of the monitor 9, and complete the ultrasonic diagnosis on the subject.

Further, if the operator causes the ultrasonic transducer 3a to perform a radial scan and guides the probe 2 following step S310, the 3D scan by the ultrasonic transducer 3a resumes. In addition, the controller 23 generates the 3D longitudinal data based on the cut points already set at step S309 and the pieces of 2D image data obtained successively by this 3D scan, and displays the 3D longitudinal image corresponding to the 3D longitudinal data on the monitor 9. In this case, the controller 23 adds the 3D longitudinal image generated by operator's guiding the probe 2 to the 3D longitudinal image $U_0$ already displayed on the screen of the monitor 9 and displays the resultant 3D longitudinal image. The controller 23 thus extends the 3D longitudinal image $U_0$ successively with the operator's operation for guiding the probe 2 during the 3D scan.

Figure 11:
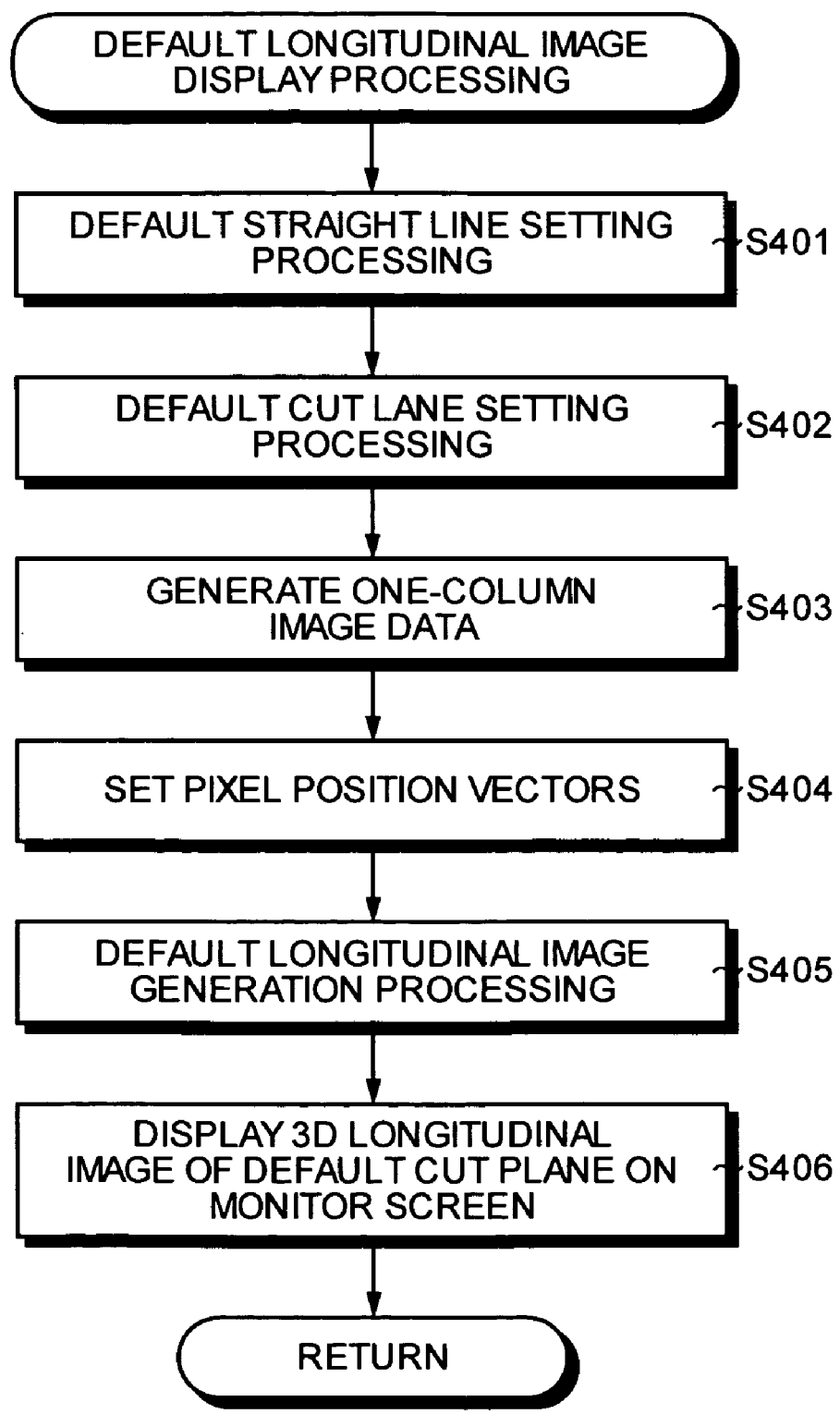
FIG. 11 is a flowchart showing respective processing steps executed until the ultrasonic diagnostic apparatus according to the second embodiment displays a 3D longitudinal image of a default cut plane on the monitor screen.
Figure 12:
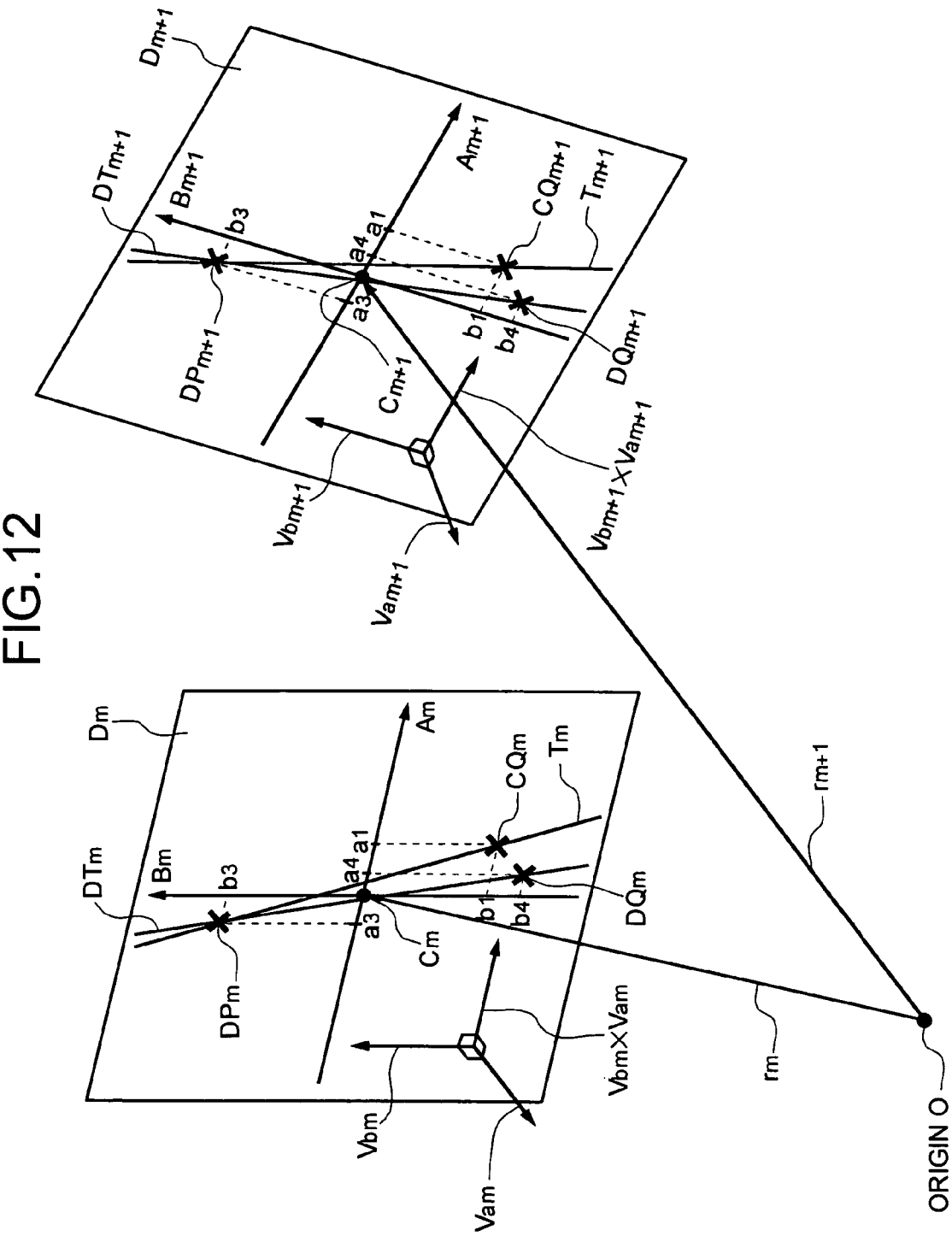
FIG. 12 is an explanatory view of a processing for setting two default points and a default straight line that passes through the two default points.

Respective processing steps executed until the controller 23 displays the 3D longitudinal image of the default cut planes on the monitor 9 is explained in detail. FIG. 11 is a flowchart showing the respective processing steps since the controller 23 sets default lines based on preset default point data until displaying the 3D longitudinal image of the default cut planes on the monitor 9 (a default longitudinal image display processing). FIG. 12 is an explanatory view of a processing for setting two default points and a default straight line that passes through the two default points on an orthogonal coordinate system of the 2D image data based on the default point data. Referring to FIGS. 11 and 12, if the orthogonal coordinate system $A_m B_m$ is set for the 2D image data $D_m$ associated with position data similarly to step S102, then the controller 23 reads the default point data 13a-1 stored in the storage unit 13a in advance, and sets default points $DP_m$ and $DQ_m$ corresponding to the default point data 13-1. For example, as shown in FIG. 12, the controller 23 sets the default point $DP_m$ at a coordinate $(a_3, b_3)$ on the orthogonal coordinate system $A_m B_m$, and sets the default point $DQ_m$ at a coordinate $(a_4, b_4)$ the orthogonal coordinate system $A_m B_m$.

If the default points $DP_m$ and $DQ_m$ have been set on the orthogonal coordinate system $A_m B_m$ of the 2D image data $D_m$, the controller 23 sets default points $DP_{m+1}$ and $DQ_{m+1}$ on the orthogonal coordinate system $A_{m+1} B_{m+1}$ of 2D image data $D_{m+1}$ adjacent to the 2D image data $D_m$ similarly to step S201. Specifically, as shown in FIG. 12, the controller 23 sets the default point $DP_{m+1}$ at the coordinate $(a_3, b_3)$ on the orthogonal coordinate system $A_{m+1} B_{m+1}$, and sets default points $DQ_{m+1}$ at the coordinate $(a_4, b_4)$ on the orthogonal coordinate system $A_{m+1} B_{m+1}$. Based on this default point setting method, the controller 23 sets default points $DP_1, DP_2, \ldots$, and $DP_n$ at respective coordinates $(a_3, b_3)$ on the orthogonal coordinate systems, sets default points $DQ_1, DQ_2, \ldots$, and $DQ_n$ at respective coordinates $(a_4, b_4)$ on the orthogonal coordinate systems for the n pieces 2D image data $D_1, D_2, \ldots$, and $D_n$. The controller 23 thereby sets the two default points for every 2D image data, and sets default straight lines $DT_1, DT_2, \ldots$, and $DT_n$ each of which passes through the two default points, for the respective pieces of 2D image data similarly to step S202 (at step S401).

If the controller 23 sets the default straight lines $DT_1, DT_2$, and $DT_n$ for the n pieces of 2D image data $D_1, D_2, \ldots$, and $D_n$, respectively, the cut plane operation unit 13c operates and outputs curved planes including the default straight lines $DT_1, DT_2, \ldots$, and $DT_n$. In this case, the controller 23 sets the default straight lines $DT_1, DT_2, \ldots$, and $DT_n$ as longitudinal plane positions of the n pieces of 2D image data arranged on the spatial coordinate system xyz, and sets the curved planes operated and output by the cut plane operation unit 13c as default cut planes on which the 3D longitudinal image is formed (at step S402).

If the controller 23 sets the default straight lines $DT_1, DT_2, \ldots$, and $DT_n$ for the n pieces of 2D image data, then the image data operation unit 13b sets pixel groups in one column and j row for the default straight lines $DT_1, DT_2, \ldots$, and $DT_n$, respectively similarly to step S204, calculates the luminances of pixels in the respective pixel groups, and generates n pieces of one-column image data $d_1, d_2, \ldots$, and $d_n$ in one column and j row for the n pieces of 2D image data $D_1, D_2, \ldots$, and $D_n$, respectively (at step S403). Thereafter, the image data operation unit 13b sets pixel position vectors of the respective pixels of the one-column image data $d_1, d_2, \ldots$, and $d_n$ similarly to step S205 (at step S404), and associates the respective pixels of the one-column image data $d_1, d_2, \ldots$, and $d_n$ with coordinates of pixels on the spatial coordinate system xyz.

If the controller 23 sets the one-column image data $d_1, d_2, \ldots$, and $d_n$ associated with the coordinates of the pixels on the spatial coordinate system xyz on the default straight lines $DT_1, DT_2, \ldots$, and $DT_n$, respectively, the image data operation unit 13b linearly interpolates respective adjacent pieces of one-column image data similarly to step S109. In addition, the image data operation unit 13b generates 3D longitudinal image data on the default cut planes set at step S402 (at step S405). The controller 23 then transmits this 3D longitudinal image data on the default cut planes to the monitor 9 through the display circuit 12 to display the 3D longitudinal image data on the default cut surface corresponding the 3D longitudinal image data on the monitor 9 (at step S406).

Figure 13:
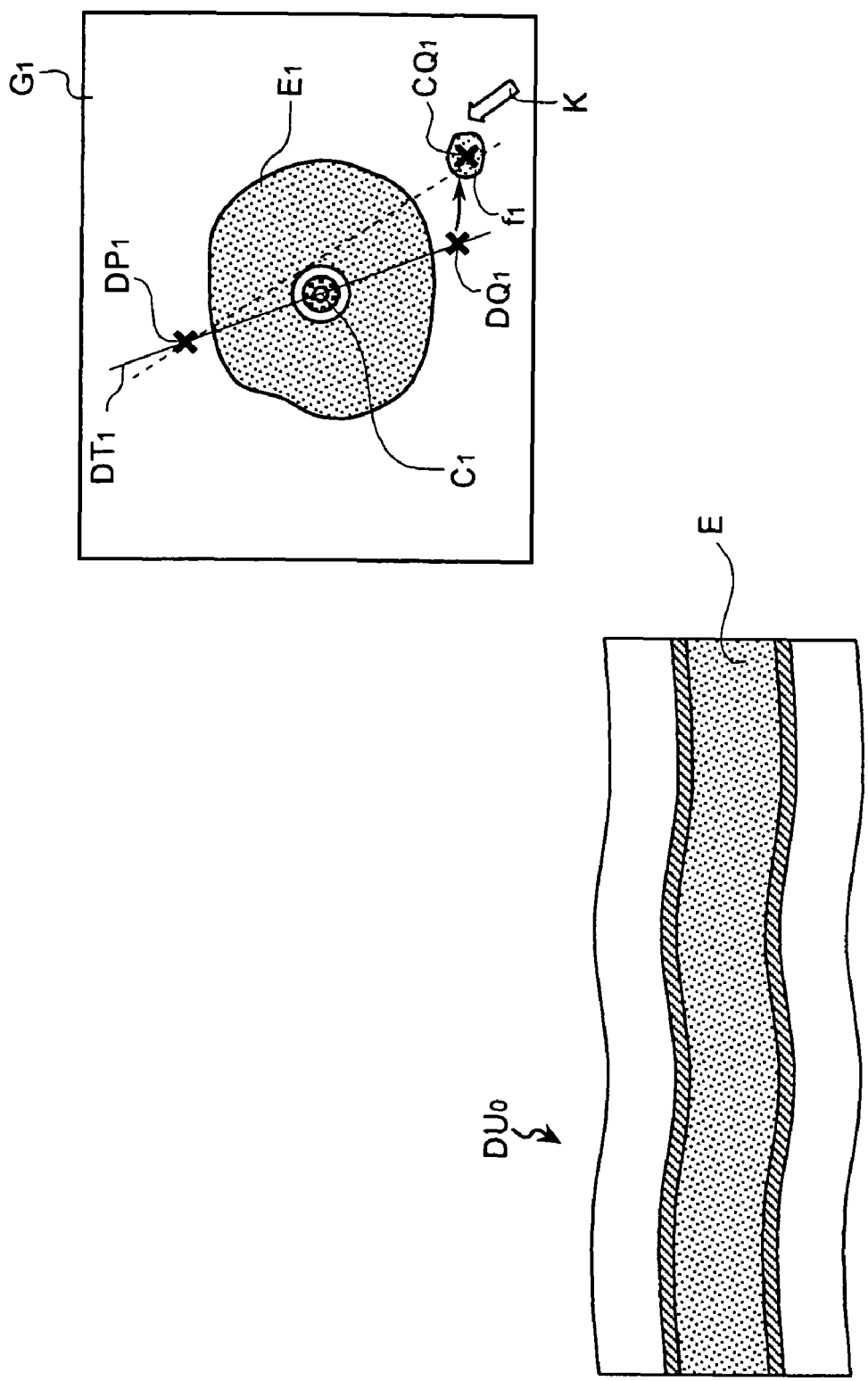
FIG. 13 depicts an example of the 3D longitudinal image of the default cut plane displayed on the monitor screen.

FIG. 13 depicts an example of the 3D longitudinal image on the default cut planes displayed on the screen of the monitor 9. Similarly to step S109, the image data operation unit 13b generates the 3D longitudinal image data on the default cut planes defined as the curved planes that include straight lines on the n pieces of 2D image data, respectively. Therefore, a 3D longitudinal image $DU_0$ of the default cut planes corresponding to this 3D longitudinal image data is a band-shaped longitudinal image having curved planes or the like according to an actual moving path, moving direction, or the like of the probe 2 that is moved into the living body when the 3D scan is performed, as shown in FIG. 13. Namely, similarly to the 3D longitudinal image $U_0$, this 3D longitudinal image $DU_0$ can represents a tomographic image that is less strained as compared with the subject in the living body on which the probe 2 performs the 3D scan, and which is substantially equal in shape to the actual subject. For example, if the operator performs a 3D scan using the probe 2 inserted into the duodenum, then the 3D longitudinal image $DU_0$ represents the duodenum image E substantially equal in shape to the actual duodenum, as shown in FIG. 13. Therefore, by performing the 3D scan while observing this 3D longitudinal image $DU_0$, the operator can highly accurately grasp the moving path, moving direction, or the like of the probe 2 that is being executing the 3D scan, and can thereby perform the 3D scan related operation without anxiety.

Further, the operator operates the input device 8, e.g., the mouse to move a cursor K to a pancreatic duct image $f_1$ on the screen, and then to depress a mouse button. As a result of this operation, the cut point $CQ_1$ is set on the pancreatic duct image $f_1$ as shown in FIG. 13. This operation for setting the cut point may be carried out using the keyboard, the touch panel, the track ball, or the joystick that realizes the input device 8 similarly to the mouse, and the cut point is set at a desired position on the screen.

If the operator inputs indication information on image display using the input device 8, the controller 23 may output and display the 3D longitudinal image $DU_0$ and the 2D ultrasonic longitudinal image $G_1$ corresponding to the 2D image data $D_1$ or a latest 2D ultrasonic longitudinal image on the same monitor screen.

Figure 14:
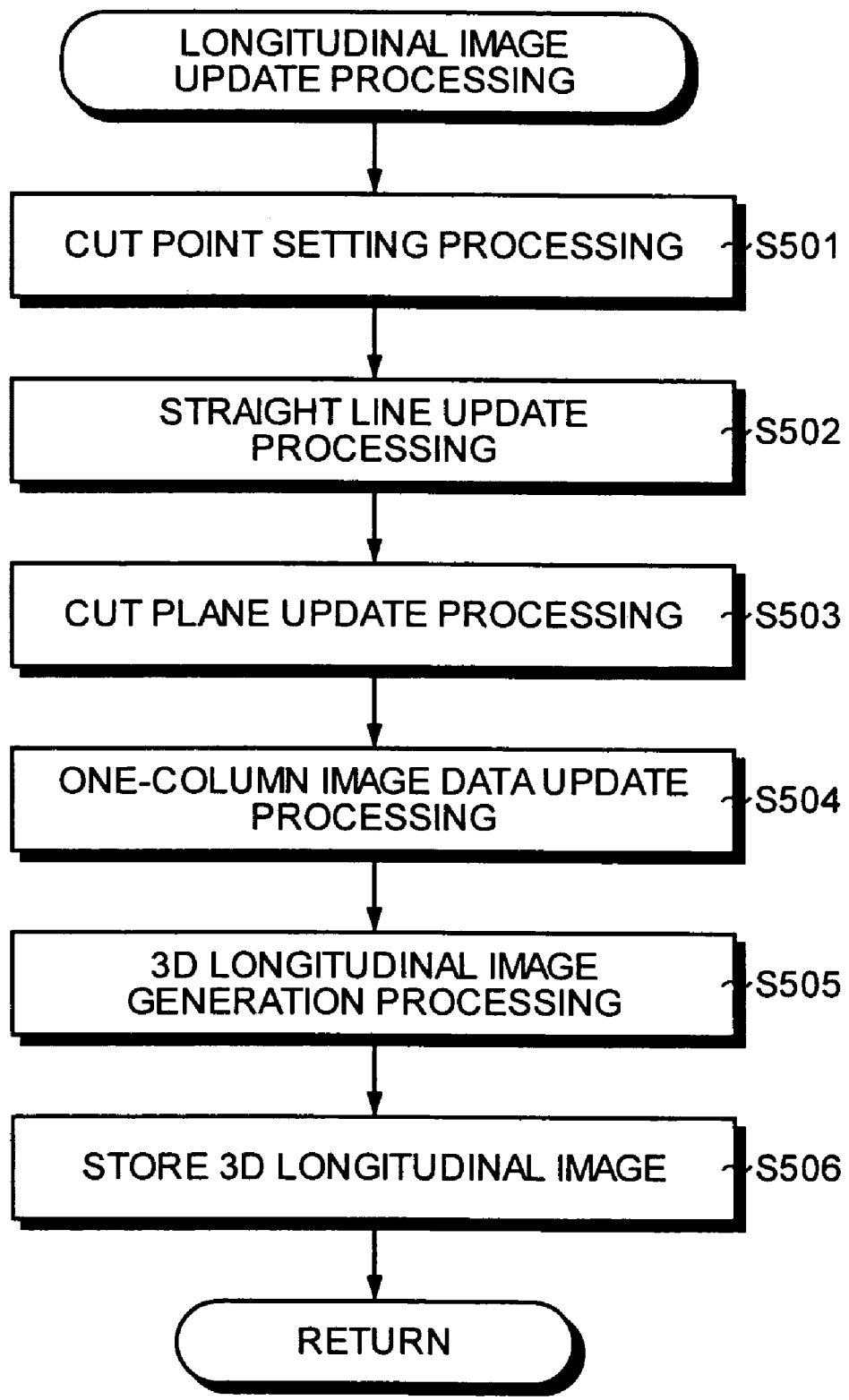
FIG. 14 is a flowchart showing processing steps executed until the ultrasonic diagnostic apparatus according to the second embodiment updates the 3D longitudinal image data on the default cut plane.
Figure 15:
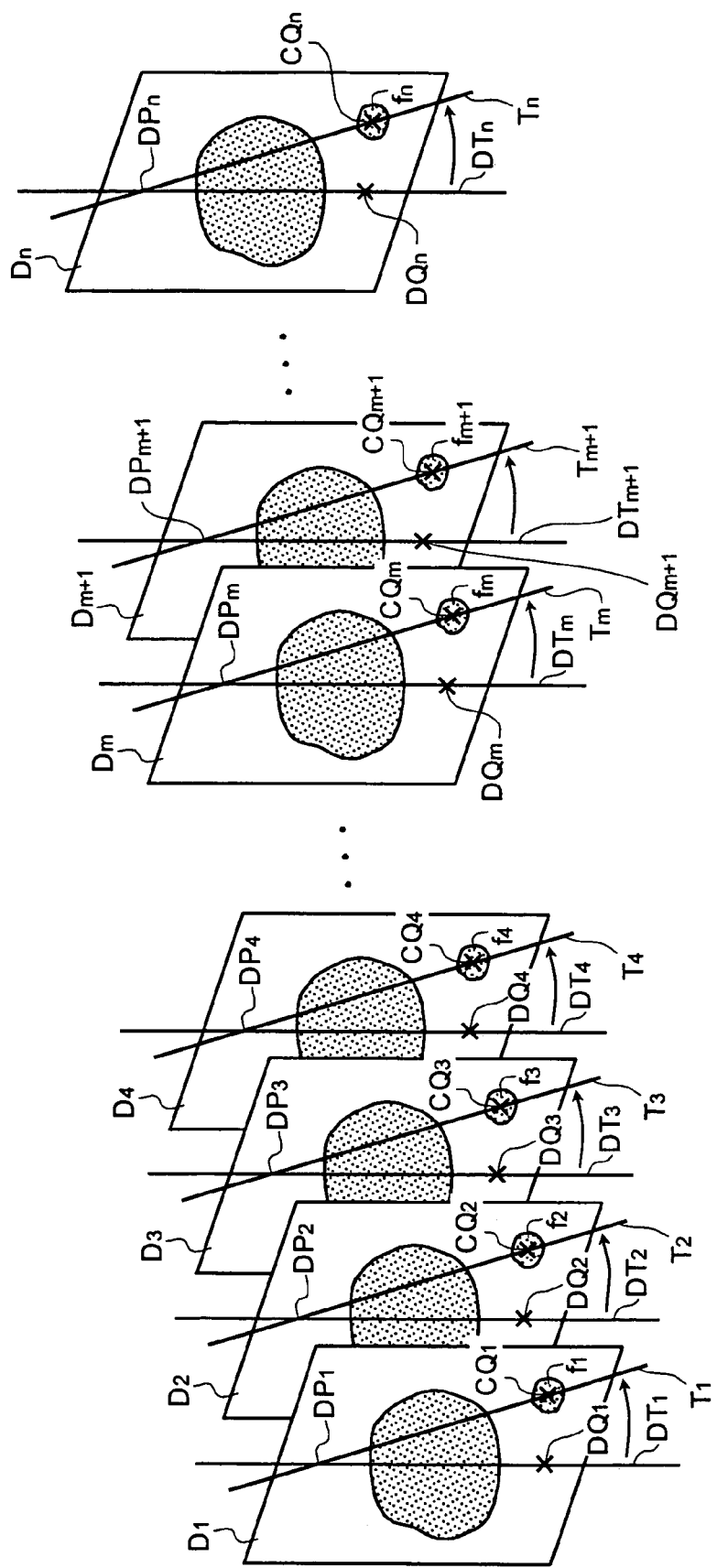
FIG. 15 is an explanatory view of a processing for updating the default straight line.

Processings at step S309 executed since the controller 23 sets the cut points corresponding to the cut point information for updating at least one of the two preset default points if the cut point information is input until updating the 3D longitudinal data on the default cut planes to the 3D longitudinal data on the updated cut planes (the longitudinal image update processing) will next be explained in detail. FIG. 14 is a flowchart showing processing steps executed since the controller 23 sets cut points obtained by updating the default points based on the input cut point information until updating the 3D longitudinal image data on the default cut planes to the 3D longitudinal image data on the updated cut planes. FIG. 15 is an explanatory view of a processing performed by the controller 23 for updating the default straight lines using the cut point information for updating the default points. An instance of updating the default points $DQ_1, DQ_2, \ldots$, and $DQ_n$ preset for the n pieces of 2D image data $D_1, D_2, \ldots$, and $D_n$ to the cut points $CQ_1, CQ_2, \ldots$, and $CQ_n$ is explained herein. However, the present invention is not limited to this instance.

Referring to FIGS. 14 and 15, if cut point information for updating the default point $DQ_m$ of desired 2D image data, e.g., the 2D image data $D_m$ to a cut point on a pancreatic duct image $f_m$ is input, the controller 23 sets the cut point $CQ_m$ corresponding to this cut point information at the coordinate $(a_1, b_1)$ corresponding to a point on the pancreatic duct image $f_m$ as shown in FIGS. 12 and 15 (at step S501), and deletes the default point $DQ_m$. Specifically, the controller 23 sets the cut points $CQ_1, CQ_2, \ldots,$ and $CQ_n$ at the coordinates $(a_1, b_1)$ on the respective orthogonal coordinate systems of the n pieces of 2D image data $D_1, D_2, \ldots,$ and $D_n$ similarly to step S201. In addition, the update processing unit 23a deletes the default points $DQ_1, DQ_2, \ldots,$ and $DQ_n$ at the coordinates $(a_4, b_4)$, thereby updating the default points $DQ_1, DQ_2, \ldots,$ and $DQ_n$ to the cut points $CQ_1, CQ_2, \ldots,$ and $CQ_n$, respectively.

If the update processing unit 23a updates the default points $DQ_1, DQ_2, \ldots,$ and $DQ_n$ to the cut points $CQ_1, CQ_2, \ldots,$ and $CQ_n$, respectively, the cut plane operation unit 13c operates and outputs straight lines $T_1, T_2, \ldots,$ and $T_n$ that pass through the default points $DP_1, DP_2, \ldots,$ and $DP_n$ and the cut points $CQ_1, CQ_2, \ldots,$ and $CQ_n$, respectively. In addition, the update processing unit 23a deletes the straight lines $DT_1, DT_2, \ldots,$ and $DT_n$ that pass through the default points $DP_1, DP_2, \ldots,$ and $DP_n$ and the default points $DQ_1, DQ_2, \ldots,$ and $DQ_n$, respectively. The update processing unit 23a thereby updates the straight lines $DT_1, DT_2, \ldots,$ and $DTn_1$ to the straight lines $T_1, T_2, \ldots,$ and $Tn_1$, as shown in FIG. 15 (at step S502).

The cut plane operation unit 13c operates and outputs cut planes including the straight lines $T_1, T_2, \ldots,$ and $T_n$ newly set at step S502. In addition, the update processing unit 23a deletes the existing default cut planes including the straight lines $DT_1, DT_2, \ldots,$ and $DT_n$, thereby updating the existing default cut planes including the straight lines $DT_1, DT_2, \ldots,$ and $DT_n$ to the cut planes including the straight lines $T_1, T_2, \ldots,$ and $T_n$ (at step S503).

If the update processing unit 23a updates the default cut planes or the cut planes, the image data operation unit 13b generates latest one-column image data $d_1, d_2, \ldots,$ and $d_n$ corresponding to the spatial coordinate system xyz on the straight lines $T_1, T_2, \ldots,$ and $T_n$ on the latest cut planes similarly to the processing steps S204 to S205. In addition, the update processing unit 23a deletes the one-column image data on the default cut planes or the cut planes before the update, thereby completes the processing for updating the n pieces of one-column image data to the latest n pieces of one-column image data generated on the respective pieces of 2D image data $D_1, D_2, \ldots,$ and $D_n$ (at step S504).

If the n pieces of one-column image data have been updated to the latest n pieces of one-column image data on the respective pieces of 2D image data $D_1, D_2, \ldots,$ and $D_n$, the image data operation unit 13b generates 3D longitudinal data using the latest one-column image data $d_1, d_2, \ldots,$ and $d_n$ similarly to step S109 (at step S505). In addition, the update processing unit 23a deletes the 3D longitudinal image data on the default cut planes or that before the update. The update processing unit 23a then stores the latest 3D longitudinal image data in the image storage unit 11 (at step S506). As a result, the longitudinal image update processing for updating the 3D longitudinal image data on the default cut planes or that before the update to the latest 3D longitudinal image data is completed.

Figure 16:
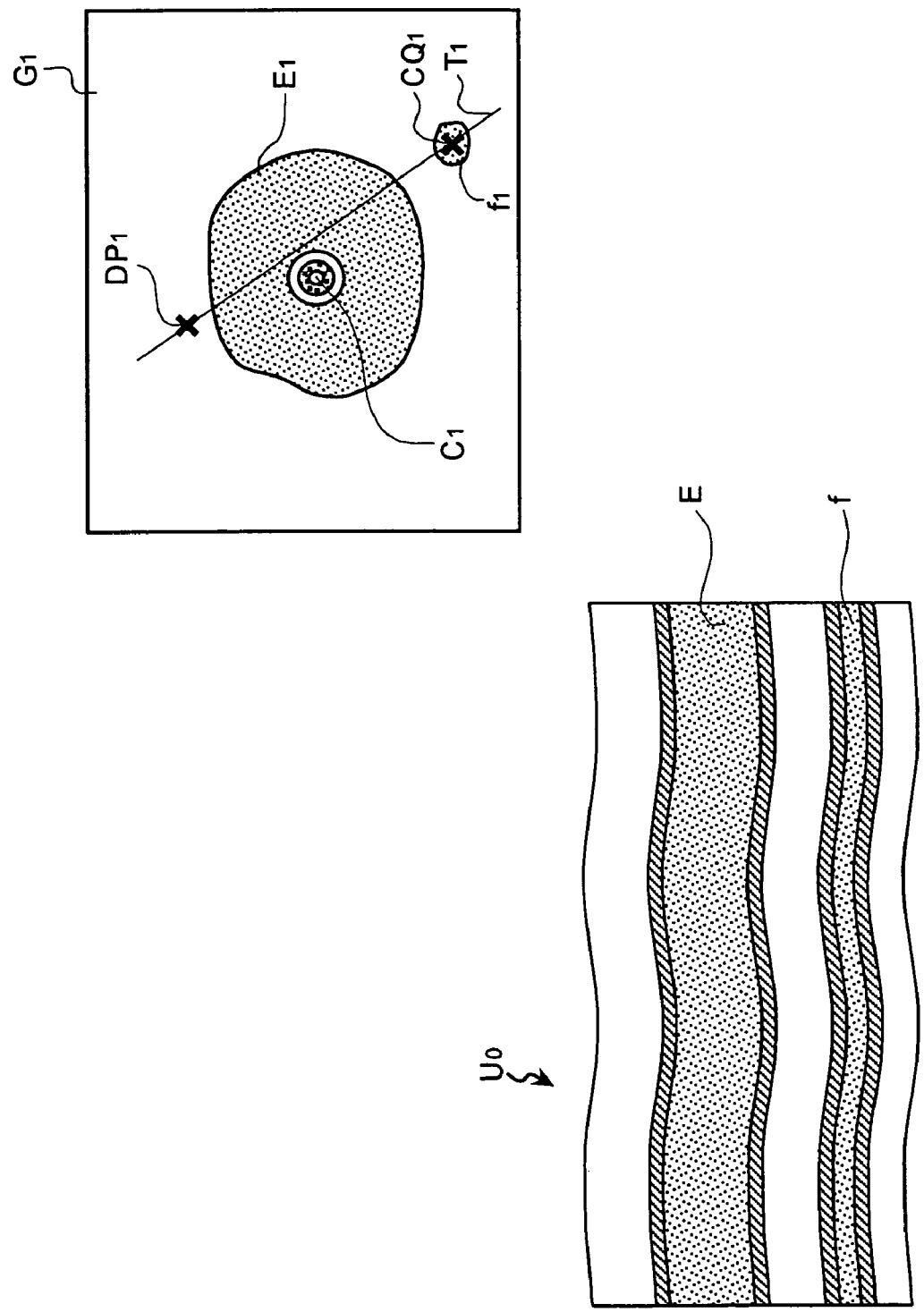
FIG. 16 depicts an example of a state in which the updated 3D longitudinal image is displayed on the monitor screen.

FIG. 16 depicts an example of a state in which the 3D longitudinal image updated by the longitudinal image update processing is displayed on the screen of the monitor 9. The controller 23 updates the straight line that determines the cut plane of one 2D image data so that the straight line passes through a desired region of interest on the one 2D image data, e.g., the pancreatic duct image $f_1$. Further, the controller 23 updates the straight lines on the n pieces of 2D image data $D_1, D_2, \ldots,$ and $D_n$ to correspond to the coordinate of the straight line, and determines the cut planes using the straight lines that pass onto pancreatic duct images $f_1, f_2, \ldots,$ and $f_n$, respectively, as shown in FIG. 15. Therefore, as shown in FIG. 16, the band-shaped 3D longitudinal image $U_0$ that is a longitudinal image of each cut plane can easily capture the pancreatic duct image f.

Figure 17:
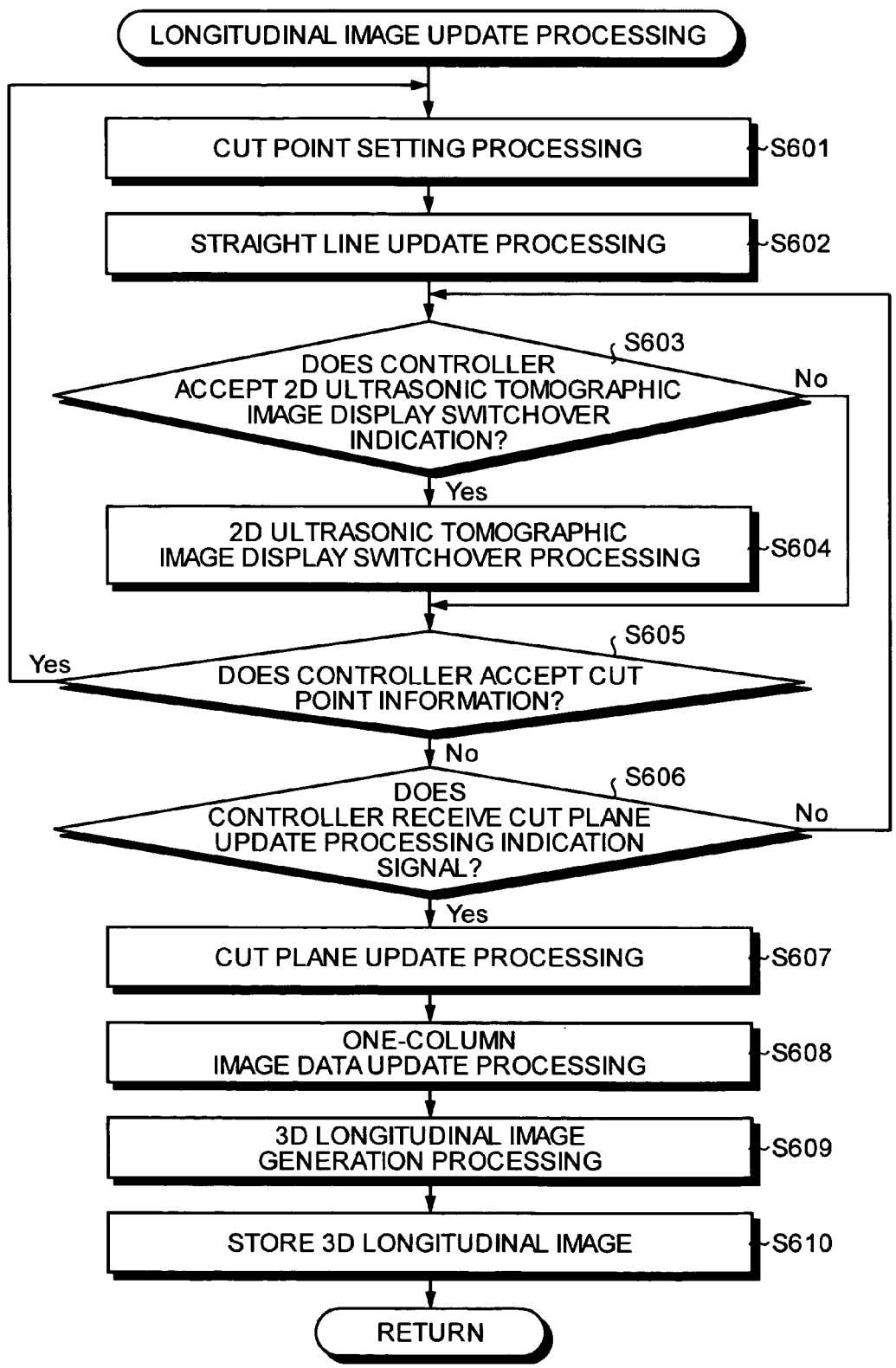
FIG. 17 is a flowchart showing processing steps executed until an ultrasonic diagnostic apparatus according to a modification of the second embodiment stores a new 3D longitudinal image.
Figure 18:
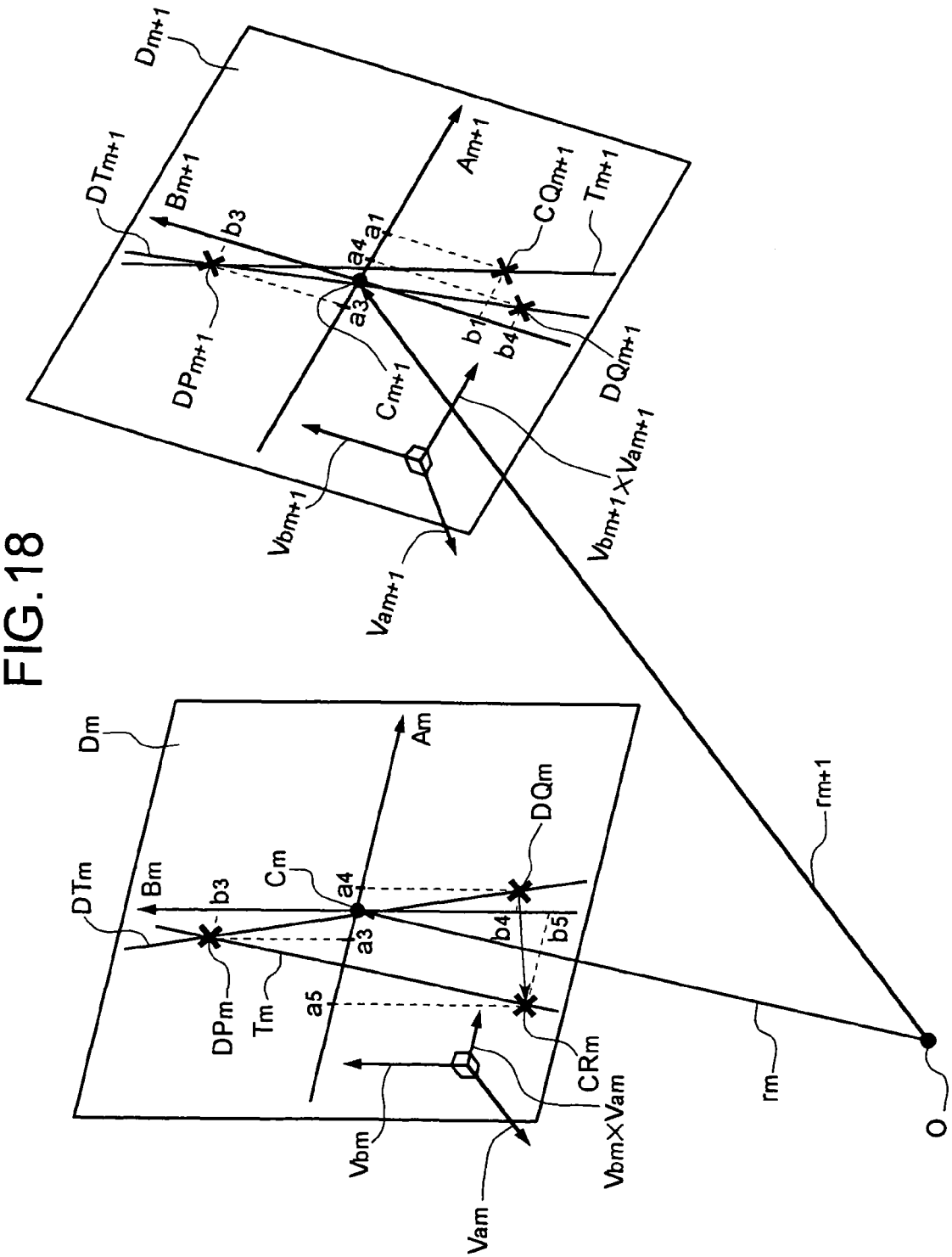
FIG. 18 is an explanatory view of a processing for updating the cut points and the straight line that passes through the cut points for each 2D image data.
Figure 19:
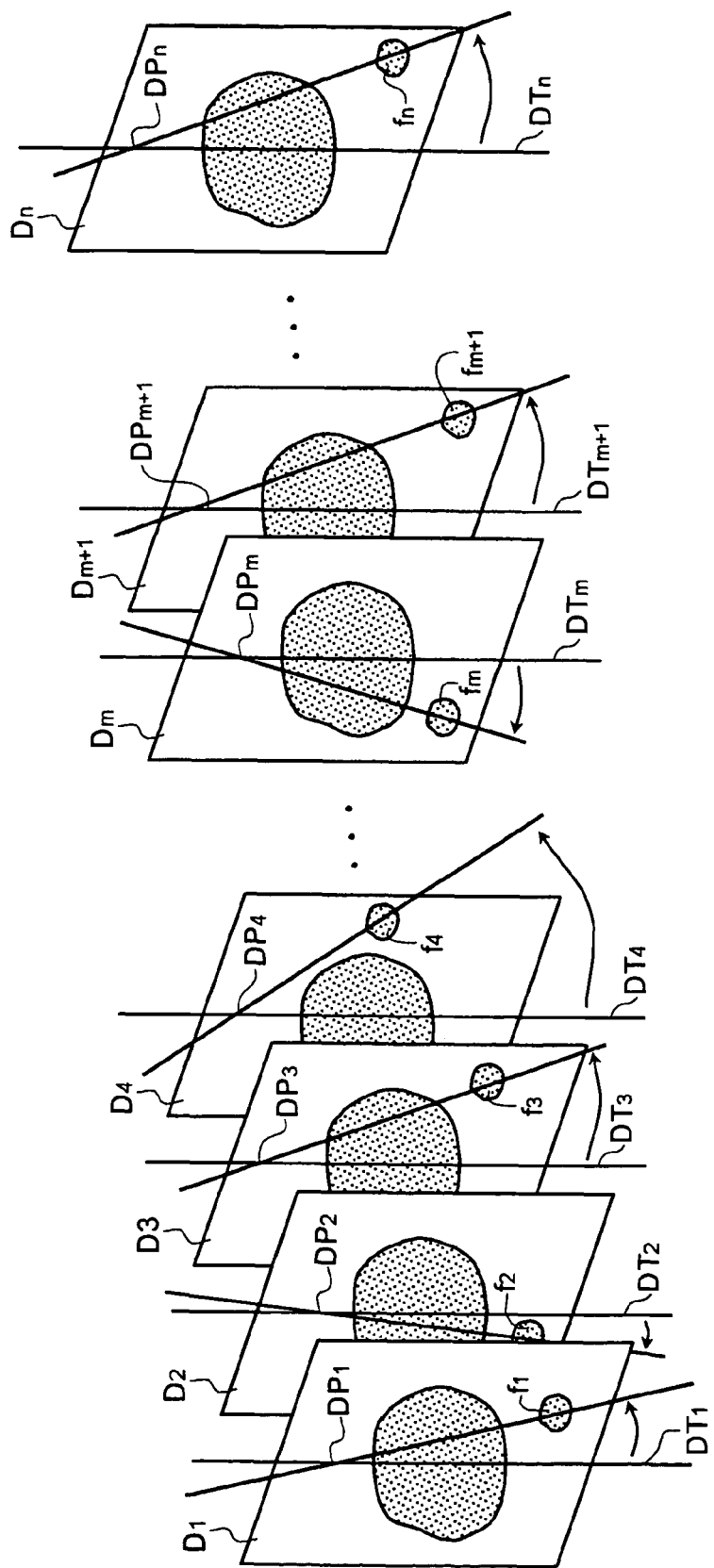
FIG. 19 is an explanatory view of a state in which straight lines on respective pieces of 2D image data are updated for each 2D image data.

In the second embodiment, if the straight line that determines the cut plane of one 2D image data is updated using the cut point information designated for the one 2D image data, then the respective straight lines on the n pieces of 2D image data $D_1, D_2, \ldots,$ and $D_n$ are updated to correspond to the updated coordinate of this straight line. Alternatively, the respective straight lines on the n pieces of 2D image data $D_1, D_2, \ldots,$ and $D_n$ may be updated for each 2D image data without associating the coordinates of the straight lines with one another. FIG. 17 is a flowchart according to a modification of the second embodiment. Namely, the flowchart of FIG. 17 shows processing steps executed since the controller 23 updates cut points and a straight line that passes through the cut points for each 2D image data using cut point information input for each 2D image data until storing a new 3D longitudinal image. FIG. 18 is an explanatory view of a processing performed by the controller 23 for updating the cut points and the straight line that passes through the cut points for each 2D image data. FIG. 19 is an explanatory view of a state in which straight lines on respective pieces of 2D image data are updated for each 2D image data.

Referring to FIGS. 17, 18, and 19, if cut point information for updating the default point $DQ_m$ of desired 2D image data, e.g., the 2D image data $D_m$ to a cut point on the pancreatic duct image $f_m$ is input, the controller 23 sets a cut point $CR_m$ corresponding to this cut point information at a corresponding coordinate $(a_5, b_5)$ on the pancreatic duct image $f_m$ (at step S601). In addition, the update processing unit 23a deletes the default point $DQ_m$. The cut plane operation unit 13c operates and outputs the straight line $T_m$ that passes through the default point $DP_m$ and the cut point $CR_m$. In addition, the update processing unit 23a deletes the straight line $DT_m$ that passes through the default point $DP_m$ and the default point $DQ_m$, thereby updating the straight line $DT_m$ to the straight line $T_m$ (at step S602).

If the processing steps S601 to S602 are executed, the controller 23 completes the update processing for the cut points and the straight line of one 2D image data, e.g., the 2D image data $D_m$. Accordingly, the operator inputs switchover indication information for switching display of the 2D ultrasonic tomographic image over to display of another 2D ultrasonic tomographic image using the input device 8. Specifically, the controller 23 receives this switchover indication information and accepts a switchover indication corresponding to this switchover indication information ("Yes" at step S603). In response to the accepted switchover indication, the controller 23 switches the display of the 2D ultrasonic tomographic image on the monitor 9 to the display of another 2D ultrasonic tomographic image (at step S604) similarly to step S107. The operator observes the 2D longitudinal image thus switched. If the operator is to change the default points or cut points set on the 2D longitudinal image, the operator inputs cut point information related to this change using the input device 8. In this case, the controller 23 accepts the input of this cut point information ("Yes" at step S605), and repeatedly executes the processing step S601 and the following.

If cut point information for updating the default point $DQ_{m+1}$ on the 2D image data $D_{m+1}$ to a cut point on a pancreatic duct image $f_{m+1}$ is input, the controller 23 sets the cut point $CQ_{m+1}$ corresponding to this cut point information at the corresponding coordinate $(a_1, b_1)$ on the pancreatic duct image $f_{m+1}$. In addition, the update processing unit 23a deletes the default point $DQ_m$. The cut plane operation unit 13c then operates and outputs the straight line $T_{m+1}$ that passes through the default point $DP_{m+1}$ and the cut point $CQ_{m+1}$. In addition, the update processing unit 23a deletes the straight line $DT_{m+1}$, that passes through the default point $DP_{m+1}$ and the default point $DQ_{m+1}$, thereby updating the straight line $DT_{m+1}$, to the straight line $T_{m+1}$. Namely, if repeatedly executing the processing steps S601 to S605 n times, the controller 23 can update the cut points and the straight lines that pass through the cut points on the respective n pieces of 2D image data $D_1, D_2, \ldots,$ and $D_n$ for each 2D image data. In this case, as shown in FIG. 19, the controller 23 can update the straight line that passes through the cut points to the straight line at a desired position for each 2D image data. The controller 23 can thereby ensure causing the straight lines to pass through the region of interest such as the pancreatic duct on the 2D image data.

If the controller 23 does not accept the 2D tomographic image switchover indication ("No" at step S603), the controller 23 turns into a standby state of waiting for input of cut point information without executing the processing at step S604. If completing the update of the cut points and the straight lines that pass through the cut points for the n pieces of 2D image data, respectively, the operator indicates start of a cut plane update processing for updating the cut planes using the updated cut point information or the like without inputting the cut point information. If so, the controller 23 does not accept the cut point information ("No" at step S605), but receives an indication signal for updating the cut planes ("Yes" at step S606). The controller 23 updates the cut planes of the n piece of 2D image data similarly to step S503 (at step S607). If the cut plane update processing indication signal is not input, then the controller 23 does not receive this indication signal ("No" at step S606) and repeatedly executes the processing step S603 and the following.

If the controller 23 updates the respective cut planes of the n pieces of 2D image data, the image data calculation unit 13b generates latest one-column image data corresponding to the spatial coordinate system xyz on the respective straight lines on the latest cut planes. In addition, the update processing unit 23a deletes the one-column image data on the default cut planes or the cut planes before the update. The update processing unit 23a thereby completes the update processing for the respective pieces of one-column image data formed on the 2D image data $D_1, D_2, \ldots,$ and $D_n$ (at step S608).

If the respective pieces of one-column image data formed on the 2D image data $D_1, D_2, \ldots,$ and $D_n$ are updated to the latest one-column image data, the image data operation unit 13b generates 3D longitudinal image data using the latest one-column image data similarly to step S109 (at step S609). In addition, the update processing unit 23a deletes the 3D longitudinal image data on the default cut planes or the 3D longitudinal image data before the update. Thereafter, the update processing unit 23a stores the latest 3D longitudinal image data in the image data storage unit 11 (at step S610). The longitudinal image update processing for updating the 3D longitudinal image data on the default cut planes or the 3D longitudinal image on the cut planes to the latest data is completed.

In the second embodiment, the instance in which one default point is updated to the new cut point is explained. However, the present invention is not limited to this instance. The two default points set on the 2D image data may be changed or the already set cut points may be changed to new cut points.

According to the second embodiment, the instance in which default point data on the default points are stored in the storage unit in advance is explained. However, the present invention is not limited to this instance. Before the 3D scan, the operator may operate the input device 8 to input the default points data.

According to the second embodiment, the pieces of 2D image data sequentially obtained by the 3D scan are cut at designated longitudinal plane positions, the adjacent pieces of one-column image data set at the longitudinal plane positions are linearly interpolated, and the longitudinal image generated by the linear interpolation is displayed on the monitor screen simultaneously with this 3D scan. Therefore, the ultrasonic diagnostic apparatus with which the operator can easily grasp the position, the moving path, or the like of the ultrasonic transducer that is being executing the 3D scan, with which the operator can thereby facilitate determining whether the desired region of interest falls within a scan range of the 3D scan, with which the operator can obtain the sense of safety during the operation of the 3D scan, and with which the operator can obtain the improved operativity of the in vivo ultrasonic diagnosis can be realized.

According to the modification of the second embodiment, the straight line that determines the longitudinal plane position of the 2D image data can be updated for each 2D image data. Therefore, even if the desired region of interest is located irregularly on each 2D image data, it is possible to ensure arranging this straight line in the desired region of interest on the 2D image data. The ultrasonic diagnostic apparatus which can easily display the longitudinal image that accurately captures the desired region of interest on the monitor screen can be thereby realized.

A third embodiment of the present invention is explained in detail. In the first embodiment, the 3D longitudinal image of the cut plane set based on the cut point information on the two cut points is displayed on the monitor screen as the band-shaped 2D tomographic image. In the third embodiment, two 2D ultrasonic tomographic images obtained first and last by a 3D scan, respectively, and a band-shaped 3D longitudinal image are used, and a 3D longitudinal image that represents a stereoscopic tomographic image is displayed on a monitor screen.

Figure 20:
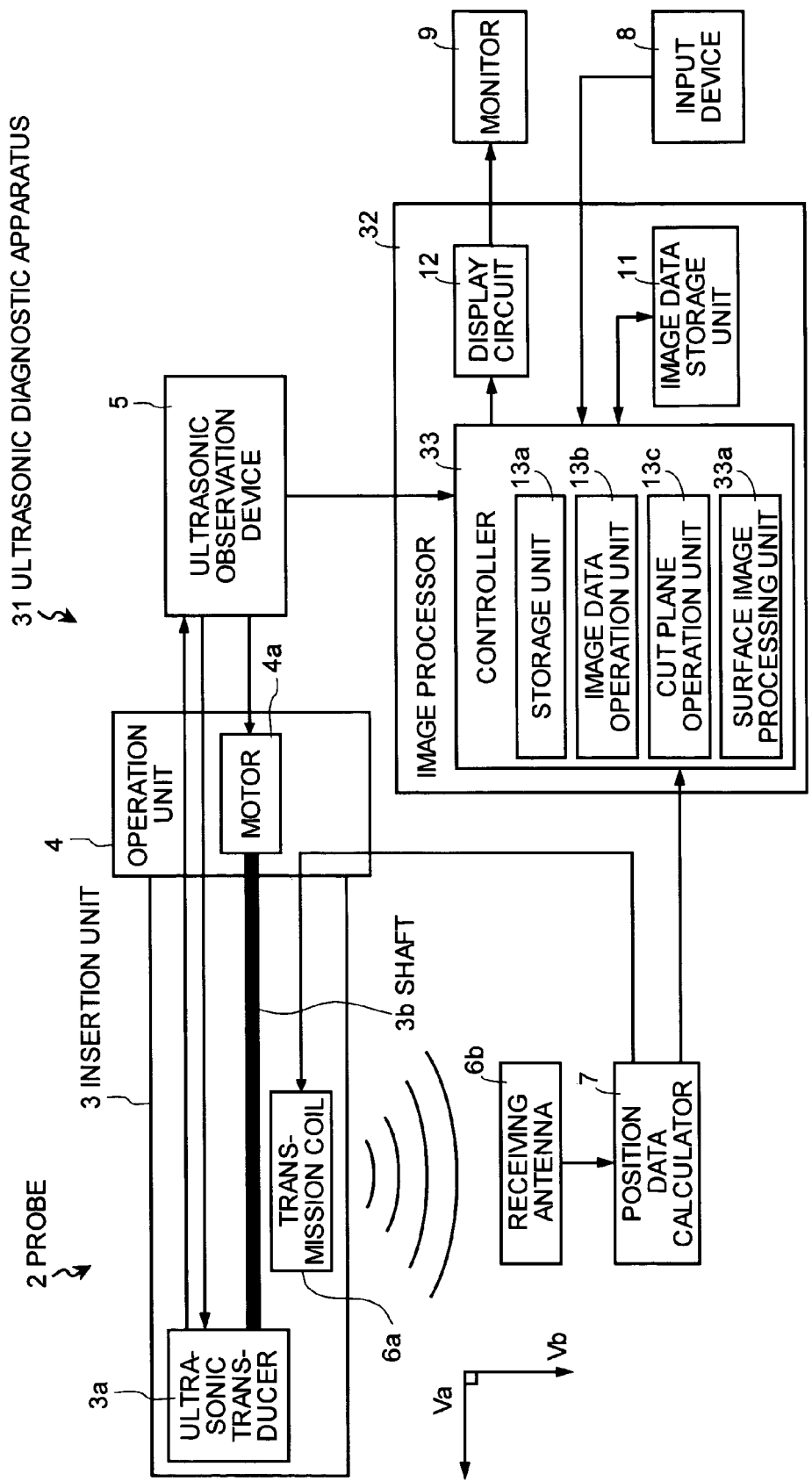
FIG. 20 is a block diagram that depicts schematic configuration of an ultrasonic diagnostic apparatus according to a third embodiment of the present invention.

FIG. 20 is a block diagram that depicts schematic configuration of an ultrasonic diagnostic apparatus according to the third embodiment. An ultrasonic diagnostic apparatus 31 shown in FIG. 20 is constituted so that an image processor 32 is provided instead of the image processor 10, and so that a controller 33 that includes a surface image processing unit 33a is provided instead of the controller 13 in the image processor 32. The controller 33 is realized, substantially similarly to the controller 13, by a ROM that stores various types of data such as a processing program, a RAM that stores each operation parameter, a CPU that executes the processing program stored in the ROM, and the like. The other constituent elements of the ultrasonic diagnostic apparatus 31 are equal to those of the ultrasonic diagnostic apparatus 1 according to the first embodiment. Like constituent elements as those according to the first embodiment are denoted by like reference symbol, respectively.

Figure 21:
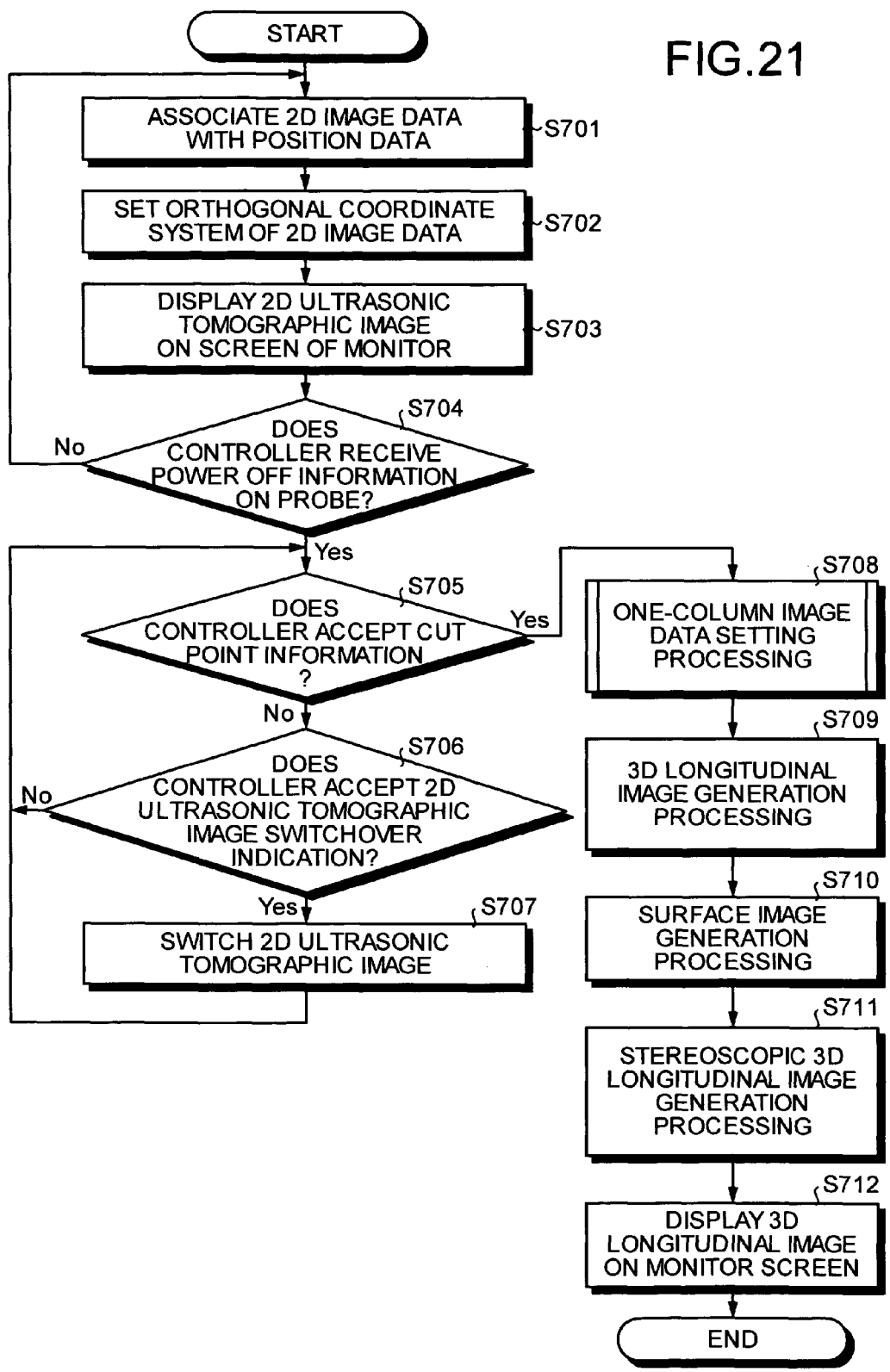
FIG. 21 is a flowchart showing respective processing steps executed until the ultrasonic diagnostic apparatus according to the third embodiment displays a stereoscopic 3D longitudinal image on the monitor screen.

FIG. 21 is a flowchart showing respective processing steps executed since the controller 33 acquires n pieces of 2D image data and n pieces of position data, sets cut planes including respective cut points, generates a 3D longitudinal image of each cut plane, i.e., a band-shaped 3D longitudinal image until displaying a 3D longitudinal image that stereoscopically represents this 3D longitudinal image on the monitor 9. Referring to FIG. 21, if the ultrasonic observation device 5 generates 2D image data based on the echo signal, and the position data calculator 7 calculates position data on the position at which this echo signal is obtained, then the controller 33 acquires the 2D image data output from the ultrasonic observation device 5 and the position data output from the position data calculator 7. In addition, the controller 33 associates the acquired 2D image data with the position data, similarly to the step 101 (at step S701).

The controller 33 arranges the 2D image data associated with this position data on the spatial coordinate system xyz, and sets an orthogonal coordinate system based on the axial vector and the plane parallel vector made to correspond for the 2D image data, similarly to the step 102 (at step S702). Thereafter, the controller 33 stores the 2D image data for which the orthogonal coordinate system is set, in the image data storage unit 11 while arranging the 2D image data on the spatial coordinate system xyz, transmits the 2D image data to the monitor 9 through the display circuit 12, and displays a 2D ultrasonic tomographic image corresponding to the 2D image data on the monitor 9 (at step S703).

If the probe 2 is executing a radial scan, that is, the power switch of the operation unit 4 is turned on, the controller 33 does not receive power-OFF information corresponding to a power-OFF state of the probe 2 ("No" at step S704). If so, the controller 33 repeatedly executes the processing step S701 and the following. Namely, if n radial scans are performed before the probe 2 is turned off, the controller 33 repeatedly executes the processing step S701 and the following n times. The controller 33 thereby acquires n pieces of 2D image data $D_1, D_2, \ldots,$ and $D_n$ associated with the respective pieces of position data, associates the orthogonal coordinate systems with the respective pieces of 2D image data $D_1, D_2, \ldots,$ and $D_n$. Further, the controller 33 stores the n pieces of 2D image data $D_1, D_2, \ldots,$ and $D_n$ thus acquired in the image data storage unit 11 while arranging the 2D image data $D_1, D_2, \ldots,$ and $D_n$ on the spatial coordinate system xyz as shown in FIG. 3.

If the operator turns off the power switch of the operation unit 4 after the n radial scans, the controller 33 receives the power-OFF information on the probe 2 ("Yes" at step S704). Thereafter, if the operator inputs switchover indication information for switching the 2D ultrasonic tomographic image displayed on the monitor screen over to another 2D ultrasonic tomographic image without performing the cut point information input operation using the input device 8, then the controller 33 does not accept the cut point information ("No" at step S705) but accepts a switchover indication corresponding to the switchover indication information ("Yes" at step S706). If so, the controller 33 reads the 2D image data stored in the image data storage unit 11 based on the switchover indication corresponding to the switchover indication information the input of which the controller 13 accepts. In addition, the controller 33 transmits this 2D image data to the monitor 9 through the display circuit 12, and switches display of the 2D ultrasonic tomographic image to display of a 2D ultrasonic tomographic image corresponding to this 2D image data (at step S707). The controller 33 repeatedly executes the processing step S705 and the following. Further, if neither the cut point information nor the switchover indication information are input to the controller 33, then the controller 33 does not accept the cut point information ("No" at step S705) and does not accept the switchover indication by the switchover indication information ("No" at step S706). If so, the controller 33 repeatedly executes the processing step S705 and the following.

On the other hand, if the operator inputs cut point information on two cut points designated as respective desired positions on a desired 2D ultrasonic tomographic image using the input device 8, the controller 33 accepts the input cut point information ("Yes" at step S705). In addition, the controller 33 sets the two cut points corresponding to the cut point information the input of which the controller 33 accepts, on the orthogonal coordinate system of the 2D image data corresponding to this 2D ultrasonic tomographic image. If the two cut points are set on the orthogonal coordinate system of one of the n piece of 2D image data, the controller 33 sets two cut points and a straight line that passes through the two cut points on each of the orthogonal coordinate systems of the n pieces of 2D image data based on the coordinate information on the two cut points similarly to step S108. In addition, the controller 33 sets the straight line as a longitudinal plane position of each of the n pieces of 2D image data arranged on the spatial coordinate system xyz.

The controller 33 calculates all pixels on each straight line thus obtained and luminances of the pixels for each of the n pieces of 2D image data, generates one-column image data in one column and j row (where j=1, 2, 3, . . . ), and sets pixel position vectors on the spatial coordinate system xyz for the pixels in each row of each one-column image data obtained. Thus, the controller 33 sets one-column image data, for which the pixel positions in the rows correspond to the coordinates of pixels on the spatial coordinate system xyz, for the n pieces of 2D image data, respectively, similarly to step S108 (at step S708).

If the controller 33 sets the one-column image data for respective pieces of 2D image data, the image data operation unit 13b linearly interpolates adjacent pieces of one-column image data using the n pieces of 2D image data for which pieces of the one-column image data are set, respectively, similarly to step S109. In addition, the image data operation unit 13b generates 3D longitudinal image data of the respective cut planes (at step S709).

Figure 22:
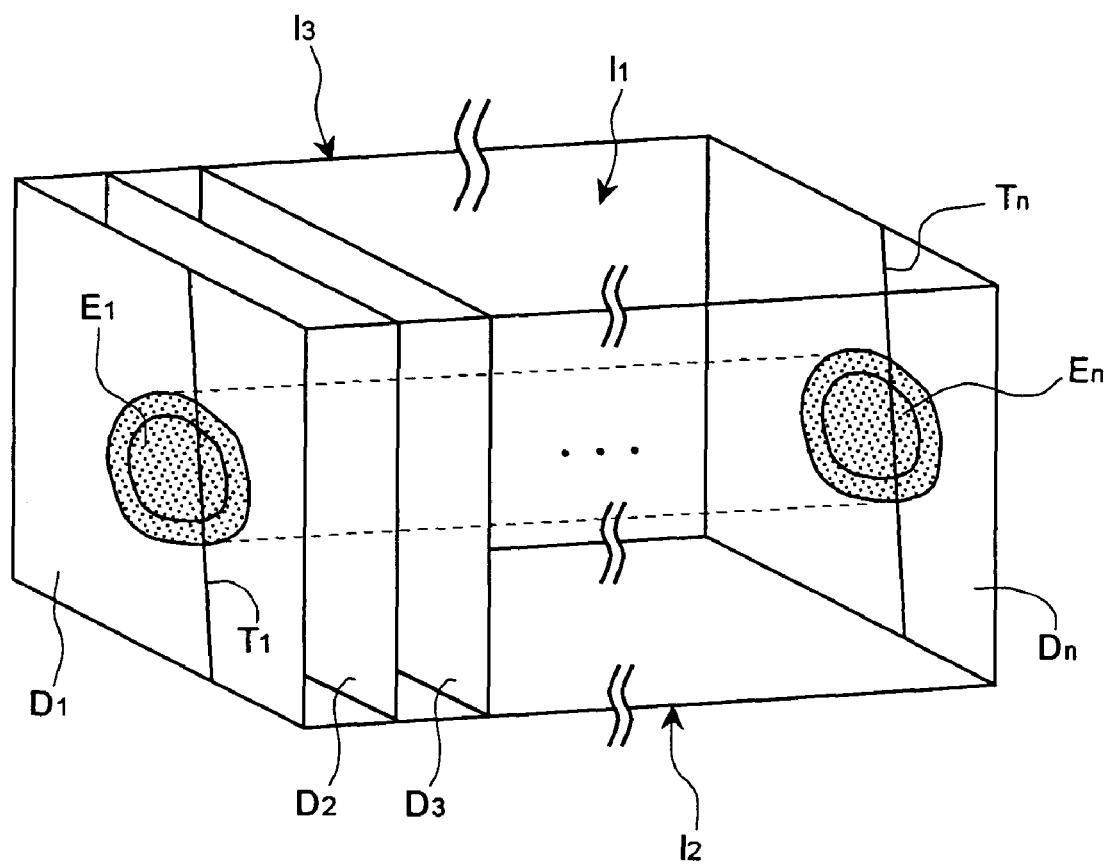
FIG. 22 is an explanatory view of a surface image generation processing.

If the image data operation unit 13b generates the 3D longitudinal image data, the surface image processing unit 33a linearly interpolates respective adjacent pieces of 2D image data for upper ends, lower ends, and side ends of the n pieces of 2D image data $D_1, D_2, \ldots,$ and $D_n$, using the n pieces of 2D image data $D_1, D_2, \ldots,$ and $D_n$ arranged on the spatial coordinate system xyz. FIG. 22 is an explanatory view of a processing performed by the plane image processing unit 33 for linearly interpolating respective adjacent pieces of 2D image data for upper ends, lower ends, and side ends of the n pieces of 2D image data $D_1, D_2, \ldots,$ and $D_n$, and for generating upper surface image data, lower surface image data, and side surface image data (a surface image generation processing). FIG. 22 typically shows a state in which the 2D image data $D_1, D_2, \ldots,$ and $D_n$ for which the straight lines $T_1, T_2, \ldots,$ and $T_n$ that determine cut planes are set, respectively are arranged on the spatial coordinate system xyz.

As shown in FIG. 22, if the adjacent pieces of 2D image data are linearly interpolated for the upper ends of the 2D image data $D_1, D_2,$ and $D_n$, the surface image processing unit 33a generates the upper surface image data $I_1$. If the adjacent pieces of 2D image data are linearly interpolated for the lower ends of the 2D image data $D_1, D_2, \ldots,$ and $D_n$, the surface image processing unit 33a generates the lower surface image data $I_2$. If the adjacent pieces of 2D image data are linearly interpolated for the side ends of the 2D image data $D_1, D_2, \ldots,$ and $D_n$, the surface image processing unit 33a generates the side surface image data $I_3$ (at step S710). It is noted that the cut planes are set as flat planes or curved planes including the straight lines $T_1, T_2, \ldots$, and $T_n$, respectively, and the cut surfaces cut 2D ultrasonic tomographic images corresponding to at least the 2D image data $D_1$ and $D_n$.

The surface image processing unit 33a performs a processing for generating 3D tomographic image data for displaying a band-shaped 3D longitudinal image (a stereoscopic 3D longitudinal image generation processing) using 3D tomographic image data SD created by the image data operation unit 13b at step S709, the upper surface image data $I_1$, the lower surface image data $I_2$, and the side surface image data $I_3$ generated by the plane image processing unit 33a at step S710, and the 2D image data $D_1$ and $D_n$ cut along the cut planes (at step S711).

Figure 23:
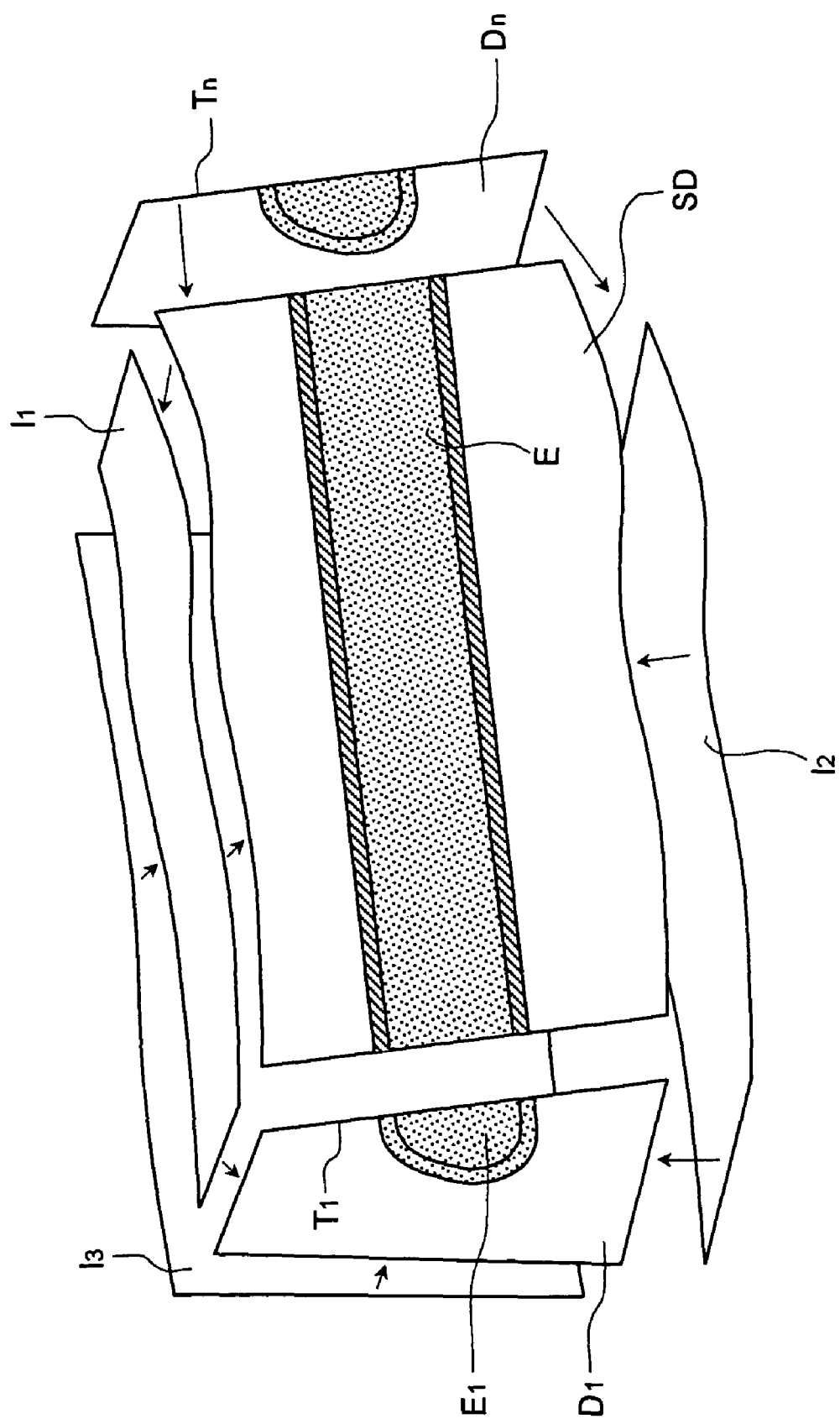
FIG. 23 is an explanatory view of a stereoscopic 3D longitudinal image generation processing.

FIG. 23 is an explanatory view of the stereoscopic 3D longitudinal image generation processing performed by the surface image processing unit 33a. As shown in FIG. 23, the surface image processing unit 33a connects the 2D image data $D_1$ to a front end of the 3D longitudinal image data SD, and the 2D image data $D_n$ to a rear end of the 3D longitudinal image data SD. The surface image processing unit 33a connects upper ends of the 3D longitudinal image data SD, the 2D image data $D_1$ and $D_n$, and the side surface image data $I_3$ to the upper surface image data $I_1$. In addition, the surface image processing unit 33a connects lower ends of the 3D longitudinal image data SD, the 2D image data $D_1$ and $D_n$, and the side surface image data 13 to the lower surface image data $I_2$. Thus, the surface image processing unit 33a generates the stereoscopic 3D longitudinal image data for representing the band-shaped 3D longitudinal image stereoscopically. If generating this stereoscopic 3D longitudinal image data, the surface image processing unit 33a connects portions of the upper surface image data $I_1$, the lower surface image data $I_2$, the side surface image data $I_3$, the 3D longitudinal image data SD, and the 2D image data $D_1$ and $D_n$, which portions correspond to the same coordinates on the spatial coordinate system xyz, respectively, to one another.

Figure 24:
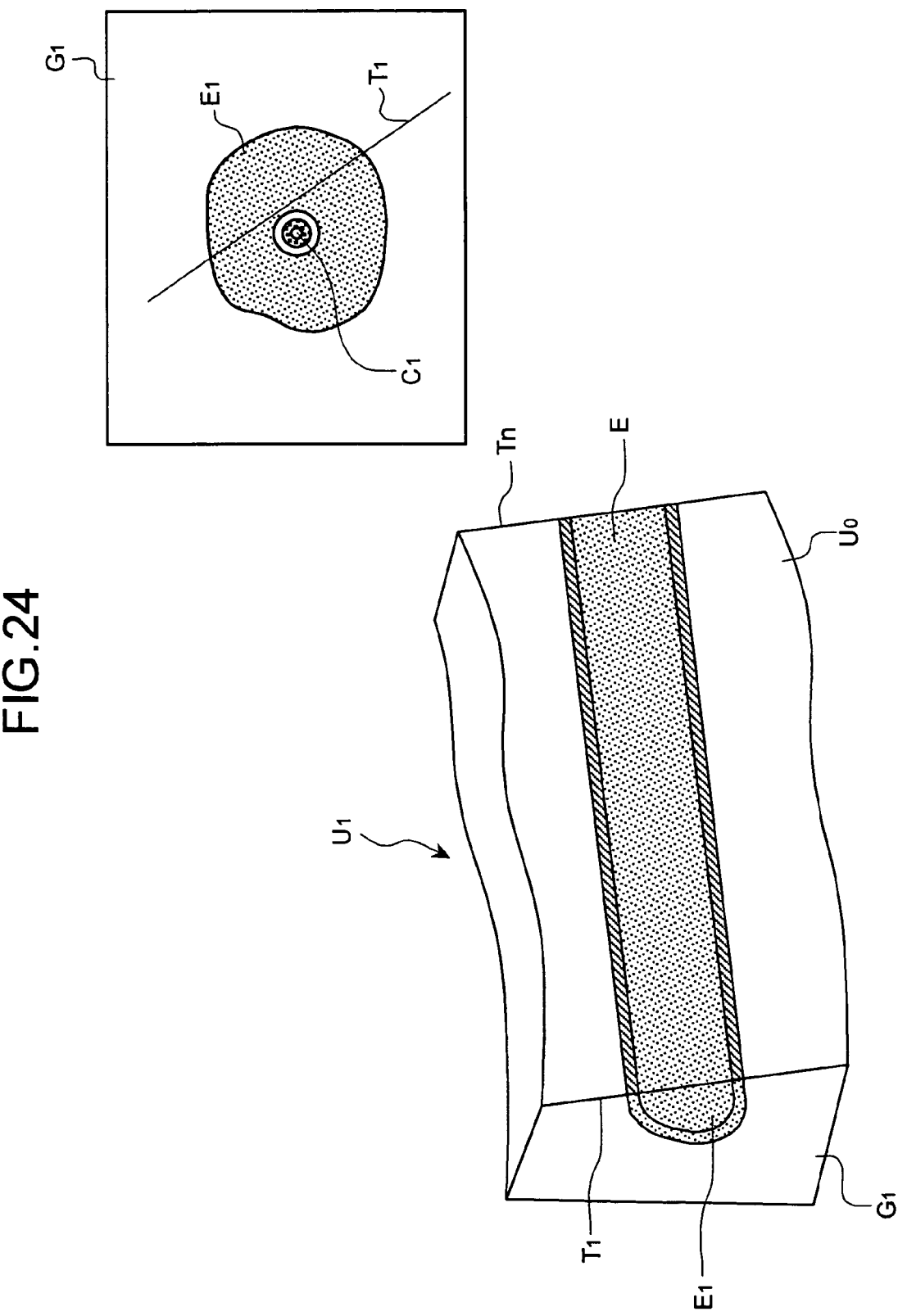
FIG. 24 depicts an example of the stereoscopic 3D longitudinal image displayed on the monitor screen.

If the surface image processing unit 33a generates the stereoscopic 3D longitudinal image data, the controller 33 transmits this stereoscopic 3D longitudinal image data to the monitor 9 through the display circuit 112 to display a stereoscopic 3D longitudinal image corresponding to this stereoscopic 3D longitudinal image data on the monitor 9 (at step S712). FIG. 24 depicts an example of a stereoscopic 3D longitudinal image displayed on the screen of the monitor 9. As shown in FIG. 24, in this stereoscopic 3D longitudinal image $U_1$, a duodenum image $E_1$ of a 2D ultrasonic tomographic image $G_1$ corresponding to the 2D image data $D_1$ and the duodenum image E of the 3D longitudinal image $U_0$ are stereoscopically connected to each other. Therefore, the stereoscopic 3D longitudinal image $U_1$ is observed as a stereoscopic tomographic image. Namely, this 3D longitudinal image $U_1$ can represents a tomographic image that is less strained as compared with the subject in the living body on which the probe 2 performs the 3D scan, and which is substantially equal in shape to the actual subject, and can stereoscopically capture a tomographic image of the region of interest or the like in the living body. This can facilitate operator's accurate grasping a state of the region of interest or the like in the living body.

If the operator inputs indication information on image display using the input device 8, the controller 33 may display and output the 3D longitudinal image $U_1$ and the 2D ultrasonic tomographic image $G_1$ on the same monitor screen based on an indication corresponding to this indication information as shown in FIG. 24. In this case, the straight line $T_1$ that determines the cut plane may be superimposed on the 2D ultrasonic tomographic image $G_1$ as an auxiliary line. The auxiliary line indicating the straight line $T_1$ corresponds to the straight line $T_1$ on the 3D longitudinal image $U_1$. Therefore, by observing the 2D ultrasonic tomographic image $G_1$ and the 3D longitudinal image $U_1$, the operator can easily grasp the positional relationship between the 2D ultrasonic tomographic image $G_1$ and the 3D longitudinal image $U_1$.

If the operator causes the ultrasonic transducer 3a to perform a radial scan and guides the probe 2 following step S712, the 3D scan using the ultrasonic transducer 3a resumes. In addition, the controller 33 generates the 3D longitudinal data based on the cut points already set at step S708 and the pieces of 2D image data obtained successively by the 3D scan, and displays a stereoscopic 3D longitudinal image including a band-shaped 3D longitudinal image corresponding to the 3D longitudinal image data on the monitor 9. In this case, the controller 33 adds the stereoscopic 3D longitudinal image generated based on the band-shaped 3D longitudinal image generated by operator's guiding the probe 2 and on the 2D ultrasonic tomographic images obtained successively by the 3D scan, to the 3D longitudinal image $U_1$ already displayed on the screen of the monitor 9 and displays the resultant 3D longitudinal image. The controller 33 thus extends the 3D longitudinal image $U_1$ successively with the operator's operation for guiding the probe 2 during the 3D scan.

In the third embodiment, the adjacent pieces of 2D image data are linearly interpolated for the upper ends, lower ends, and side ends of the n pieces of 2D image data arranged on the spatial coordinate system xyz, and the upper plane image, the lower plane image, and the side plane image are thereby formed. However, the present invention is not limited to this instance. An image processing such as linear interpolation may be performed on all pixels between the respective adjacent pieces of 2D image data, thereby forming the upper plane image, the lower plane image, and the side plane image.

According to the third embodiment, the 2D ultrasonic tomographic image obtained first by the 3D scan and the 2D ultrasonic tomographic image obtained last by the 3D scan are connected to the front end and the rear end of the 3D longitudinal image of the cut surfaces set based on the cut suface information, i.e., the band-shaped 3D longitudinal image, respectively, thereby generating the stereoscopic 3D longitudinal image. Therefore, it is possible to realize the ultrasonic diagnostic apparatus which can display a tomographic image that is less strained as compared with the subject in the living body on which the probe 2 performs the 3D scan, which is substantially equal in shape to the actual subject, which can stereoscopically capture the tomographic image of the region of interest or the like in the living body, and which can facilitate operator's accurate grasping a state of the region of interest or the like in the living body. If the operator uses this ultrasonic diagnostic apparatus, the operator can easily observe the image which accurately captures the state of the region of interest or the like in the living body. Accordingly, an in vivo ultrasonic diagnosis can be carried out efficiently.

A fourth embodiment of the present invention is explained in detail. In the third embodiment, the stereoscopic 3D longitudinal image that represents the stereoscopic tomographic image is displayed on the monitor screen using the 2D ultrasonic tomographic images obtained first and last by the 3D scan, respectively and the band-shaped 3D longitudinal image. In the fourth embodiment, a cut plane is set based on cut point information, the cut plane is rotated by a preset step angle, and a stereoscopic 3D longitudinal image that represents a stereoscopic tomographic image is displayed on the monitor screen using a band-shaped longitudinal image of the rotated cut plane and 2D ultrasonic tomographic images obtained first and last by a 3D scan, respectively.

Figure 25:
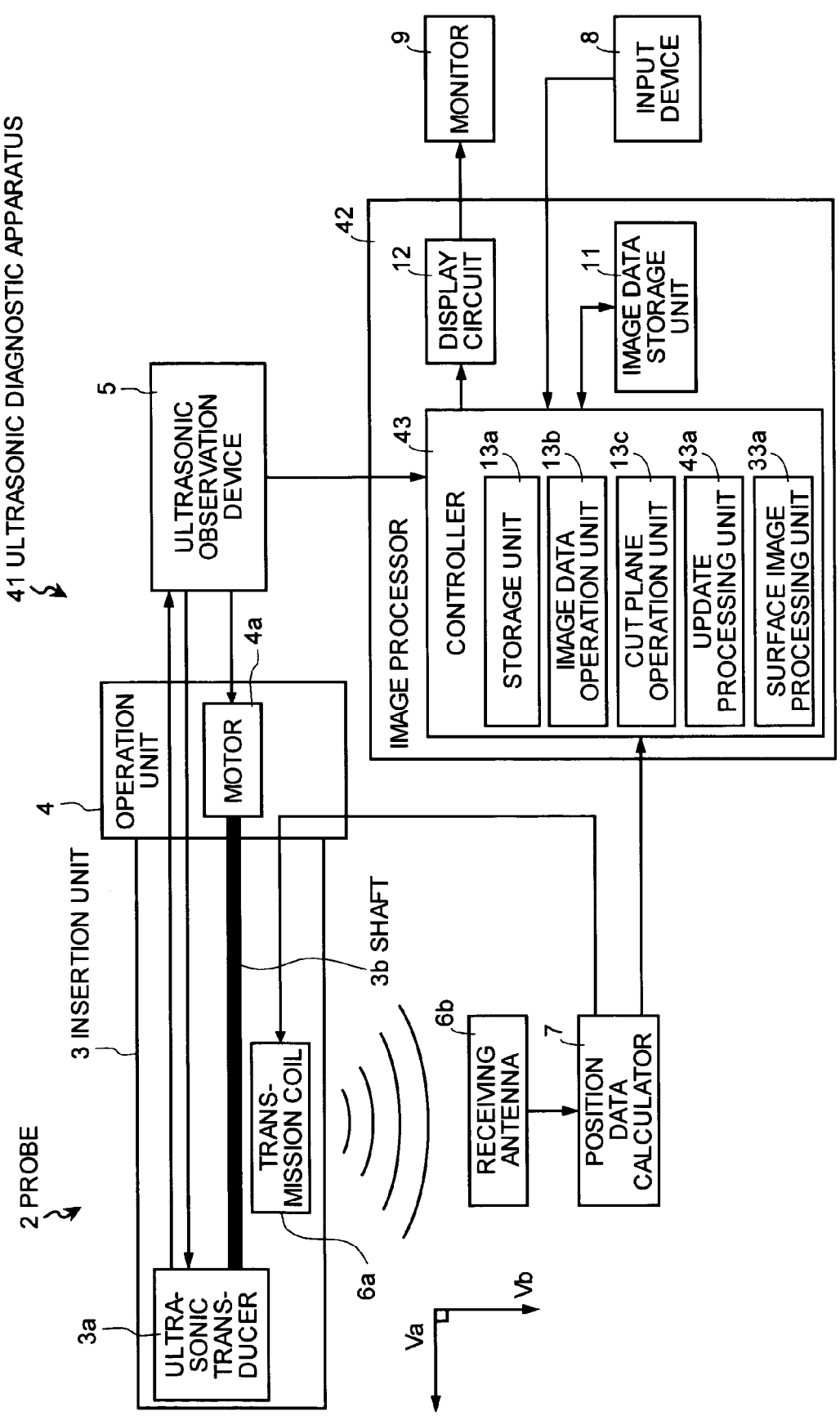
FIG. 25 is a block diagram that depicts schematic configuration of an ultrasonic diagnostic apparatus according to a fourth embodiment of the present invention.

FIG. 25 is a block diagram that depicts schematic configuration of an ultrasonic diagnostic apparatus according to the fourth embodiment. The ultrasonic diagnostic apparatus 41 shown in FIG. 20 is constituted so that an image processor 42 is provided instead of the image processor 32, and so that a controller 43 that includes an update processing unit 43a is provided instead of the controller 33 in the image processor 42. The controller 43 is realized, substantially similarly to the controller 33, by a ROM that stores various types of data such as a processing program, a RAM that stores each operation parameter, a CPU that executes the processing program stored in the ROM, and the like. The other constituent elements of the ultrasonic diagnostic apparatus 41 are equal to those of the ultrasonic diagnostic apparatus 31 according to the third embodiment. Like constituent elements as those according to the third embodiment are denoted by like reference symbol, respectively.

Figure 26:
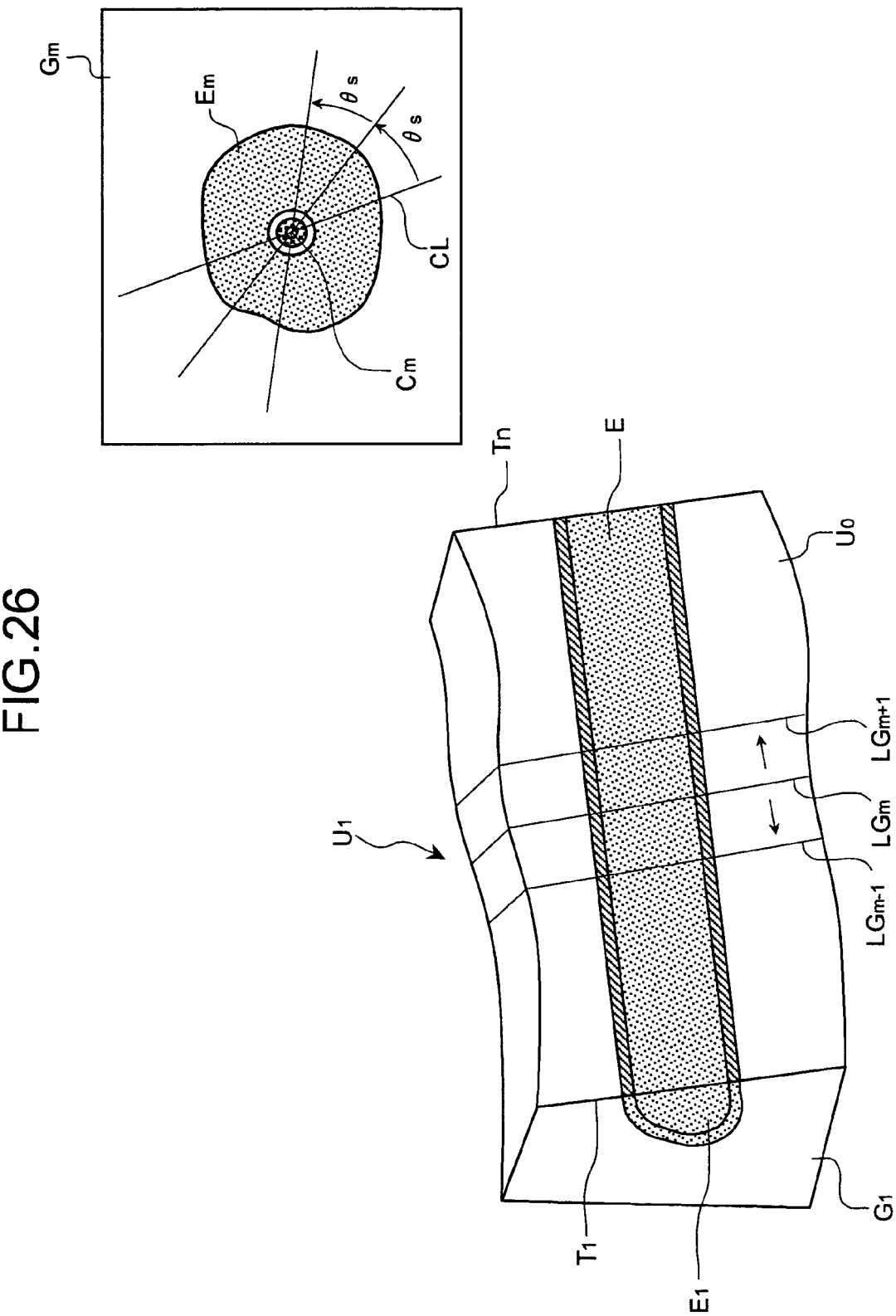
FIG. 26 depicts an example of a stereoscopic 3D longitudinal image and a 2D ultrasonic tomographic image displayed by the ultrasonic diagnostic apparatus according to the fourth embodiment on the screen of the monitor.

FIG. 26 depicts an example of a stereoscopic 3D longitudinal image and a 2D ultrasonic tomographic image displayed on the screen of the monitor 9. As shown in FIG. 26, in this stereoscopic 3D longitudinal image $U_1$, similarly to the third embodiment, the duodenum image $E_1$ of the 2D ultrasonic tomographic image $G_1$ corresponding to the 2D image data $D_1$ and the duodenum image E of the band-shaped 3D longitudinal image $U_0$ are stereoscopically connected to each other. In addition, the 2D ultrasonic tomographic image $G_m$ and the stereoscopic 3D longitudinal image $U_1$ are displayed on the same monitor screen. The controller 43 displays a straight line $LG_m$ that indicates a position of the 2D ultrasonic tomographic image $G_m$ on the 3D longitudinal image $U_1$ based on indication information input by the operator while operating the input device 8. The controller 43 also displays a cut line CL corresponding to a cut plane on which the 3D longitudinal image $U_0$ that is one plane of the 3D longitudinal image $U_1$ is formed based on the indication information input by the operator while operating the input device 8. The cut line CL is a straight line that passes the image center $C_m$ of the 2D ultrasonic tomographic image $G_m$.

If the operator operates the input device 8 to input indication information for rotating the cut line CL displayed on the 2D ultrasonic tomographic image $G_m$ in a predetermined direction, then the controller 43 reads a preset step angle $\theta_s$ from the storage unit 13a in response to an indication corresponding to this indication information. In addition, the controller 43 rotates the cut line CL by the read step angle $\theta_s$ in the predetermined direction, with a counterclockwise direction set as a positive direction, and the image center $C_m$ set as a rotation center. If so, the image data operation unit 13b generates 3D longitudinal image data on the cut plane corresponding to the rotated cut line CL. The update processing unit 43a then performs a 3D longitudinal image data update processing for updating the 3D longitudinal image data thus generated to latest 3D longitudinal image data similarly to the second embodiment. As a result, the controller 43 displays the stereoscopic 3D longitudinal image on the monitor 9 using a band-shaped 3D longitudinal image corresponding to the latest 3D longitudinal image data obtained by the update processing performed by the update processing unit 43a and the 2D ultrasonic tomographic images $G_1$ and $G_n$, similarly to the third embodiment. Namely, if rotating the cut line CL, the controller 43 updates the cut plane according to rotation of this cut line CL, and updates the 3D longitudinal image data on this cut plane, and reconstructs a stereoscopic 3D longitudinal image using the updated 3D longitudinal image data. Thereafter, the controller 43 updates the display of the image to display of the reconstructed stereoscopic 3D longitudinal image.

The operator can input the indication information for rotating the cut line CL by the step angle $\theta_s$ in the predetermined direction whenever the operator depresses a key on a keyboard, for example, by a key operation or a button operation on the input device 8. The controller 43 rotates the cut line CL by the step angle $\theta_s$ in the predetermined direction whenever this indication information is input. The controller 43 then reconstructs the stereoscopic 3D longitudinal image, and completes the processing for updating the display of this 3D longitudinal image.

If the operator operates the input device 8 to input indication information for switching over the 2D ultrasonic tomographic image $G_m$ displayed on the same screen as the 3D longitudinal image $U_1$, the controller 43 reads the 2D image data from the storage unit 13a in response to an indication corresponding to this indication information. In addition, the controller 43 switches the display of the image to display of a 2D ultrasonic tomographic image corresponding to this 2D image data. For example, if the indication information for switching the 2D ultrasonic tomographic image $G_m$ over to the 2D ultrasonic tomographic image $G_{m-1}$ is input, the controller 43 reads the 2D image data $D_{m-1}$ corresponding to the 2D ultrasonic tomographic image $G_{m-1}$ from the image data storage unit 11. In addition, the controller 43 displays the 2D ultrasonic tomographic image $G_{m-1}$ on the monitor 9. In this case, the update processing unit 43a updates the display of the 2D ultrasonic tomographic image from that of the 2D ultrasonic tomographic image $G_m$ to that of the 2D ultrasonic tomographic image $G_{m-1}$ and updates the straight line $LG_m$ displayed on the 3D longitudinal image $U_1$ to a straight line $LG_{m-1}$. Likewise, if the indication information for switching the 2D ultrasonic tomographic image $G_m$ to the 2D ultrasonic tomographic image $G_{m+1}$ is input, the controller 43 reads the 2D image data $D_{m+1}$ corresponding to the 2D ultrasonic tomographic image $G_{m+1}$ from the image data storage unit 11. In addition, the controller 43 displays the 2D ultrasonic tomographic image $G_{m+1}$ on the monitor 9. In this case, the update processing unit 43a updates the display of the 2D ultrasonic tomographic image from that of the 2D ultrasonic tomographic image $G_m$ to that of the 2D ultrasonic tomographic image $G_{m+1}$, and updates the straight line $LG_m$ displayed on the 3D longitudinal image $U_1$ to a straight line $LG_{m+1}$.

Namely, if the indication information for switching over the display of the 2D ultrasonic tomographic image on the screen whenever the operator operates depresses a key on the keyboard, for example, by the key operation or the button operation on the input device 8, the controller 43 performs the processing for updating the display of the 2D ultrasonic tomographic image on the screen, and for updating the straight line $LG_m$ displayed on the 3D longitudinal image $U_1$ to the straight line that indicates the position of the new 2D ultrasonic tomographic image to which the display is updated whenever this indication information is input. Further, if the indication information for updating the straight line $LG_m$ displayed on the 3D longitudinal image $U_1$ is input whenever the operator depresses the key on the keyboard, for example, by the key operation or button operation on the input device, then the controller 43 can update this straight line $LG_m$ to another straight line (e.g., the straight line $L_{m-1}$ or $LG_{m+1}$) and update the display of the 2D ultrasonic tomographic image on the screen to the display of the 2D ultrasonic tomographic image corresponding to the position of the updated straight line on the 3D longitudinal image $U_1$ whenever this indication information is input.

Furthermore, if the operator causes the ultrasonic transducer 3a to perform a radial scan and guides the probe 2 after the stereoscopic 3D longitudinal image and the 2D ultrasonic tomographic image are displayed on the same screen, the 3D scan using the ultrasonic transducer 3a resumes. In addition, the controller 43 generates the 3D longitudinal data on the cut plane based on the already set cut points and the pieces of 2D image data obtained successively by the 3D scan, and displays a stereoscopic 3D longitudinal image including a band-shaped 3D longitudinal image corresponding to the 3D longitudinal image data on the monitor 9. In this case, the controller 43 adds the stereoscopic 3D longitudinal image generated based on the band-shaped 3D longitudinal image generated by operator's guiding the probe 2 and on the 2D ultrasonic tomographic images obtained successively by the 3D scan, to the 3D longitudinal image $U_1$ already displayed on the screen of the monitor 9 and displays the resultant 3D longitudinal image. The controller 43 thus extends the 3D longitudinal image $U_1$ successively with the operator's operation for guiding the probe 2 during the 3D scan.

In the fourth embodiment, the stereoscopic 3D longitudinal image generated based on a plurality of pieces of 2D image data and the 2D ultrasonic tomographic image corresponding to any one of these pieces of 2D image data are displayed and output on the same screen. The straight line corresponding to the position of the 2D ultrasonic tomographic image on the stereoscopic 3D longitudinal image is displayed on the stereoscopic 3D longitudinal image. In addition, the cut line corresponding to the cut plane of the band-shaped 3D longitudinal image which the stereoscopic 3D longitudinal image includes is displayed on the 2D ultrasonic tomographic image. Furthermore, the stereoscopic 3D longitudinal image is updated so that stereoscopic 3D longitudinal image includes, as its one plane, the 3D longitudinal image of the cut plane corresponding to the rotated cut line when the cut line is rotated. In addition, if this 2D ultrasonic tomographic image is updated over to the other 2D ultrasonic tomographic image, the straight line on the stereoscopic 3D longitudinal image is switched to the straight line which indicates the position of the other 2D ultrasonic tomographic image on the stereoscopic 3D longitudinal image. Therefore, it is possible to realize the ultrasonic diagnostic apparatus which can facilitate operator's grasping the positional relationship between the stereoscopic 3D longitudinal image and the 2D ultrasonic tomographic image which are displayed and output on the same screen, and which can thereby easily display and output the tomographic image which accurately captures the region of interest such as the characteristic site or the affected site, e.g., the tumor in the living body. If the operator uses this ultrasonic diagnostic apparatus, the operator can easily locate the desired region of interest.

A fifth embodiment of the present invention is explained in detail. In the first to the fourth embodiments, the ultrasonic diagnostic apparatus is constituted to generate and output the tomographic image of the subject obtained by cutting the curved plane along the moving path or moving direction of the probe 2 which performs the 3D scan. In the fifth embodiment, the ultrasonic diagnostic apparatus is constituted to further set two measurement points designated on this tomographic image on the spatial coordinate system, and to measure a distance between the two measurement points.

Figure 27:
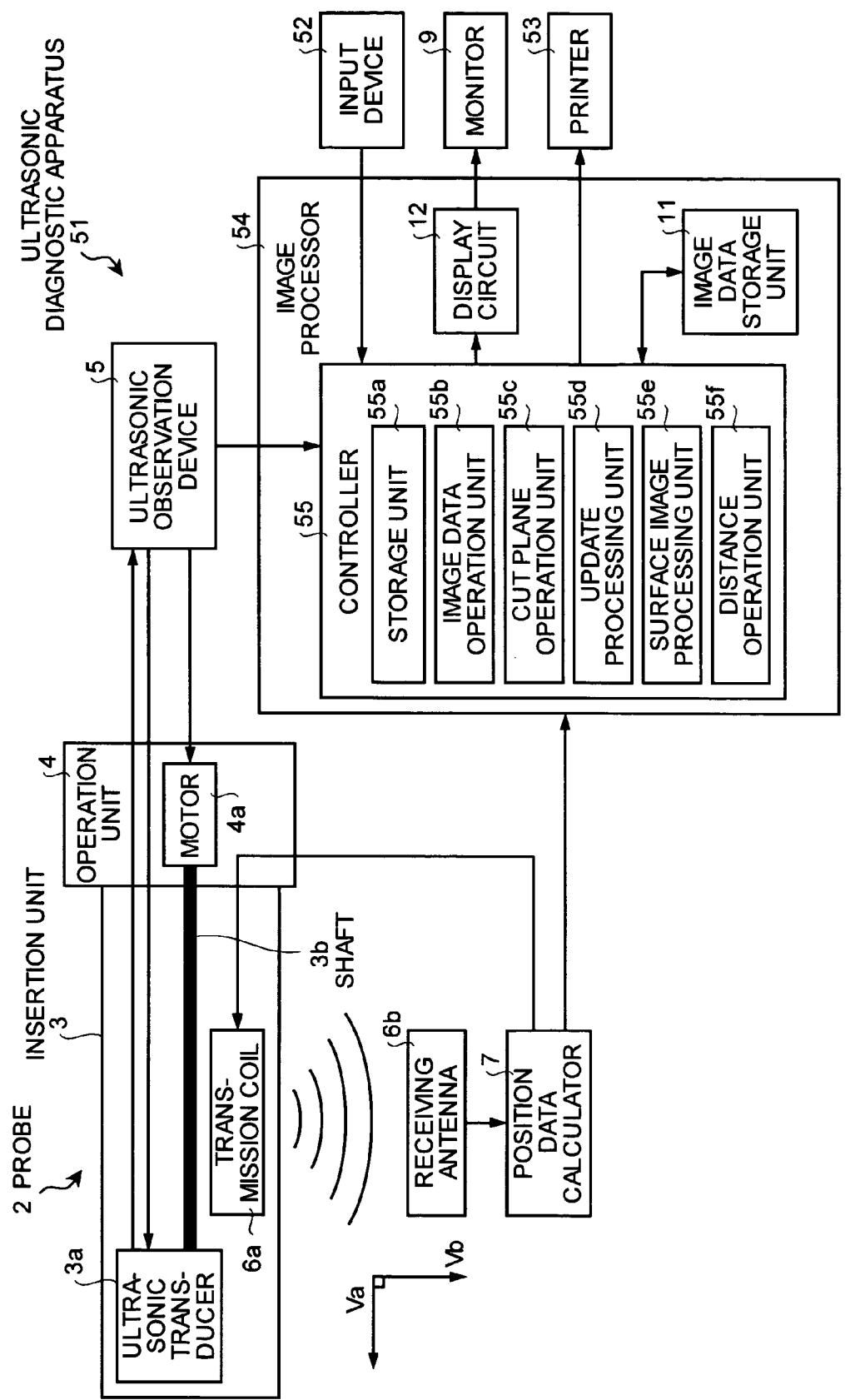
FIG. 27 is a block diagram that depicts schematic configuration of an ultrasonic diagnostic apparatus according to a fifth embodiment of the present invention.

FIG. 27 is a block diagram that depicts schematic configuration of an ultrasonic diagnostic apparatus according to the fifth embodiment. This ultrasonic diagnostic apparatus 51 is constituted so that an input device 52 is provided instead of the input device 8, and so that an image processor 54 is provided instead of the image processor 42, as compared with the ultrasonic diagnostic apparatus according to the fourth embodiment. In addition, a controller 55 instead of the controller 43 is provided in the image processor 54. The controller 55 includes a storage unit 55a instead of the storage unit 13a, an image data operation unit 55b instead of the image data operation unit 13b, a cut plane operation unit 55c instead of the cut plane operation unit 13c, an update processing unit 55d instead of the update processing unit 43a, a surface image processing unit 55e instead of the plane unit processing unit 33a, and a distance operation unit 55f. The ultrasonic diagnostic unit 51 further includes a printer 53. The printer 53 is electrically connected to the controller 55. The other constituent elements of the ultrasonic diagnostic apparatus 51 are equal to those of the ultrasonic diagnostic apparatus 41 according to the fourth embodiment. Like constituent elements as those according to the third embodiment are denoted by like reference symbol, respectively.

The input device 52 is realized by a keyboard, a touch panel, a track ball, a mouse, a joystick, or the like, or a combination thereof. The input device 52 inputs the cut point information, designated point information on coordinate information on points designated (designated points) on 2D image data generated by the ultrasonic observation device 55, angle information for designating rotation angles of various longitudinal images or various tomographic images displayed on the monitor screen, measurement point information on coordinate information on points (measurement points) for designating a region (measurement region) for measuring geometric values such as lengths, areas, and volumes relative to the various longitudinal images or the various tomographic images displayed on the monitor screen, various pieces of indication information on an image display processing on the monitor 9, and various indication processings related to a print output processing for printing the measurement results onto a paper or the like, to the image processor 54.

If the input device 52 is, for example, the keyboard or the touch panel, then the input device 52 inputs or selects a numeric value corresponding to the cut point information, the designated point information, or the measurement point information, or directly inputs a coordinate position displayed on the screen of the monitor 9 or the touch panel in a state in which the input device 52 accepts input of each information. The cut point information, the designated point information, the angle information, or the measurement point information is thereby input to the input device 52. If the input device 52 is, for example, the track ball, the mouse, or the joystick, then the input device 52 selects a numeric value corresponding to the cut point information, the designated point information, the angle information, or the measurement point information or directly inputs the coordinate position displayed on the screen of the monitor 9 in a state in which the input device 52 accepts input of each information. The cut point information, the designated point information, or the measurement point information is thereby input to the input device 52. Further, the input device 52 selects a numeric value corresponding to the angle information or performs the drag operation, thereby inputting the angle information corresponding to an angle according to a moving amount of a cursor or the like. For example, the angle information indicating that, if the operator causes the input device 52 to execute this drag operation and the cursor is moved upward on the monitor screen by a predetermined amount, the longitudinal image or the tomographic image is rotated in a positive direction by an angle according to the predetermined amount is input to the input device 52. The angle information indicating that, if the operator causes the input device 52 to execute the drag operation and the cursor is moved downward on the monitor screen by the predetermined amount, the longitudinal image or the tomographic image is rotated in a negative direction by the angle according to the predetermined amount is input to the input device 52. The angle information indicating that, if the cursor is moved rightward on the monitor screen, the longitudinal image or the tomographic image is rotated in the positive direction by the angle according to the predetermined amount is input to the input device 52. The angle information indicating that, if the cursor is moved leftward on the monitor screen, the longitudinal image or the tomographic image is rotated in the negative direction by the angle according to the predetermined amount is input to the input device 52.

The image processor 54 is realized by a well-known computer that includes various recording mediums such as a RAM, a ROM, and a hard disk, and a CPU. The image processor 54 includes the image data storage unit 11, the display circuit 12, and the controller 13. The image data storage unit 11 is realized by an IC memory such as a RAM, an EEPROM, and a flash memory, and various storage device which can write and read data such as a hard disk drive or a magneto-optic disk drive. The image data storage unit 11 stores various pieces of image data input from the controller 55 under control of the controller 55. In addition, if the controller 55 generates various pieces of longitudinal image data or tomographic image data, the image data storage unit 11 stores the longitudinal image data or tomographic image data under control of the controller 55.

The controller 55 is realized by a ROM that stores various types of data such as a processing program, a RAM that stores each operation parameter, a CPU that executes the processing program stored in the ROM, and the like substantially similarly to the controller 43. The controller 55 includes the storage unit 55a, the image data operation unit 55b, the cut plane operation unit 55c, the update processing unit 55d, the surface image processing unit 55e, and the distance operation unit 55f. The storage unit 55a is composed by the ROM and the RAM, and stores not only the processing program and operation parameters but also the position data which the controller 55 sequentially receives from the position data calculator 7. The spatial coordinate system xyz is set to the controller 55 in advance, and the storage unit 55a stores setting data on this spatial coordinate system xyz. The storage unit 55a also stores default point data on an initial longitudinal position of each 2D image data arranged on the spatial coordinate system xyz. The controller 55 sets a default cut plane that is a cut plane at this initial longitudinal position based on this default point data.

Further, when the ultrasonic transducer 3a sequentially transmits n echo signals obtained by n radial scans (where n=1, 2, 3, . . . ) to the ultrasonic observation device 5, then the controller 55 grasps timings at which the ultrasonic observation device 5 generates n pieces of 2D image data based on the n echo signals, respectively, and grasps pieces of position data sequentially received from the position data calculator 7 for the respective timings. Thereafter, the controller 55 sequentially receives the n pieces of 2D image data from the ultrasonic observation device 5, and associates the 2D image data generated at each timing, with the position data received at the same timing for each 2D image data. By doing so, the controller 55 ensures associating the position data corresponding to the position at which each radial scan is performed, with the 2D image data generated based on the echo signal generated by this radial scan.

Figure 28:
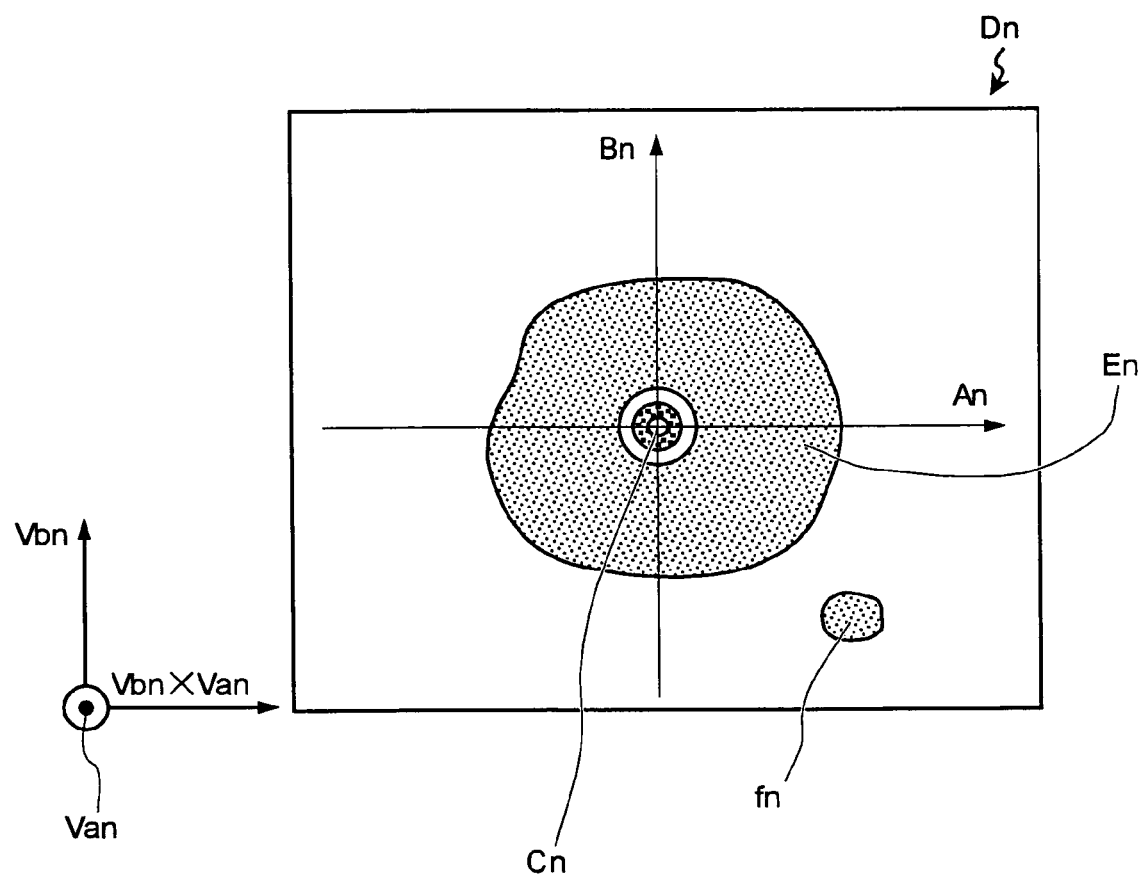
FIG. 28 depicts an example of 2D image data associated with position data.

FIG. 28 depicts an example of $n^{th}$ 2D image data associated with the position data by the controller 55 if the controller 55 sequentially receives the n pieces of 2D image data from the ultrasonic observation device 5. An instance in which the operator inserts the insertion unit 3 into the duodenum of the subject, a radial scan is performed by the ultrasonic transducer 3a, the insertion unit 3 is gradually guided in the insertion axis direction, and this subject is thereby scanned three-dimensionally is explained hereafter. However, this is not intended to limit the present invention.

As shown in FIG. 28, the $n^{th}$ 2D image data $D_n$ includes the duodenum image En that shows a cross section of the duodenum and the pancreatic duct image fn that shows a cross section of the pancreatic duct. As already explained, the controller 55 associates the 2D image data $D_n$ with the position data received at the timing at which the 2D image data $D_n$ is generated. In this case, the controller 55 sets the axial vector $V_{an}$ as a normal vector of the plane corresponding to the 2D image data $D_n$. In addition, the controller 55 sets the plane parallel vector $V_{bn}$ as a direction vector that is parallel to this plane and which indicates a predetermined direction relative to the axial vector $V_{an}$, e.g., a direction of 12 o'clock on this plane. Further, the controller 55 sets the position vector $r_n$ which indicates the image center $C_n$ of the 2D image data $D_n$. Thus, the controller 55 can set an orthogonal coordinate system composed by an axis parallel to the plane parallel vector $V_{bn}$ and an axis parallel to an outer product vector ($V_{bn} \times V_{an}$) with the image center $C_n$ set as an origin. The outer product vector ($V_{bn} \times V_{an}$) can be calculated by an outer product between the plane parallel vector $V_{bn}$ and the axial vector $V_{an}$.

Likewise, the controller 55 associates (n−1) pieces of 2D image data $D_1, D_2, \ldots,$ and $D_{n-1}$ received sequentially from the ultrasonic observation device 5, with the position data, respectively. Thus, the axial vectors $V_{a1}, V_{a2}, \ldots$ and $V_{an}$, the plane parallel vectors $V_{b1}, V_{b2}, \ldots,$ and $V_{bn}$, and the position vectors $r_1, r_2, \ldots,$ and $r_n$ are set to the n pieces of 2D image data $D_1, D_2, \ldots,$ and $D_n$, respectively.

Figure 29:
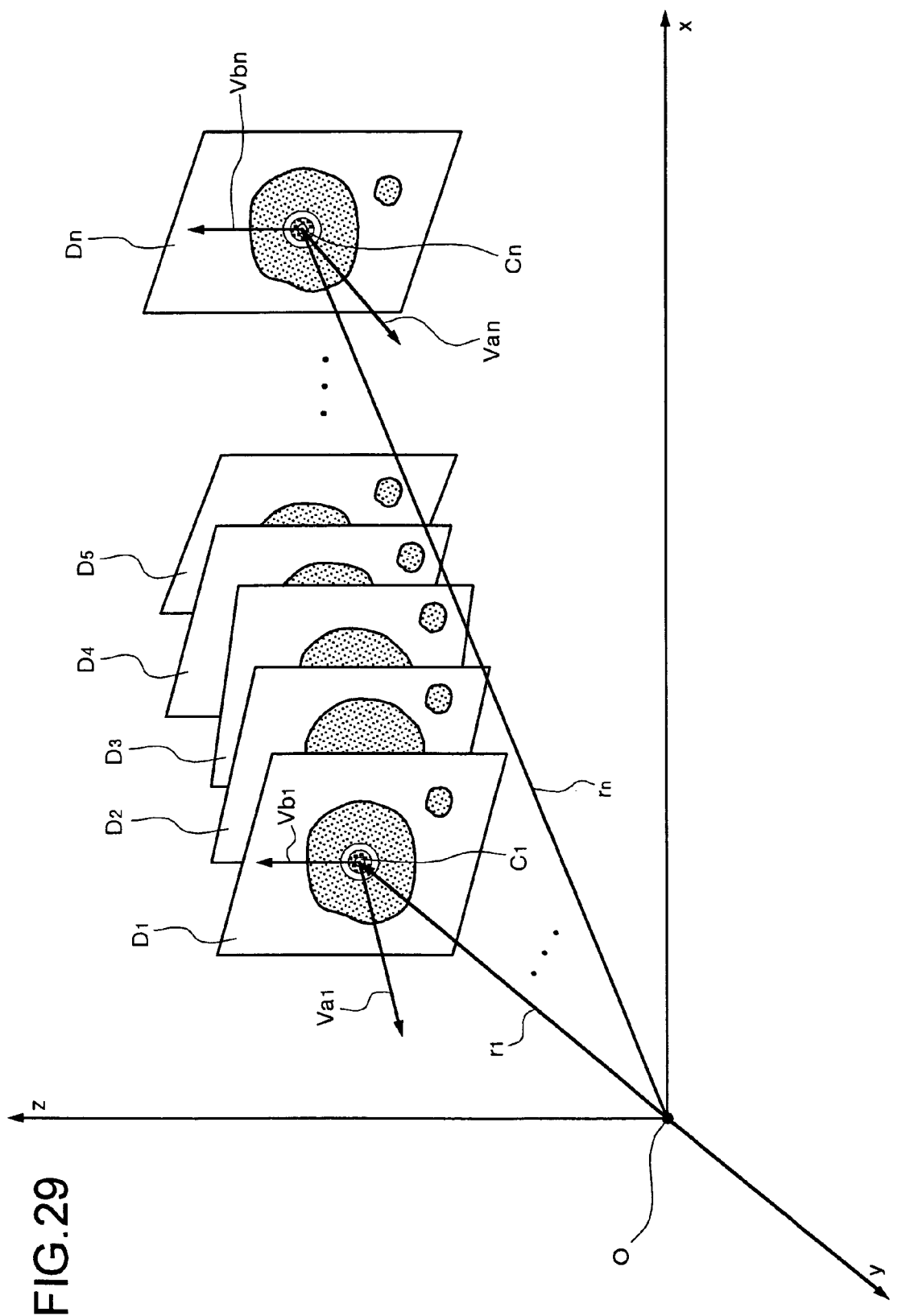
FIG. 29 is an explanatory view of an operation for arranging pieces of 2D image data associated with respective pieces of position data on the spatial coordinate system.

FIG. 29 is an explanatory view of an operation performed by the controller 55 for arranging the n pieces of 2D image data associated with the respective pieces of position data on the spatial coordinate system xyz. As shown in FIG. 29, if the controller 55 associates the n pieces of 2D image data $D_1, D_2, \ldots,$ and $D_n$ with the respective pieces of position data, the controller 13 arranges the 2D image data $D_1, D_2, \ldots,$ and $D_n$ on the spatial coordinate system xyz based on the spatial coordinate system xyz and the position data associated with the respective pieces of 2D image data, both of which are read from the storage unit 55a. The axial vectors $V_{a1}, V_{a2}, \ldots,$ and $V_{an}$, the plane parallel vectors $V_{b1}, V_{b2}, \ldots,$ and $V_{bn}$, and the position vectors $r_1, r_2, \ldots,$ and $r_3$ which constitute the pieces of position data determine the respective positions and direction of the 2D image data $D_1, D_2, \ldots,$ and $D_n$ arranged on the spatial coordinate system xyz. Therefore, the controller 55 can arrange the n pieces of 2D image data $D_1, D_2, \ldots,$ and $D_{bn}$ on the spatial coordinate system xyz so that a positional relationship of the 2D image data is substantially equal to an actual positional relationship when the ultrasonic transducer 3a performs a radial scan three-dimensionally. Thereafter, the controller 55 stores the n pieces of 2D image data $D_1, D_2, \ldots,$ and $D_{bn}$, for which the arrangement relationship on the spatial coordinate system xyz is set, in the image storage unit 11.

Figure 30:
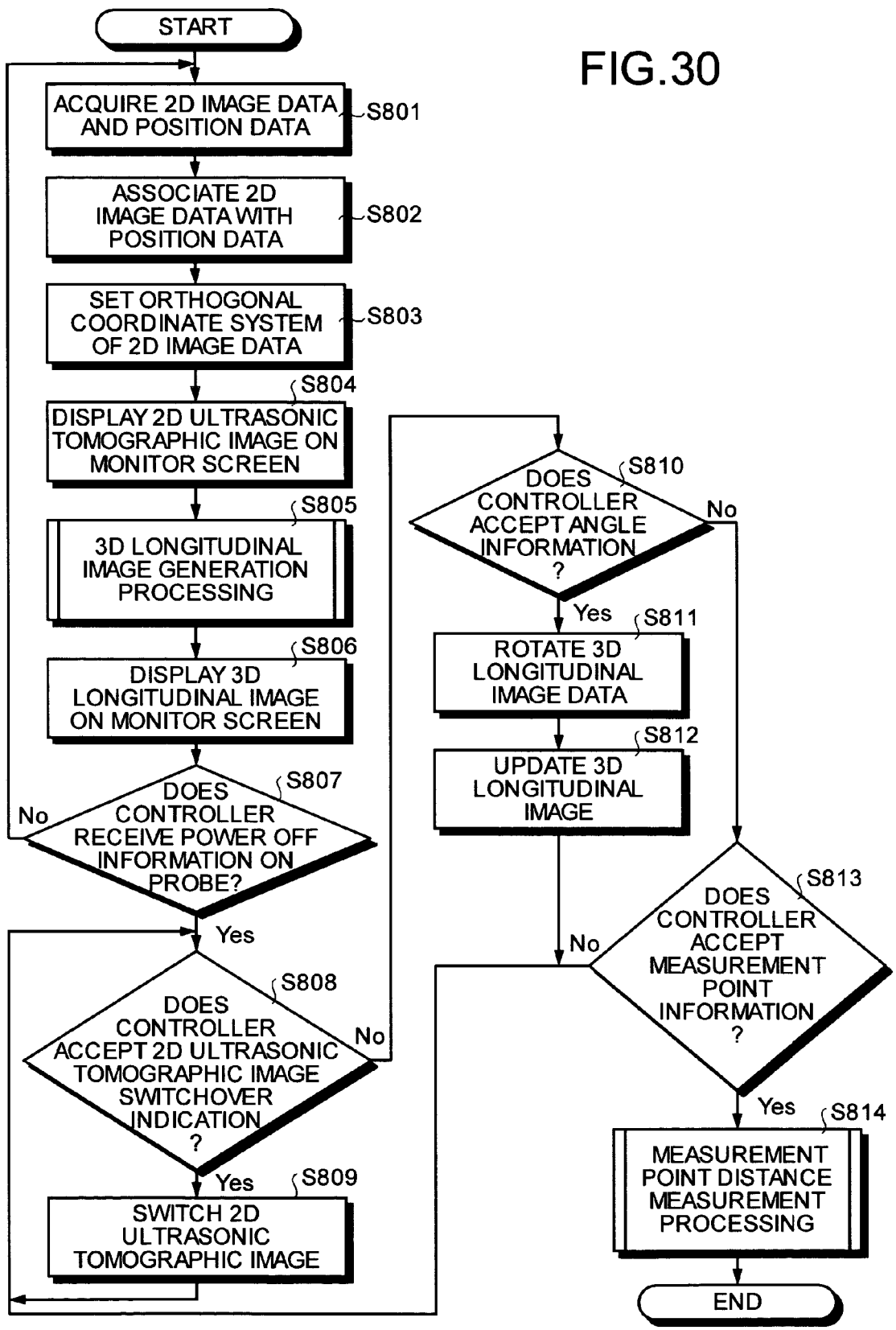
FIG. 30 is a flowchart showing processing steps executed until measuring a distance between measurement points on this 3D longitudinal image.
Figure 31:
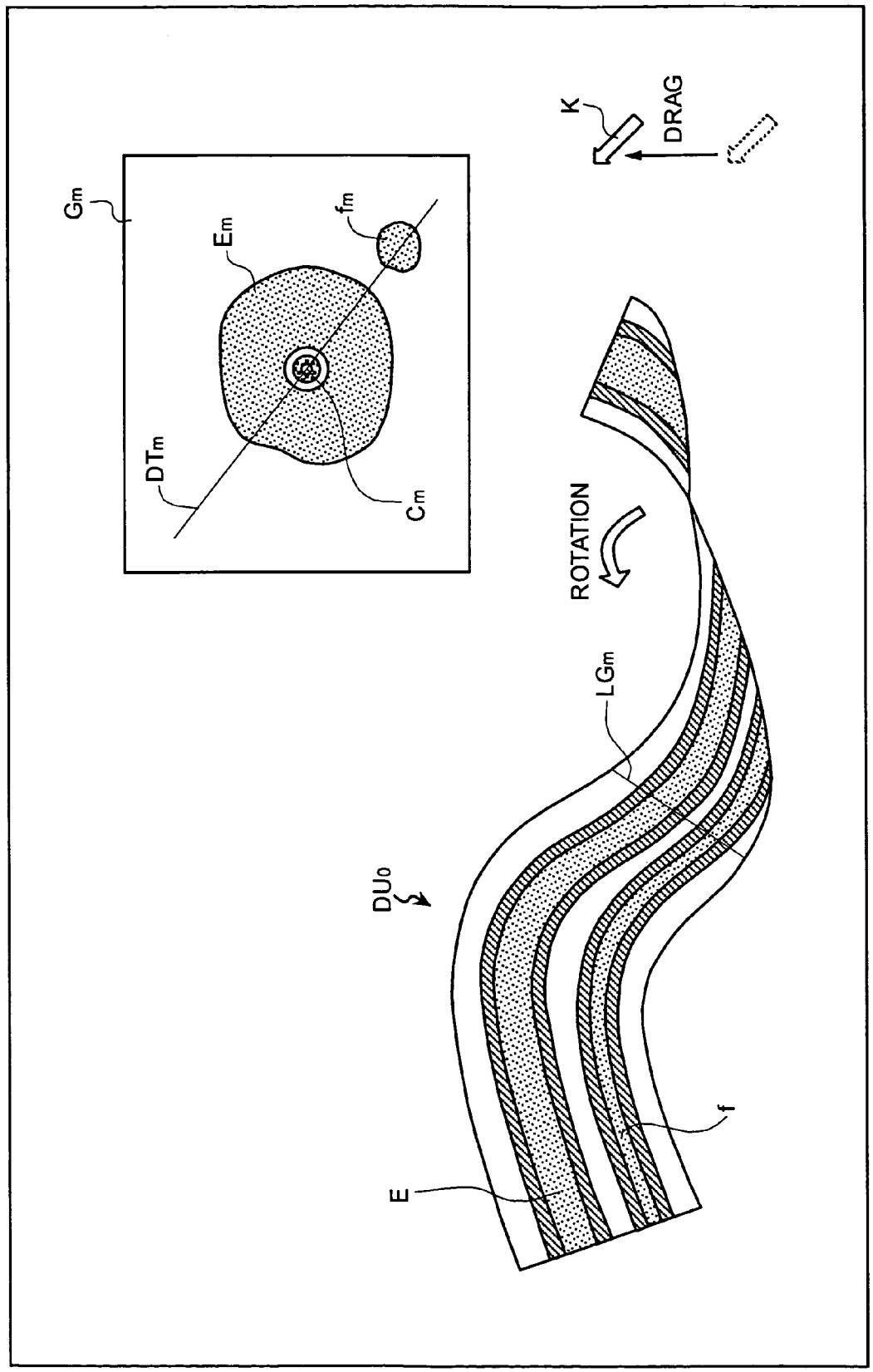
FIG. 31 depicts an example of a state in which the 3D longitudinal image and the 2D ultrasonic tomographic image are displayed on the screen of the monitor.

FIG. 30 is a flowchart that depicts processing steps executed since the controller 55 acquires the n pieces of 2D image data generated based on the n echo signals as a result of the n radial scans and the position data corresponding to the respective positions at which the radial scans are performed, until generating 3D longitudinal image data including a longitudinal image of a preset default cut plane, displaying a 3D longitudinal image corresponding to the 3D longitudinal data on the monitor 9, and then measuring the distance (measurement point distance) between the two measurement points designated on this 3D longitudinal image. FIG. 31 depicts an example of a state in which the 3D longitudinal image and the 2D ultrasonic tomographic image are displayed on the screen of the monitor 9.

Referring to FIG. 30, if the ultrasonic observation device 5 generates 2D image data based on the echo signal, and the position data calculator 7 calculates position data on the position at which this echo signal is obtained, then the controller 55 grasps the timing at which the 2D image data is generated based on this echo signal, and acquires the 2D image data output from the ultrasonic observation device 5 and the position data output from the position data calculator 7 (at step S801). In this case, the controller 55 associates the timing at which this acquired 2D image data is generated, with the position data acquired from the position data calculator 7.

The controller 55 associates the 2D image data generated at the grasped timing, with the position data acquired at the timing using the 2D image data and the position data thus acquired (at step S802). Thereafter, the controller 55 arranges the 2D image data associated with this position data on the spatial coordinate system xyz, and sets an orthogonal coordinate system based on the axial vector and the plane parallel vector made to correspond for the 2D image data (at step S803). Specifically, as shown in FIG. 28, the controller 55 sets the orthogonal coordinate system $A_nB_n$ composed by the axis ($B_n$ axis) in parallel to the plane parallel vector $V_{bn}$ and the axis ($A_n$ axis) in parallel to the outer product vector ($V_{bn} \times V_{an}$), with the image center $C_n$ set as the origin, for the 2D image data $D_n$ (where n=1, 2, 3, . . . ).

Thereafter, the controller 55 stores the 2D image data for which the orthogonal coordinate system is set, in the image data storage unit 11 while arranging the 2D image data on the spatial coordinate system xyz, transmits the 2D image data to the monitor 9 to display a 2D ultrasonic tomographic image corresponding to the 2D image data on the monitor 9 (at step S804).

The controller 55 sets a default straight line corresponding to the initial longitudinal position on the orthogonal coordinate system of each 2D image data arranged on the spatial coordinate system xyz based on the default point data stored in the storage unit 55a in advance. In addition, the controller 55 sets a curved plane formed by segments of the 2D image data cut by the default straight line as a default cut plane. Further, the controller 55 generates one-column image data on the default straight line thus set, arranges and interpolates the one-column image data, and generates 3D longitudinal image data including a longitudinal image of the default cut plane (at step S805). The controller 55 then stores the generated 3D longitudinal image data in the image data storage unit 11, and transmits the 3D longitudinal image data to the monitor through the display circuit 12 to display a band-shaped 3D longitudinal image corresponding to the 3D longitudinal image data on the monitor 9 (at step S806).

If the probe 2 is executing a radial scan, that is, the power switch of the operation unit 4 is turned on, the controller 55 does not receive power-OFF information corresponding to a power-OFF state of the probe 2 ("No" at step S807). If so, the controller 55 repeatedly executes the processing step S801 and the following. Namely, if n radial scans are performed before the probe 2 is turned off, the controller 55 repeatedly executes the processing step S801 and the following n times. The controller 55 thereby acquires n pieces of 2D image data $D_1, D_2, \ldots,$ and $D_n$ associated with the respective pieces of position data, associates the orthogonal coordinate systems with the respective pieces of 2D image data $D_1, D_2, \ldots,$ and $D_n$. Further, the controller 55 stores the n pieces of 2D image data $D_1, D_2, \ldots,$ and $D_n$ thus acquired in the image data storage unit 11 while arranging the 2D image data $D_1, D_2, \ldots,$ and $D_n$ on the spatial coordinate system xyz.

Furthermore, the controller 55 sets default straight lines on the n pieces of 2D image data $D_1, D_2, \ldots,$ and $D_n$ stored in the image data storage unit 11, and one-column image data on each default straight line. Based on the n pieces of one-column image data, the controller 55 generates 3D longitudinal image data including the longitudinal images of the default cut planes set for the n pieces of 2D image data $D_1, D_2, \ldots,$ and $D_n$. The controller 55 transmits this 3D longitudinal image data to the monitor 9 through the display circuit 12 to display a 3D longitudinal image corresponding to the 3D longitudinal image data on the monitor 9. In this case, the controller 55 displays the band-shaped 3D longitudinal image $DU_0$ having curved planes, twists, or the like as shown in FIG. 31.

The 3D longitudinal image $DU_0$ is generated as the longitudinal image of the default cut planes including the default straight lines set on the orthogonal coordinate systems of the n pieces of 2D image data $D_1, D_2, \ldots,$ and $D_n$. Therefore, the 3D longitudinal image $DU_0$ is a band-shaped longitudinal image having curved planes or the like according to an actual moving path, moving direction, or the like of the probe 2 that is moved into the living body when the 3D scan is performed. Therefore, the 3D longitudinal image $DU_0$ represents a tomographic image that is less strained as compared with the subject in the living body on which the probe 2 performs the 3D scan, and which is substantially equal in shape to the actual subject. If the default straight line $DT_m$ on one 2D image data among the n pieces of 2D image data is set to pass through the duodenum image $E_m$ and the pancreatic duct image $f_m$ captured by the 2D ultrasonic tomographic image $G_m$ corresponding to the 2D image data $D_m$, then the 3D longitudinal image $DU_0$ can represent the duodenum image E substantially equal in shape to the actual duodenum and the pancreatic duct image f substantially equal in shape to the actual pancreatic duct.

If the operator inputs indication information on image display using the input device 52, the controller 55 may display and output the 3D longitudinal image $DU_0$ and the 2D ultrasonic tomographic image $G_m$ on the same monitor screen based on the indication by this indication information. If so, the duodenum image $E_m$, the pancreatic duct image $f_m$, the image center $C_m$, and the default straight line $DT_m$ are displayed on the 2D ultrasonic tomographic image $G_m$, and this default straight line $DT_m$ corresponds to the longitudinal position of the 3D longitudinal image $DU_0$ displayed on the same monitor screen. Further, the straight line $LG_m$ that indicates a position of the 2D ultrasonic tomographic image $G_m$ displayed on the same monitor screen as that on which the 3D longitudinal image $DU_0$ is displayed, on the 3D longitudinal image $U_0$ is displayed on this 3D longitudinal image DUO. It is noted that the straight line $LG_m$ corresponds to this 2D longitudinal tomographic image $G_m$. Due to this, if the 2D ultrasonic tomographic image $G_m$ is switched over to another 2D ultrasonic tomographic image, the straight line $LG_m$ is moved to a position corresponding to another 2D ultrasonic tomographic image.

If the operator turns off the power switch of the operation unit 4 after the n radial scans, the controller 55 receives the power-OFF information on the probe 2 ("Yes" at step S807) and turns into a standby state of waiting to accept the 2D longitudinal tomographic image switchover indication, the angle information for designating the rotation angle of the 3D longitudinal image, or the measurement point information. Thereafter, if the operator inputs indication information for indicating that the 2D ultrasonic tomographic image displayed on the monitor screen is switched over to another 2D ultrasonic tomographic image, then the controller 13 accepts a 2D longitudinal tomographic image switchover indication corresponding to the switchover indication information ("Yes" at step S808). If so, the controller 55 reads the 2D image data stored in the image data storage unit 11 based on the switchover indication by the switchover indication information the input of which the controller 55 accepts. In addition, the controller 55 transmits this 2D image data to the monitor 9 through the display circuit 12. The display circuit 12 performs various processings such as D/A conversion on the 2D image data. The update processing unit 55*d* displays the 2D ultrasonic tomographic image corresponding to this 2D image data on the monitor screen in place of the 2D tomographic image already displayed (at step S809). The controller 55 then repeatedly executes the processing step S808 and the following.

If the operator performs an input operation for inputting the angle information for designating the rotation angle of the 3D longitudinal image displayed on the monitor screen, then the controller 55 does not accept the switchover indication corresponding to the switchover indication information ("No" at step S808) but accepts this angle information. If so, the controller 55 sets an angle corresponding to this accepted angle information as the rotation angle of the 3D longitudinal image. In addition, the controller 55 rotates the 3D longitudinal image data corresponding to the 3D longitudinal image displayed on the monitor screen by this rotation angle, with a desired straight line preset on the spatial coordinate system xyz, e.g., a straight line that passes through the image center of the 2D image data set as a rotation axis (at step S811). The controller 55 thereby rotates the longitudinal plane of the 3D longitudinal image data before rotation by this rotation angle, and generates the 3D longitudinal image data after the rotation including the longitudinal plane obtained by the rotation. The update processing unit 55*d* updates the 3D longitudinal image data before the rotation to the 3D longitudinal image data after the rotation.

If the 3D longitudinal image data is updated to the 3D longitudinal image data after the rotation, the controller 55 transmits this 3D longitudinal image data after the rotation to the monitor 9 through the display circuit 12. At the same time, the update processing unit 55*d* displays the 3D longitudinal image corresponding to the 3D longitudinal image data after the rotation in place of the 3D longitudinal image already displayed. The controller 55 thereby updates the 3D longitudinal image before the rotation to the 3D longitudinal image after the rotation successively according to the operator's angle information input operation (at step S812). The controller 55 then executes the processing step S808 and the following repeatedly.

For example, as shown in FIG. 31, if the operator performs the drag operation using the input device 52 to move a cursor k upward by a predetermined amount, the 3D longitudinal image $DU_0$ is rotated by an angle according to this predetermined amount in a predetermined positive direction, e.g., counterclockwise direction around the rotation axis. Namely, if the operator inputs the angle information using the input device 52, the 3D longitudinal image $DU_0$ is rotated in the predetermined directing according to the angle corresponding to this angle information. Therefore, even if the 3D longitudinal image DUO includes the curved planes, the twists, or the like, the operator can easily observe all the tomographic images and longitudinal images captured by the 3D longitudinal image $DU_0$, including hidden portions hidden by the curved planes or twists. Further, if the operator inputs indication information on image magnification or image reduction using the input device 52, the controller 55 magnifies or reduces the 3D longitudinal image $U_0$ in accordance with an input amount input to the input device 52.

If the operator performs an input operation for inputting the measurement point information for designating desired measurement points on the 3D longitudinal image displayed on the monitor screen, then the controller 55 does not accept the switchover indication corresponding to the switchover indication information ("No" at step S808), does not accept the angle information ("No" at step 810), but accepts this measurement point information ("Yes" at step S813). If so, the controller 55 sets two measurement points on the 3D longitudinal image data using the measurement point information input by operator's operating the input device 52. In addition, the controller 55 operates and outputs an Euclidian distance between the two measurement points (a measurement point distance), displays and outputs or prints out the obtained operation result as a measurement result of the measurement point distance (at step S814). Details of a processing performed since the measurement points are set on the 3D longitudinal image data until the measurement result of the measurement point distance is displayed and output or printed out (a measurement point distance measurement processing) is explained later.

If the operator does not perform the input operation for inputting the switchover indication information, the angle information, and the measurement point information using the input device 52, then the controller 55 does not accept the switchover indication information ("No" at step S808), does not accept the angle information ("No" at step S810), does not accept the measurement point information ("No" at step S813), and repeatedly executes the processing step 808 and the following.

Figure 32:
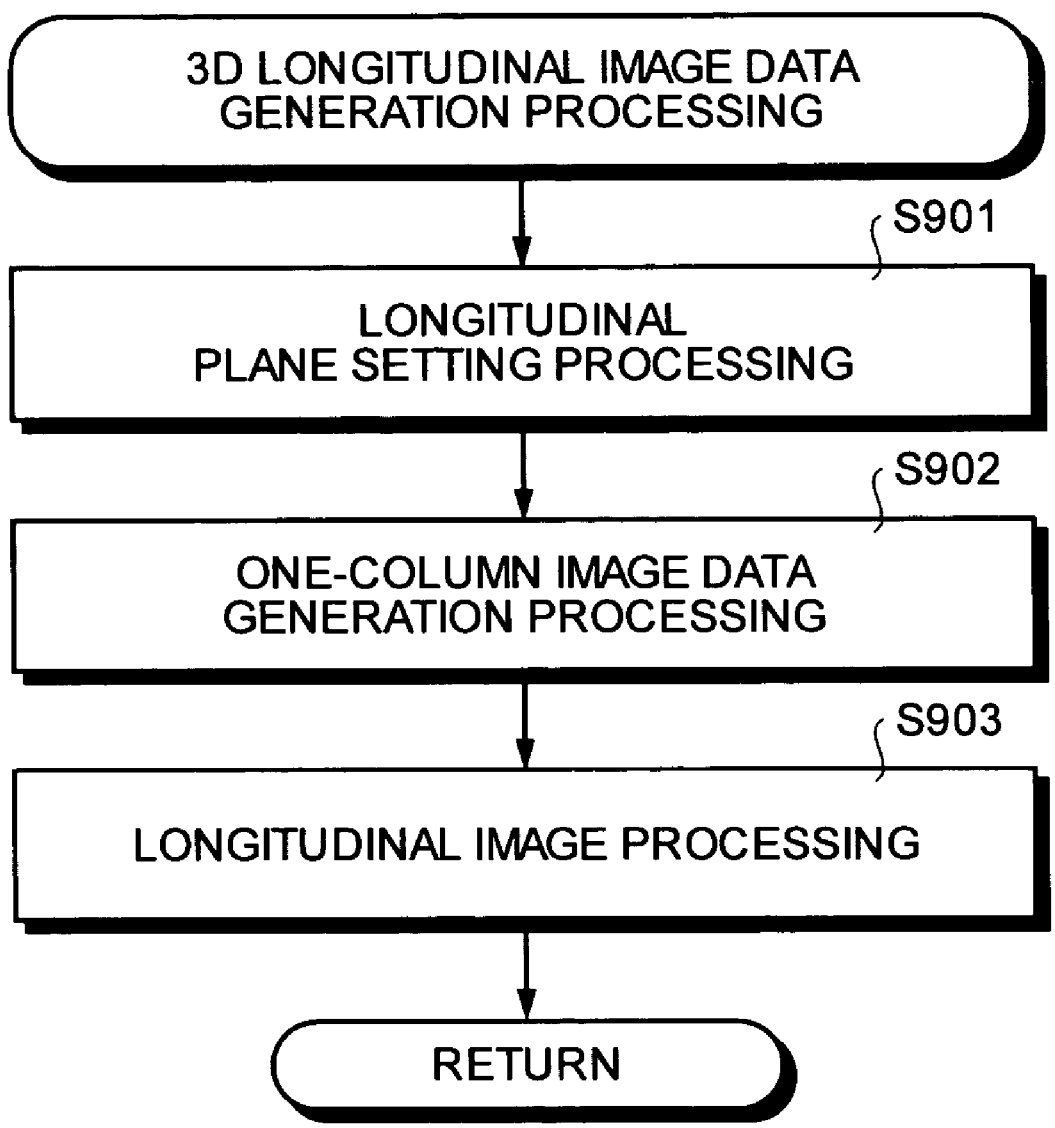
FIG. 32 is a flowchart showing respective processing steps executed until a 3D longitudinal image data generation processing is completed.
Figure 33:
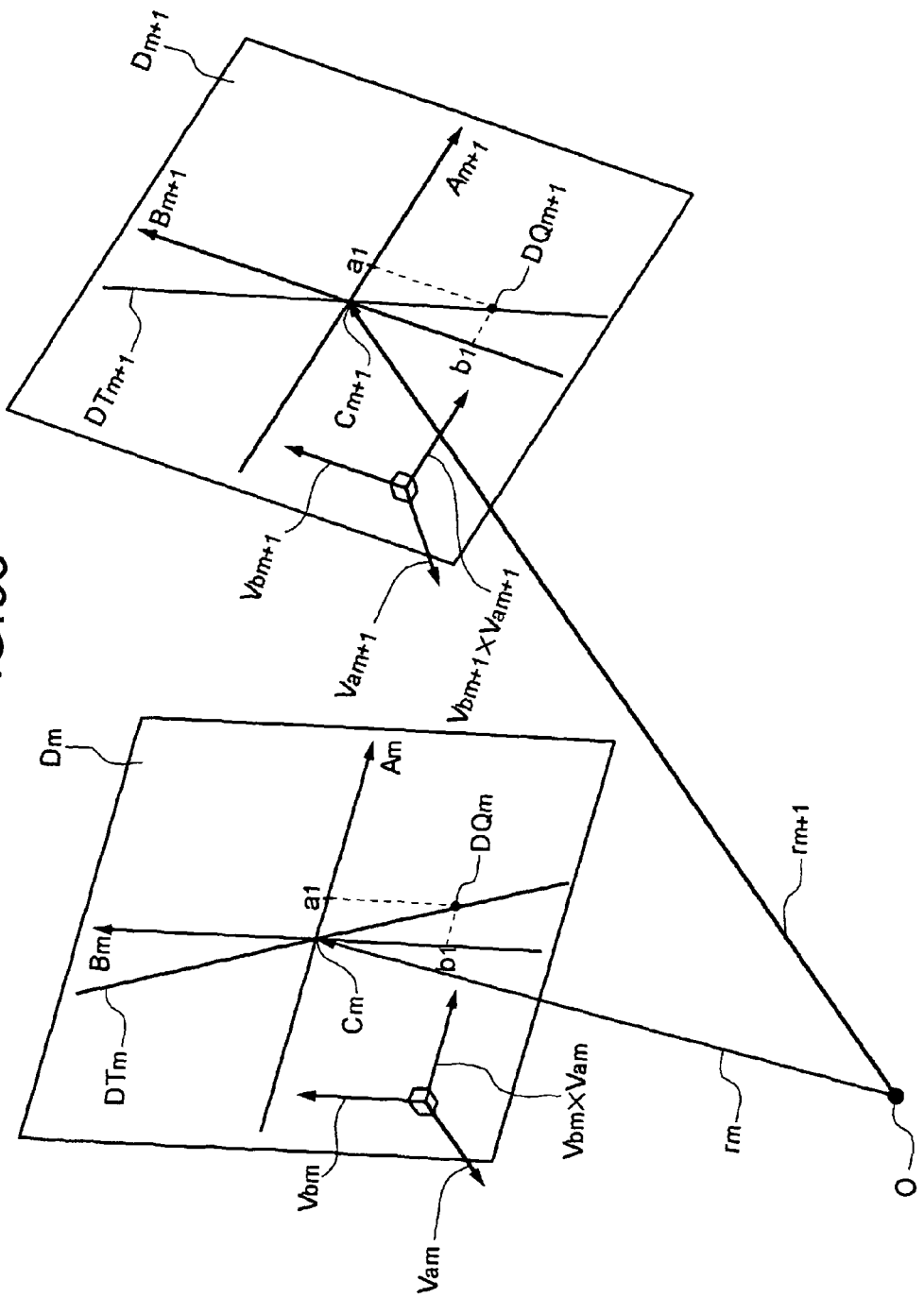
FIG. 33 is an explanatory view of a longitudinal plane setting processing.
Figure 34:
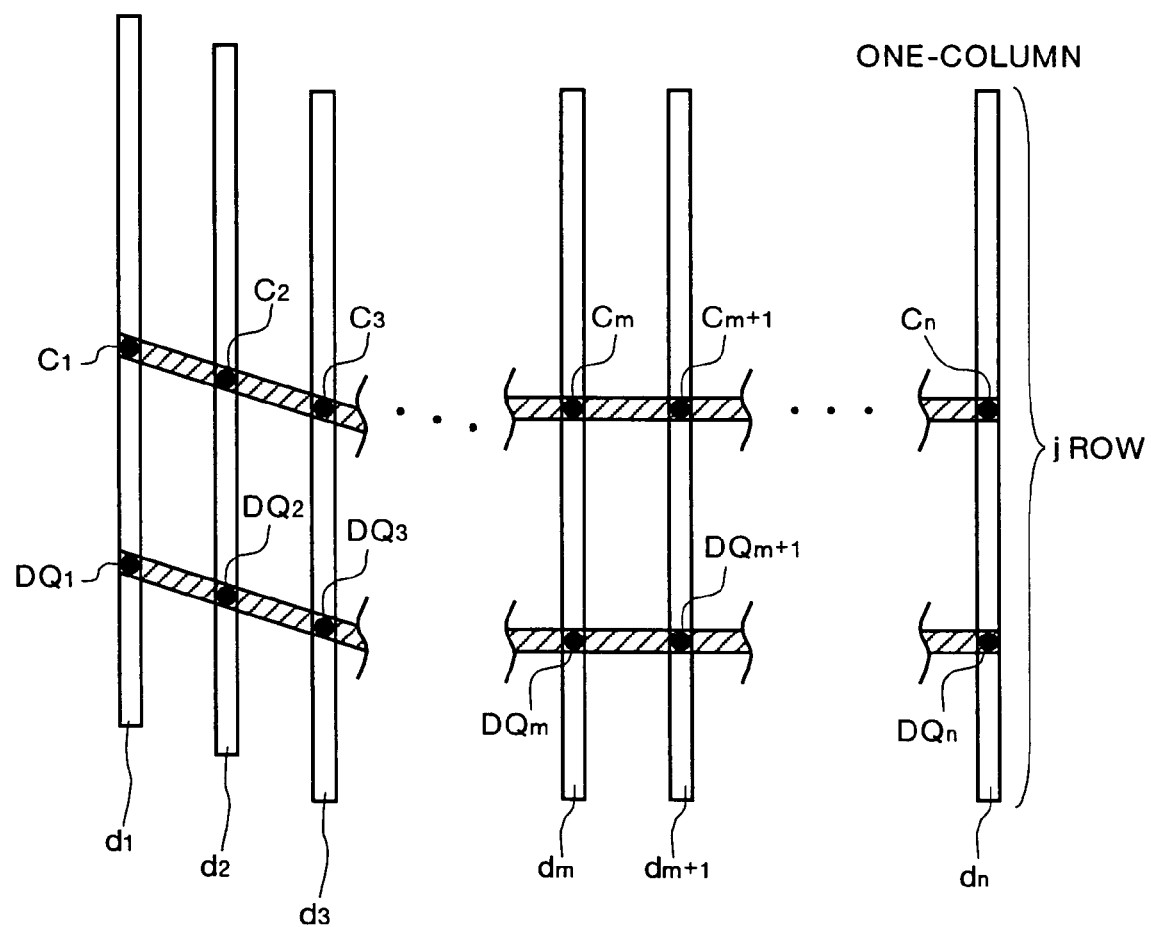
FIG. 34 is an explanatory view of a longitudinal image processing.

A processing performed by the controller 55 at step S805 since the controller 55 sets the default cut planes of the n pieces of 2D image arranged on the spatial coordinate system xyz until generating the 3D longitudinal image data including the longitudinal images of the default cut planes (a 3D longitudinal image data generation processing) is explained. FIG. 32 is a flowchart showing respective processing steps executed until the controller 55 completes the 3D longitudinal image data generation processing based on the n pieces of 2D image data arranged on the spatial coordinate system xyz and the preset default point data. FIG. 33 is an explanatory view of a processing for setting the default straight line on the orthogonal coordinate system of each of the n pieces of 2D image data, and for setting the default cut plane based on the default straight line (a longitudinal plane setting processing). FIG. 34 is an explanatory view of a processing performed by the image data operation unit 55*b* for interpolating the respective adjacent pieces of one-column image data using pieces of one-column image data generated on the n pieces of 2D image data, and for generating the longitudinal image of the default cut plane set by the longitudinal plane setting processing (a longitudinal image processing). In FIG. 34, for convenience of explanation with reference to the drawing, the one-column image data $d_1, d_2, \ldots,$ and $d_n$ are drawn to be on the same plane and parallel to one another. Actually, they are not always present on the same plane and not always parallel to one another.

Referring to FIG. 32, if the orthogonal coordinate system based on the axial vector and the plane parallel vector is set for each of the n pieces of 2D image data by the processing at step S803, the controller 55 reads the default point data stored in the storage unit 55a in advance. In addition, the controller 55 sets the default straight line based on this default point data on the orthogonal coordinate system of each of the n pieces of 2D image data. If coordinate information on longitudinal positions based on this default point data correspond to, for example, the coordinate $(a_1, b_1)$ on the orthogonal coordinate system of the 2D image data and the image center, the controller 55 sets the default point $DQ_m$ at the coordinate $(a_1, b_1)$ on the orthogonal coordinate system $A_mB_m$ of the 2D image data $D_m$ and the image center $C_m$ that is the origin on the orthogonal coordinate system $A_mB_m$ as points corresponding to the longitudinal position, as shown in FIG. 33. In addition, the controller 55 operates and outputs the default straight line $DT_m$ that passes through the default point $DQ_m$ and the image center $C_m$, and sets the obtained default straight line $DT_m$ as a straight line corresponding to the longitudinal position. It is noted that the integer m is the integer which satisfies $1 \leq m \leq (n-1)$. In addition, the orthogonal coordinate system $A_mB_m$ is the orthogonal coordinate system that is composed by the $B_m$ axis in parallel to the plane parallel vector $V_{bm}$ and the $A_m$ axis in parallel to the outer product vector $(V_{bm} \times V_{am})$, with the image center $C_m$ set as the origin, as already explained.

If the default straight line $DT_m$ has been set on the orthogonal coordinate system $A_mB_m$ of the 2D image data $D_m$, the controller 55 sets the default straight line $DT_{m+1}$ on the orthogonal coordinate system $A_{m+1}B_{m+1}$ of the 2D image data $D_{m+1}$ adjacent to the 2D image data $D_m$. Specifically, similarly to the instance of the default straight line $DT_m$, the controller 55 sets the default point $DQ_{m+1}$ at the coordinate $(a_1, b_1)$ on the orthogonal coordinate system $A_{m+1}B_{m+1}$ and the image center $C_{m+1}$ that is the origin on the orthogonal coordinate system $A_{m+1}B_{m+1}$ as points corresponding to the longitudinal positions. In addition, the controller 55 operates and outputs the default straight line $DT_{m+1}$ that passes through the default point $DQ_{m+1}$ and the image center $C_{m+1}$, and sets the obtained default straight line $DT_{m+1}$ as the straight line corresponding to the longitudinal position. Based on this default straight line setting method, the controller 55 sets default points $DQ_1, DQ_2, \ldots,$ and $DQ_n$ at respective coordinates $(a_1, b_1)$ on the orthogonal coordinate systems, sets image centers $C_1, C_2, \ldots,$ and $C_n$ that are origins of the orthogonal coordinate systems for the n pieces 2D image data $D_1, D_2, \ldots,$ and $D_n$. The controller 55 also sets default straight lines $DT_1, DT_2, \ldots,$ and $DT_n$ which pass through the default points $DQ_1, DQ_2, \ldots,$ and $DQ_n$ and the image centers $C_1, C_2, \ldots,$ and $C_n$, respectively. Thereafter, the cut plane operation unit 55c connects respective points on the default points $DQ_1, DQ_2, \ldots,$ and $DQ_n$ to one another so that coordinates of the points are equal relative to the image centers $C_1, C_2, \ldots,$ and $C_n$, thereby operating and outputting a curved planes including the default points $DQ_1, DQ_2, \ldots,$ and $DQ_n$. The controller 55 sets the curved planes operated and output by the cut plane operation unit 55c as the default cut planes (at step S901).

If the controller 55 sets the default straight lines $DT_1, DT_2, \ldots,$ and $DT_n$ for the n pieces of 2D image data $D_1, D_2, \ldots,$ and $D_n$, respectively, then the image data operation unit 55b sets pixel groups in one column and j row for the default straight lines $DT_1, DT_2, \ldots,$ and $DT_n$. In addition, the image data operation unit 55b calculates the luminances of pixels (voxels or pixels) in the respective pixel groups, and generates n pieces of one-column image data $d_1, d_2, \ldots,$ and $d_n$ in one column and j row for the n pieces of 2D image data $D_1, D_2, \ldots,$ and $D_n$, respectively (at step S902). The one-column image data $d_1, d_2, \ldots,$ and $d_n$ correspond to the default straight lines $DT_1, DT_2, \ldots,$ and $DT_n$, respectively. Therefore, the image data operation unit 55b can obtain positions of the respective pixels of the one-column image data $d_1, d_2, \ldots,$ and $d_n$ as pixel position vectors on the spatial coordinate system xyz. For example, the image center $C_m$ and the orthogonal coordinate system $A_mB_m$ are present on the spatial coordinate system xyz, and a position vector $O(DQ_m)$ of the default point $DQ_m$ set at the coordinate $(a_1, b_1)$ on the orthogonal coordinate system $A_mB_m$ of the 2D image data $D_m$ can be, therefore, calculated using the coordinate $(a_1, b_1)$ of this default point $DQ_m$ and the position vector $r_m$ of the image center $C_m$, as represented by the following Equation (3).

$$O(DQ_m) = r_m + a_1(V_{bm} \times V_{am}) + b_1 V_{bm} \quad (3)$$

In this calculation, each point on the default straight line $DT_m$ is operated and output by linearly interpolating or exterpolating the point to the default straight line $DT_m$ using a distance of the point to the default point $DQ_m$ and a distance of the point to the image center $C_m$, and Equation (3). Namely, the image data operation unit 55b can calculate the position of each pixel of the one-column image data $d_m$ as a position vector on the spatial coordinate system xyz by using the distance of the pixel position to the default point $DQ_m$, the distance of the pixel position to the image center $C_m$, and Equation (3). The image data operation unit 55b can set the pixel position vectors of the respective pixels of the one-column image data $d_1, d_2, \ldots,$ and $d_n$ by performing the same operation processings for the n pieces of one-column image data $d_1, d_2, \ldots,$ and $d_n$.

If the controller 55 sets the two arbitrary points on the orthogonal coordinate system as the respective default points and sets the straight line that passes through the two arbitrary points as the default straight line for each of the n pieces of 2D image data $D_1, D_2, \ldots,$ and $D_n$, the cut plane operation unit 55c operates and outputs the curved plane corresponding to the default cut plane similarly to the default straight lines $DT_1, DT_2, \ldots,$ and $DT_n$. In this case, the image data operation unit 55b can calculate the position of each pixel of the one-column image data generated on the respective n pieces of 2D image data as the position vector on the spatial coordinate system xyz using distances of the pixel position to the two arbitrary points and position vectors of the two arbitrary points, similarly to the one-column image data $d_1, d_2, \ldots,$ and $d_n$.

The image data operation unit 55b interpolates respective adjacent pieces of one-column image data using the one-column image data $d_1, d_2, \ldots,$ and $d_n$ for which the pixel position vectors are set. As explained, the one-column image data $d_1, d_2, \ldots,$ and $d_n$ are arranged on the spatial coordinate system xyz based on the axial vectors and plane parallel vectors of the respective pieces of 2D image data $D_1, D_2, \ldots$ and $D_n$. As a result, the two arbitrary default points corresponding to the longitudinal positions include the same coordinate components on the respective coordinate systems on the 2D image data $D_1, D_2, \ldots,$ and $D_n$. For example, the image centers $C_1, C_2, \ldots,$ and $C_n$ include the same coordinate components on the respective coordinate systems on the 2D image data $D_1, D_2, \ldots,$ and $D_n$. The default points $D_1, D_2, \ldots,$ and $D_n$ include the same coordinate components on the respective coordinate systems on the 2D image data $D_1, D_2, \ldots,$ and $D_n$. Therefore, if the image data operation unit 55b interpolates the respective adjacent pieces of one-column image data of the one-column image data $d_1, d_2, \ldots,$ and $d_n$, the image data operation unit 55b linearly interpolates the respective adjacent pixels equal in pixel position determined by the number of rows from respective reference points from the two arbitrary default points.

For example, as shown in FIG. 34, the image data operation unit 55b linearly interpolates the respective adjacent pixels equal in pixel position to the image centers $C_1, C_2, \ldots,$ and $C_n$ and interpolates the respective adjacent pixels equal in pixel position to the default points $DQ_1, DQ_2, \ldots,$ and $DQ_n$. In addition, the image data operation unit 55b linearly interpolates a pixel located in an $i^{th}$ row (where i=1, 2, ..., j) from the image center $C_m$ and in a $k^{th}$ row (where k=1, 2, ..., j) from the default point $DQ_m$, and a pixel located in the $i^{th}$ row (where i=1, 2, ..., j) from the image $C_{m+1}$, and in the $k^{th}$ row (where k=1, 2, ..., j) from the default point $DQ_{m+1}$. The image data operation unit 55b performs the same processings for all the pixels set on the respective pieces of one-column image data $d_1, d_2, \ldots,$ and $d_n$. The image data operation unit 55b can thereby interpolate all the adjacent pieces of one-column image data of the n pieces of one-column image data $d_1, d_2, \ldots,$ and $d_n$. Accordingly, the image data operation unit 55b can generate the 3D longitudinal image data corresponding to the band-shaped longitudinal image of the default cut planes including the respective default straight lines $DT_1, DT_2, \ldots,$ and $DT_n$ (step S903). If the image data operation unit 55b is to linearly interpolate the respective adjacent pixels of the adjacent one-column image data $d_m$ and $d_{m+1}$ (where m=1, 2, ..., n−1), the image data operation unit 55b interpolates luminances of the respective adjacent pixels equal in pixel position on the one-column image data $d_m$ and $d_{m+1}$, thereby determining luminances between the respective adjacent pixels.

Figure 35:
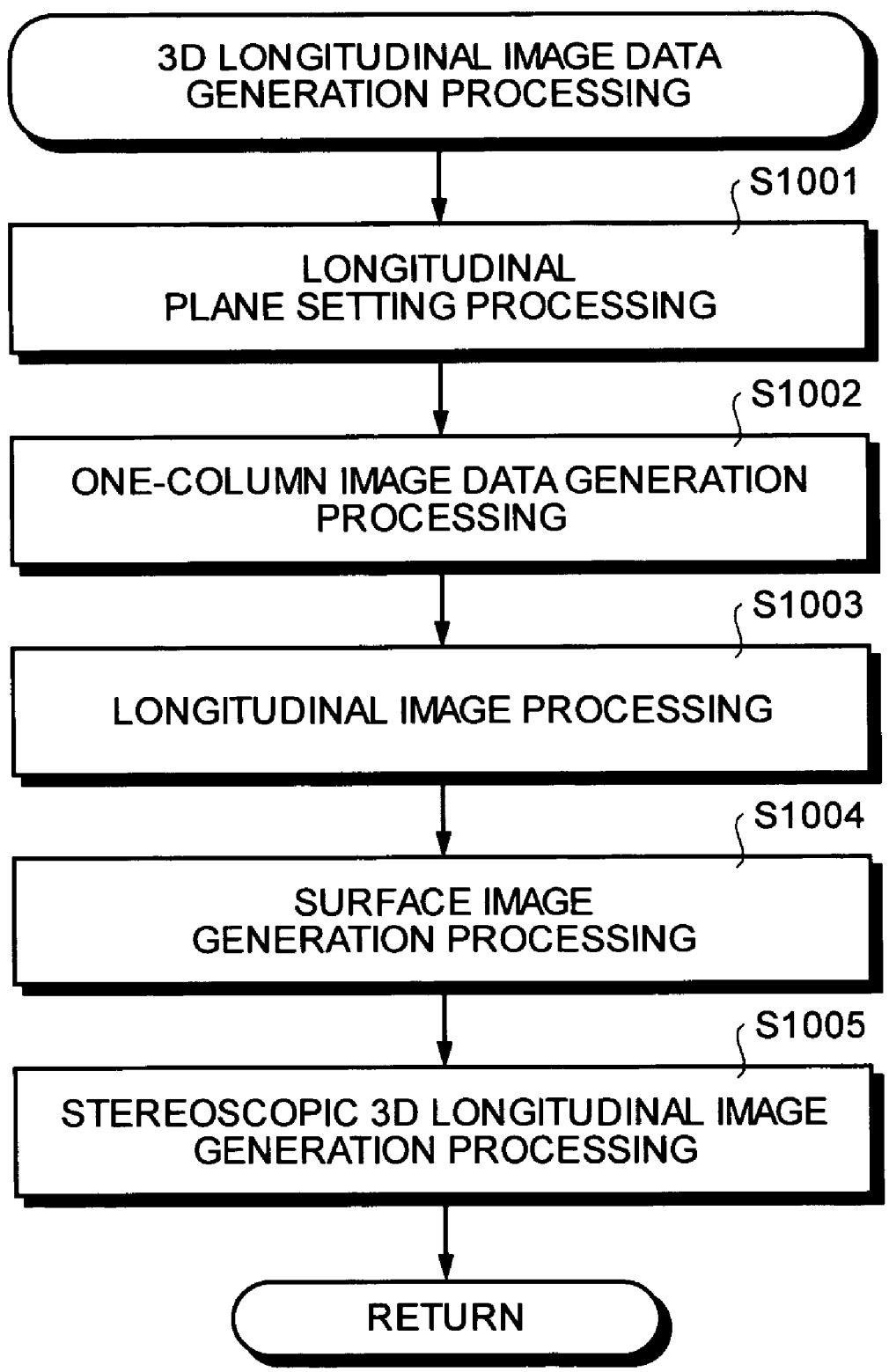
FIG. 35 is a flowchart showing respective processing steps executed until generating stereoscopic 3D longitudinal data including a band-shaped longitudinal image.
Figure 36:
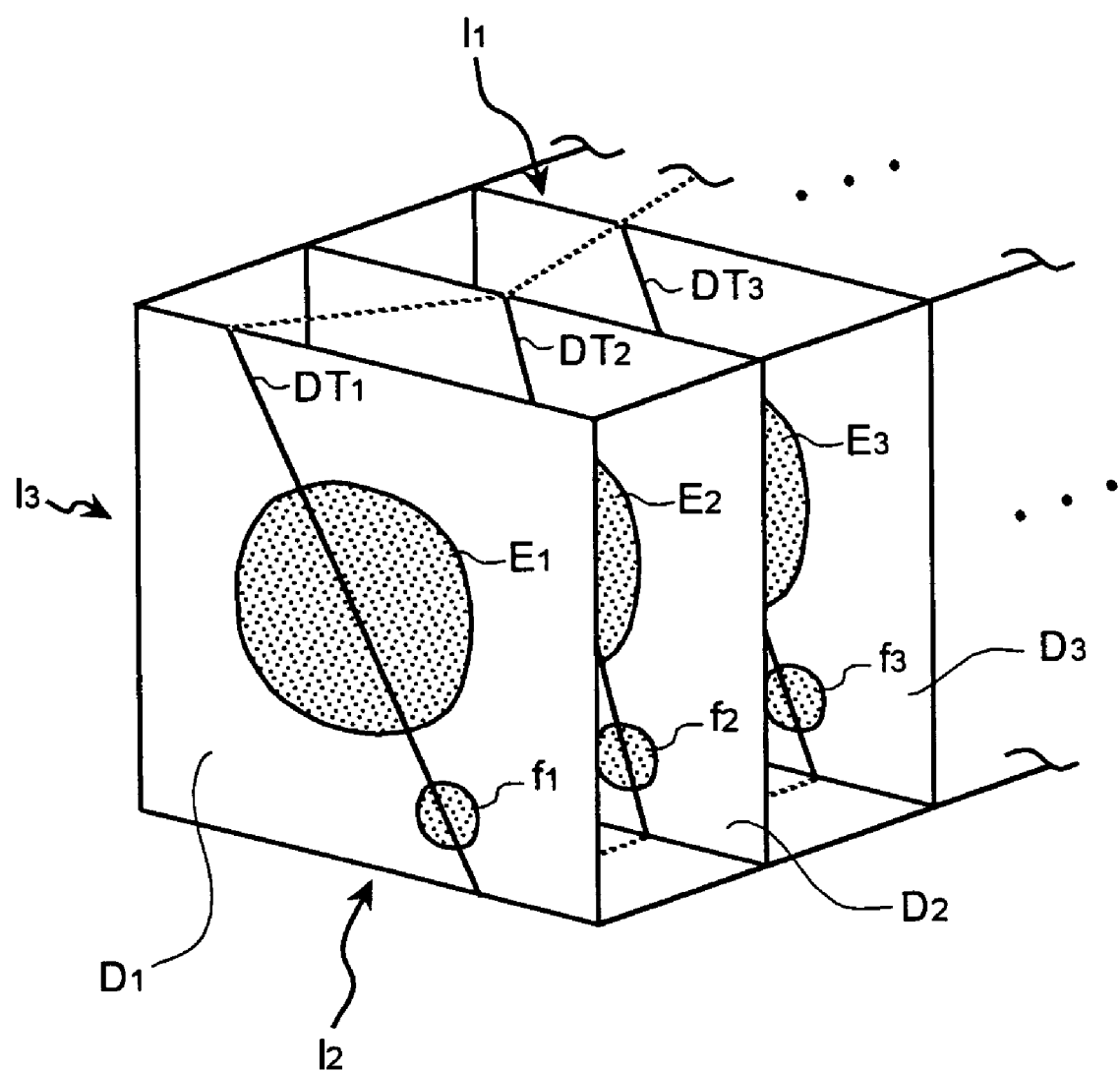
FIG. 36 is an explanatory view of a surface image generation processing including generation of longitudinal images of default cut planes.

The surface image processing unit 55e generates 3D longitudinal image data corresponding to a stereoscopic longitudinal image including, as one surface, the band-shaped longitudinal image using the 3D longitudinal image data corresponding to the band-shaped longitudinal image generated by the image data operation unit 55b by the longitudinal image processing, and the n pieces of 2D image data arranged on the spatial coordinate system xyz. FIG. 35 is a flowchart showing a processing for generating 3D longitudinal image data. Specifically, if the controller 55 generates the default cut planes of n pieces of 2D image data arranged on the spatial coordinate system xyz and 3D longitudinal image data corresponding to the band-shaped longitudinal image of the default cut planes, then the surface image processing unit 55e generates the 3D longitudinal image data corresponding to the stereoscopic longitudinal image including, as one surface, this band-shaped longitudinal image using the 3D longitudinal image data corresponding to the band-shaped longitudinal image and the n pieces of 2D image data. FIG. 36 is an explanatory view of a processing performed by the surface image processing unit 55e for linearly interpolating adjacent pieces of 2D image data for upper ends, lower ends, and side ends of the n pieces of 2D image data, and for generating upper surface image data, lower surface image data, and side surface image data (a surface image generation processing). FIG. 36 typically shows a state in which the n pieces of 2D image data for which the default straight line that show default cut planes are set, are arranged on the spatial coordinate system xyz.

Referring to FIGS. 35 and 36, if the orthogonal coordinate system based on the axial vector and the plane parallel vector is set for each of the n pieces of 2D image data by the processing at step S803, the controller 55 executes the same processing as that at step S S901 to S903 to set the respective default straight lines and default cut planes of the n pieces of 2D image data. In addition, the controller 55 generates one-column image data on each default straight line, and generates 3D longitudinal image corresponding to the band-shaped longitudinal image of this default cut plane using the respective pieces of one-column image data (at steps S1001 to S1003).

As shown in FIG. 36, the surface image processing unit 55e linearly interpolates respective adjacent pieces of 2D image data and generates upper surface image data $I_1$ for the upper ends of the 2D image data $D_1, D_2, \ldots,$ and $D_n$ for which the default straight lines $DT_1, DT_2, \ldots,$ and $DT_n$ are set. The surface image processing unit 55e linearly interpolates respective adjacent pieces of 2D image data and generates the lower surface image data $I_2$ for the lower ends of the 2D image data $D_1, D_2, \ldots,$ and $D_n$. The surface image processing unit 55e linearly interpolates respective adjacent pieces of 2D image data and generates the side surface image data $I_3$ for the side ends of the 2D image data $D_1, D_2, \ldots,$ and $D_n$ (at step S1004).

Thereafter, the surface image processing unit 55e performs a stereoscopic 3D longitudinal image generation processing using the 3D longitudinal image data corresponding to the band-shaped longitudinal image generated at step S1003, the upper surface image data $I_1$, the lower surface image data $I_2$, and the side surface image data $I_3$ generated at step S1004, and the 2D image data $D_1$ and $D_n$ cut on the default cut plane set at step S1001. The surface image processing unit 55e thereby generates the 3D longitudinal image data corresponding to the stereoscopic 3D longitudinal image including, as one surface, the band-shaped longitudinal image, e.g., the band-shaped 3D longitudinal image $DU_0$ (at step S1005). If the surface image processing unit 55e generates the 3D longitudinal image data corresponding to this stereoscopic 3D longitudinal image, the surface image processing unit 55e connects portions of the upper surface image data $I_1$, the lower surface image data $I_2$, the side surface image data $I_3$, the 3D longitudinal image data corresponding to the band-shaped longitudinal image, and the 2D image data $D_1$ and $D_n$, which portions correspond to the same coordinates on the spatial coordinate system xyz, respectively, to one another.

Figure 37:
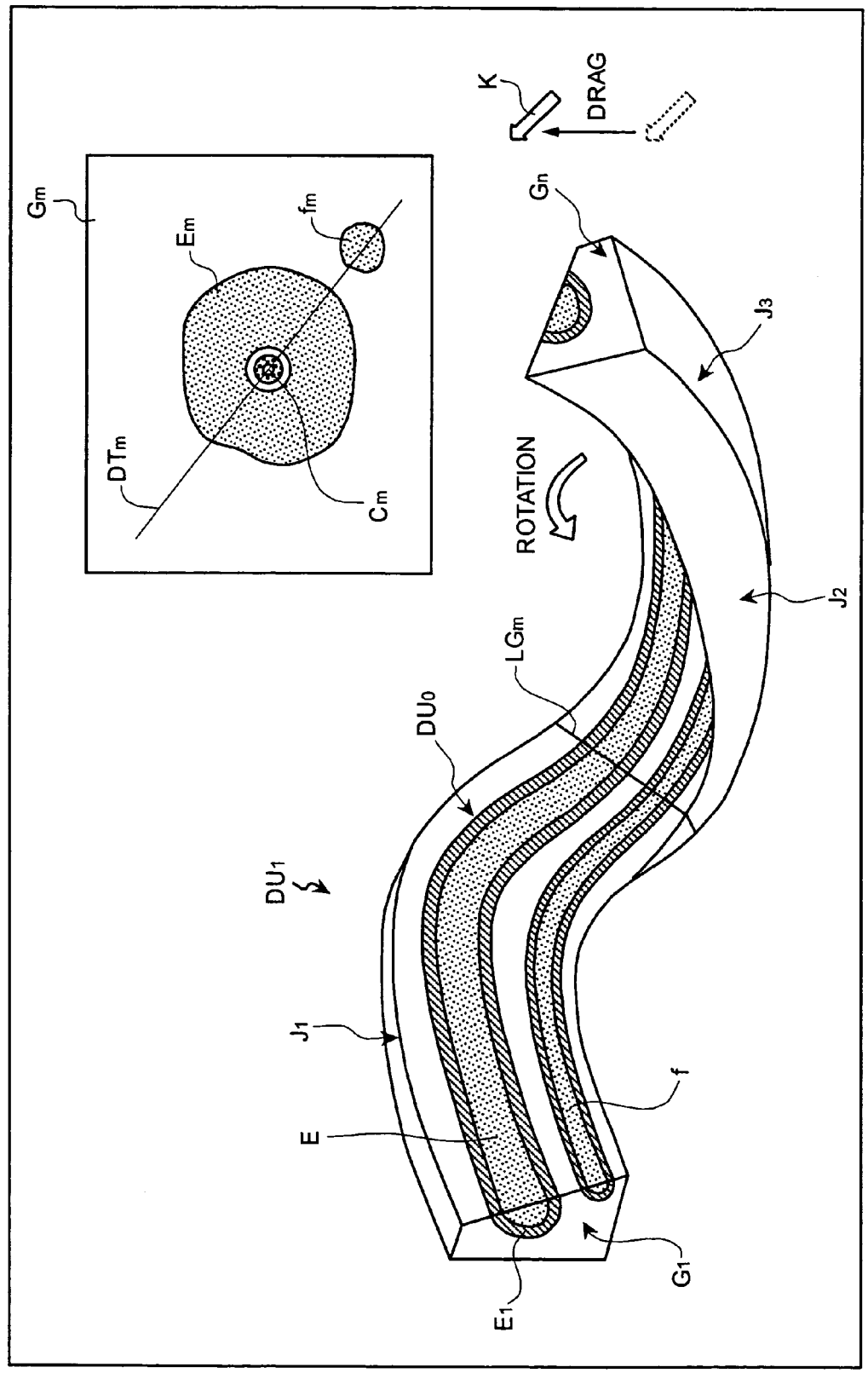
FIG. 37 depicts an example of a state in which the stereoscopic 3D longitudinal image including the band-shaped longitudinal image is displayed on the screen of the monitor.

The controller 55 transmits the 3D longitudinal image data generated by the surface image processing unit 55e by the stereoscopic 3D longitudinal image generation processing at step S1005 to the monitor 9, thereby making it possible to display the stereoscopic 3D longitudinal image corresponding to this 3D longitudinal image data on the monitor 9, similarly to step S806. Namely, if the respective processing steps S1001 to S1005 are executed in place of step S S901 to S903 as the processing at step S805, the 3D longitudinal image data corresponding to the stereoscopic 3D longitudinal image including, as one surface, the band-shaped longitudinal image can be generated by the controller 55. FIG. 37 depicts an example of a state in which the stereoscopic 3D longitudinal image including, as one surface, the band-shaped longitudinal image is displayed on the screen of the monitor 9. In FIG. 37, a stereoscopic 3D longitudinal image $DU_1$ including the band-shaped 3D longitudinal image $DU_0$ is shown in place of the 3D longitudinal image $DU_0$ shown in FIG. 31. In addition, similarly to FIG. 31, the 2D ultrasonic tomographic image $G_m$ is displayed on the same monitor screen.

In FIG. 37, the 3D longitudinal image $DU_1$ is constituted so that portions of the band-shaped 3D longitudinal image $DU_0$, an upper plane image $J_1$ corresponding to the upper surface image data $I_1$, a lower plane image $J_2$ corresponding to the lower surface image data $I_2$, a side plane image $J_3$ corresponding to the side surface image data $I_3$, and 2D image data $G_1$ and $G_n$ corresponding to the 2D image data $D_1$ and $D_n$, which portions correspond to the same coordinates on the spatial coordinate system xyz, respectively, are connected to one another. Therefore, for example, the duodenum $E_1$ on this 2D ultrasonic tomographic image $G_1$ and the duodenum E on the 3D longitudinal image $DU_0$ are connected to each other stereoscopically. Thus, the 3D longitudinal image $DU_1$ represents a stereoscopic duodenum approximated in shape to the actual duodenum. That is, the 3D longitudinal image $DU_1$ stereoscopically represents the longitudinal image which includes longitudinal planes having curved planes, twists, or the like according to the actual moving path or moving direction of the probe 2 moved in the living body during the 3D scan, which is less strained as compared with the subject in the living body on which the probe 2 performs the 3D scan, and which is substantially equal in shape to the actual subject.

If the operator inputs angle information using the input device 52, the 3D longitudinal image $DU_1$ displayed on the monitor screen is rotated in the predetermined direction according to the angle corresponding to this angle information, similarly to the 3D longitudinal image DUO. Therefore, even if the 3D longitudinal image $DU_1$ includes the curved planes, the twists, or the like, the operator can easily observe all the tomographic images and longitudinal images captured by the 3D longitudinal image $DU_1$ including hidden portions hidden by the curved planes or twists. Further, if the operator inputs indication information on image magnification or image reduction using the input device 52, the controller 55 magnifies or reduces the 3D longitudinal image $DU_1$ in accordance with an input amount input to the input device 52.

Figure 38:
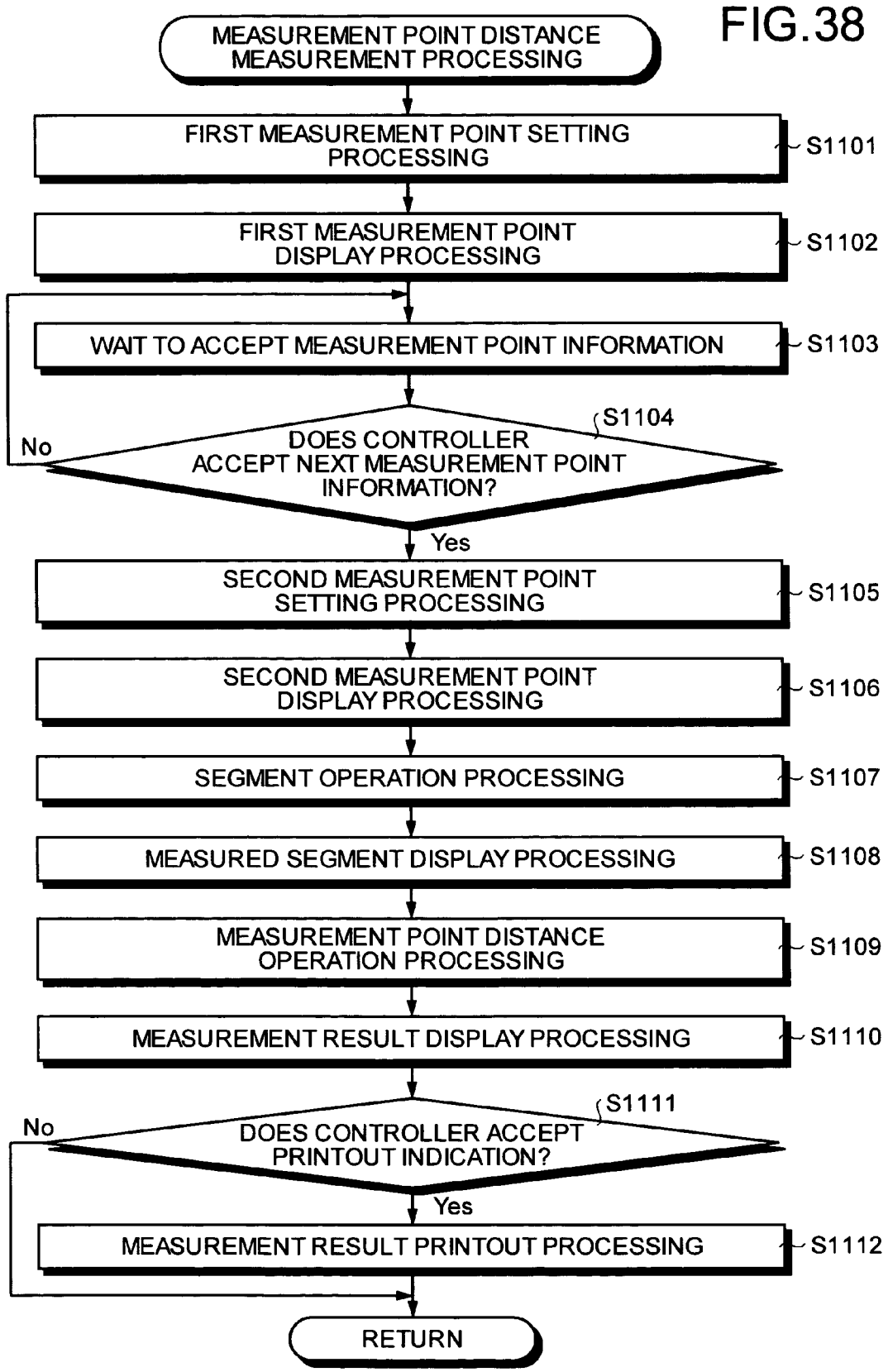
FIG. 38 is a flowchart showing respective processing steps executed until the ultrasonic diagnostic apparatus according to the fifth embodiment completes a measurement point distance measurement processing in detail.
Figure 39:
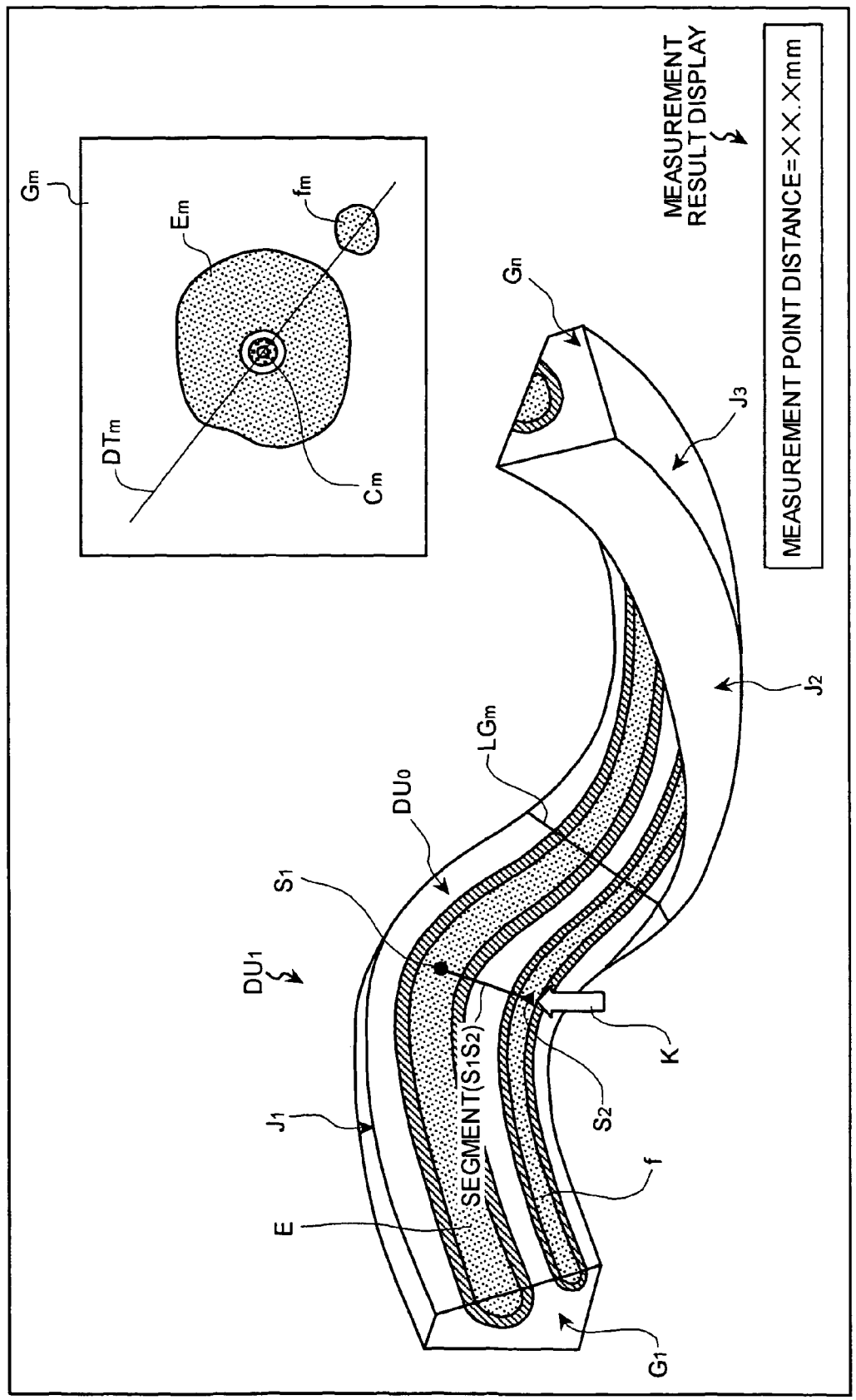
FIG. 39 depicts an example of display of the monitor when the measurement point distance is calculated by two measurement points set on the 3D longitudinal image.

Respective processing steps executed until the controller 55 completes the measurement point distance measurement processing at step S814 is explained in detail. FIG. 38 is a flowchart showing the respective processing steps executed until the controller 55 completes the measurement point distance measurement processing at step S814 in detail. FIG. 39 depicts an example of the display of the monitor 9 when the controller 55 sets two measurement points on the 3D longitudinal image $DU_1$ and calculates the measurement point distance by the two measurement points. Before the controller 55 starts the measurement point distance measurement processing, the operator observes the 3D longitudinal image displayed on the screen of the monitor 9. If the 3D longitudinal image does not display a desired measurement region, then the operator performs, for example, a drag processing using the input device 52, e.g., the mouse, and inputs angle information on the angle for rotating this 3D longitudinal image. If so, the controller 55 performs the processing at step S810 to S812 to rotate this 3D longitudinal image in the predetermined direction corresponding to the moving direction of the cursor by this drag operation by an angle according to a moving amount of the cursor.

Referring to FIGS. 38 and 39, if the operator uses the input device 52, e.g., the mouse, to move the cursor K displayed on the screen of the monitor 9 to a predetermined position on the 3D longitudinal image $DU_1$, to designate the desired position, and to input measurement point information corresponding to this desired position, then the controller 55 accepts this measurement point information, and sets a measurement point $S_1$ including coordinate component indicated by this measurement point information on the 3D longitudinal image data corresponding to the 3D longitudinal image $DU_1$ as a first measurement point (at step S1101). In this case, the controller 55 sets the measurement point $S_1$ as a point on the 3D longitudinal image data present on the spatial coordinate system xyz. Therefore, vector components of a position vector $OS_1$ of the measurement point $S_1$ on the spatial coordinate system xyz are represented by the following Equation (4) using an x component, a y component, and a z component of the spatial coordinate system xyz.

$$OS_1=(x_1,y_1,z_1) \quad (4)$$

The controller 55 then allocates a marker (a first measurement marker) that indicates the measurement point $S_1$ to the coordinate on the 3D longitudinal image data at which the measurement point $S_1$ is set. Further, while superimposing the first measurement marker on the 3D longitudinal image $DU_1$ corresponding to this 3D longitudinal image data, the controller 55 displays this first measurement marker on the monitor 9 (at step S1102). The controller 55 turns into a standby state of waiting to accept input of measurement point information on a measurement point to be designated next (at step S1103). If the operator does not input the next measurement point information while operating the input device 52, then the controller 5 does not accept the next measurement point information ("No" at step S1104), and maintains this standby state until the next measurement point information is input by operator's input operation.

If the operator operates the input device 52 to input the next measurement point information similarly to the measurement point $S_1$, the controller 55 accepts the input next measurement point information ("Yes" at step S1104). In addition, the controller 55 sets a measurement point $S_2$ including coordinate components indicated by this measurement point information on the 3D longitudinal image data corresponding to the 3D longitudinal image $DU_1$ as a second measurement point, similarly to step S1101 (at step S1105). In this case, vector components of a position vector $OS_2$ of the measurement point $S_2$ on the spatial coordinate system xyz are represented by the following Equation (5) using the x component, the y component, and the z component of the spatial coordinate system xyz, similarly to the measurement point $S_1$.

$$OS_2=(x_2,y_2,z_2) \quad (5)$$

The controller 55 then allocates a marker (a second measurement marker) that indicates the measurement point $S_2$ to the coordinate on the 3D longitudinal image data at which the measurement point $S_2$ is set, similarly to step S1102. Further, while superimposing the second measurement marker on the 3D longitudinal image $DU_1$ corresponding to this 3D longitudinal image data, the controller 55 displays this second measurement marker on the monitor 9 (at step S1106).

Thereafter, the controller 55 operates and outputs a segment that connects the measurement points $S_1$ and $S_2$ to each other based on the respective vector components of the position vectors $OS_1$ and $OS_2$ of the measurement points $S_1$ and $S_2$ set on the 3D longitudinal image data (at step S1107). The controller 55 sets the obtained segment ($S_1S_2$) on the 3D longitudinal image data, and displays an auxiliary line indicating the segment ($S_1S_2$) on the monitor 9 while superimposing the segment ($S_1S_2$) on the 3D longitudinal image $DU_1$ corresponding to the 3D longitudinal image data (at step S1108).

Furthermore, the distance operation unit 55*f* operates and outputs a measurement point distance between the measurement points $S_1$ and $S_2$ based on the respective vector components of the position vectors $OS_1$ and $OS_2$ of the measurement points $S_1$ and $S_2$ set on the 3D longitudinal image data (at step S1109). If the measurement points $S_1$ and $S_2$ are set on the 3D longitudinal image data, the distance operation unit 55*f* can operate and output the measurement point distance between the measurement points $S_1$ and $S_2$. Therefore, this measurement point distance operation processing may be performed before the operation processing for the segment ($S_1S_2$) at step S1107. It is noted that this measurement point distance is the Euclidean distance between the measurement points $S_1$ and $S_2$ and corresponds to a length of the segment ($S_1S_2$) obtained based on the measurement point $S_1$ and $S_2$. Accordingly, the distance operation unit 55*f* operates and outputs this measurement point distance $|S_1S_2|$ based on the respective vector components of the position vectors $OS_1$ and $OS_2$ of the measurement points $S_1$ and $S_2$, which vectors are represented by Equations (4) and (5), as represented by the following Equation (6).

$$|S_1S_2|=\{(x_1-x_2)^2+(y_1-y_2)^2+(z_1-z_2)^2\}^{1/2} \quad (6)$$

The controller 55 converts the measurement point distance operated and output at step S1109 into value in a desire unit, and displays the resultant value on the monitor 9 as a measurement result (at step S1110). In this case, as shown in FIG. 39, the controller 55 displays the measurement result on the same monitor screen as the 3D longitudinal image $DU_1$ for which the measurement point distance is measured. Thereafter, if the operator operates the input device 52 to input indication information for printing out the measurement result of this measurement point distance onto a paper or the like, the controller 55 accepts a printout indication based on this indication information ("Yes" at step S1111). In addition, the controller 55 transmits measurement result information on the measurement point distance to the printer 53, and controls the printer 53 to output a measurement result corresponding to the transmitted measurement result information (at step S1112). In this case, the printer 53 prints out the measurement result corresponding to the received measurement result information onto a paper or the like under control of the controller 55. On the other hand, if the operator does not operate the input device 52 to input this printout indication information, the controller 55 does not accept the printout indication ("No" at step S1111). In other words, the controller 55 accomplishes this measurement point distance measurement processing without controlling the printer 53 to print out the measurement result.

It is preferable that the controller 55 allocate the first measurement marker and the second measurement marker onto the 3D longitudinal image data in different manners. Specifically, as shown in FIG. 39, the controller 55 allocates the first measurement marker that is, for example, round and yellow onto the 3D longitudinal image data as a marker that indicate the measurement point $S_1$. In addition, while superimposing the first marker on the 3D longitudinal image $DU_1$ corresponding to this 3D longitudinal image data, the first measurement marker is displayed on the screen of the monitor 9. Likewise, the controller 55 allocates the second measurement marker that is, for example, triangular and Mars yellow onto the 3D longitudinal image data as a marker that indicate the measurement point $S_2$. In addition, while superimposing the second marker on the 3D longitudinal image $DU_1$ corresponding to this 3D longitudinal image data, the second measurement marker is displayed on the screen of the monitor 9. This enables the operator to easily discriminate the first measurement marker and the second measurement marker displayed on the screen of the monitor 9 from each other.

If the operator switches the 2D ultrasonic tomographic image displayed on the same monitor screen as the 3D longitudinal image, e.g., the 2D ultrasonic tomographic image $G_m$ shown in FIG. 39, over to a desired 2D tomographic image, and designates measurement points on each of a plurality of desired 2D ultrasonic tomographic images displayed sequentially, the controller 55 sets measurement points on 2D image data corresponding to the respective pieces of 2D ultrasonic tomographic image on which the measurement points are designated. In addition, the distance operation unit 55f operates and outputs a measurement point distance spread over different 2D ultrasonic tomographic images based on the vector components of the position vectors of the measurement points set on the respective pieces of 2D image data.

Figure 40:
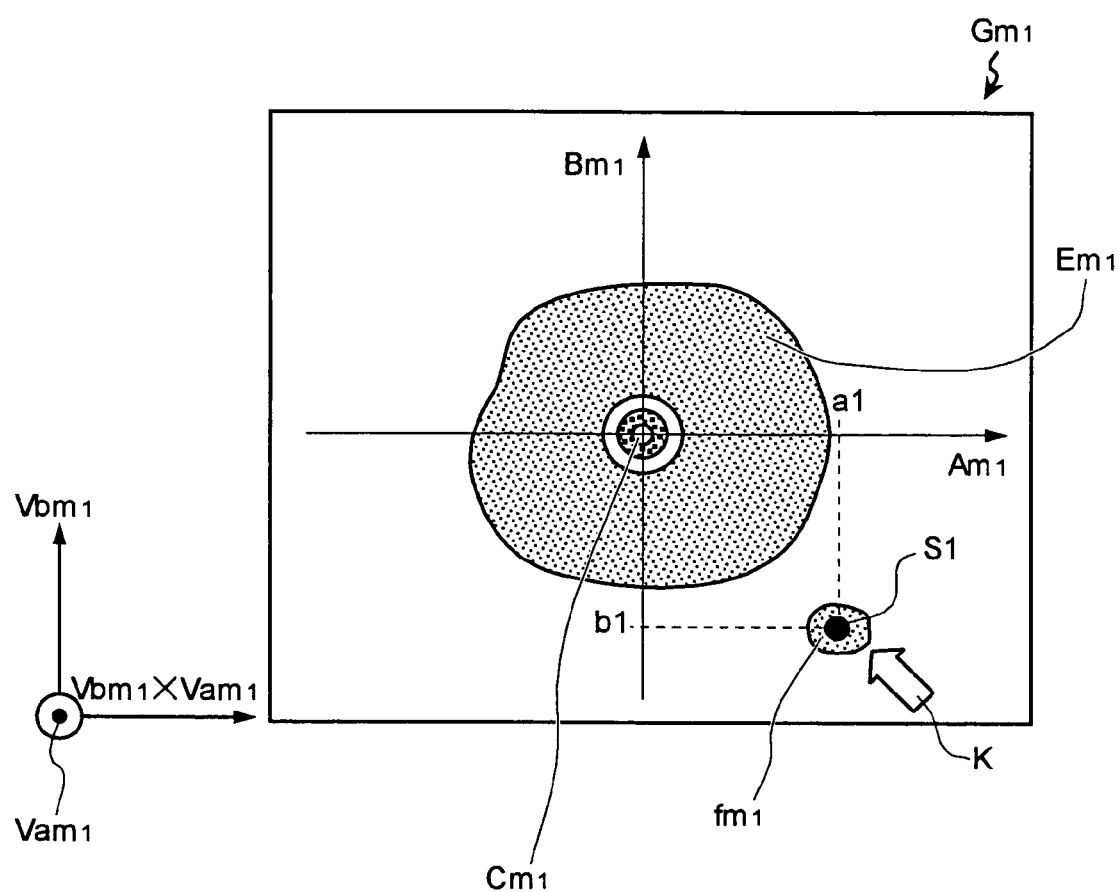
FIG. 40 is an explanatory view of an operation for setting a first measurement point on the 2D ultrasonic tomographic image.
Figure 41:
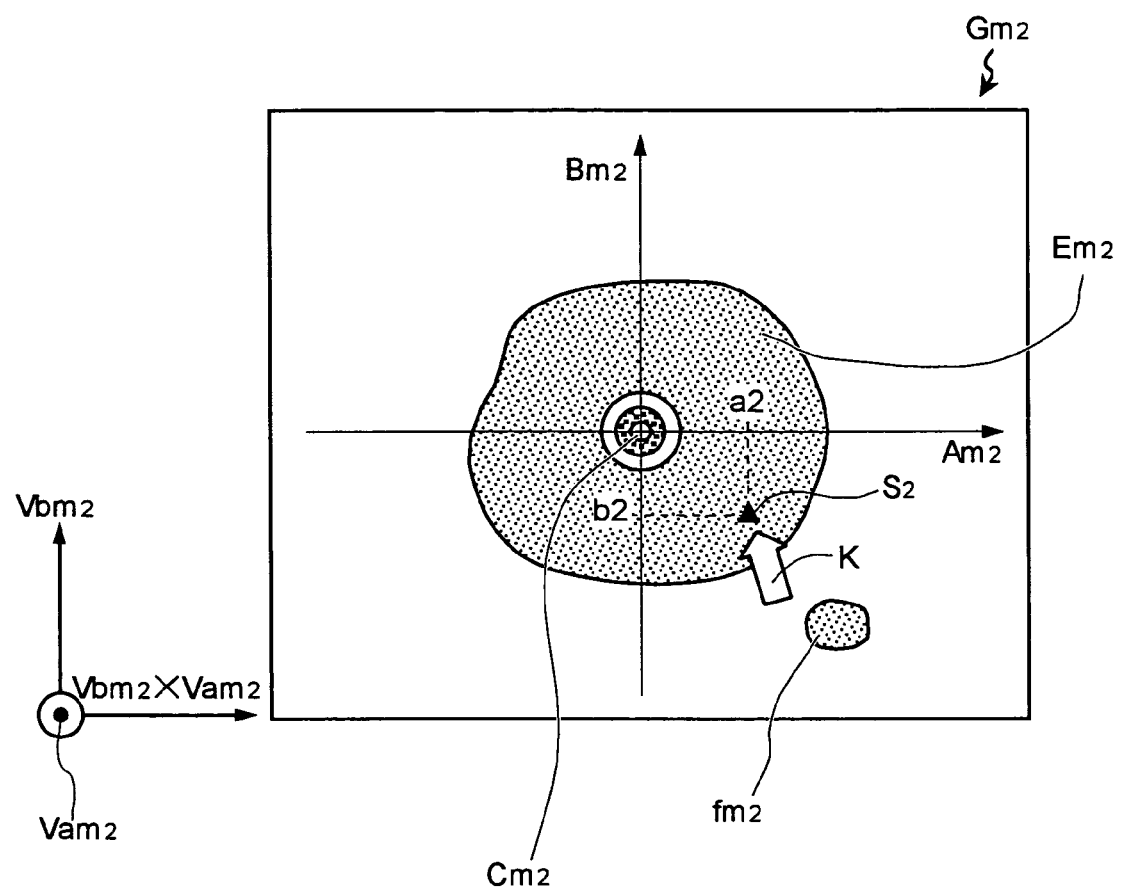
FIG. 41 is an explanatory view of an operation for setting a second measurement point on another 2D ultrasonic tomographic image.
Figure 42:
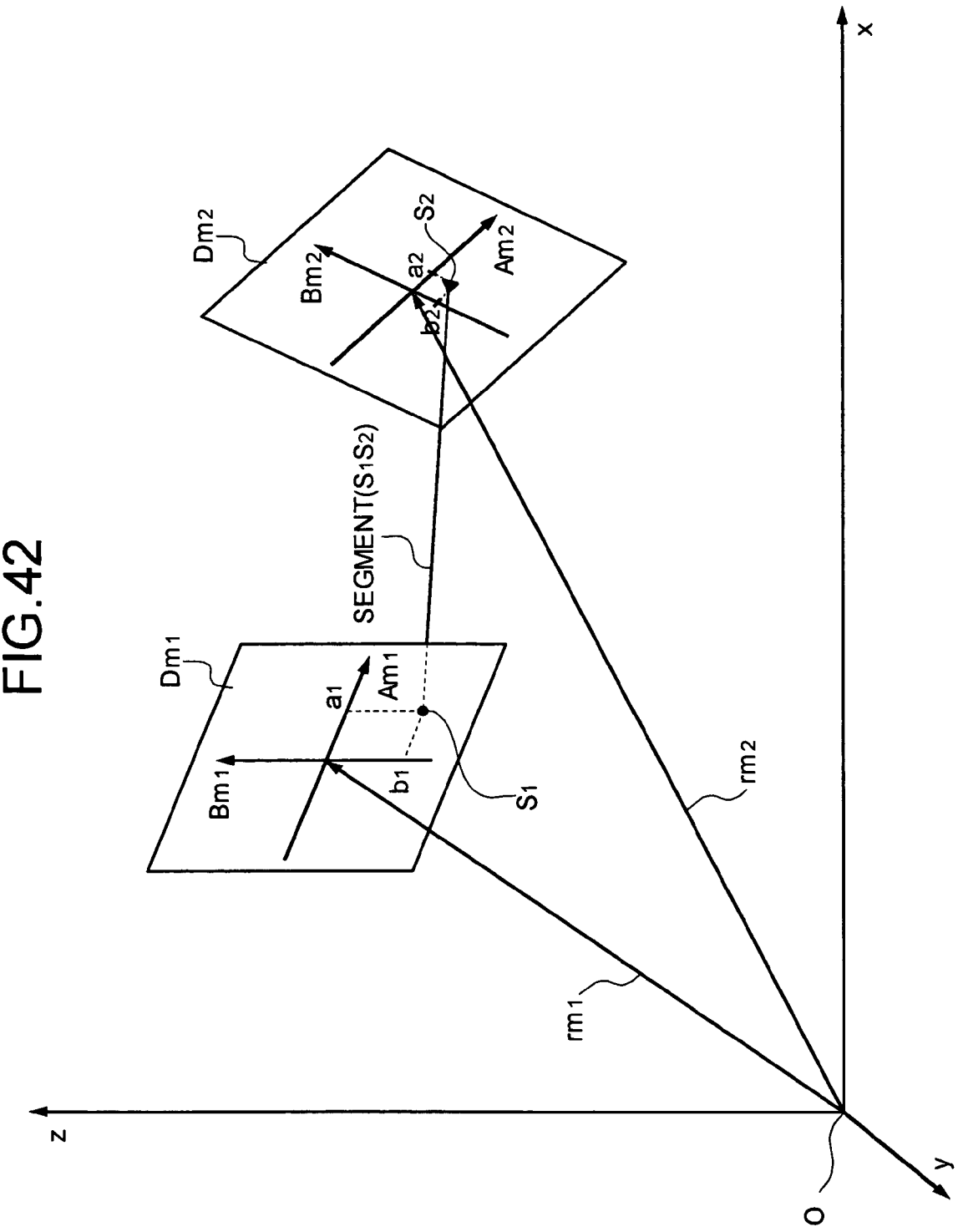
FIG. 42 is an explanatory view of a processing for operating and outputting the measurement point distance based on the two measurement points set on different pieces of 2D image data, respectively.

FIG. 40 is an explanatory view of an operation for designating the measurement point $S_1$ on the 2D ultrasonic tomographic image $G_{m1}$ corresponding to the 2D image data $D_{m1}$ among the n pieces of 2D image data. FIG. 41 is an explanatory view of an operation for designating the measurement point $S_2$ on the 2D ultrasonic tomographic image $G_m$ corresponding to the 2D image data $D_{m2}$ among the n pieces of 2D image data. FIG. 42 is an explanatory view of a processing for operating and outputting the measurement point position distance based on the measurement point $S_1$ designated on the 2D image data $D_{m1}$ and the measurement point $S_2$ designated on the 2D image data $D_{m2}$.

Referring to FIGS. 40, 41, and 42, if the operator operates the input device 52 to input switchover indication information for displaying the 2D ultrasonic tomographic image $G_{m1}$ on the monitor screen, the controller 55 performs the same processing as that at step S809 to display the 2D ultrasonic tomographic image $G_{m1}$ on the monitor screen 9. If the operator then operates the input device 52 to move the cursor K on the monitor screen to a desired position on the 2D ultrasonic tomographic image $G_{m1}$, and inputs measurement point information for designating the first measurement point $S_1$ to the desired position, the controller 55 performs the respective processings at steps S1101 and S1102, thereby displaying the first measurement marker which indicates the measurement point $S_1$ at this desired position. In this case, the controller 55 sets the measurement position $S_1$ at the coordinate $(a_1, b_1)$ on an orthogonal coordinate system $A_{m1}B_{m1}$ of the 2D image data $D_{m1}$ corresponding to this desired position. In addition, as shown in FIG. 40, the controller 55 displays the first measurement marker which indicates the measurement position $S_1$ at this desired position, e.g., on a pancreatic duct image $f_{m1}$.

Thereafter, if the operator operates the input device 52 to input switchover indication information for displaying the 2D ultrasonic tomographic image $G_{m2}$ on the monitor screen, the controller 55 performs the same processing at step S809 to display the 2D ultrasonic tomographic image $G_{m2}$ on the monitor screen. If the operator then operates the input device 52 to move the cursor K on the monitor screen to a desired position on the 2D ultrasonic tomographic image $G_{m2}$, and inputs measurement point information for designating the second measurement point $S_2$ to the desired position, the controller 55 performs the respective processings at steps S1105 and S1106, thereby displaying the second measurement marker which indicates the measurement point $S_2$ at this desired position. In this case, the controller 55 sets the measurement position $S_2$ at the coordinate $(a_2, b_2)$ on an orthogonal coordinate system $A_{m2}B_{m2}$ of the 2D image data $D_{m2}$ corresponding to this desired position. In addition, as shown in FIG. 41, the controller 55 displays the second measurement marker which indicates the measurement position $S_2$ at this desired position, e.g., on a duodenum image $E_{m2}$.

If the controller 55 sets the measurement point $S_1$ at the coordinate $(a_1, b_1)$ on the orthogonal coordinate system $A_{m1}B_{m1}$ of the 2D image data $D_{m1}$ and sets the measurement point $S_2$ at the coordinate $(a_2, b_2)$ on the orthogonal coordinate system $A_{m2}B_{m2}$ of the 2D image data $D_{m2}$, the distance operation unit 55f performs the same processing as that at step S1109. The distance operation unit 55f thereby operates and outputs the length of the segment $(S_1S_2)$ shown in FIG. 42, i.e., the measurement point distance between these measurement points $S_1$ and $S_2$. It is noted that the orthogonal coordinate systems $A_{m1}B_{m1}$ and $A_{m2}B_{m2}$ of the respective pieces of 2D image data $D_{m1}$ and $D_{m2}$ are present on the spatial coordinate system xyz. Therefore, the coordinate $(a_1, b_1)$ on the orthogonal coordinate system $A_{m1}B_{m1}$ and the coordinate $(a_2,$ $b_2$) on the orthogonal coordinate system $A_{m2}B_{m2}$ can be expressed using the x component, the y component, and the z component of the spatial coordinate system xyz, as represented by Equation (3).

Thereafter, the controller 55 executes the processing step S1110 and the following, and displays the measurement result of this measurement point distance on the monitor 9 or controls the printer 53 to output the measurement result of this measurement point distance onto a paper or the like. Accordingly, by executing the respective processing steps, the controller 55 can accomplish the processing for measuring the measurement point distance spread over different 2D ultrasonic tomographic images.

Further, if the controller 55 regards the position of the cursor K as a virtual measurement point $S_2$, calculates the length to the segment ($S_1S_2$), and displays the measurement result on the monitor 9 while the operator operates the input device 52 to move the cursor K on the screen to the desired position on the 2D ultrasonic tomographic image $G_{m2}$, the operator can recognize the distance between the measurement points $S_1$ and $S_2$ in real time.

If the operator causes the ultrasonic transducer 3a to perform a radial scan and guides the probe 2 following step S809, S812, or S814, the 3D scan using the ultrasonic transducer 3a resumes. In addition, the controller 55 repeatedly executes the processing step S801 and the following. In this case, the controller 55 adds the stereoscopic 3D longitudinal image generated by operator's guiding the probe 2 to the 3D longitudinal image already displayed on the screen of the monitor 9 and displays the resultant 3D longitudinal image. The controller 55 thus extends the 3D longitudinal image successively with the operator's operation for guiding the probe 2 during the 3D scan.

According to the fifth embodiment, the transmission coil is arranged near the ultrasonic transducer incorporated into the tip end of the probe. In addition, the position data calculator calculates the position data on the radial scan using this ultrasonic transducer, based on the magnetic field output from the transmission coil. However, the present invention is not limited to this method. The position data calculator may calculate the position data on the radial scan using the ultrasonic transducer by detecting a movement acceleration of the ultrasonic transducer when the operator guides this probe, and by performing an integral processing or the like on the movement acceleration.

According to the fifth embodiment, the transmission coil which generates the magnetic field is arranged near the ultrasonic transducer within the probe. If the magnetic field generated by the transmission coil is to be detected by the reception antenna, the position of this transmission coil is detected. However, the present invention is not limited to this method. The transmission coil may be arranged at the position of the reception antenna in place of the reception antenna, and a reception coil having directivities of an ultrasonic vibration insertion direction and a direction perpendicular to the insertion direction may be arranged near the ultrasonic transducer within the probe. In addition, a position of this reception coil may be detected.

According to the fifth embodiment, a plurality of pieces of 2D image data obtained by the 3D scan are associated with associated with the respective pieces of position data related to the positions and the directions relative to which the 3D can is performed. These pieces of 2D image data thus associated with the respective pieces of position data are arranged on the predetermined spatial coordinate system. The curved planes corresponding to the moving path or moving direction of the probe during the 3D scan are set as the cut planes on which the longitudinal images of the pieces of 2D image data are formed, respectively. In addition, the longitudinal image of the subject is displayed on each cut plane. Furthermore, the measurement point distance is operated and output based on the coordinate information on the respective measurement points set on the longitudinal images of the subject displayed and output onto the monitor screen. Therefore, the ultrasonic diagnostic apparatus which can generate the tomographic image of the subject by accurately tracing the moving path or moving direction of the probe during the 3D scan, which can easily display and output the longitudinal image substantially equal in shape to the actual subject, and which can accurately measure a desired distance, e.g., a diameter or a distance, of the desired region of interest, such as the characteristic site or the affected site, on this longitudinal image even if the probe 2 performs the 3D scan while being curved and moved along the shape of the living body, or even if the probe performs the 3D scan while being twisted and moved dependently on the operator's operation such as the insertion or the guiding, can be realized.

If the operator uses this ultrasonic diagnostic apparatus, then the operator can easily acquire the longitudinal image substantially equal in shape to the actual subject and can easily measure the accurate distance between the measurement points designated in the region of interest on this longitudinal image by artificially inserting or guiding the probe 2 that is executing the radial scan within the living body without using a drive or the like which inserts or draws out the probe 2 into or from the interior of the living body. Accordingly, the operator can accurately grasp a shape, a size, or a position of an affected site before a surgical operation. The ultrasonic diagnostic apparatus is thereby useful for determination of a surgical operation plan or a cutting range. Besides, the operator can determine more accurately and more objectively a temporal treatment effect of an anticancer agent, radiotherapy, or the like on the affected site.

A sixth embodiment of the present invention is explained in detail. In the fifth embodiment, the ultrasonic diagnostic apparatus is constituted so as to generate the longitudinal image of the subject on the curved plane according to the moving path or moving direction of the probe which performs the 3D scan, to set the two measurement points designated on this longitudinal image on the spatial coordinate system, and to measure the measurement point distance based on the two measurement points. In the sixth embodiment, an ultrasonic diagnostic apparatus is constituted so as to interpolate respective adjacent pieces of 2D image data among a plurality of pieces of 2D image data arranged on the spatial coordinate system to generate 3D image data, to set a plane designated on this 3D image data as a cut plane, and to measure a distance between two measurement points designated on a longitudinal image on the cut plane.

Figure 43:
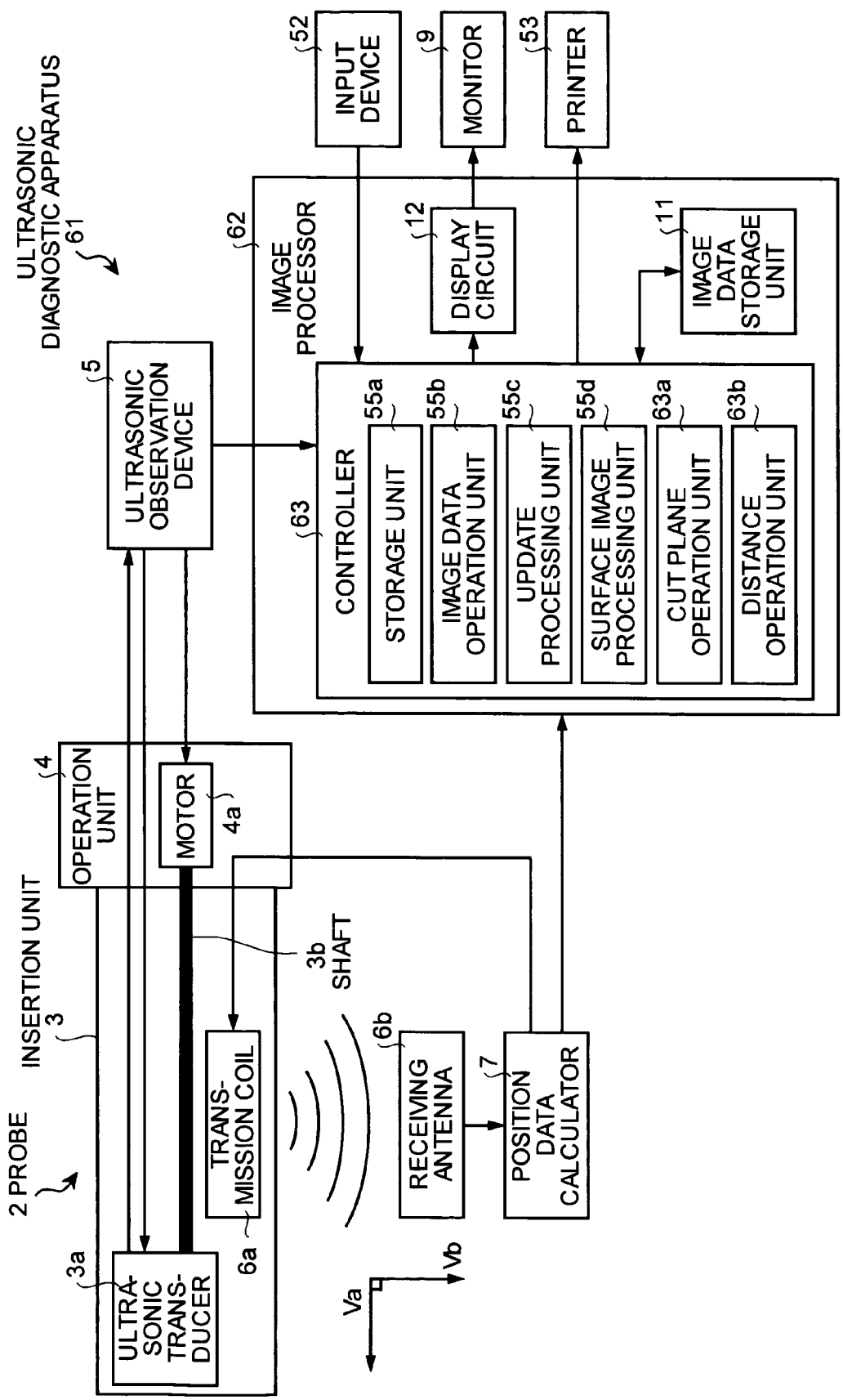
FIG. 43 is a block diagram that depicts schematic configuration of an ultrasonic diagnostic apparatus according to a sixth embodiment of the present invention.

FIG. 43 is a block diagram that depicts schematic configuration of the ultrasonic diagnostic apparatus according to the sixth embodiment of the present invention. The ultrasonic diagnostic apparatus 61 shown in FIG. 43 is constituted as follows, as compared with the ultrasonic diagnostic apparatus 51 according to the fifth embodiment. An image processor 62 is provided instead of the image processor 54. The image processor 62 includes a controller 63 instead of the controller 55. The controller 63 includes a cut plane operation unit 63a instead of the cut plane operation unit 55c and a distance operation unit 63b instead of the distance operation unit 55f. The controller 63 is realized by a ROM that stores various types of data such as a processing program, a RAM that stores each operation parameter, a CPU that executes the processing program stored in the ROM, and the like, substantially similarly to the controller 55. The other constituent elements of the ultrasonic diagnostic apparatus 61 are equal to those of the ultrasonic diagnostic apparatus 51 according to the fifth embodiment. Like constituent elements as those according to the fifth embodiment are denoted by like reference symbol, respectively.

Figure 44:
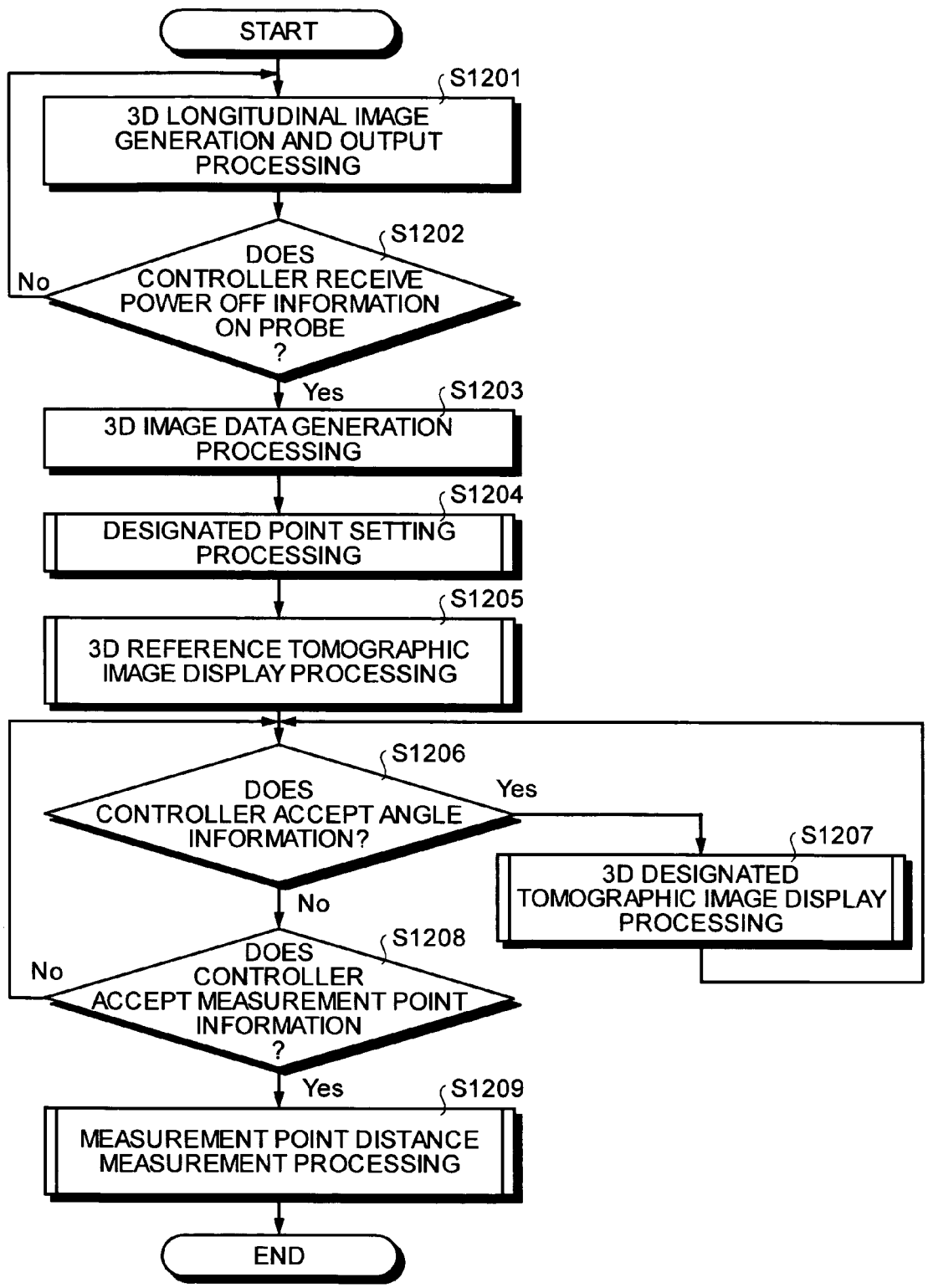
FIG. 44 is a flowchart showing respective processing steps executed until a measurement point distance between the two measurement points designated on a 3D reference tomographic image or a 3D designated tomographic image is measured.

FIG. 44 is a flowchart showing respective processing steps executed since the controller 63 displays a band-shaped or stereoscopic 3D longitudinal image on the monitor 9, generates 3D image data using n pieces of 2D image data on the spatial coordinate system xyz, and sets two measurement points on a longitudinal image generated based on this 3D image data until measuring a measurement point distance by the two measurement points. Referring to FIG. 44, if the ultrasonic observation device 5 generates 2D image data based on the echo signal and the position data calculator 7 calculates position data on a position at which this echo signal is obtained, the controller 63 executes the respective processing steps S801 to S806. The controller 63 thereby displays a 2D ultrasonic tomographic image on the monitor 9, and a band-shaped 3D longitudinal image or a stereoscopic 3D longitudinal image including, as one surface, the band-shaped 3D longitudinal image to be displayed on the screen of the monitor 9 (at step S1201).

Thereafter, if the controller 63 does not receive the power-OFF information on the probe 2 ("No" at step S1202), the controller 63 repeatedly executes the processing step S1201 and the following, similarly to step S807. If the controller 63 receives the power-OFF information on the probe 2 ("Yes" at step S1202), the image data operation unit 55b performs a well-known image processing such as interpolation between respective pieces of 2D image data or averaging of overlapped portions using the n pieces of 2D image data arranged on the spatial coordinate system xyz to thereby generate 3D image data on the spatial coordinate system xyz before receiving this power-OFF information (at step S1203). The controller 63 stores the 3D image data generated by the image data operation unit 55b in the image data storage unit 11. This 3D image data includes n pieces of 2D image data $D_1$, $D_2, \ldots,$ and $D_n$ as plane tomographic image data perpendicular to the respective axial vectors $V_{a1}, V_{a2}, \ldots,$ and $V_{an}$, and is composed by many cells (voxels) corresponding to 3D coordinates on the spatial coordinate system xyz. As the voxels, pieces of image data corresponding to luminances are set, respectively.

The controller 63 reads desired 2D image data from the image data storage unit 11 in response to indication information on an image display processing input from the input device 52. In addition, the controller 63 transmits this 2D image data to the monitor 9 through the display circuit 12 to display a 2D ultrasonic tomographic image corresponding to this 2D image data on the monitor 9. If a desired 2D ultrasonic tomographic image is displayed on the screen of the monitor 9, then the operator operates the input device 52 to designate a desired position on the 2D ultrasonic tomographic image using, for example, a cursor displayed on the screen of the monitor 9, and to input designated point information corresponding to this desired position. The controller 63 sets a desired point on the 2D image data corresponding to the 2D ultrasonic tomographic image based on the designated point information input from the input device 52. The operator performs this designated point information input operation at least twice, whereby the controller 63 sets at least two designated points corresponding to the respective pieces of input designated point information on each of the n pieces of 2D image data $D_1, D_2, \ldots,$ and $D_n$ (at step S1204).

If the controller 63 sets the at least two designated points corresponding to the respective pieces of input designated point information on each of the n pieces of 2D image data $D_1$, $D_2, \ldots,$ and $D_n$, the cut plane operation unit 63a operates and outputs a straight line that passes through the two designated points thus set and operates and outputs a plane including the two designated points and a reference set point read from the storage unit 55a. The controller 63 sets this plane as a reference cut plane serving as a rotation reference plane, and sets this straight line as a rotation axis of the reference cut plane. Alternatively, the cut plane operation unit 63a may operate and output a plane which includes the two designated points and which includes a reference normal vector read from the storage unit 55a.

Thereafter, the image data operation unit 55b generates 3D tomographic image data (3D reference tomographic image data) including the 2D tomographic image data on this reference cut plane, using the 3D image data which the controller 63 reads from the image data storage unit 11. The controller 63 stores the 3D reference tomographic image data generated by the image data operation unit 55b in the image data storage unit 11, and transmits the 3D reference tomographic image data to the monitor 9 through the display circuit 12. Thus, the controller 63 displays a 3D reference tomographic image corresponding to the 3D reference tomographic image data on the monitor 9 (at step S1205).

The operator observes the 3D reference tomographic image displayed on the screen of the monitor 9 and checks whether a desired region of interest is displayed on the screen of the monitor 9. If the desired region of interest is not displayed on the screen of the monitor 9, the operator operates the input device 52 to input angle information to the controller 63. For example, the operator moves the cursor to a predetermined position on the monitor screen using the mouse. Thereafter, if a mouse button is depressed, the controller 63 is switched into a standby state of waiting to accept input of the angle information. If the operator then performs a drag operation or the like and inputs the angle information from the input device 52, the controller 63 accepts the angle information input from the input device 52 ("Yes" at step S1206). If so, the cut plane operation unit 63a operates and outputs a plane obtained by rotating the reference cut plane by an angle corresponding to the angle information input from the input device 52 based on the angle and the designated point information. The controller 63 sets this plane as a designated cut plane. The image data operation unit 55b generates 3D tomographic image data (3D designated tomographic image data) including the 2D longitudinal image data on this designated cut plane, using the 3D image data which the controller 63 reads from the image data storage unit 11. The controller 63 stores the 3D designated tomographic image data generated by the image data operation unit 55b in the image data storage unit 11, and transmits this 3D designated tomographic image data to the monitor 9 through the display circuit 12. Thus, the controller 63 displays a 3D designated tomographic image corresponding to this 3D designated tomographic image data on the monitor 9 (at step S1207).

Thereafter, the operator observes the 3D designated tomographic image displayed on the screen of the monitor 9 and checks whether a desired region of interest is displayed on the screen of the monitor 9. If the desired region of interest is not displayed on the screen of the monitor 9, the operator operates the input device 52 to input angle information to the controller 63, similarly to the instance of the 3D reference tomographic image. The controller 63 accepts the angle information input from the input device 52, and repeatedly executes the processing steps S1206 and the following. Namely, the controller 63 repeatedly executes the processing step S1206 and the following until the operator confirms that the desired region of interest is displayed on the screen of the monitor 9.

On the other hand, if the operator observes the 3D reference tomographic image displayed on the screen of the monitor 9 and confirms that the desired region of interest is displayed on the screen of the monitor 9, then the operator does not input the angle information to the controller 63 but inputs measurement point information on the measurement points designated on each of various tomographic images displayed on the screen of the monitor 9. In this embodiment, the controller 63 does not accept the angle information ("No" at step S1206) but accepts the measurement point information ("Yes" at step S1208). The controller 63 then accomplishes the measurement point distance measurement processing based on the two designated points set on each tomographic image (at step S1209).

If the operator does not operate the input device 52 to input the angle information and the measurement point information, then the controller 63 does not accept the angle information ("No" at step S1206), does not accept the measurement point information ("No" at step S1208), but repeatedly executes the processing step S1206 and the following. If so, the controller 63 controls the monitor 9 to maintain a state in which the 3D reference tomographic image or 3D designated tomographic image is displayed on the monitor screen until the controller accepts the angle information or the measurement point information input by the operator's input operation.

Figure 45:
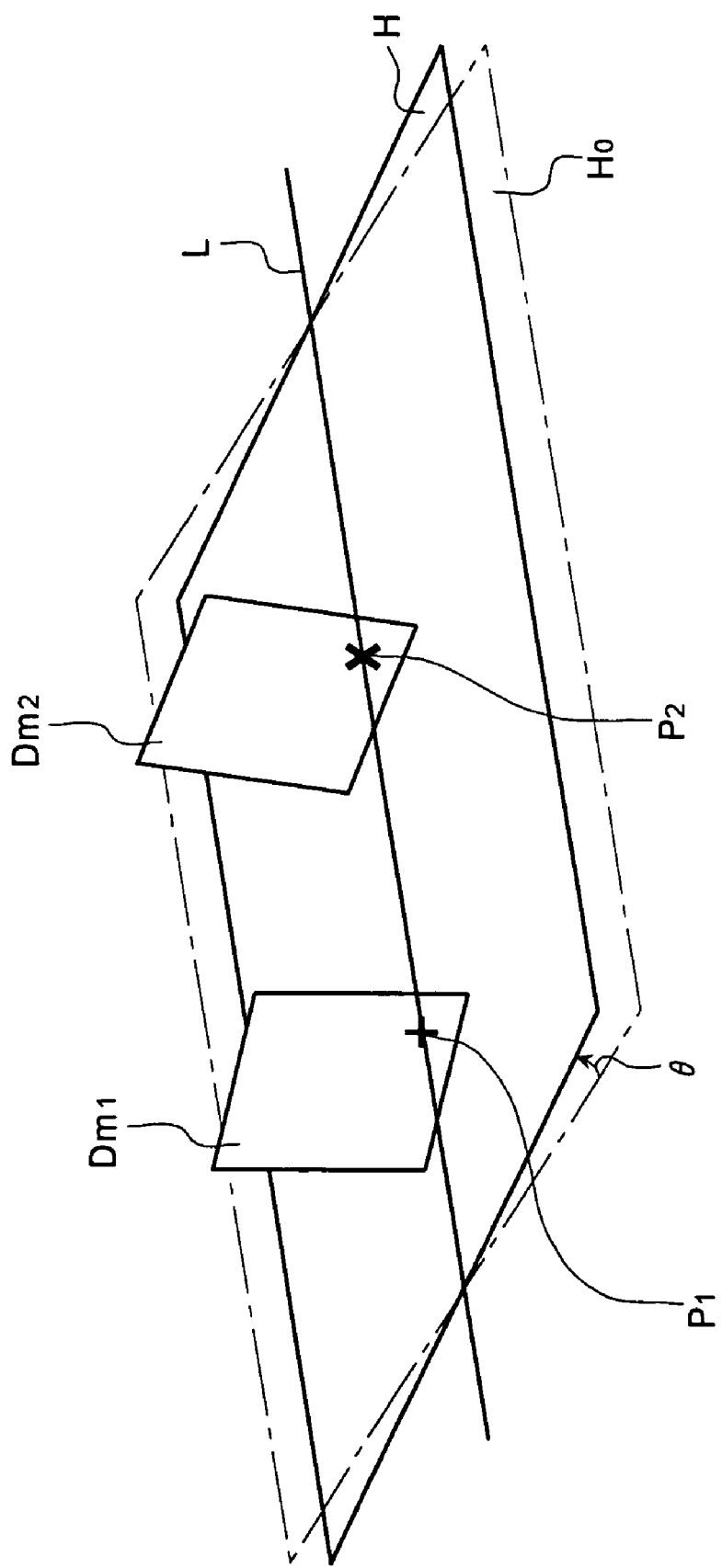
FIG. 45 is an explanatory view of a setting of the straight line that passes through the two designated points set on the 2D image data and that of a reference cut plane.

The processing performed by the cut plane operation unit 63a for operating and outputting the straight line that passes through the two designated points and the reference cut plane that includes the two designated points and the reference set point set in advance if the controller 63 sets the two designated points on each 2D image data is explained in detail. FIG. 45 is an explanatory view of a setting of the straight line that passes through the two designated points set on the 2D image data and that of the reference cut plane. As shown in FIG. 45, the controller 63 sets designate point $P_1$ and $P_2$ on the 2D image data $D_{m1}$ and $D_{m2}$ included in the n pieces of 2D image data, respectively based on the designated point information input from the input device 52. It is noted that the 2D image data $D_{m1}$ is $m1^{th}$ 2D image data of the n pieces of 2D image data arranged on the spatial coordinate system xyz, and that the 2D image data $D_{m2}$ is $m2^{th}$ 2D image data of the n pieces of 2D image data arranged on the spatial coordinate system xyz. In addition, integers m1 and m2 are positive integers equal to or smaller than an integer n, and the integer m1 is smaller than the integer m2.

The cut plane operation unit 63a operates and outputs a straight line L that passes through the designated points $P_1$ and $P_2$ based on coordinate information on the designated point $P_1$ and coordinate information on the designated point $P_2$. In addition, the cut plane operation unit 63a operates and outputs a plane that includes the designated points $P_1$ and $P_2$ and a preset reference set point (not shown) based on the coordinate information on the designated point $P_1$, that on the designated point $P_2$, and that on the reference set point. In this case, the controller 63 sets this plane as a reference cut plane $H_0$ and sets the straight line L as the rotation axis of the reference cut plane $H_0$, as shown in FIG. 45. In other words, the reference cut plane $H_0$ is a rotation reference plane of a cut plane which includes the straight line L as the rotation axis and on which the 3D image data generated at step S1203 is cut. Therefore, if the controller 63 accepts the angle information input from the input device 52, then the cut plane operation unit 63a operates and outputs a plane obtained by rotating the reference cut plane $H_0$ by an angle $\theta$ corresponding to this angle information, and the controller 63 sets this plane as the designated cut plane H.

Alternatively, the cut plane operation unit 63a may operate and output a plane including the designated points $P_1$ and $P_2$ based on the respective pieces of coordinate information on the designated points $P_1$ and $P_2$ and the preset reference normal vector (not shown). If so, similarly to the instance of using the reference set point, the controller 63 can set the reference cut plane $H_0$. Details of a method for setting the reference set point, the reference normal vector, and the reference cut plane $H_0$ is explained later.

Figure 46:
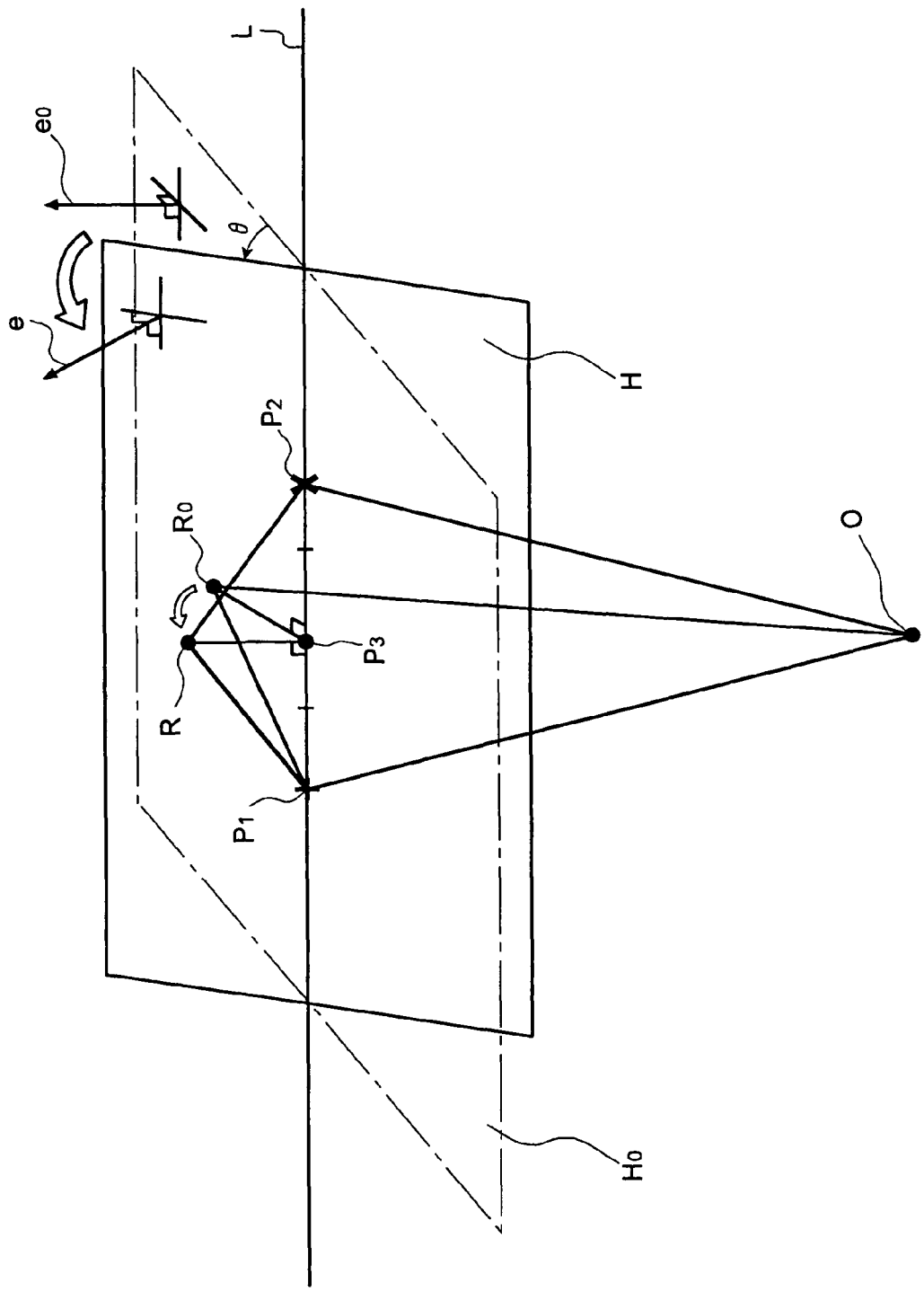
FIG. 46 is an explanatory view of a processing for operating and outputting a designated cut plane.

The processing performed by the cut plane operation unit 63a for operating and outputting the plane obtained by rotating the reference cut plane $H_0$ by the angle $\theta$ using the angle $\theta$ corresponding to the angle information input to the controller 63, that is, the designated cut plane H is explained in detail. FIG. 46 is an explanatory view of the processing performed by the cut plane operation unit 63a for operating and outputting the designated cut plane H obtained by rotating the reference cut plane $H_0$ around the straight line L set as the rotation axis by the angle $\theta$. As shown in FIG. 46, the reference cut plane $H_0$ includes a unit normal vector $e_0$ determined by using the designated points $P_1$ and $P_2$ and the reference set point or using the reference normal vector. The designated cut plane H is a plane obtained by rotating the reference cut plane $H_0$ by the angle $\theta$ around the straight line L set as the rotation axis. Therefore, by using a unit normal vector e obtained by rotating the unit normal vector $e_0$ by the angle $\theta$ around the straight line L set as the rotation axis, and the designated points $P_1$ and $P_2$, the cut plane operation unit 63a can operate and output the designated cut plane H.

As shown in FIG. 46, a point $P_3$ is assumed as a midpoint of a segment that connects the designated point $P_1$ to the designated point $P_2$. A reference set point $R_0$ is assumed as a point on the reference cut plane $H_0$ which point constitutes a segment of a unit length perpendicular to the straight line L and connecting the point $P_3$ to the reference set point $R_0$. A point R is assumed as a point on the designated cut plane H which point is obtained by rotating the reference set point $R_0$ by the angle $\theta$ around the straight line L set as the rotation axis. Based on this assumption, the unit normal vector e of the designated cut plane H is calculated using respective position vectors $OP_1$ and $OP_2$ of the designated points $P_1$ and $P_2$ and a position vector OR of the point R, as represented by the following Equation (7).

$$e = (OP_2 - OP_1) \times (OR - OP_1) / |(OP_2 - OP_1) \times (OR - OP_1)| \quad (7)$$

Further, since the point $P_3$ is assumed as the midpoint of the segment that connects the designated point $P_1$ to the designated point $P_2$, a position vector $OP_3$ of the point $P_3$ is calculated as represented by the following Equation (8).

$$OP_3 = (OP_1 + OP_2)/2 \quad (8)$$

If a unit vector of a vector $P_1P_2$ is assumed as t, the unit vector t is calculated as represented by the following Equation (9).

$$t = (OP_2 - OP_1)/|OP_2 - OP_1| \quad (9)$$

If so, a vector $P_3R$ is calculated using the position vectors $OP_1$ and $OP_2$, the unit vector t, and the angle $\theta$, as represented by the following Equation (10).

$$P_3R = \{(OP_1 \times OP_2)/|OP_1 \times OP_2|\} \cos\theta + \{t \times (OP_1 \times OP_2)/|t \times (OP_1 \times OP_2)|\} \sin\theta \quad (10)$$

Accordingly, the position vector OR is calculated using Equations (8) to (10) as represented by the following Equation (11).

$$OR = OP_3 + P_3R \quad (11)$$
$$= (OP_1 + OP_2)/2 +$$
$$\{(OP_1 \times OP_2)/|OP_1 \times OP_2|\}\cos\theta +$$
$$\{(OP_2 - OP_1)/|OP_2 - OP_1|\} \times$$
$$\{(OP_1 \times OP_2)/|OP_1 \times OP_2|\}\sin\theta$$

According to Equations (7) and (11), the cut plane operation unit 63a can operate and output the unit normal vector e using the respective position vectors $OP_1$ and $OP_2$ of the designated points $P_1$ and $P_2$ and the angle θ that is the rotation angle of the reference cut plane $H_0$. Namely, the cut plane operation unit 63a can operate and output the unit normal vector e using the designated point information and the angle information received by the controller 63, and operate and output the designated cut plane H using the designated point information and the unit normal vector e. It is noted, however, that the cut plane operation unit 63a operates and outputs the reference cut plane $H_0$ when this angle θ is zero. That is, the position vector $OR_0$ of the reference set point $R_0$ can be calculated by assigning zero to Equation (11) as the angle θ. Further, the reference normal vector $e_0$ can be calculated based on Equation (7) using the position vector OR when the angle θ is zero (that is, the position vector $OR_0$) and the position vectors $OP_1$ and $OP_2$. The reference cut plane $H_0$ is operated and output as the plane that includes the designated points $P_1$ an $P_2$ and the reference set point $R_0$, and that has the reference normal vector $e_0$ as a normal. Based on this method, the reference set point $R_0$, the reference normal vector $e_0$, and the reference cut plane $H_0$ are set. In this example, the reference cut plane $H_0$ is geometrically a plane that crosses a plane including the origin O and the designated points $P_1$ and $P_2$ perpendicularly.

If a normal library software for generating 3D images is installed in the controller 63, the controller 63 can cut the 3D image data, which is located on the spatial coordinate system xyz, on the designated cut plane H and generate the 3D designated tomographic image on the designated cut plane H as long as the unit normal vector e and a distance between the origin O and the designated cut plane H are input to the controller 63. The distance between the origin O and the designated cut plane H is calculated using an inner product between the unit normal vector e and the position vector OP, or an inner product between the unit normal vector e and the position vector $OP_2$. Therefore, the controller 63 can obtain the designated cut plane H using the designated point information and the angle information input from the input device 52 based on Equations (7) and (11). In addition, the controller 63 can generate the 3D designated tomographic image data on the designated cut plane H. Specifically, whenever the operator performs the drag operation or the like using the input device 52, the controller 63 sequentially accepts angle information according to a moving amount of the cursor as a result of this drag operation or the like, and rotates the reference cut plane $H_0$ according to the sequentially accepted angle information. The controller 63 thereby sequentially obtains designated cut planes, and generates or updates the 3D designated tomographic image data on each of the obtained designated cut planes. The controller 63 then displays a 3D designated tomographic image corresponding to the 3D designated tomographic image data on the monitor 9.

Figure 47:
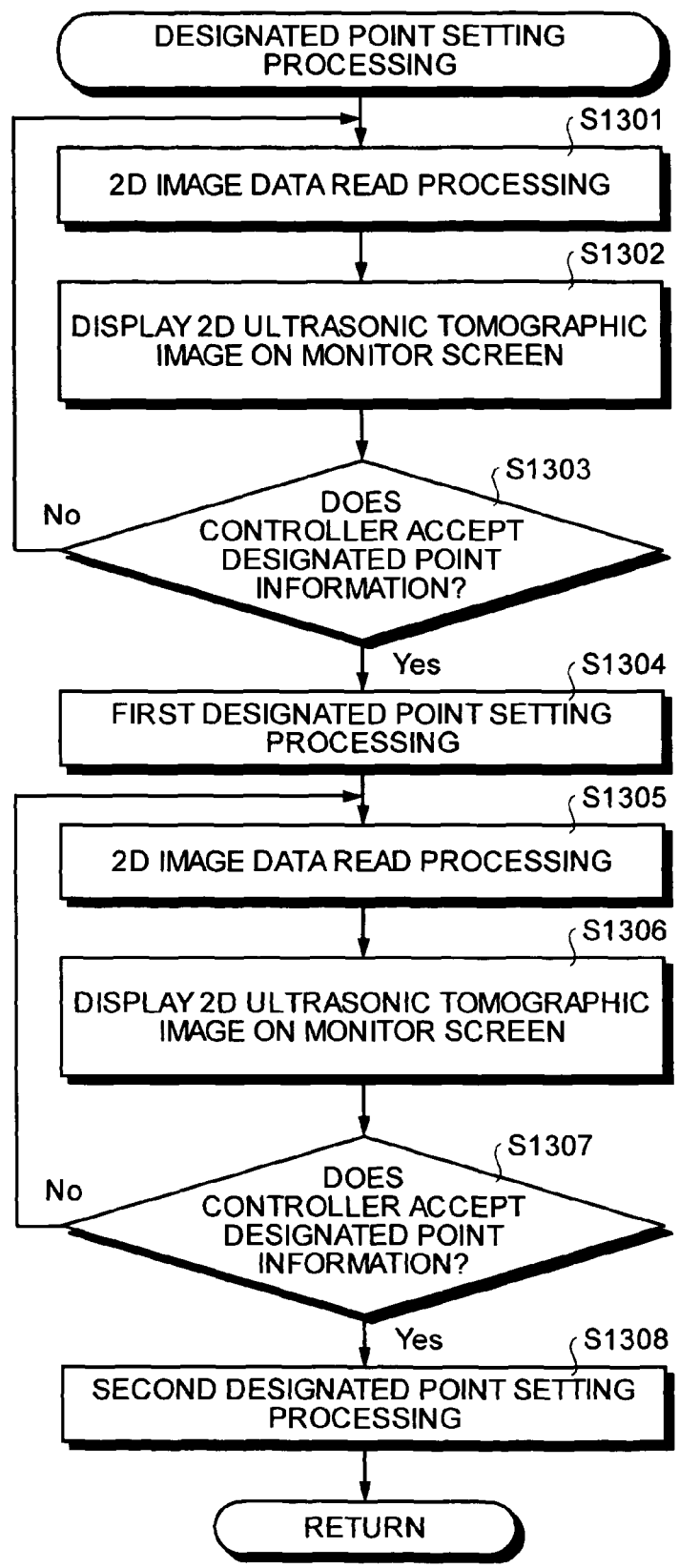
FIG. 47 is a flowchart showing processing steps executed until a designated point setting processing is completed.
Figure 48:
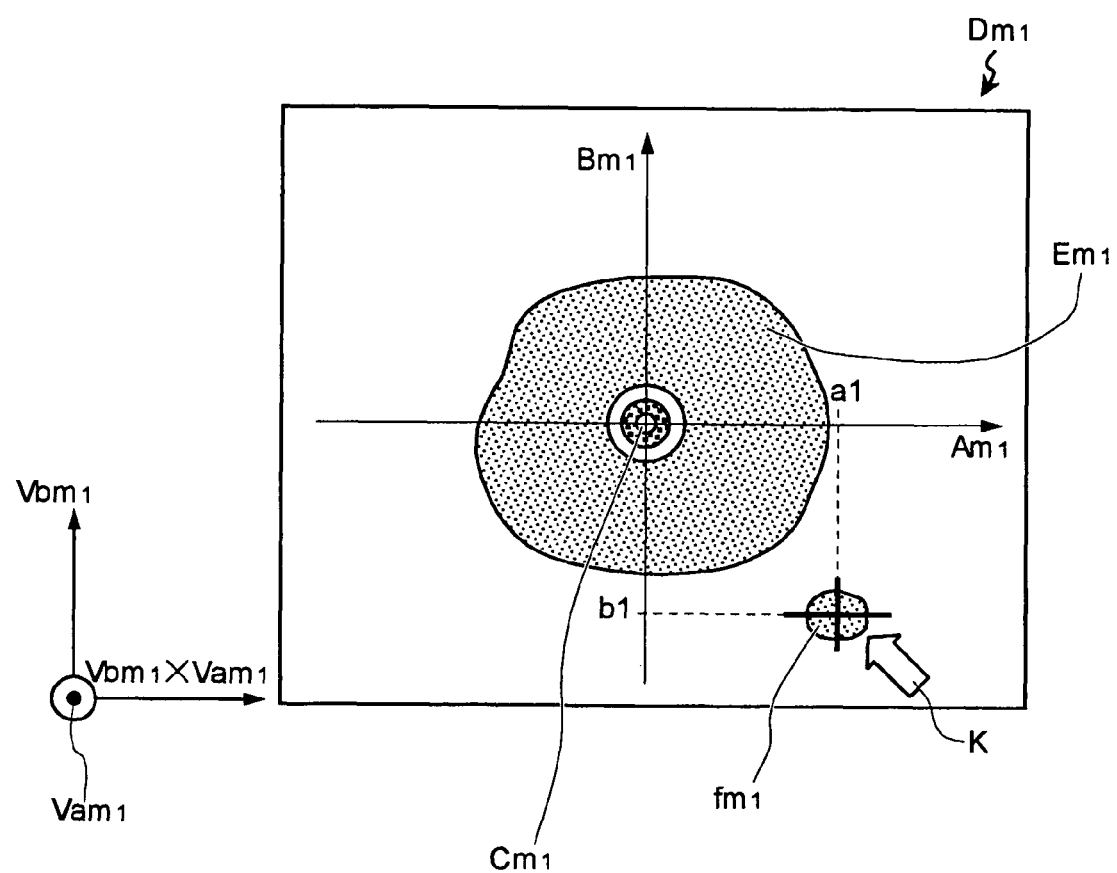
FIG. 48 is an explanatory view of a first designated point setting processing.
Figure 49:
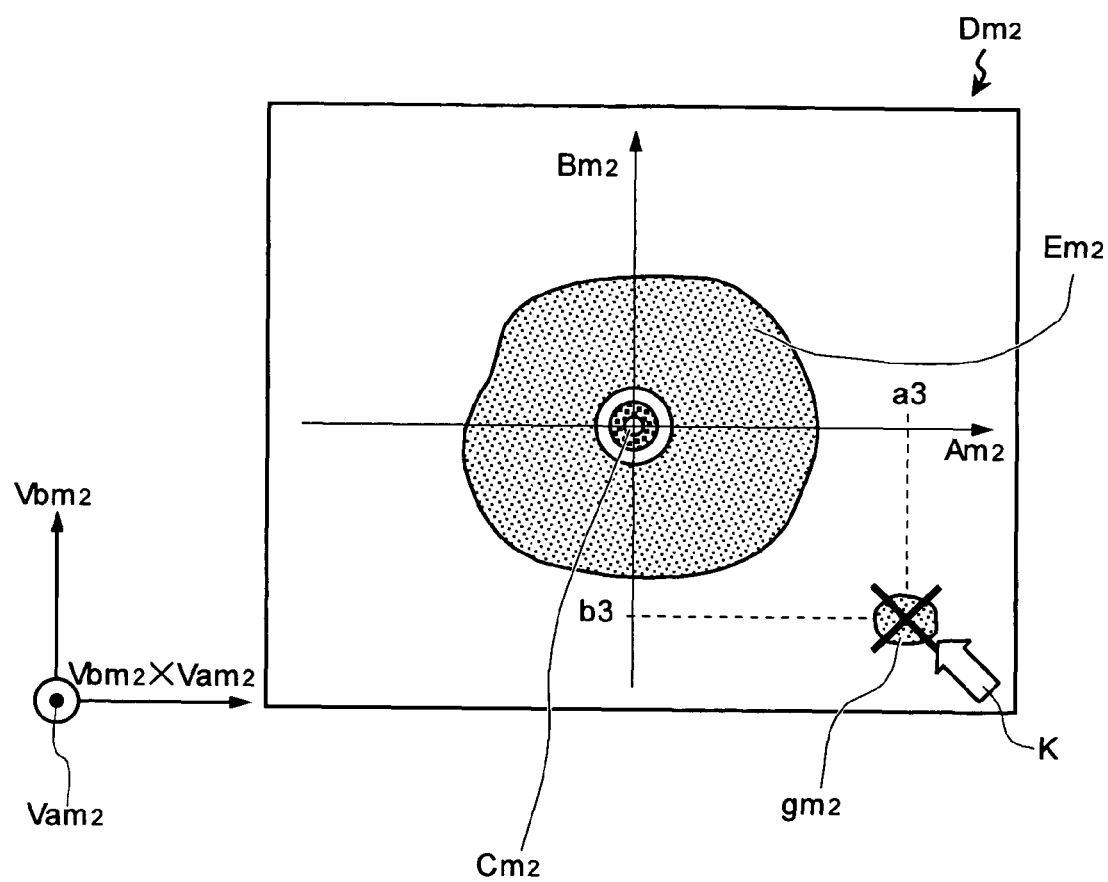
FIG. 49 is an explanatory view of a second designated point setting processing.

The processing performed by the controller 63 at step S1204 for setting the designated points on the 2D image data using the designated point information input from the input device 52 (designated point setting processing) is explained in detail. FIG. 47 is a flowchart showing processing steps executed until the controller 63 completes the designated point setting processing. FIG. 48 is an explanatory view of a processing for setting the designated point $P_1$ on the 2D image data $D_{m1}$ (a first designated point setting processing). FIG. 49 is an explanatory view of a processing for setting the designated point $P_2$ on the 2D image data $D_{m2}$ (a second designated point setting processing).

Referring to FIGS. 47, 48, and 49, the controller 63 reads desired 2D image data, e.g., 2D image data $D_{m1}$ from the image data storage unit 11 in response to a switchover indication corresponding to 2D ultrasonic tomographic image switchover indication information input by the operator as indication information on the image display processing, similarly to step S809 (at step S1301). In addition, the controller 63 transmits the 2D image data $D_{m1}$ to the monitor 9 through the display circuit 12 to display a 2D ultrasonic tomographic image corresponding to the 2D image data $D_{m1}$ on the monitor 9 (at step S1302).

The operator checks whether the desired region of interest is displayed on this 2D ultrasonic tomographic image. If the desired region of interest is not displayed, the operator operates the input device 52 to input switchover indication information for switching the present 2D ultrasonic tomographic image to another 2D ultrasonic tomographic image to the controller 63. In this case, the controller 63 does not accept the designated point information ("No" at step S1303) and repeatedly executes the processing step S1301 and the following.

If the operator confirms that the desired region of interest, e.g., the pancreatic duct image $f_{m1}$ shown in FIG. 48, is displayed, then the operator operates the input device 52 to move, for example, the cursor K displayed on the screen of the monitor 9 toward the pancreatic duct image $f_{m1}$ and to input designated point information for designating the designated point $P_1$ on the pancreatic duct image $f_{m1}$. In this case, the controller 63 accepts the designated point information input by the operator's input operation ("Yes" at step S1303), and sets the designated point $P_1$ at a coordinate corresponding to the pancreatic duct image $f_{m1}$ on the 2D image data $D_{m1}$ (at step S1304). Thereafter, the controller 63 allocates a marker (the first marker) indicating the designated point $P_1$ onto the coordinate set as the designated point $P_1$. While superimposing the first marker on the 2D ultrasonic tomographic image corresponding to the 2D image data $D_{m1}$, the controller 63 displays the first marker on the monitor 9.

As explained, the controller 63 can set the orthogonal coordinate system composed by the axis parallel to the plane parallel vector $V_{bn}$ and the axis parallel to the outer product vector $(V_{bn} \times V_{an})$ with the image center $C_n$ set as an origin, for the 2D image data $D_n$. Therefore, as shown in FIG. 48, the orthogonal coordinate system $A_{m1}B_{m1}$ composed by the axis $B_{m1}$ parallel to the plane parallel vector $V_{bm1}$ and the axis $A_{m1}$ parallel to the outer product vector $(V_{bm1} \times V_{am1})$ with an image center $C_{m1}$ set as an origin is set on the 2D image data $D_{m1}$. The controller 63 sets the designated point $P_1$ at the coordinate $(a_1, b_1)$ corresponding to the pancreatic duct image $f_{m1}$ on the 2D image data $D_{m1}$. Accordingly, the position vector $OP_1$ of the designated point $P_1$ is calculated using this coordinate $(a_1, b_1)$ and a position vector $r_{m1}$ of the image center $C_{m1}$, and based on the fact that each of the axial vector $V_{am1}$ and the plane parallel vector $V_{bm1}$ has a unit length, by the following Equation (12).

$$OP_1 = r_{m1} + a_1(V_{bm1} \times V_{am1}) + b_1 V_{bm1} \quad (12)$$

It is noted that the outer vector $(V_{bm1} \times V_{am1})$ corresponds to the direction vector of the axis $A_{m1}$, and that the plane vector $V_{bm1}$ corresponds to the direction vector of the axis $B_{m1}$. As can be seen, the coordinate $(a_1, b_1)$ corresponding to the designated point $P_1$ can be expressed by a coordinate composed by three components on the spatial coordinate system xyz. That is, the controller 63 sets the designated point $P_1$ on the 2D image data $D_{m1}$ as the point on the spatial coordinate system xyz.

The operator then operates the input device 52 to input switchover indication information for switching the present 2D ultrasonic tomographic image to another 2D ultrasonic tomographic image to the controller 63. The controller 63 reads desired 2D image data, e.g., 2D image data $D_{m2}$ from the image data storage unit 11 based on this switchover indication information, similarly to step S809 (at step S1305). In addition, the controller 63 transmits the 2D image data $D_{m2}$ to the monitor 9 through the display circuit 12 to display a 2D ultrasonic tomographic image corresponding to the 2D image data $D_{m2}$ on the monitor 9 (at step S1306). The operator checks whether the region of interest is displayed on this 2D ultrasonic tomographic image. If the desired region of interest is not displayed, the operator operates the input device 52 to input switchover indication information for switching the present 2D ultrasonic tomographic image to another ultrasonic tomographic image to the controller 63. In this case, the controller 63 does not accept the designated point information ("No" at step S1307) but repeatedly executes the processing step S1305 and the following.

If the operator confirms that the desired region of interest, e.g., a bile duct image $g_{m2}$ shown in FIG. 49, is displayed on the screen of the monitor 9, then the operator operates the input device 52 to move, for example, the cursor K displayed on the screen of the monitor 9 toward the bile duct image $g_{m2}$, and to input the designated point information for designating the designating point $P_2$ on the bile duct image $g_{m2}$. In this case, the controller 63 accepts this designated point information by the operator's input operation ("Yes" at step S1307). In addition, the controller 63 sets the designated point $P_2$ at a coordinate corresponding to the bile duct $g_{m2}$ on the 2D image data $D_{m2}$ (at step S1308).

It is noted that the orthogonal coordinate system $A_{m2}B_{m2}$ composed by the axis $B_{m2}$ parallel to the plane parallel vector $V_{bm2}$ and the axis $A_{m2}$ parallel to the outer product vector $(V_{bm2} \times V_{am2})$ with an image center $C_{m2}$ set as an origin is set on the 2D image data $D_{m2}$, similarly to the instance of the designated point $P_1$. As shown in FIG. 49, the controller 63 sets the designated point $P_2$ at the coordinate $(a_3, b_3)$ corresponding to a bile duct image $g_{m2}$ on the 2D image data $D_{m2}$. Accordingly, the position vector $OP_2$ of the designated point $P_2$ is calculated using this coordinate $(a_3, b_3)$ and a position vector $r_{m2}$ of the image center $C_{m2}$, and based on the fact that each of the axial vector $V_{am2}$ and the plane parallel vector $V_{bm2}$ has a unit length, by the following Equation (13).

$$OP_2 = r_{m2} + a_2(V_{bm2} \times V_{am2}) + b_2 V_{bm2} \quad (13)$$

That is, the controller 63 sets the designated point $P_2$ on the 2D image data $D_{m2}$ as the point on the spatial coordinate system xyz. Thereafter, the controller 63 allocates a marker (the second marker) indicating the designated point $P_2$ onto the coordinate set as the designated point $P_2$. While superimposing the second marker on the 2D ultrasonic tomographic image corresponding to the 2D image data $D_{m2}$, the controller 63 displays the second marker on the monitor 9.

Similarly to the instances of the first measurement marker and the second measurement marker, it is preferable that the controller 63 allocate the first marker and the second marker onto the 2D image data in different manners. Specifically, as shown in FIG. 48, the controller 63 allocates the first marker that is, for example, "+" shaped and red onto the 2D image data $D_{m1}$ as a marker that indicate the designated point $P_1$. In addition, while superimposing the first marker on the 2D ultrasonic tomographic image corresponding to the 2D image data $D_{m1}$, the first marker is displayed on the screen of the monitor 9. Likewise, the controller 63 allocates the second measurement marker that is, for example, "x" shaped and green onto the 2D image data $D_{m2}$ as a marker that indicate the designated point $P_2$. In addition, while superimposing the second marker on the 2D ultrasonic tomographic image corresponding to the 2D image data $D_{m2}$, the second marker is displayed on the screen of the monitor 9. This enables the operator to easily discriminate the first marker and the second marker displayed on the screen of the monitor 9 from each other.

Figure 50:
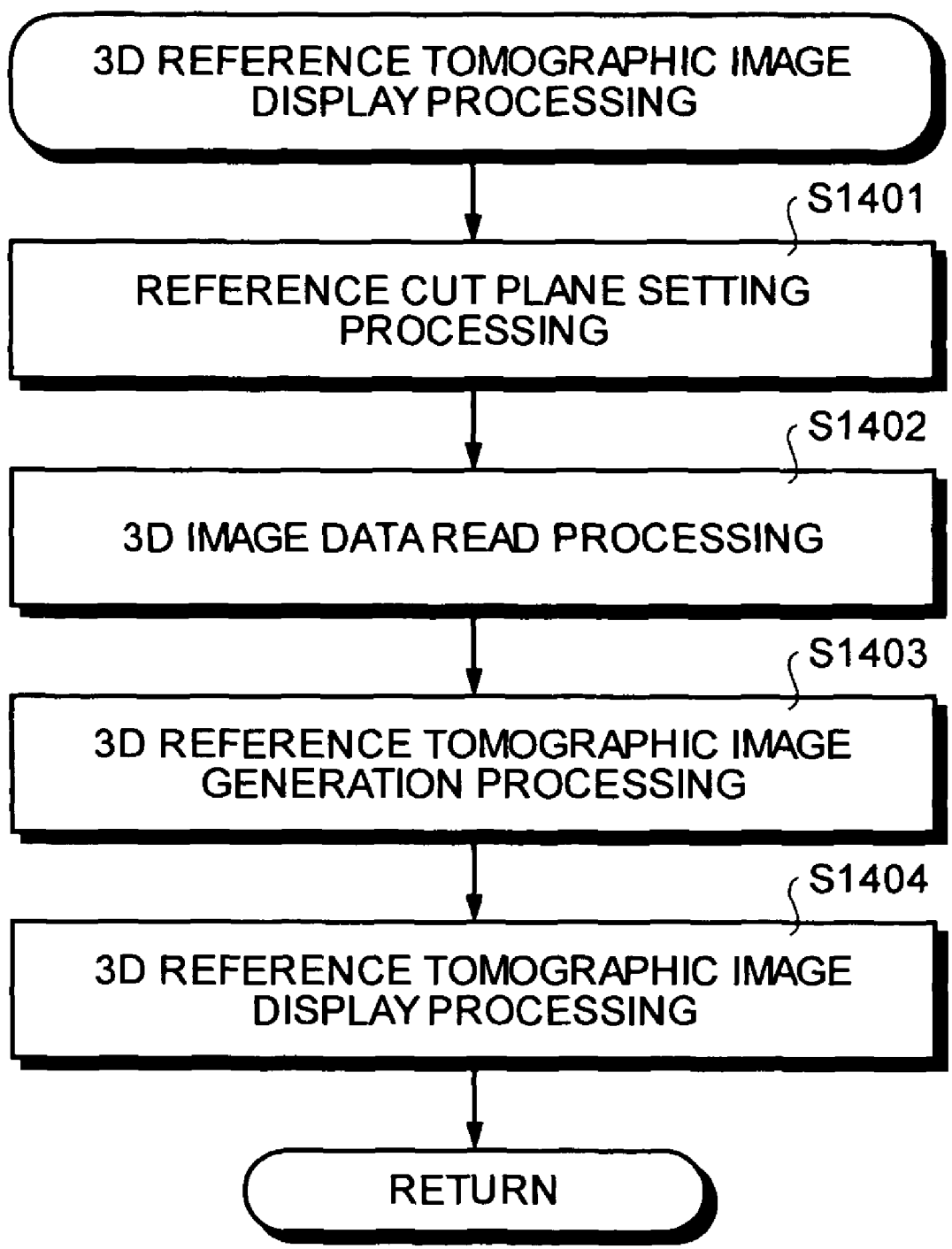
FIG. 50 is a flowchart showing processing steps executed until a 3D reference tomographic image display processing is completed in detail.
Figure 51:
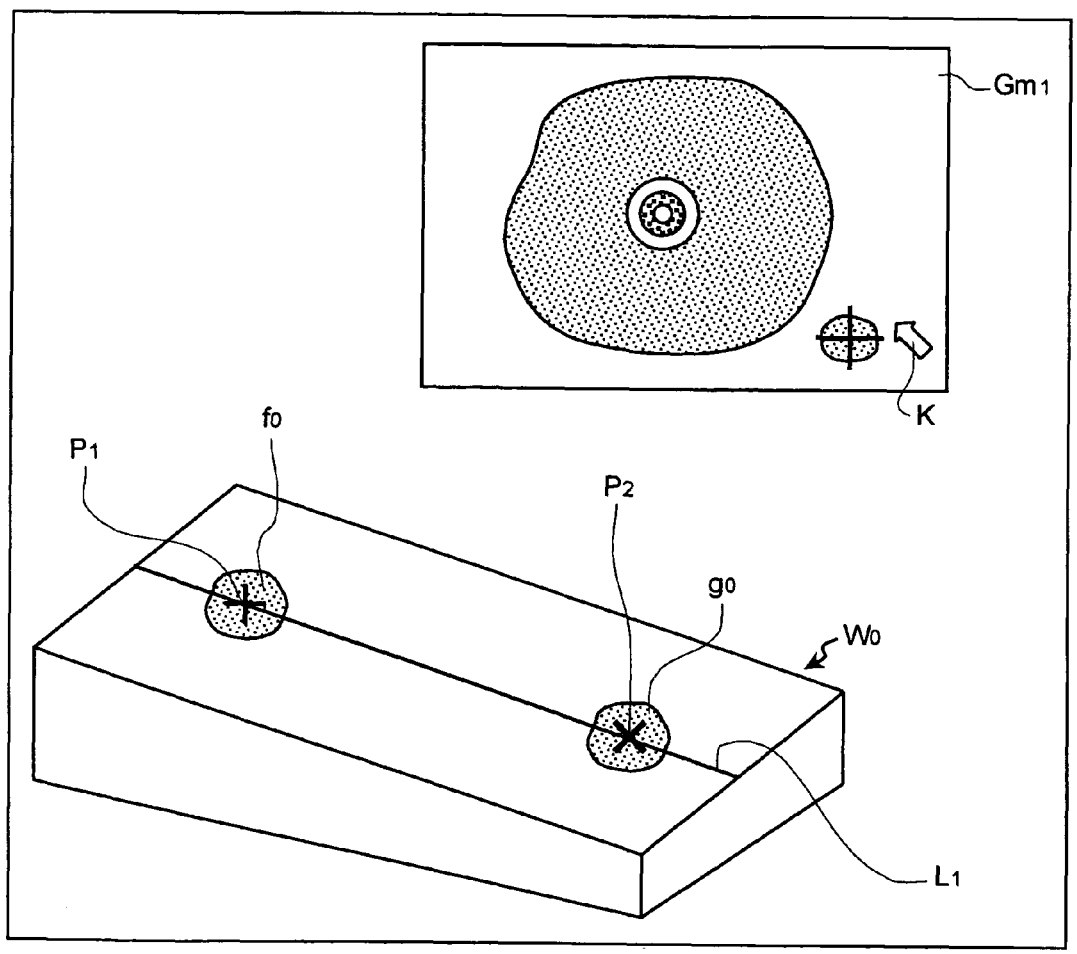
FIG. 51 is an explanatory view of a state in which a 3D reference tomographic image is displayed on the monitor screen.

The processing performed by the controller 63 at step S1205 for setting the reference cut plane and the rotation axis of the reference cut plane using the two designated points thus set, generating the 3D reference tomographic image data on the set reference cut plane, and then displaying the 3D reference tomographic image corresponding to the 3D reference tomographic image data on the monitor 9 (3D reference tomographic image display processing) is explained in detail. FIG. 50 is a flowchart showing processing steps executed until the controller 63 completes the 3D reference tomographic image display processing in detail. FIG. 51 is an explanatory view of a state in which the controller 63 displays the 3D reference tomographic image on the monitor screen.

Referring to FIGS. 50 and 51, if the controller 63 performs the processing at step S1204 to set the designated points $P_1$ and $P_2$ on, for example, the 2D image data $D_{m1}$ and the 2D image data $D_{m2}$, respectively, the cut plane operation unit 63a operates and outputs the straight line L that passes through the designated points $P_1$ and $P_2$ using the designated point information as shown in FIG. 45. In addition, the cut plane operation unit 63a operates and outputs the plane that includes the reference set point read from the storage unit 55a and the designated points $P_1$ and $P_2$ or the plane that includes the reference normal vector read from the storage unit 55a and the designated points $P_1$ and $P_2$. In this case, the controller 63 sets the plane operated and output by the cut plane operation unit 63 as the reference cut plane $H_0$, and the straight line L as the rotation axis of the reference cut plane $H_0$ (at step S1401).

The controller 63 reads the 3D image data generated at step S1203 from the image data storage unit 11 (at step S1402). The image data operation unit 55b generates 3D reference tomographic image data on the reference cut plane $H_0$ using this 3D image data (at step S1403). The controller 63 stores the 3D reference tomographic image data generated by the image data operation unit 55b in the image data storage unit 11. In addition, the controller 63 transmits the 3D reference tomographic image data to the monitor 9 through the display circuit 12. Thus, the controller 63 displays a 3D reference tomographic image $W_0$ corresponding to the 3D reference tomographic image data on the monitor 9 (at step S1404).

In this case, as shown in FIG. 51, the controller 63 displays a pancreatic duct tomographic image $f_0$ corresponding to the pancreatic duct image of the 2D image data and a bile duct tomographic image $g_0$ corresponding to the bile duct image of the 2D image data on the 3D reference tomographic image $W_0$. In addition, the controller 63 displays the designated point $P_1$ indicated by the first marker, the designated point $P_2$ indicated by the second marker, and an auxiliary line $L_1$ corresponding to the straight line L on the pancreatic duct tomographic image $f_0$ or the bile duct tomographic image $g_0$ while being superimposed thereon. It is preferable that the controller 63 display the first marker and the second marker on the monitor 9 in different manners. Specifically, the controller 63 displays the first marker that is, for example, "+" shaped and red on the monitor 9 while superimposing the first marker on the pancreatic duct tomographic image $f_0$. The controller 63 also displays the second marker that is, for example, "×" shaped and green on the monitor 9 while superimposing the second marker on the bile duct tomographic image $g_0$. Further, as shown in FIG. 51, the controller 63 controls the monitor 9 to output the 3D reference tomographic image $W_0$ and a desired 2D ultrasonic tomographic image on the same screen. By doing so, the 3D reference tomographic image $W_0$ and the desired 2D tomographic image, e.g., a 2D ultrasonic tomographic image $G_{m1}$ corresponding to the 2D image data $D_{m1}$ are output and displayed on the same monitor screen without superimposing on each other.

As can be seen, the controller 63 controls the first marker on the 2D ultrasonic tomographic image $G_{m1}$ and the first marker on the 3D reference tomographic image $W_0$ to be displayed on the screen of the monitor 9 in the same manner, and controls the first marker and the second marker to be displayed on the screen of the monitor 9 in different manners. Therefore, as shown in FIG. 51, for example, if the 2D ultrasonic tomographic image $G_{m1}$ on which the "+" shaped and red first marker that indicates the pancreatic duct is displayed is displayed on the screen of the monitor 9, a position of this first marker can be easily associated with that of the "+" shaped and red first marker displayed on the pancreatic duct tomographic image $f_0$ of the 3D reference tomographic image $W_0$. As a result, it is possible to prevent the pancreatic duct indicated by the first marker from being confused with the bile duct indicated by the second marker.

Figure 52:
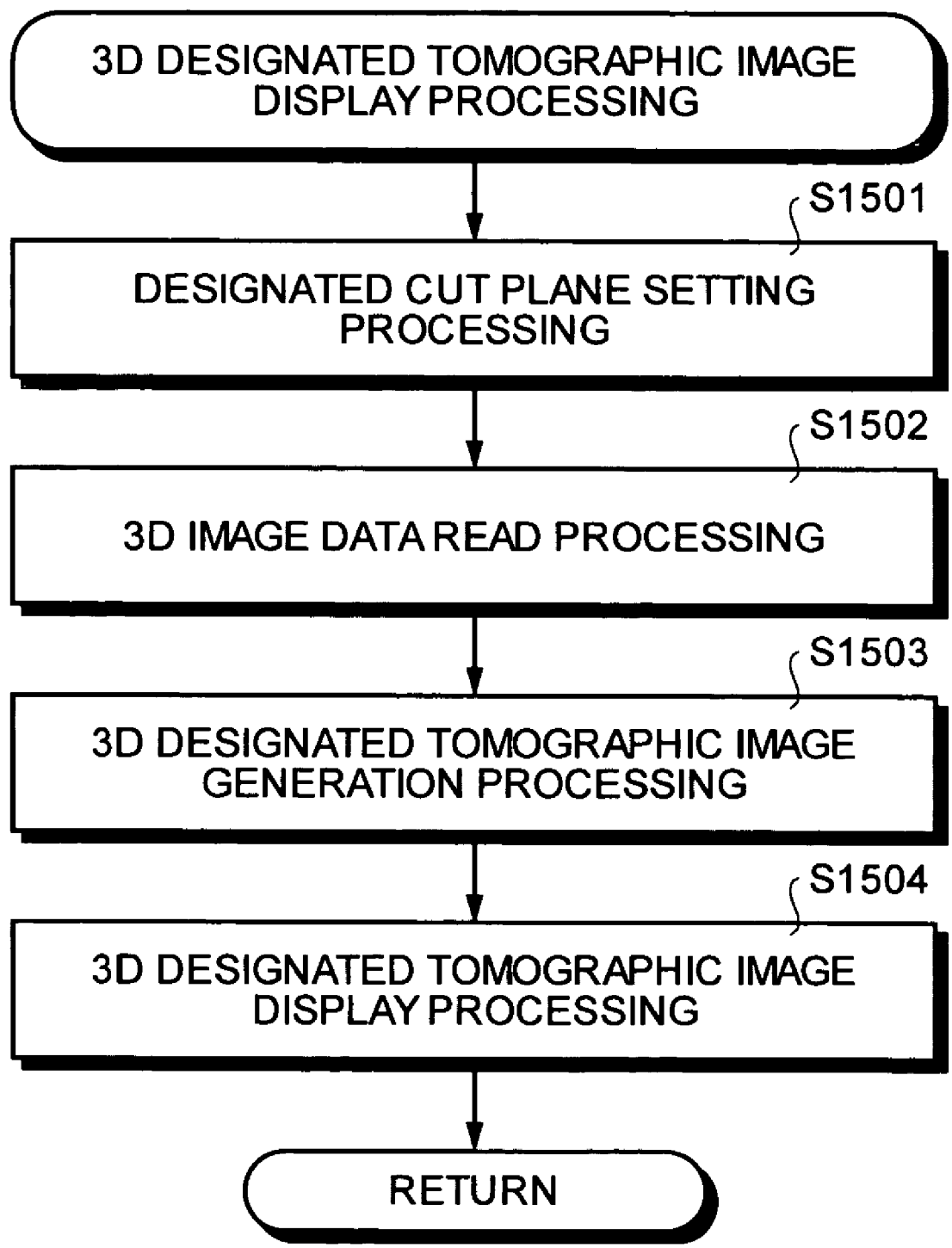
FIG. 52 is a flowchart showing processing steps executed until a 3D designated tomographic image display processing is completed in detail.
Figure 53:
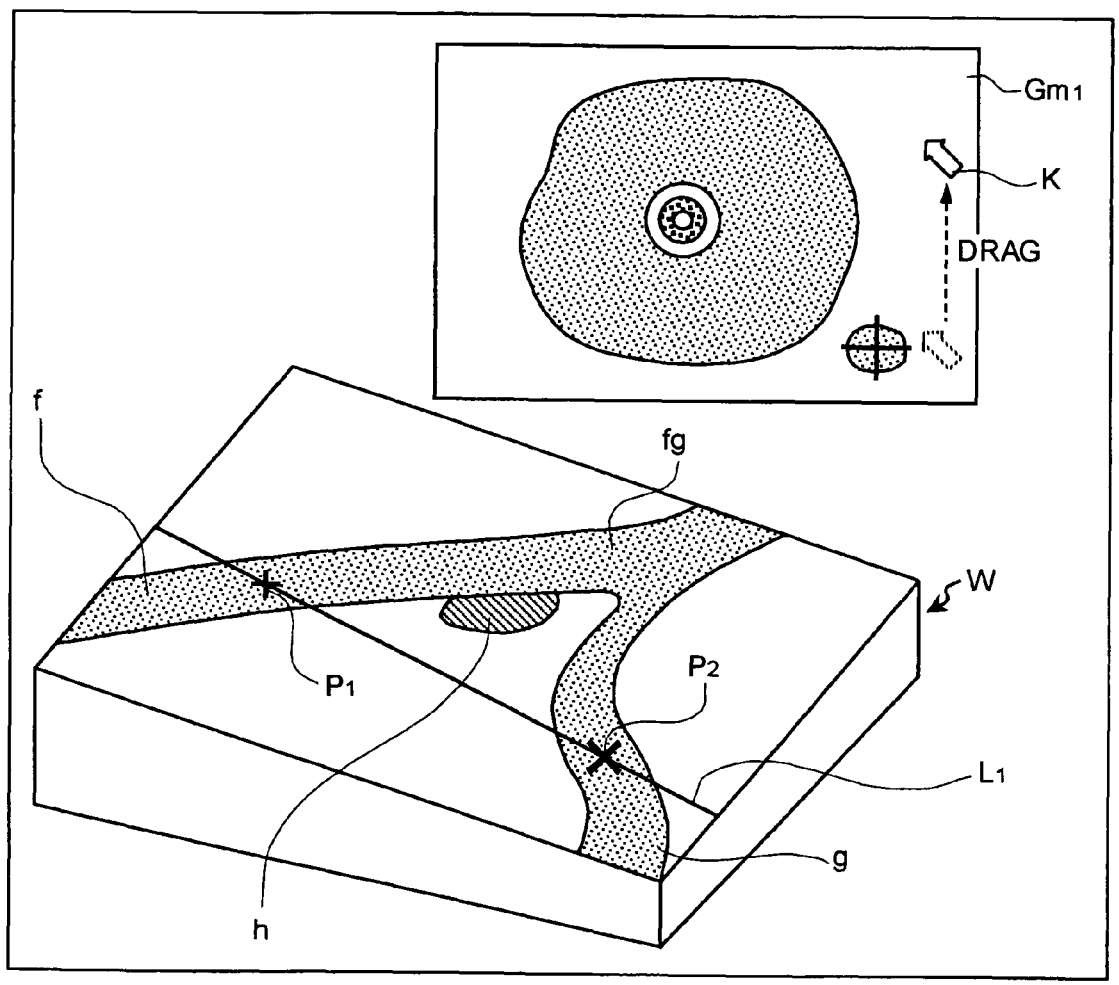
FIG. 53 is an explanatory view of a state in which a 3D designated tomographic image is displayed on the monitor screen.

The processing at step S1207 executed since the controller 63 sets the designated cut plane using the designated point information and the angle information, and generates the 3D designated tomographic image data on the designated cut plane thus set, until displaying the 3D designated tomographic image corresponding to the 3D designated tomographic image data (3D designated tomographic image display processing) is explained in detail. FIG. 52 is a flowchart showing processing steps executed until the controller 63 completes the 3D designated tomographic image display processing in detail. FIG. 53 is an explanatory view of a state in which the controller 63 displays the 3D designated tomographic image on the monitor screen.

Referring to FIGS. 52 and 53, the operator performs the drag operation or the like using the input device 52 to move the cursor K on the monitor 9 in a predetermined direction, e.g., a vertical direction of the screen and to input the angle θ according to the moving amount and moving direction of this cursor K as the angle information. In addition, the controller 63 accepts this angle information. If so, the cut plane operation unit 63a operates and outputs the plane obtained by rotating the reference cut plane $H_0$ around the straight line L set as the rotation axis by the angle θ, based on the angle θ corresponding to this angle information and the designated point information. The controller 63 sets the plane thus operated and output as the designated cut plane H (at step S1501). In this case, the cut plane operation unit 63a operates and outputs the designated cut plane H based on Equations (7) and (11), and using the angle θ and the respective pieces of coordinate information on the designated points $P_1$ and $P_2$.

If the designated cut plane H is set, the controller 63 reads the 3D image data generated at step S1203 from the image data storage unit 11 (at step S1502). The image data operation unit 55b then generates the 3D designated tomographic image data on the designated cut plane H using this 3D image data (at step S1503). The controller 63 stores the 3D designated tomographic image data generated by the image data operation unit 55b in the image data storage unit 11, and transmits the 3D designated tomographic image data to the monitor 9 through the display circuit 12. Thus, the controller 63 displays a 3D designated tomographic image W corresponding to this 3D designated tomographic image data on the monitor 9 (at step S1504).

In this case, as shown in FIG. 53, the controller 63 displays the pancreatic duct tomographic image f corresponding to the pancreatic duct image of the 2D image data, the bile duct tomographic image g corresponding to the bile duct image of the 2D image data, and a bile duct-to-pancreatic duct junction image fg that is a tomographic image of a junction between the bile duct and the pancreatic duct (a bile duct-to-pancreatic duct junction) of the 3D designated tomographic image data. Further, the controller 63 displays the designated point $P_1$ indicated by the first marker, the designated point $P_2$ indicated by the second marker, and the auxiliary line $L_1$ corresponding to the straight line L on the monitor screen while superimposing them on the pancreatic duct tomographic image f or the bile duct tomographic image g. Similarly to the instance of the 3D reference tomographic image $W_0$, it is preferable that the controller 63 display the first marker and the second marker on the screen in different manners. The controller 63 displays the first marker that is, for example, "+" shaped and red on the monitor screen while superimposing the first marker on the pancreatic duct tomographic image f, and the second marker that is, for example, "×" shaped and green on the monitor screen while superimposing the second marker on the bile duct tomographic image g. As shown in FIG. 53, the controller 63 controls the monitor 9 to output the 3D designated tomographic image W and the desired 2D ultrasonic tomographic image on the same monitor screen. By so controlling, the 3D designated tomographic image W and the desired 2D ultrasonic tomographic image, e.g., the 2D ultrasonic tomographic image $G_{m1}$ corresponding to the 2D image data $D_{m1}$ are output and displayed on the same monitor screen so as not to be superimposed on each other.

Therefore, if the operator performs the drag operation or the like using the input device 52 to input indication information for rotating the reference cut plane $H_0$ of the 3D reference tomographic image $W_0$ on which both the tomographic image of the pancreatic duct and that of the bile duct are displayed, i.e., to input the angle information on the angle θ by which the reference cut plane $H_0$ is rotated around the straight line L set as the rotation axis, the tomographic image approximated to the actual shape of the region of interest such as the bile duct-to-pancreatic duct junction image fg that is the characteristic site or the tumor tomographic image h that is the affected site can be easily obtained, as shown in FIG. 53. If a processing rate of the controller 63 is high enough at steps S1501 to S1504, the 3D designated tomographic image data on the designated cut plane having the rotation angle that changes according to an input amount by the drag operation is successively output to the monitor 9 synchronously with this drag operation. The operator can, therefore, further easily obtain the tomographic image of the region of interest such as the bile duct-to-pancreatic duct junction image fg or the tumor tomographic image h.

Figure 54:
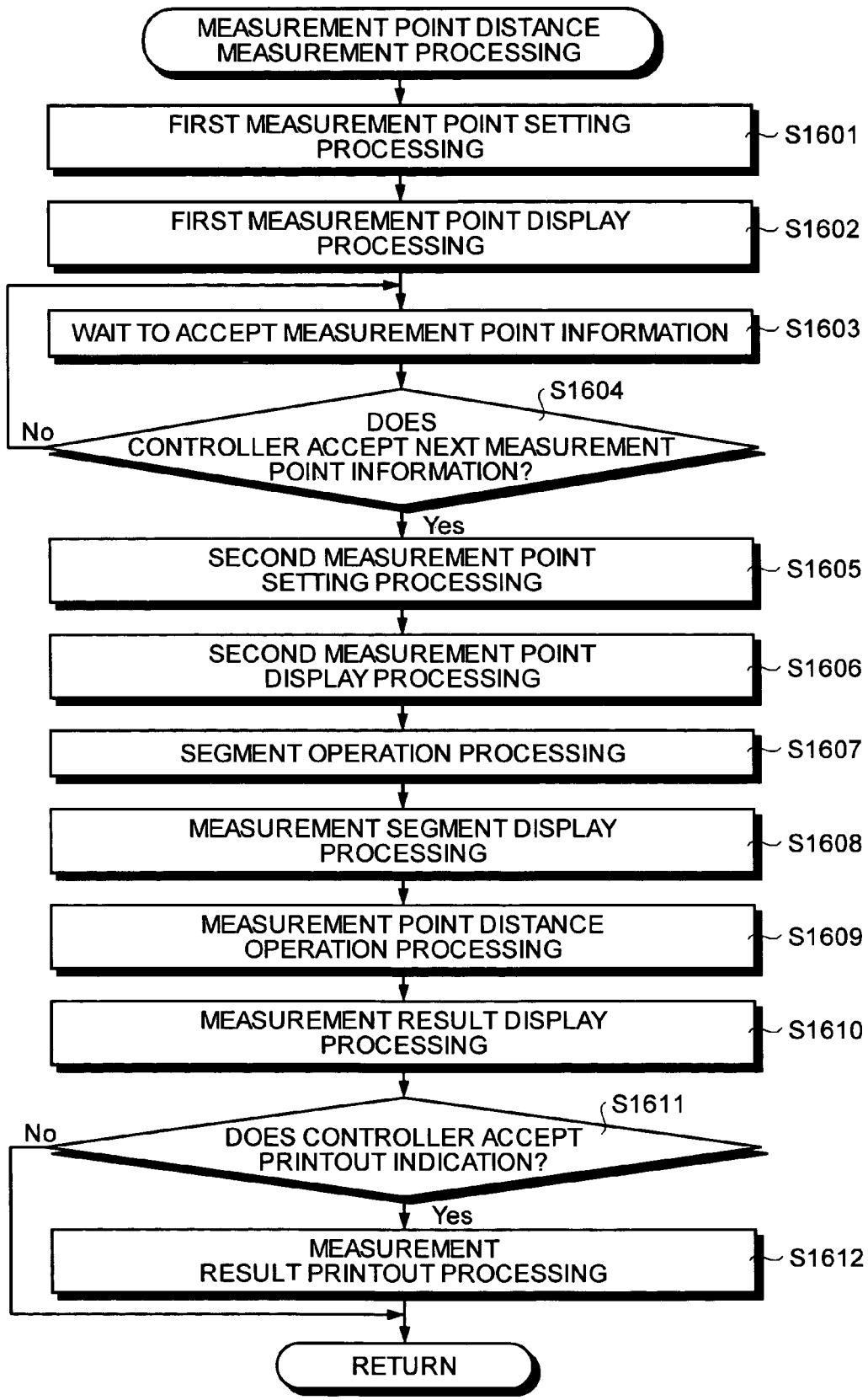
FIG. 54 is a flowchart showing respective processing steps executed until the ultrasonic diagnostic apparatus according to the sixth embodiment completes a measurement point distance measurement processing in detail.
Figure 55:
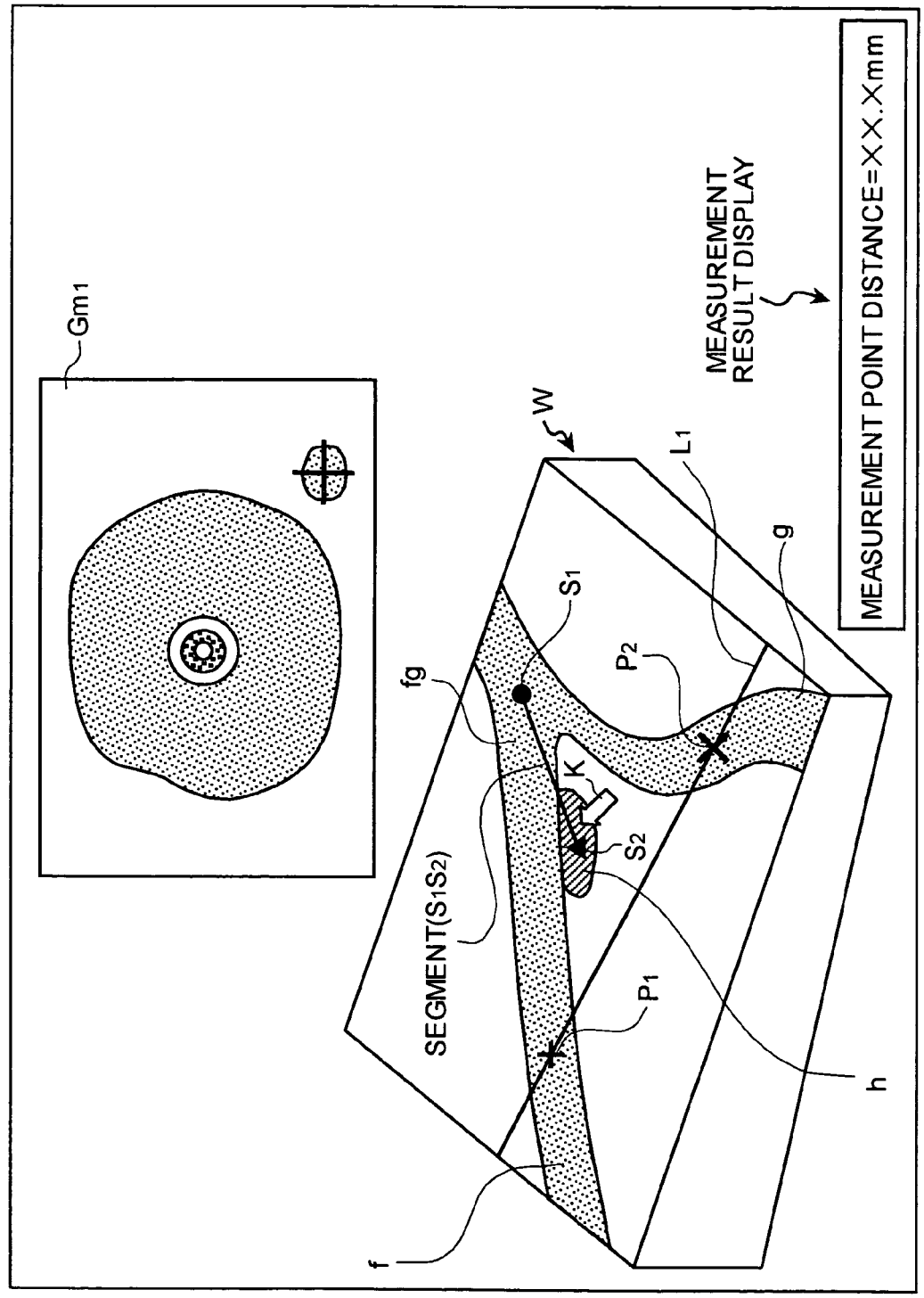
FIG. 55 depicts an example of display of the monitor if the measurement point distance between the two measurement points set on the 3D designated tomographic image is measured.

Respective processing steps executed until the controller 63 completes the measurement point distance measurement processing at step S1209 is explained in detail. FIG. 54 is a flowchart showing the respective processing steps executed until the controller 63 completes the measurement point distance measurement processing on the two measurement points designated on the 3D reference tomographic image or the 3D designated tomographic image in detail. FIG. 55 depicts an example of display of the monitor 9 if the controller 63 sets two measurement points on the 3D designated tomographic image W, on which the tumor tomographic image h that is the tomographic image of the region of interest is displayed, and measures a measurement point distance by the two measurement points.

Referring to FIGS. 54 and 55, if the operator operates the input device 52, e.g., the mouse to move the cursor displayed on the screen of the monitor 9 to a desired position on the 3D reference tomographic image or the 3D designated tomographic image, to designate the desired position, and to input measurement point information corresponding to the desired position, the controller 63 accepts this measurement point information. In addition, the controller 63 performs the same processing as that at steps S1101 to S1103. Namely, the controller 63 sets the measurement point $S_1$ based on this measurement point information, displays the first measurement marker indicating the measurement position $S_1$ at this desired position, and then turns into a standby state of waiting to accept the next measurement point information (at steps S1601 to S1603). In this case, the controller 63 displays the first measurement marker indicating the first measurement point $S_1$ at, for example, the position of the bile duct-to-pancreatic duct joint image fg on the 3D designated tomographic image W while superimposing the first measurement marker on the bile duct-to-pancreatic duct joint image fg. If the operator does not operate the input device 52 to input the next measurement point information, then the controller 63 does not accept the next measurement point information ("No" at step S1604) but maintains this standby state.

If the operator operates the input device 52 to input the next measurement information for designating a measurement point at the next desired position, similarly to the instance of the measurement point $S_1$, the controller 63 accepts the input of the next measurement point information ("Yes" at step S1604). In addition, the controller 63 performs the same processing as that at steps S1105 to S1108. Namely, the controller 63 sets the measurement point $S_2$ based on this next measurement point information as the second measurement position, and displays a second measurement marker indicating the measurement position $S_2$ at this another desired position. Further, the controller 63 operates and outputs the segment $(S_1S_2)$ that connects the measurement points $S_1$ to $S_2$, and displays an auxiliary line indicating the segment $(S_1S_2)$ thus obtained on the monitor screen (at steps S1605 to S1608). In this case, the controller 63 displays the second measurement marker indicating measurement point $S_2$ at the position of the tumor tomographic image h on the 3D designated tomographic image W, which position is designated as this another desired position, and displays the auxiliary line indicating the segment $(S_1S_2)$ on the 3D designated tomographic image W while superimposing the auxiliary line on the 3D designated tomographic image W.

The distance measurement unit 63b performs the same processing as that at steps S1109 and S1110. Namely, the distance measurement unit 63b operates and outputs the measurement point distance based on the measurement points $S_1$ and $S_2$ set by the controller 63. In addition, as shown in FIG. 55, the distance measurement unit 63b converts the obtained measurement point distance into a value in a desired unit as a measurement result, and displays the measurement result on the monitor 9 (at steps S1609 and 1610). Thereafter, if the operator operates the input device 52 to input indication information on a printout indication for printing out the measurement result of the measurement point distance onto a paper or the like, the controller 63 accepts a printout indication base on this indication information ("Yes" at step S1611). In addition, the controller 63 performs the same processing as that at step S1112 to control the printer 53 to output the measurement result of the measurement point distance (at step S1612). If the operator does not operate the input device 52 to input the printout indication information, the controller 63 does not accept the printout indication ("No" at step S1611). That is, the controller 63 completes this measurement point distance measurement processing without controlling the printer 53 to output the measurement result of the measurement point distance. As a consequence, the operator can easily locate the tumor tomographic image h as the region of interest, accurately measure the distance between the bile duct-to-pancreatic duct joint image fg that is the characteristic site and the tumor tomographic image h, and thereby efficiently performs an ultrasonic diagnosis on the subject.

Further, while the operator operates the input device 52 to move the cursor K on the screen to a desired position on the 2D ultrasonic tomographic image $G_{m2}$, the controller 63 regards the position of the cursor K as the virtual measurement point $S_2$, operates a length of the segment $(S_1S_2)$, and displays the measurement result on the monitor 9. If so, the operator can recognize the distance between the measurement points $S_1$ and $S_2$ at real time.

If the operator operates the input device 52 to input indication information for indicating deletion of the first marker, the second marker, the auxiliary line, the first measurement marker, the second measurement marker, or the 2D ultrasonic tomographic image from the monitor screen, then the controller 63 may control the monitor 9 to delete the first marker, the second marker, the auxiliary line, the first measurement marker, the second measurement marker, or the 2D ultrasonic tomographic image in response to an indication based on this indication information. If the operator operates the input device 52 to input indication information for indicating re-display of the first marker, the second marker, the auxiliary line, the first measurement marker, the second measurement marker, or the 2D ultrasonic tomographic image on the monitor screen, the controller 63 may control the monitor 9 to re-display the first marker, the second marker, the auxiliary line, the first measurement marker, the second measurement marker, or the 2D ultrasonic tomographic image in response to an indication based on this indication information. If the operator operates the input device 52 to input switchover indication information for indicating switching of the 2D ultrasonic tomographic image displayed on the same monitor screen as the 3D reference tomographic image or the 3D designated tomographic image to another 2D ultrasonic tomographic image, the controller 63 may control the monitor 9 to switch the 2D ultrasonic tomographic image displayed on the monitor screen to another 2D ultrasonic tomographic image in response to an indication based on this indication information.

In the sixth embodiment of the present invention, the instance of setting the two measurement points at the respective desired positions on the 3D designated tomographic image is explained. However, the present invention is not limited to this instance. The two measurement points may be set at respective desired positions on the 3D reference tomographic image, and operate and output the measurement point distance for the two measurement points. The two measurement points may be set at respective desired positions on the 2D ultrasonic tomographic image, and operate and output the measurement point distance for the two measurement points.

According to the sixth embodiment of the present invention, the ultrasonic diagnostic apparatus constituted as follows can be realized. That is, the 3D image data is generated using a plurality of pieces of 2D image data associated with the respective pieces of position data on the moving path or moving direction of the probe 2 which performs the 3D scan. If the designated point information for designating the two designated points on the desired 2D ultrasonic tomographic image is input, the designated points corresponding to the designated point information are set on each 2D image data corresponding to the 2D ultrasonic tomographic image. The reference cut plane including these two designated point and the rotation axis of the reference cut plane that passes through the two designated points are operated and output. Based on this 3D image data and the reference cut plane, the 3D reference tomographic image on the reference cut plane is displayed on the monitor screen. Further, if the angle information on the desired rotation angle of the reference cut plane is input, the designated cut plane obtained by rotating this reference cut plane by the angle corresponding to the angle information is operated and output. Thereafter, based on this 3D image data and the designated point information, the 3D designated tomographic image on the designated cut plane is displayed on the monitor screen. Furthermore, if the two measurement points are designated at the respective desired positions on the 3D reference tomographic image or the 3D designated tomographic image displayed on the monitor screen, the measurement point distance that is the Euclidean distance between the two measurement points is operated and output based on the respective pieces of coordinate information corresponding to the desired positions. Therefore, the tomographic image of the region of interest such as the characteristic site in the living body, e.g., the bile duct-to-pancreatic duct joint or the affected side, e.g., the tumor can be easily displayed on and output to the one monitor screen. In addition, the length of the region of interest can be accurately measured.

The operator can easily locate the tomographic image of the region of interest, accurately grasp the size, the length, or the positional relationship in the living body of the located region of interest using the ultrasonic diagnostic apparatus. The in vivo ultrasonic diagnosis can be thereby carried out efficiently. Accordingly, if the operator appropriately selects the 3D designated tomographic image and the measurement points, then the operator can acquire more accurately and more objectively information as to at a position of how distant (in millimeters) from the bile duct-to-pancreatic duct joint the affected site is present, by what length (in millimeters) the affected site spreads along a blood vessel such as the bile duct or the pancreatic duct, or how a largest diameter (in millimeters) of the affected site is. The ultrasonic diagnostic apparatus is thus useful for determination of a surgical operation plan or a cutting range before a surgical operation. Besides, the operator can determine more accurately and more objectively a treatment effect of an anticancer agent, a radiation therapy, or the like on the affected site with the passage of time.

A seventh embodiment of the present invention is explained in detail. In the sixth embodiment, if the two measurement points are designated on the respective desired positions on the desired tomographic image, the measurement points are set at the coordinates corresponding to the desired positions. In addition, the measurement point distance for the two measurement points is operated and output. In the seventh embodiment, an ultrasonic diagnostic apparatus is constituted so that if at least three measurement points are designated at respective desired positions on a desired tomographic image, then the measurement points are set at coordinates corresponding to the desired positions, and so that a length such as a peripheral length of a measurement range determined by the at least three measurement points is operated and output.

Figure 56:
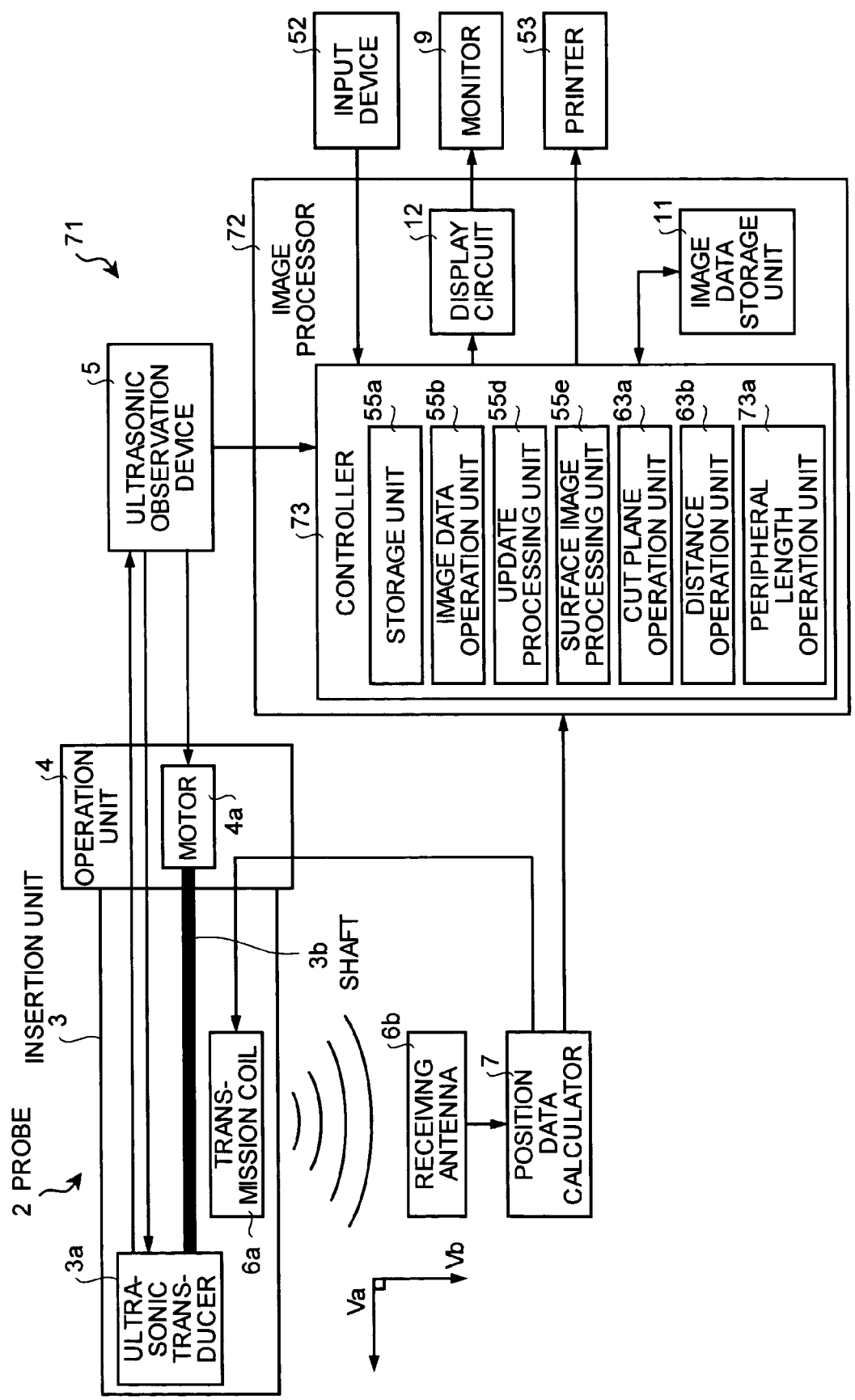
FIG. 56 is a block diagram that depicts schematic configuration of an ultrasonic diagnostic apparatus according to a seventh embodiment of the present invention.

FIG. 56 is a block diagram that depicts schematic configuration of the ultrasonic diagnostic apparatus according to the seventh embodiment of the present invention. The ultrasonic diagnostic apparatus 71 shown in FIG. 56 is constituted as follows, as compared with the ultrasonic diagnostic apparatus 61 according to the sixth embodiment. An image processor 72 is provided instead of the image processor 62. The image processor 72 includes a controller 73 instead of the controller 63. The controller 73 additionally includes a peripheral length operation unit 73a. The controller 73 is realized by a ROM that stores various types of data such as a processing program, a RAM that stores each operation parameter, a CPU that executes the processing program stored in the ROM, and the like, substantially similarly to the controller 63. The other constituent elements of the ultrasonic diagnostic apparatus 71 are equal to those of the ultrasonic diagnostic apparatus 61 according to the sixth embodiment. Like constituent elements as those according to the sixth embodiment are denoted by like reference symbol, respectively.

Figure 57:
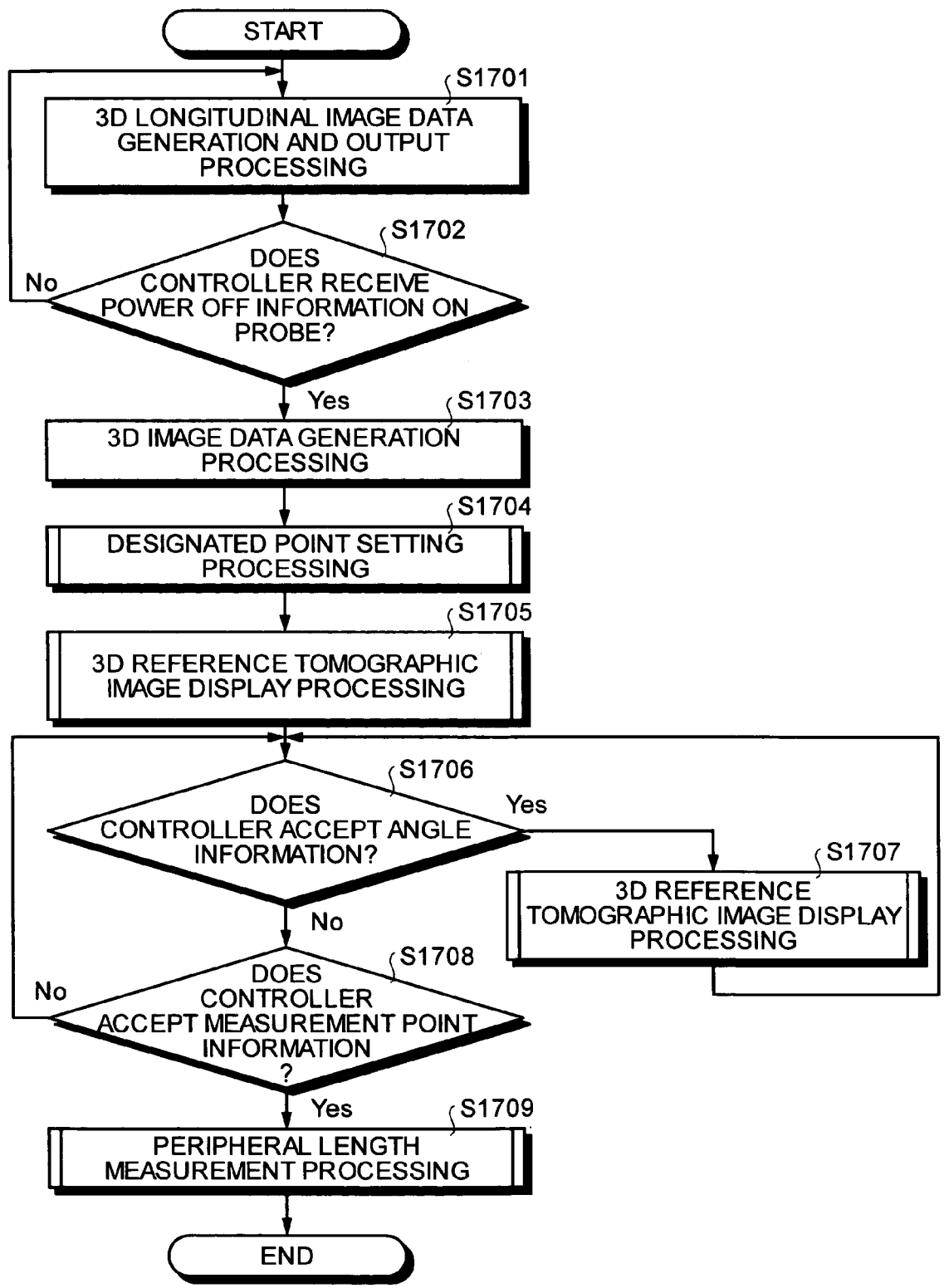
FIG. 57 is a flowchart showing respective processing steps executed until a peripheral length of a measurement range set on the 3D reference tomographic image or the 3D designated tomographic image is measured.

FIG. 57 is a flowchart showing respective processing steps executed since the controller 73 displays a band-shaped or stereoscopic 3D longitudinal image on the screen of the monitor 9, generates 3D image data using n pieces of 2D image data on the spatial coordinate system xyz, and sets at least three measurement points on 3D reference tomographic image data or 3D designated tomographic image data generated based on this 3D image data until measuring a peripheral length of a measurement range surrounded by the at least three measurement points. Referring to FIG. 57, if the ultrasonic observation device 5 generates 2D image data based on the echo signal and the position data calculator 7 calculates position data on a position at which this echo signal is obtained, the controller 73 executes the respective processing steps S1701 to S1707 similarly to steps S1201 to S1207.

Thereafter, the operator observes the 3D reference tomographic image or the 3D designated tomographic image displayed on the screen of the monitor 9 and checks whether a desired region of interest is displayed on the screen of the monitor 9. If confirming that the desired region of interest is displayed on the screen of the monitor 9, the operator operates the input device 52 to perform an operation for inputting measurement point information on measurement points designated on each tomographic image displayed on the monitor screen to the controller 73 without performing an operation for inputting the angle information to the controller 73. In this case, the controller 73 does not accept the angle information ("No" at step S1706) but accepts the measurement point information ("Yes" at step S1708). The controller 73 then sets at least three measurement points on the 3D reference tomographic image data or the 3D designated tomographic image data, and operates and outputs the peripheral length of the measurement range surrounded by the at least three measurement points. In addition, the controller 73 displays and outputs or prints out an operation result obtained as a measurement result of the peripheral length (at step S1709). Details of a processing performed since the measurement points are set on the 3D reference tomographic image or the 3D designated tomographic image until the measurement result of the peripheral length is displayed and output or printed out (a peripheral length measurement processing) is explained later.

If the operator does not operate the input device 52 to input the angle information and the measurement point information, then the controller 73 does not accept the angle information ("No" at step S1706), does not accept the measurement point information ("No" at step S1708), but repeatedly executes the processing step S1706 and the following. In this case, the controller 73 controls the monitor 9 to maintain a state in which the 3D reference tomographic image or 3D designated tomographic image is displayed on the monitor screen until the controller 73 accepts the angle information or the measurement point information input by the operator's input operation.

Figure 58:
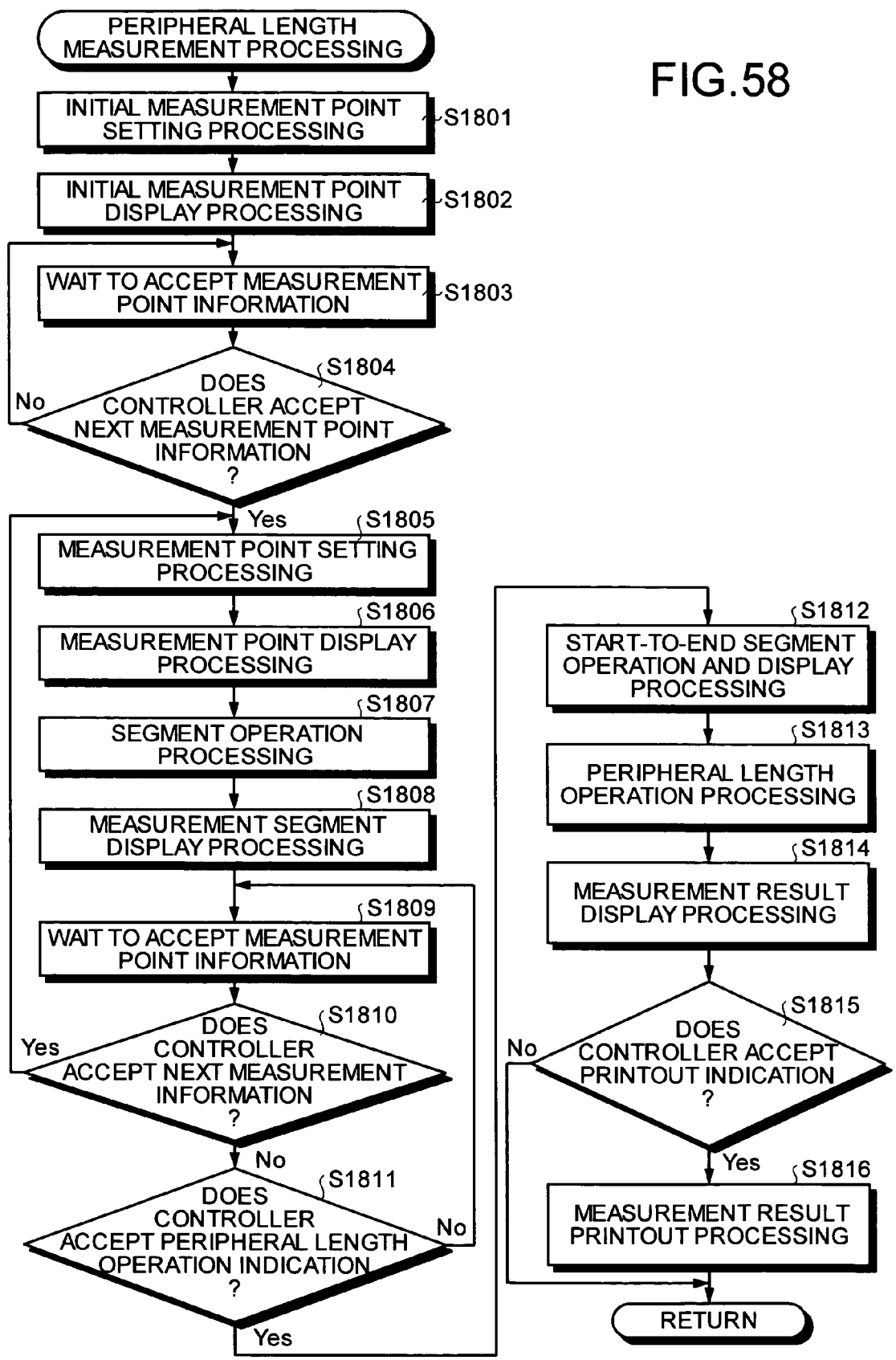
FIG. 58 is a flowchart showing respective processing steps executed a peripheral length measurement processing is completed in detail.
Figure 59:
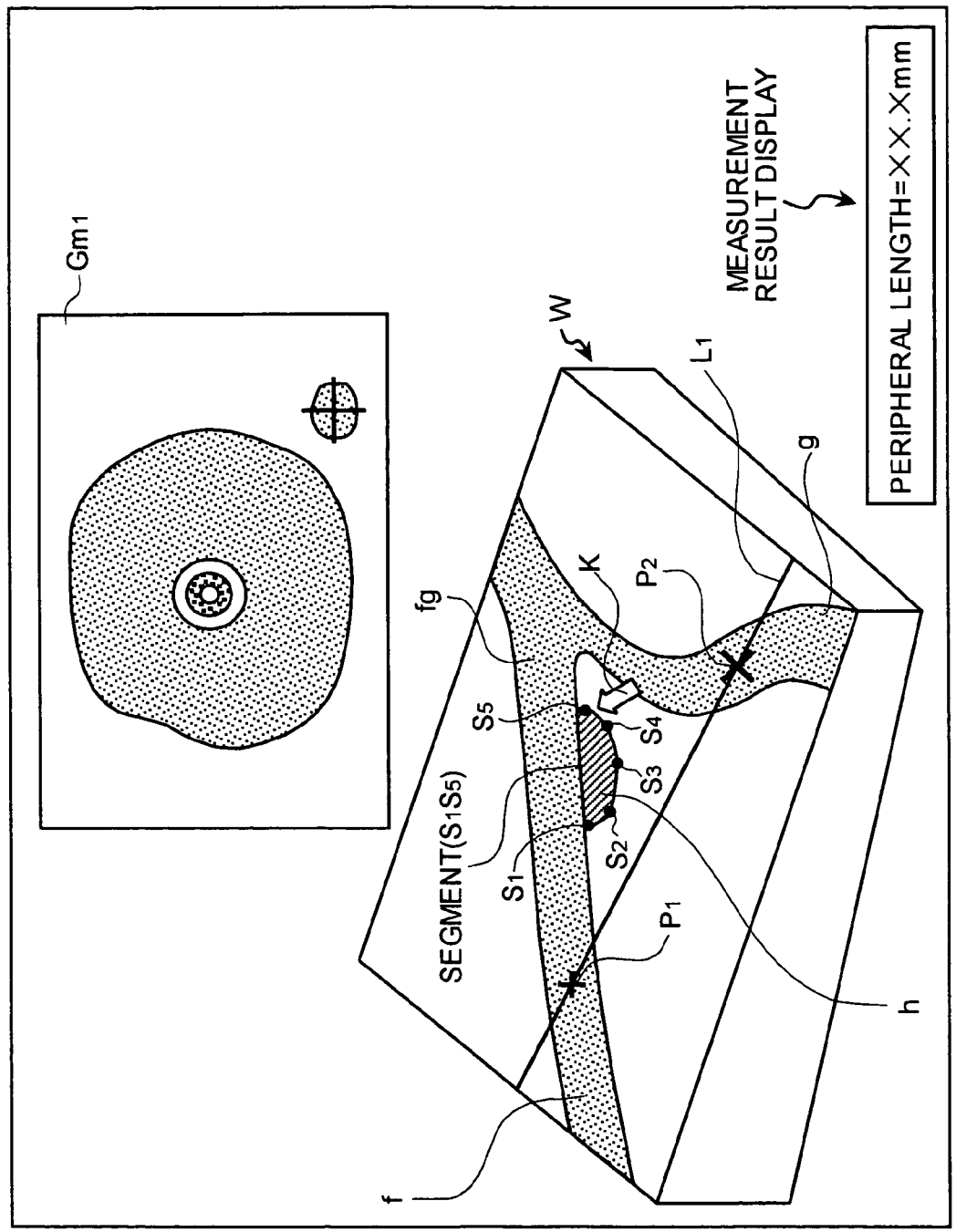
FIG. 59 depicts an example of display of the monitor if the peripheral length of a measurement range set on the 3D designated tomographic image is measured.

Respective processing steps executed until the controller 73 completes the peripheral length measurement processing at step S1709 is explained in detail. FIG. 58 is a flowchart showing the respective processing steps executed until the controller 73 completes the peripheral length measurement processing related to the peripheral length of the measurement range designated on the 3D reference tomographic image or the 3D designated tomographic image in detail. FIG. 59 depicts an example of the display of the monitor 9 if the controller 73 sets a predetermined number of, for example, five measurement points on the 3D designated tomographic image W on which the tumor tomographic image h that is the tomographic image of the region of interest is displayed, and measures the peripheral length of the measurement range surrounded by the five measurement points.

Referring to FIGS. 58 and 59, if the operator operates the input device 52, e.g., the moue, to move the cursor displayed on the screen of the monitor 9 to a desired position on the 3D reference tomographic image or the 3D designated tomographic image, to designate the desired position, and to input measurement point information corresponding to the desired position, then the controller 73 accepts this measurement point information, and performs the same processing as that at steps S1601 to S1603. Specifically, the controller 73 sets the measurement point $S_1$ based on this measurement point information as an initial measurement point, displays the first measurement marker indicating the measurement point $S_1$ at this desired position, and turns into a standby state of waiting to accept the next measurement point information (at steps S1801 to S1803). As shown in FIG. 59, for example, the controller 73 displays the first measurement marker indicating the measurement point $S_1$ at a position, designated as the desired position, near a boundary between the tumor tomographic image h and the pancreatic duct tomographic image f on the 3D designated tomographic image while superimposing the first measurement marker on the 3D designated tomographic image W. If the operator does not operate the input device 52 to input the next measurement point information, then the controller 73 does not accept the next measurement point information ("No" at step S1804) but maintains this standby state.

If the operator operates the input device 52 to input the next measurement position information for designating the measurement position at another desired position, then the controller 73 accepts the input next measurement point information ("Yes" at step S1804), and performs the same processing as that at steps S1605 to S1608. Specifically, the controller 73 sets the measurement point $S_2$ based on this next measurement point information as the second measurement point, and displays the second measurement marker indicating the measurement point $S_2$ at this another desired position. Further, the controller 73 operates and outputs the segment ($S_1S_2$) that connects the measurement point $S_1$ and $S_2$ to each other, and displays an auxiliary line indicating the obtained segment ($S_1S_2$) on the monitor screen (at steps S1805 to S1808). As shown in FIG. 59, for example, the controller 73 displays the second measurement marker indicating the measurement position $S_2$ at the position, designated as this another desired position, near surroundings of the tumor tomographic image h on the 3D designated tomographic image W while superimposing the second measurement marker on the image W. In addition, the controller 73 displays the auxiliary line indicating the segment ($S_1S_2$) on the monitor screen while superimposing the auxiliary line on the 3D designated tomographic image W. The controller 73 then turns into a standby state of waiting to accept the next measurement point information (at step S1809).

If the operator operates the input device 52 to input the next measurement point information, then the controller 73 accepts this next measurement point information ("Yes" at step S1810), and repeatedly executes the processing step S1805 and the following. Namely, the controller 73 repeatedly executes the processing steps S1805 to S1809 for each of pieces of measurement point information successively input by operator's input operation. As a result, the controller 73 sets measurement points according to the number of the times of the operator's input operation on the 3D reference tomographic image data or the 3D designated tomographic image data. If performing the processing at step S1807, the controller 73 operates and outputs a segment that connects a newly set measurement point to the measurement point set just before the new measurement point.

If the operator operates the input device 52 to designate, for example, the measurement point $S_1$ near the boundary between the tumor tomographic image h and the pancreatic duct tomographic image f, and to designate measurement points $S_2$ to $S_5$ to surround the tumor tomographic image h, the controller 73 sets the measurement points $S_1$ to $S_5$ on the 3D designated tomographic image data corresponding to the respective operator's designated positions. In addition, as shown in FIG. 59, a first marker to a fifth marker corresponding to the measurement positions $S_1$ to $S_5$, respectively, are displayed on the monitor screen while superimposing the first to the fifth markers on the 3D designated tomographic image W so as to surround the tumor tomographic image h. If the measurement point $S_2$ is newly set, the controller 73 operates and outputs an auxiliary line corresponding to the segment ($S_1S_2$) between the measurement point $S_2$ and the measurement point $S_1$ set just before the measurement point $S_2$. In addition, the controller 73 displays the auxiliary line corresponding to the segment ($S_1S_2$) on the monitor screen while superimposing the auxiliary line on the 3D designated tomographic image W. If the measurement point $S_3$ is newly set, the controller 73 operates and outputs a segment ($S_2S_3$) between the measurement point $S_3$ and the measurement point $S_2$ set just before the measurement point $S_3$, similarly to the instance of the segment ($S_1S_2$). In addition, the controller 73 displays an auxiliary line corresponding to the segment ($S_2S_3$) on the monitor screen while superimposing the auxiliary line on the 3D designated tomographic image W. If the measurement point $S_4$ is newly set, the controller 73 operates and outputs a segment ($S_3S_4$) between the measurement point $S_4$ and the measurement point $S_3$ set just before the measurement point $S_4$, similarly to the segment ($S_1S_2$). In addition, the controller 73 displays an auxiliary line corresponding to the segment ($S_3S_4$) on the monitor screen while superimposing the auxiliary line on the 3D designated tomographic image W. If the measurement point $S_5$ is newly set, the controller 73 operates and outputs a segment ($S_4S_5$) between the measurement point $S_5$ and the measurement point $S_4$ set just before the measurement point $S_5$, similarly to the segment $(S_1S_2)$. In addition, the controller 73 displays an auxiliary line corresponding to the segment $(S_4S_5)$ on the monitor screen while superimposing the auxiliary line on the 3D designated tomographic image W.

If the operator does not operate the input device 52 to input the next measurement point information and to input indication information for indicating operation and output of the peripheral length of the measurement range surrounded by the at least three measurement points (peripheral length operation indication information), then the controller 73 does not accept the next measurement point information ("No" at step S1810) and does not accept a peripheral length operation indication corresponding to the peripheral length operation indication information ("No" at step S1811). If so, the controller 73 repeatedly executes the processing step S1809 and the following.

On the other hand, if the operator operates the input device 52 to input the peripheral length operation indication information without inputting the next measurement point information, then the controller 72 does not accept the next measurement point information ("No" at step S1810), but accepts the peripheral length operation indication corresponding to the peripheral length operation indication information ("Yes" at step S1811). Thereafter, the controller 73 operates and outputs a start-to-end point segment that connects the initial measurement point set at step S1801 to a latest measurement point set before the peripheral length operation indication is accepted, that is, the last measurement point. In addition, the controller 73 displays an auxiliary line corresponding to the start-to-end point segment on the screen (at step S1812). For example, if the five measurement points $S_1$ to $S_5$ are successively input in all by the operator's input operation, then the controller 73 operates and outputs a segment $(S_1S_5)$ that connects the measurement point $S_1$ to the measurement point $S_5$ and displays an auxiliary line corresponding to the obtained segment $(S_1S_5)$ on the screen.

The distance operation unit 63b then operates and outputs Euclidean lengths between the respective pairs of measurement points, i.e., a length of each segment obtained at step S1807, and a length of the start-to-end point segment obtained at step S1812 based on respective pieces of coordinate information on the measurement points set by the operation unit 73. It is noted that the measurement points set by the controller 73 on the 3D reference tomographic image data or the 3D designated tomographic image data can be represented by position vectors on the spatial coordinate system xyz, similarly to the measurement points set on the 3D longitudinal image data. This results from the fact that the 3D reference tomographic image data or the 3D designated tomographic image data is present on the spatial coordinate system xyz. Accordingly, the distance operation unit 63b can operate and output the length of each segment and that of the start-to-end point segment using the vector components of the position vectors of the respective measurement points typically represented by Equation (4) and (5) based on Equation (6).

If the distance operation unit 63b operates and outputs the length of each segment and that of the start-to-end point segment, then the peripheral length operation unit 73a adds up all the lengths of the respective segment and that of the start-to-end point segment operated and output by the distance operation unit 63b, and operates and outputs the peripheral length of the measurement range surrounded by the measurement points set by the controller 73 (at step S1813). As shown in FIG. 59, for example, if the controller 73 sets the measurement points $S_1$ to $S_5$ so as to surround the tumor tomographic image h, the peripheral length operation unit 73a adds up the length of the segment $(S_1S_2)$, the length of the segment $(S_2S_3)$, the length of the segment $(S_3S_4)$, the length of the segment $(S_4S_5)$, and the length of the start-to-end point segment $(S_1S_5)$ operated and output by the distance operation unit 63b. The peripheral length operation unit 73a thereby operates and outputs the peripheral length of the measurement range surrounded by the measurement points $S_1$ to $S_5$, i.e., the peripheral length of the tumor tomographic image h. Thereafter, the controller 73 converts the peripheral length operated and output by the peripheral length operation unit 73a into a value in a desired unit, and displays the peripheral length on the monitor 9 as a measurement result (at step S1814).

If the controller 73 accepts the peripheral length operation indication while setting only two measurement points, then the distance operation unit 63b operates and outputs the Euclidean distance between these two measurement points. In addition, the peripheral length operation unit 73a operates and output the Euclidean distance operated and output by the distance operation unit 63b as the peripheral length. In other words, if the controller 73 accepts the peripheral length operation indication while setting only two measurement points, the distance operation unit 63b and the peripheral length operation unit 73a operate and output a distance equal to the measurement point distance.

If the operator operates the input device 52 to input indication information for indicating printout of this peripheral length measurement result onto a paper or the like, the controller 73 accepts a printout indication corresponding to the indication information ("Yes" at step S1815). In addition, the controller 73 performs the same processing as that at step S1612 to control the printer 53 to output this peripheral length measurement result (at step S1816). If the operator does not operate the input device 52 to input the indication information on this printout indication, the controller 73 does not accept the printout indication ("No" at step S1815). That is, the controller 73 completes this peripheral length measurement processing without controlling the printer 53 to print out the measurement result. If this peripheral length measurement processing is completed, then the operator can accurately measure the peripheral length of the tumor tomographic image h located as the region of interest, and thereby highly accurately estimate the size of the affected site such as the tumor before a surgical operation.

Figure 60:
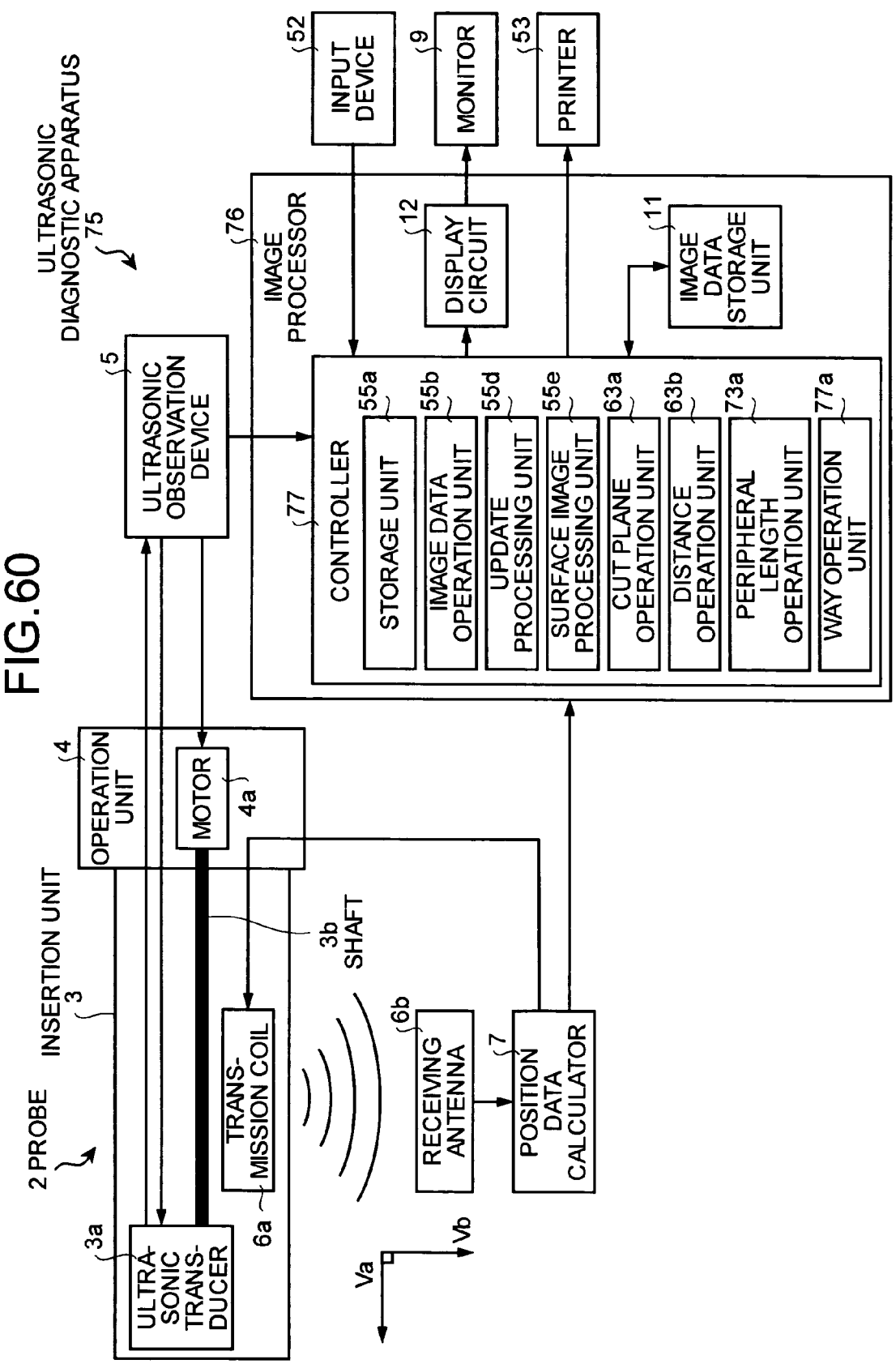
FIG. 60 is a block diagram that depicts schematic configuration of an ultrasonic diagnostic apparatus according to a modification of the seventh embodiment.

In the seventh embodiment, the peripheral length of the measurement range is measured based on the respective pieces of coordinate information on the measurement points set on the 3D designated tomographic image. However, the present invention is not limited to this method. A way determined by these measurement points may be measured. FIG. 60 is a block diagram that depicts schematic configuration of an ultrasonic diagnostic apparatus according to a modification of the seventh embodiment of the present invention. This ultrasonic diagnostic apparatus 75 is constituted as follows, as compared with the ultrasonic diagnostic apparatus 71 according to the seventh embodiment. An image processor 76 is provided instead of the image processor 72. The image processor 76 includes a controller 77 instead of the controller 73. The controller 77 additionally includes a way operation unit 77a. The controller 77 is realized by a ROM that stores various types of data such as a processing program, a RAM that stores each operation parameter, a CPU that executes the processing program stored in the ROM, and the like, substantially similarly to the controller 73. The other constituent elements of the ultrasonic diagnostic apparatus 75 are equal to those of the ultrasonic diagnostic apparatus 71 according to the seventh embodiment. Like constituent elements as those according to the seventh embodiment are denoted by like reference symbol, respectively.

If the controller 77 is to complete a processing for operating and outputting a way determined by the measurement points set on the 3D designated tomographic image based on the respective pieces of coordinate information on these measurement points, and then displaying and outputting or printing out an obtained way measurement result (a way measurement processing), the controller 77 performs this way measurement processing in place of the peripheral length measurement processing (step S1709) among the respective processing steps (steps S1701 to S1709) executed until completing the peripheral length measurement processing shown in FIG. 57.

Figure 61:
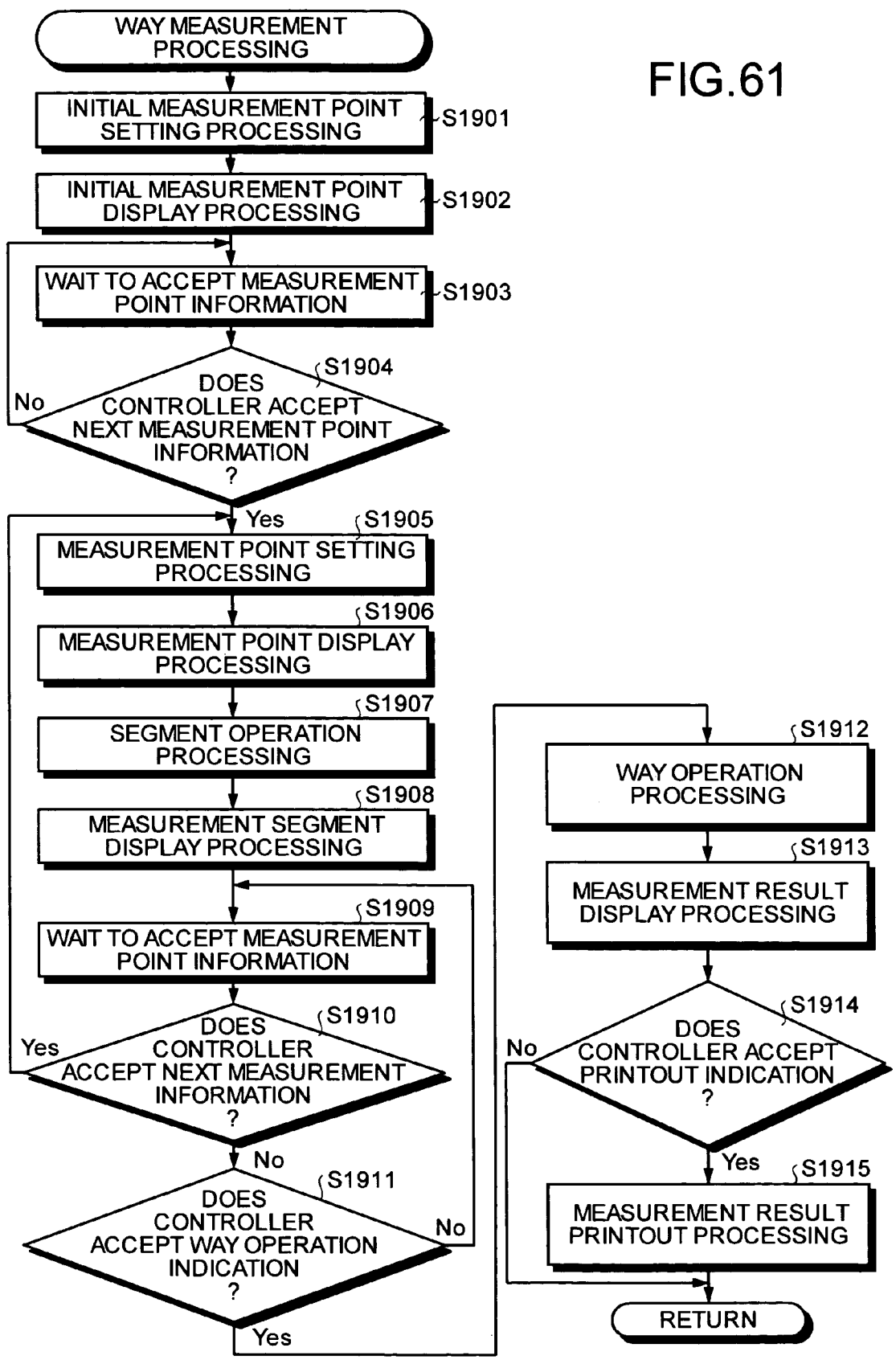
FIG. 61 is a flowchart showing respective processing steps executed a way measurement processing is completed in detail.
Figure 62:
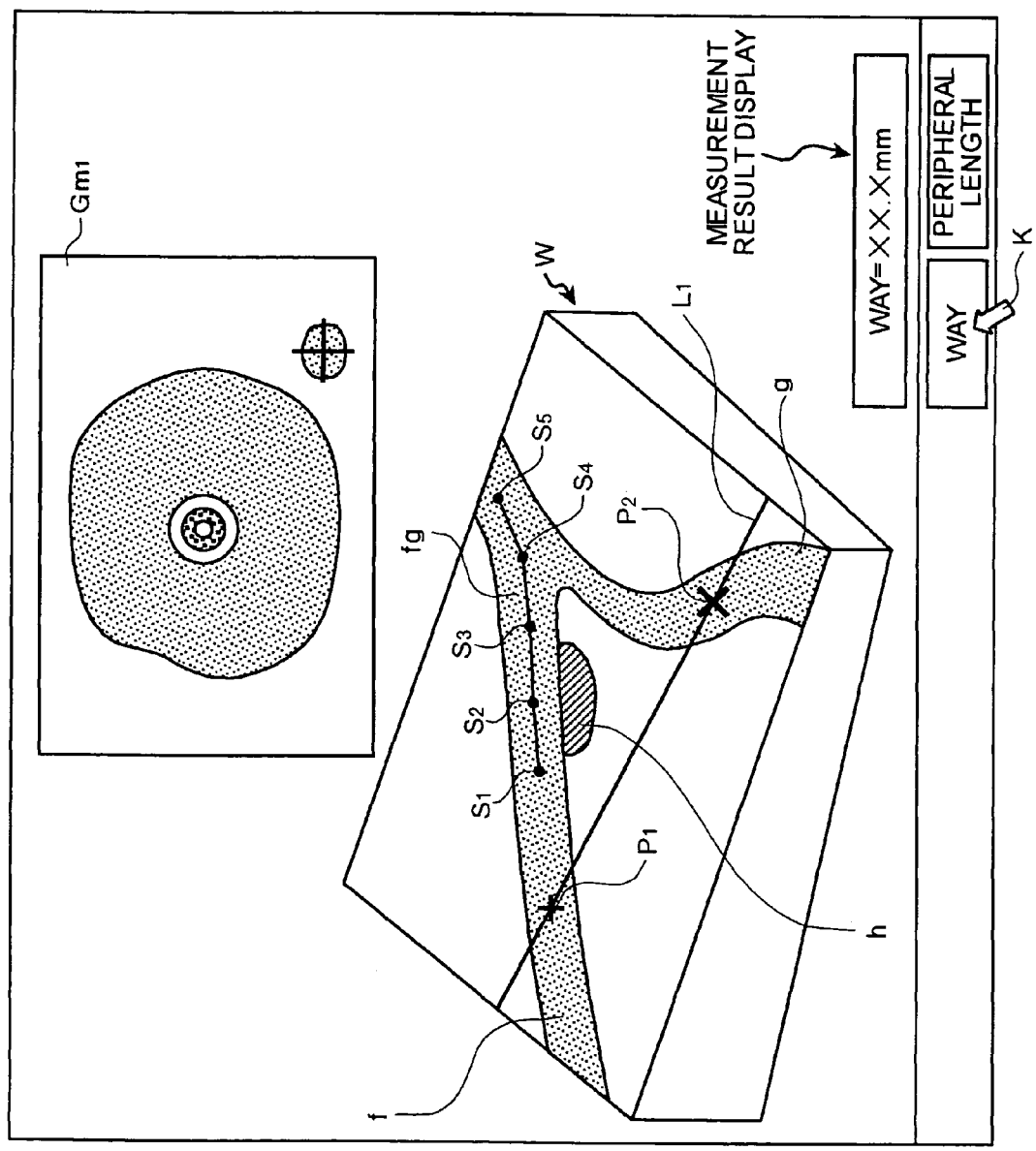
FIG. 62 depicts an example of display of the monitor if a way determined by measuring points set on the 3D designated tomographic image is measured.

FIG. 61 is a flowchart that explains respective processing steps executed until the controller 77 completes this way measurement processing. FIG. 62 depicts an example of the display of the monitor 9 if the controller 77 sets a desired number of, e.g., five measuring points on the 3D designated tomographic image W on which the tumor tomographic image h that is the tomographic image of the region of interest is displayed, and measures the way determined by the five measuring points. Referring to FIGS. 61 and 62, if the operator operates the input device 52, e.g., the mouse to move the cursor displayed on the screen of the monitor 9 to each desired position on the 3D reference tomographic image or the 3D designated tomographic image, to successively designate the desired positions, and to successively input pieces of measurement point information corresponding to the respective desired positions, the controller 77 performs the same processing as that at steps S1801 to S1810. Specifically, the controller 77 sets measurement points according to the number of times of operator's input operation at the respective desired positions on the 3D reference tomographic image data or the 3D designated tomographic image data, and displays markers indicating the respective measurement points. Thereafter, the controller 77 sequentially operates and outputs the segments that connect the set measurement points to one another, and displays the auxiliary lines indicating the respective segments (at steps S1901 to S1910).

If the operator operates the input device 52 to designate the measurement point $S_1$ on the pancreatic duct image f near the tumor tomographic image h, and to sequentially designate the measurement points $S_2$ to $S_5$ toward the bile duct-to-pancreatic duct point image fg, the controller 77 sets the measurement points $S_1$ to $S_5$ on the 3D designated tomographic image data corresponding to the respective operator's designated positions. In addition, as shown in FIG. 62, the first to the fifth measurement markers corresponding to the measurement points $S_1$ to $S_5$, respectively, are displayed on the screen while superimposing the first to the fifth markers on the 3D designated tomographic image W so as to form a series of polygonal lines from the position on the pancreatic duct tomographic image f near the tumor tomographic image h toward the position on the bile duct-to-pancreatic duct joint image fg. Further, similarly to the peripheral length measurement processing, the controller 77 operates and outputs the segments $(S_1S_2)$, $(S_2S_3)$, $(S_3S_4)$, and $(S_4S_5)$, and displays the respective auxiliary lines corresponding to the segments $(S_1S_2)$, $(S_2S_3)$, $(S_3S_4)$, and $(S_4S_5)$ on the monitor screen while superimposing the auxiliary lines on the 3D designated tomographic image W.

If the operator does not operate the input device 52 to input the next measurement point information and to input indication information for indicating operation and output of the way determined by at least three measurement points (way operation indication information), then the controller 77 does not accept the next measurement point information ("No" at step S1910) and does not accept a way operation indication corresponding to the way operation indication information ("No" at step S1911). If so, the controller 77 turns into a standby state of waiting to accept the measurement point information (at step S1909), and then repeatedly executes the processing step S1910 and the following.

On the other hand, if the operator operates the input device 52 to input the way operation indication information without inputting the next measurement point information, then the controller 77 does not accept the next measurement point information ("No" at step S1910), but accepts the way operation indication corresponding to the way operation indication information ("Yes" at step S1911). Thereafter, the distance operation unit 63b operates and outputs Euclidean distances between the respective pairs of measurement points, i.e., the lengths of the respective segments obtained at step S1907 by using each coordinate information of the plurality of measurement points set by the control 77, similarly to step S1813. If the controller 77 accepts the way operation indication, the controller 77 does not perform an operation processing and a display and output processing for the start-to-end point segment similar to the processing at step S1812. Accordingly, the distance operation unit 63b does not operate and output the length of the start-to-end point segment differently from step S1813.

This way operation indication information is input by the operator's input operation, for example, when the operator operates the mouse or the like to move the cursor K to an icon "WAY" corresponding to the way operation indication, and click this icon "WAY", that is, selects the icon "WAY" as shown in FIG. 62.

If the distance operation unit 63b operates and outputs the lengths of the respective segments, the way operation unit 77a adds up all the lengths of the segments operated and output by the distance operation unit 63b, and operates and outputs the way determined by the measurement points set by the controller 77 (at step S1912). As shown in FIG. 62, for example, if the controller 77 sets the measurement points $S_1$ to $S_5$ so as to form a series of polygonal lines from the position on the pancreatic duct tomographic image f toward the position on the bile duct-to-pancreatic duct joint image fg, then the way operation unit 77a adds up all the lengths of the segments $(S_1S_2)$, $(S_2S_3)$, $(S_3S_4)$, and $(S_4S_5)$ operated and output by the distance operation unit 63b. The way operation unit 77a thereby operates and outputs the way determined by the measurement points $S_1$ to $S_5$, i.e., the way within the pancreatic duct from neighborhoods of the tumor tomographic image h to the bile duct-to-pancreatic duct joint image fg. Thereafter, the controller 77 converts the way operated and output by way operation unit 77a into a value in a desired unit, and displays the resultant value as the measurement result on the screen of the monitor 9 (at step S1913).

If the controller 77 accepts the peripheral length operation indication while setting only the two measurement points, then the distance operation unit 63b operates and outputs the Euclidean distance based on the two measurement points. In addition, the way operation unit 77a operates and outputs the Euclidean distance operated and output by the distance operation unit 63b as the way. Namely, the distance operation unit 63b and the way operation unit 77a operate and output the same distance as the measurement point distance if the controller 77 accepts the peripheral length indication while the controller 77 sets only the two measurement points.

If the operator operates the input device 52 to input indication information for indicating printout of a way measurement result onto a paper or the like, the controller 77 accepts a printout indication based on this indication information ("Yes" at step S1914). In addition, the controller 77 performs the same processing as that at step S1816 to control the printer 53 to output this way measurement result (at step S1915). On the other hand, if the operator does not the input device 52 to input this printout indication information, the controller 77 does not accept the printout indication ("No" at step S1914). In other words, the controller 77 completes the way measurement processing without controlling the printer 53 to print out the measurement result. If this way measurement processing is completed, the operator can accurately measure, for example, the way within the pancreatic duct from the tumor tomographic image h located as the region of interest to the bile duct-to-pancreatic duct joint image fg as shown in FIG. 62. The operator can thereby estimate an accurate positional relationship or the like with respect to the affected site such as the tumor within the living body.

Figure 63:
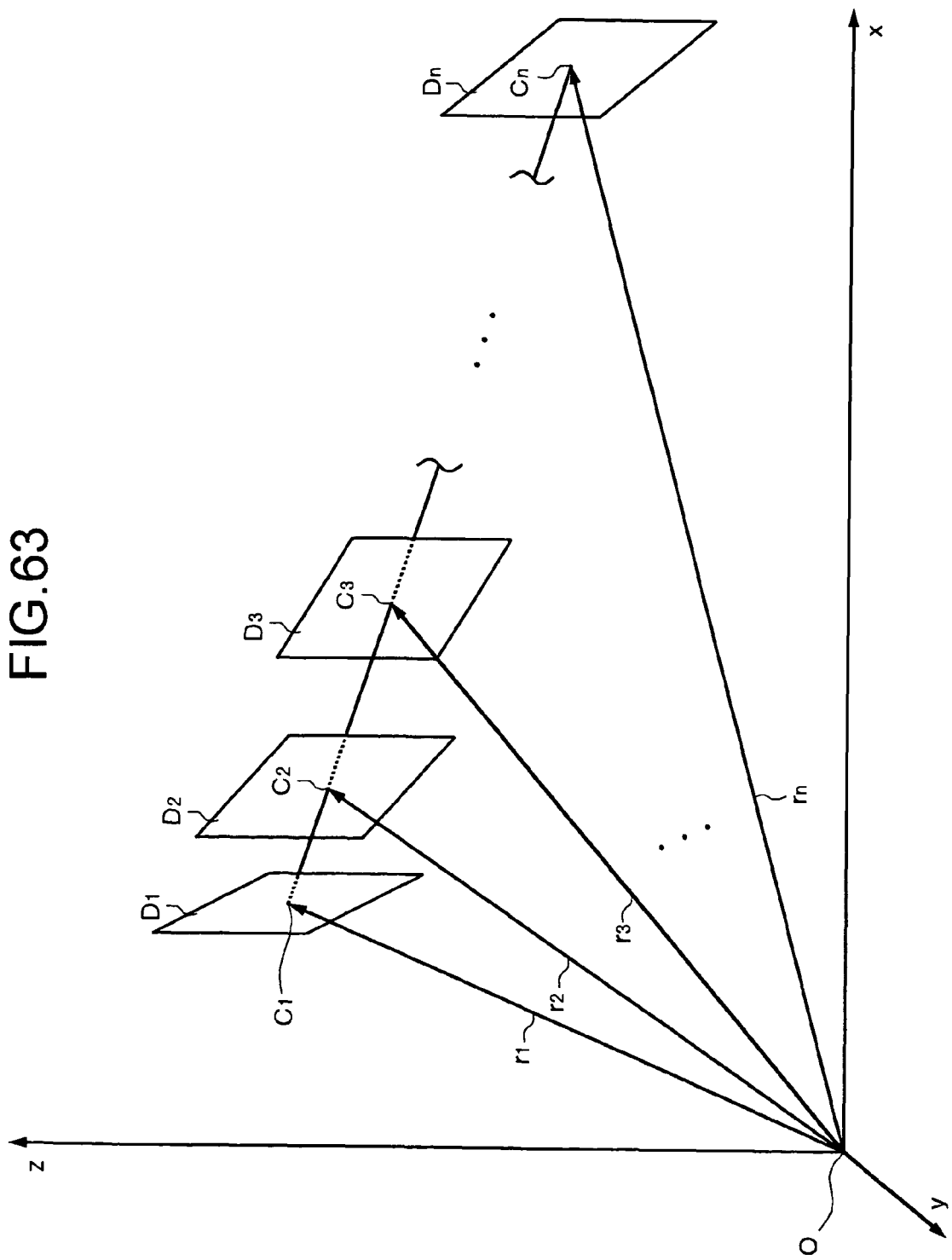
FIG. 63 is an explanatory view of a processing performed for calculating a moving path length of a probe during a 3D scan.

If operating and outputting the Euclidean distances between the respective pairs of the image centers $C_1$, $C_2$, ..., and $C_n$ of the n pieces of 2D image data $D_1$, $D_2$, ..., and $D_3$ associated with the pieces of position data, the controller 7 can calculate the way among the 2D image data $D_1$, $D_2$, ..., and $D_3$, that is, a moving path length of the probe 2 when the probe 2 performs an in vivo 3D scan. FIG. 63 is an explanatory view of a processing performed by the controller 77 for calculating the moving path length of the probe 2 during the 3D scan. Referring to FIG. 63, the 2D image data $D_1$, $D_2$, ..., and $D_n$ are arranged on the spatial coordinate system xyz, as explained. The position vectors $r_1$, $r_2$, ..., and $r_n$ are set to the respective image centers $C_1$, $C_2$, ... and $C_n$, as explained. The position vectors $r_1$, $r_2$, ..., and $r_n$ are vectors that are present on the spatial coordinate system xyz. Therefore, the distance operation unit 63b can operate and output the Euclidean distances between the respective pairs of the image centers $C_1$, $C_2$, ..., and $C_n$ by performing the same processing as that at step S1912. The way operation unit 77a can operate and output the way among the 2D image data $D_1$, $D_2$, ..., and $D_n$, that is, the moving path length of the probe 2.

In the seventh embodiment and the modification of the seventh embodiment, the instance of performing the peripheral length measurement processing or the way measurement processing using the respective pieces of coordinate information on a plurality of measurement points designated at the desired positions on the 3D designated tomographic image is explained. However, the present invention is not limited to the instance. The peripheral length measurement processing or the way measurement processing can be performed using the respective pieces of coordinate information on a plurality of measurement points designated at the desired positions on the 3D reference tomographic image or the 2D ultrasonic tomographic image.

Figure 64:
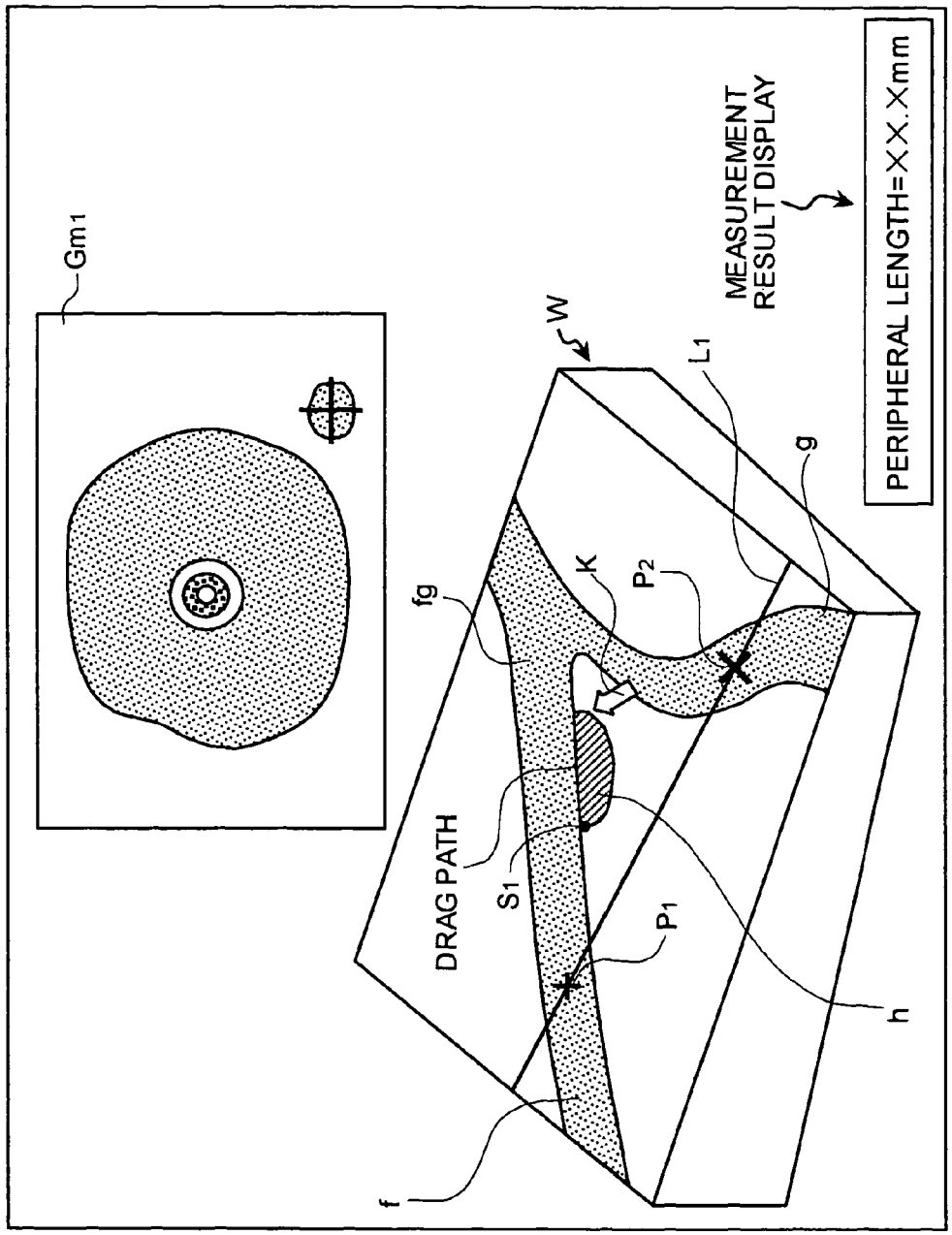
FIG. 64 is a typical view illustrating an operation for measuring the peripheral length of the measurement range or the way determined based on a drag path.

In the seventh embodiment and the modification of the seventh embodiment, the operator uses the input device 52 to set the measurement points on the 3D designated tomographic image, and the peripheral length of the measurement range or the way determined by these measurement points is measured based on the respective pieces of coordinate information on the measurement points. However, the present invention is not limited to this instance. The peripheral length of the measurement range or the way determined based on a drag path drawn by the drag operation using the input device 52 may be measured. FIG. 64 is a typical view illustrating an operation performed by the controller 77 for measuring the peripheral length of the measurement range or the way determined based on a drag path.

As shown in FIG. 64, the operator operates the input device 52, e.g., the mouse, to designate the first measurement point $S_1$ at the position near the boundary between the tumor tomographic image h and the pancreatic duct tomographic image f displayed on the screen of the monitor 9. The operator then performs a drag operation for moving the cursor K to a desired direction so as to surround the tumor tomographic image h while depressing the mouse button. In this example, the controller 77 counts the number of pixels of tomographic image data corresponding to the drag path drawn by this drag operation while the operator is dragging the mouse. The controller 77 then multiplies the count value obtained by this count processing by an actual size of one pixel, thereby operating and outputting the way corresponding to this drag path. Thereafter, the controller 77 converts the operated and output way into a value in a predetermined unit, to display the resultant converted way on the screen of the monitor 9. At the same time, the controller 77 displays a curve of the drag path by this drag operation on the screen of the monitor 9 while superimposing the curve on the 3D designated tomographic image W. The pixel of the tomographic image data is set as a square having a length and a width equal to actual size. The size of the tomographic image data per pixel is calculated by dividing a lateral (or longitudinal) length of a region displayed on the 2D ultrasonic tomographic image in the living body by the number of pixels of the 2D ultrasonic tomographic image data in the lateral direction (or longitudinal direction).

Further, a radius from the designated measurement point $S_1$ is set to the controller 77 in advance. When the operator moves the cursor K within this radius and stops depressing the mouse button during this drag operation, the controller 77 connects this measurement point $S_1$ to a point at which the operator stops depressing the mouse button. In this example, the controller 77 automatically closes this drag path to form a closed curve, and counts the number of pixels of the tomographic image data corresponding to the closed curve. The controller 77 multiplies the count value obtained by this counting processing with the actual size of the tomographic image data per pixel, thereby operating and outputting a peripheral length of the closed curve corresponding to this drag path. Thereafter, similarly to the peripheral length measurement processing, the controller 77 converts the operated and output peripheral length into a value in the predetermined unit, and displays the resultant converted value on the screen of the monitor 9. At the same time, the controller 77 displays the closed curve formed by this drag operation on the screen of the monitor 9 while superimposing the closed curve on the 3D designated tomographic image W.

According to the seventh embodiment, the ultrasonic diagnostic apparatus is constituted as follows. The 3D reference tomographic image or the 3D designated tomographic image is displayed on the screen of the monitor 9 based on the 3D image data generated using a plurality of pieces of 2D image data associated with the pieces of position data on the moving path or moving direction of the probe 2 which performs the 3D scan. If at least three measurement points are designated at the respective desired positions on the 3D reference tomographic image or the 3D designated tomographic image, the peripheral length of the measurement range surrounded by the at least three measurement points based on the respective pieces of coordinate information corresponding to the desired positions. Therefore, the ultrasonic diagnostic apparatus which can easily display and output the tomographic images of the region of interest such as the characteristic site in the living body, e.g., the bile duct-to-pancreatic duct joint or the affected site, e.g. the tumor on one monitor screen, and which can accurately measure the peripheral length of this region of interest can be realized. If the operator uses this ultrasonic diagnostic apparatus, the operator can easily locate the tomographic image of this region of interest, accurately grasp the peripheral length of the region of interest thus located, and highly accurately estimate the magnitude of the region of interest before a surgical operation.

Accordingly, if the operator appropriately selects the 3D designated longitudinal image on which the pancreatic duct and the bile duct are displayed simultaneously, the operator can acquire more accurately and more objectively information as to at a position of how distant (in millimeters) from the bile duct-to-pancreatic duct joint the affected site is present, by what length (in millimeters) the affected site spreads along a blood vessel such as the bile duct or the pancreatic duct, or how a largest diameter (in millimeters) of the affected site is. The ultrasonic diagnostic apparatus is thus useful for determination of a surgical operation plan or a cutting range before a surgical operation.

According to the modification of the seventh embodiment, the ultrasonic diagnostic apparatus is constituted as follows. If at least three measurement points are designated at the respective desired positions on the 3D reference tomographic image or the 3D designated tomographic image displayed on the screen of the monitor 9, the way determined by the at least three measurement points is operated and output. Therefore, the ultrasonic diagnostic apparatus which can accurately measure the desired way in the living body toward the region of interest such as the characteristic site or the affected site in the living body can be realized. If the operator uses this ultrasonic diagnostic apparatus, the operator can accurately measure the way in the living body from, for example, the characteristic site to the affected site, accurately grasp the positional relationship between the desired regions of interest in the living body, and promptly and properly perform the in vivo ultrasonic diagnosis. Accordingly, if the operator appropriately selects the 3D designated tomographic image and the measurement points, the operator can acquire more accurately and more objectively information as to, for example, at a position of how distant (in millimeters) from the bile duct-to-pancreatic duct joint the affected site is present or by what length (in millimeters) the affected site spreads along a blood vessel such as the bile duct or the pancreatic duct. The ultrasonic diagnostic apparatus is thus useful for determination of a surgical operation plan or a cutting range before a surgical operation.

Moreover, the ultrasonic diagnostic apparatus according to the seventh embodiment is constituted to operate and output the way among the respective image centers of a plurality of pieces of 2D image data associated with the pieces of position data on the moving path or moving direction of the probe which performs the 3D scan. Therefore, even if the probe performs the in vivo 3D scan as the probe moves in the living body while being curved or twisted, the moving path of this probe can be accurately measured.

An eighth embodiment of the present invention is explained in detail. In the seventh embodiment, if at least three measurement points are designated at the respective desired positions on the desired tomographic image, the measurement points are set at the respective coordinates corresponding to the desired positions. In addition, the length such as the peripheral length of the measurement range determined by at least three measurement points is operated and output. In the eighth embodiment, an area of the measurement range determined by the at least three measurement points is operated and output.

Figure 65:
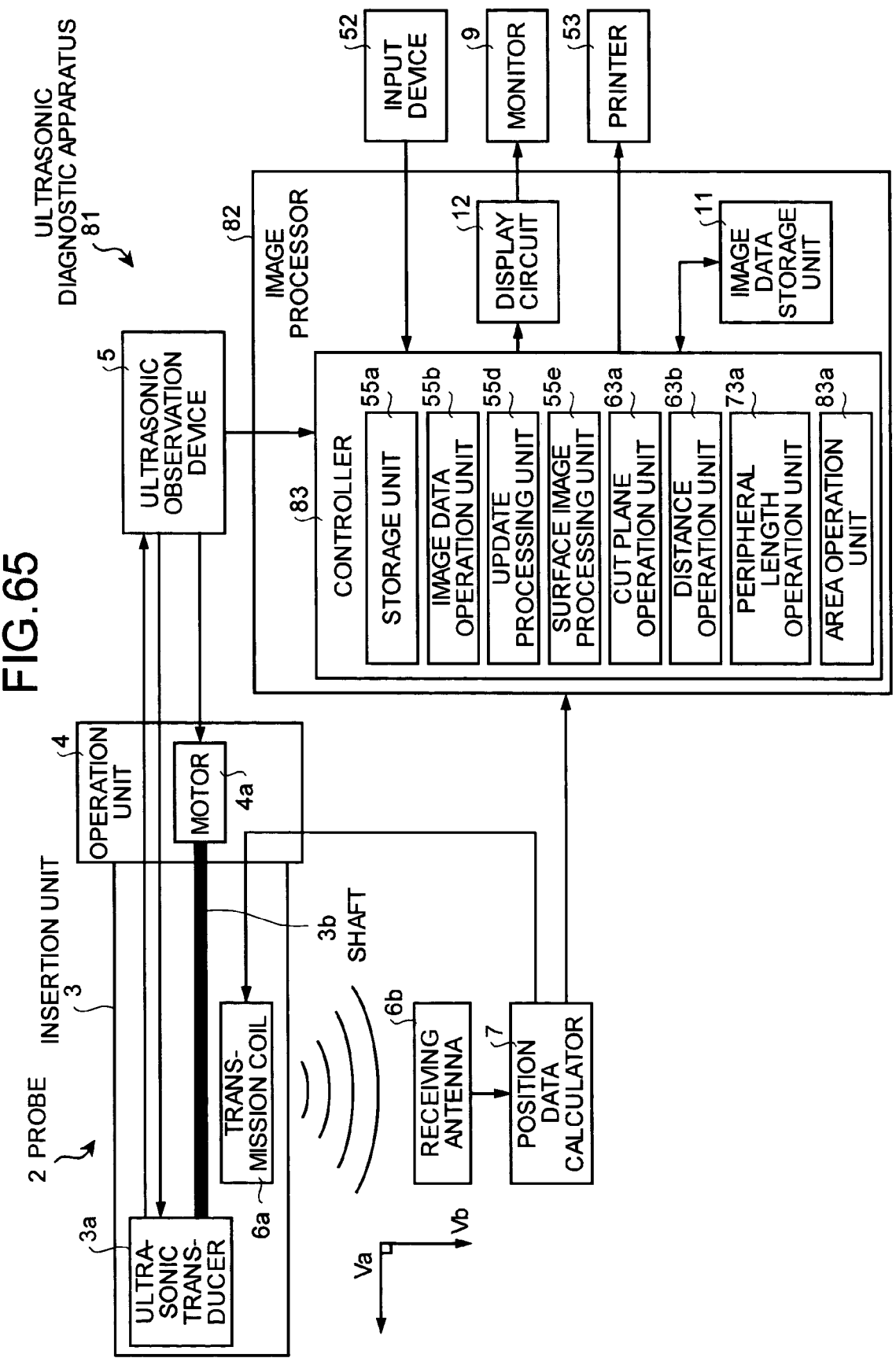
FIG. 65 is a block diagram that depicts schematic configuration of an ultrasonic diagnostic apparatus according to an eighth embodiment of the present invention.

FIG. 65 is a block diagram that depicts schematic configuration of an ultrasonic diagnostic apparatus according to the eighth embodiment of the present invention. The ultrasonic diagnostic apparatus 81 shown in FIG. 65 is constituted as follows. As compared with the ultrasonic diagnostic apparatus 71 according to the seventh embodiment, an image processor 82 is provided instead of the image processor 72. The image processor 82 includes a controller 83 instead of the controller 73. The controller 83 additionally includes an area operation unit 83a. The controller 83 is realized by a ROM that stores various types of data such as a processing program, a RAM that stores each operation parameter, a CPU that executes the processing program stored in the ROM, and the like, substantially similarly to the controller 73. The other constituent elements of the ultrasonic diagnostic apparatus 81 are equal to those of the ultrasonic diagnostic apparatus 71 according to the seventh embodiment. Like constituent elements as those according to the seventh embodiment are denoted by like reference symbol, respectively.

Figure 66:
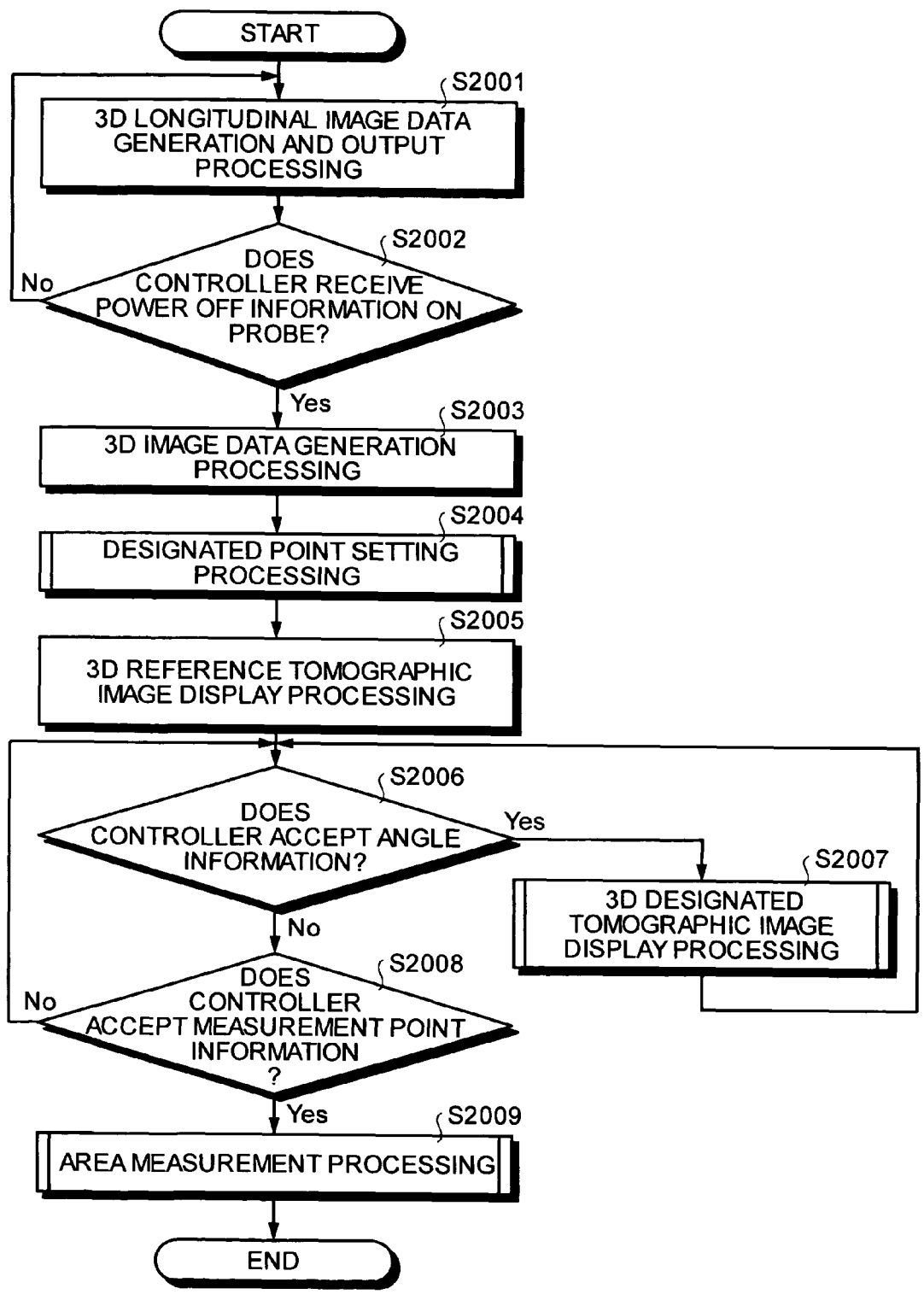
FIG. 66 is a flowchart showing respective processing steps executed until an area of a measurement range set on the 3D reference tomographic image or the 3D designated tomographic image is measured.

FIG. 66 is a flowchart showing respective processing steps executed since the controller 83 displays a band-shaped or stereoscopic 3D longitudinal image on the monitor 9, generates 3D image data using n pieces of 2D image data on the spatial coordinate system xyz, and sets at least three measurement points on 3D reference tomographic image data or 3D designated tomographic image data generated based on this 3D image data until measuring an area of a measurement range surrounded by the at least three measurement points. Referring to FIG. 66, if the ultrasonic observation device 5 generates 2D image data based on the echo signal and the position data calculator 7 calculates position data on a position at which this echo signal is obtained, the controller 83 executes respective processing steps S2001 to S2007 similarly to steps S1701 to S1707.

Thereafter, the operator observes the 3D reference tomographic image or the 3D designated tomographic image displayed on the screen of the monitor 9 and checks whether the desired region of interest is displayed on the screen of the monitor 9. If confirming that the desired region of interest is displayed on the screen of the monitor 9, the operator operates the input device 52 to perform an operation for inputting measurement point information on measurement points designated on the tomographic image displayed on the monitor screen to the controller 83 without performing an operation for inputting the angle information to the controller 83. In this case, the controller 83 does not accept the angle information ("No" at step S2006) but accepts the measurement point information ("Yes" at step S2008). The controller 83 then sets at least three measurement points on the 3D reference tomographic image data or the 3D designated tomographic image data using the measurement point information input by operator's operating the input device 52. In addition, the controller 83 operates and outputs the area of the measurement range surrounded by the three measurement points. Further, the controller 83 displays and outputs or prints out an operation result obtained as a measurement result of the area (at step S2009). Details of a processing performed since the measurement points are set on the 3D reference tomographic image data or the 3D designated tomographic image data until the measurement result of the area is displayed and output or printed out (an area measurement processing) is explained later.

If the operator does not operate the input device 52 to input the angle information and the measurement point information, then the controller 83 does not accept the angle information ("No" at step S2006), does not accept the measurement point information ("No" at step S2008), but repeatedly executes the processing step S2006 and the following. In this case, the controller 83 controls the monitor 9 to maintain a state in which the 3D reference tomographic image or 3D designated tomographic image is displayed on the monitor screen until the controller 83 accepts the angle information or the measurement point information input by the operator's input operation.

Figure 67:
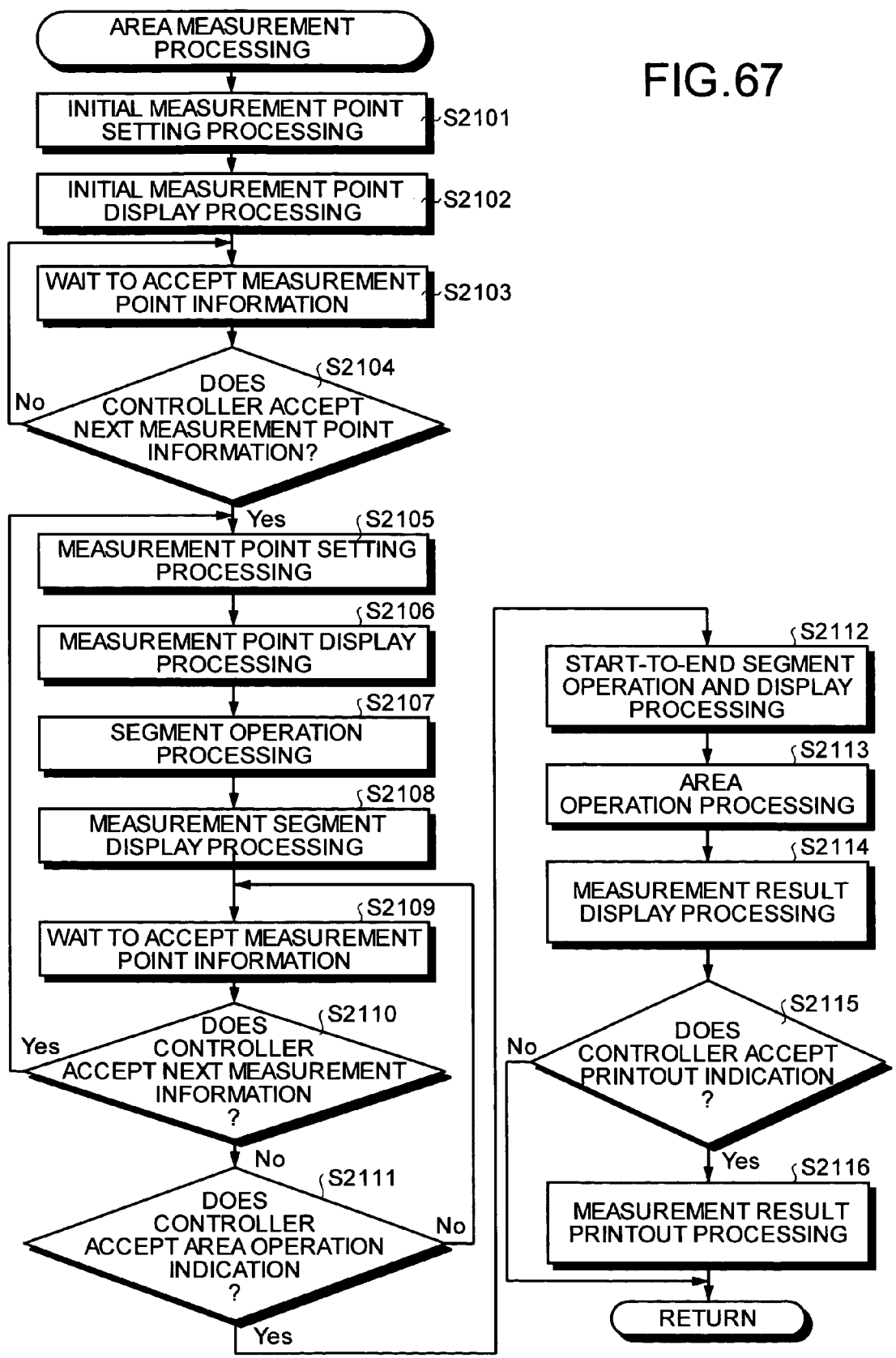
FIG. 67 is a flowchart showing respective processing steps executed until an area measurement processing is completed in detail.
Figure 68:
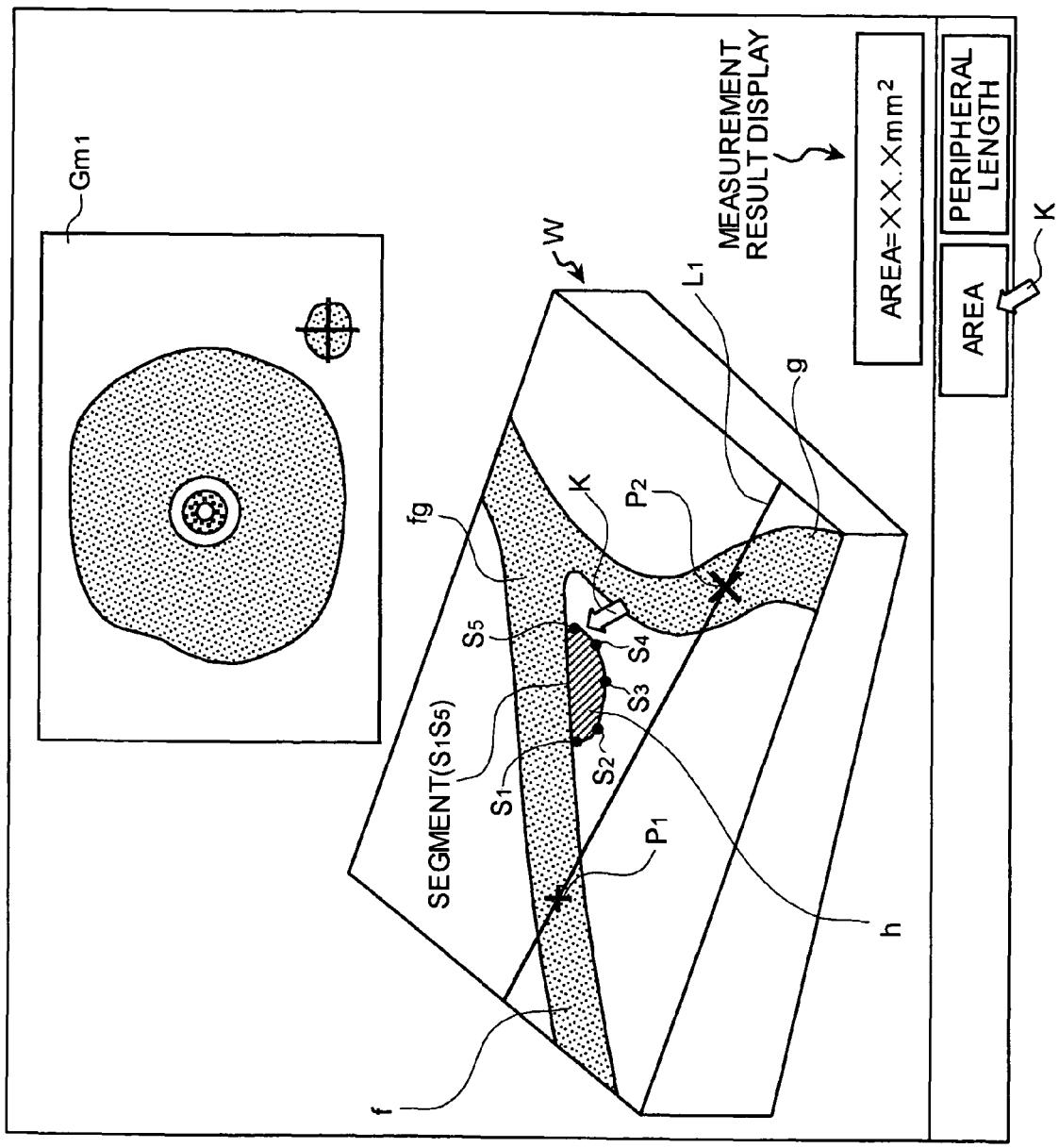
FIG. 68 depicts an example of display of the monitor if the area of the measurement range set on the 3D designated tomographic image is measured.

Respective processing steps executed until the controller 83 completes the area measurement processing at step S2009 is explained in detail. FIG. 67 is a flowchart showing the respective processing steps executed until the controller 83 completes the area measurement processing related to the area of the measurement range designated on the 3D reference tomographic image or the 3D designated tomographic image in detail. FIG. 68 depicts an example of the display of the monitor 9 if the controller 83 sets a predetermined number of, for example, five measurement points on the 3D designated tomographic image W on which the tumor tomographic image h that is the tomographic image of the region of interest is displayed, and measures the area of the measurement range surrounded by the five measurement points.

Referring to FIGS. 67 and 68, if the operator operates the input device 52, e.g., the moue, to move the cursor displayed on the screen of the monitor 9 to each desired position on the 3D reference tomographic image or the 3 designated tomographic image, to successively designate the desired positions, and to successively input measurement point information corresponding to each desired point, the controller 83 performs the same processing as that at steps S1801 to S1810. Specifically, the controller 83 sets measurement points according to the number of times of the operator's input operation and displays markers indicating the measurement positions at the desired positions on the 3D reference tomographic image data or the 3D designated tomographic image data, respectively. The controller 83 then operates and outputs segments that sequentially connect the measurement points thus set, and displays auxiliary lines that indicate the respective segments (at steps S2101 to S2110).

If the operator operates the input device 52 to designate the measurement point $S_1$ at, for example, the position near the boundary between the tumor tomographic image h and the pancreatic duct tomographic image f, and designates the measurement points $S_2$ to $S_5$ so as to surround the tumor tomographic image h, the controller 83 sets the measurement points $S_1$ to $S_5$ on the 3D designated tomographic image data corresponding to the respective operator's designated positions. Further, as shown in FIG. 68, the controller 83 displays a first measurement marker to a fifth measurement marker corresponding to the measurement points $S_1$ to $S_5$, respectively, while superimposing the first to the fifth measurement markers on the 3D designated tomographic image W. Similarly to the instance of the peripheral length measurement processing, the controller 83 operates and outputs the segments $(S_1S_2)$, $(S_2S_3)$, $(S_3S_4)$, and $(S_4S_5)$. In addition, the controller 83 displays auxiliary lines corresponding to the segments $(S_1S_2)$, $(S_2S_3)$, $(S_3S_4)$, and $(S_4S_5)$, respectively, while superimposing the auxiliary lines on the 3D designated tomographic image W.

If the operator does not operate the input device 52 to input the next measurement point information and to input indication information for operating and outputting the area of the measurement range surrounded by at least three measurement points (area operation indication information), then the controller 83 does not accept the next measurement point information ("No" at step S2110) and does not accept a peripheral length operation indication corresponding to the peripheral length operation indication information ("No" at step S2111). If so, the controller 83 repeatedly executes the processing step S2109 and the following.

On the other hand, if the operator operates the input device 52 to input the area operation indication information without inputting the next measurement point information, then the controller 82 does not accept the next measurement point information ("No" at step S2110), but accepts the area operation indication corresponding to the area operation indication information ("Yes" at step S2111). Thereafter, the controller 83 performs the same processing as that at step S1812. Namely, the control unit 83 operates and outputs a start-to-end point segment that connects the initial measurement point set at step S2101 to the latest measurement point set before the area operation indication is accepted, that is, the last measurement point. In addition, the controller 83 displays an auxiliary line corresponding to the start-to-end point segment on the screen (at step S2112). For example, if the five measurement points $S_1$ to $S_5$ are successively input in all by the operator's input operation, then the controller 83 operates and outputs the segment $(S_1S_5)$ that connects the measurement point $S_1$ to the measurement point $S_5$ and displays an auxiliary line corresponding to the obtained segment $(S_1S_5)$ on the screen at step S2112.

If the controller 83 accepts the area operation indication, the area operation unit 83a operates and outputs the area of the measurement range (polygon) surrounded by the at least three measurement points set at steps S2101 to S2110 based on the respective pieces of coordinate information on the at least three measurement points (at step S2113). The controller 83 coverts the area of the measurement range operated and output by the area operation unit 83a into a value in a desired unit as a measurement result, and displays the resultant value on the screen of the monitor 9 (at step S2114). It is noted, however, that, if this polygon is formed by at least four measurement points, the controller 83 divides an interior of this polygon to a plurality of triangles using three out of the at least four measurement points. If so, the area operation unit 83a operates and outputs areas of the respective triangles divided by the controller 83 based on the respective coordinate information on the measurement points that form these triangles. Further, the area operation unit 83a adds up all the areas of the triangles thus obtained, thereby operating and outputting an area of this polygon. Details of the processing performed by the controller 83 for dividing the interior of the polygon formed by the at least four measurement points into a plurality of triangles is explained later.

It is noted that the measurement points set by the controller 83 on the 3D reference tomographic image data or the 3D designated tomographic image data can be represented by position vectors on the spatial coordinate system xyz, similarly to the measurement points set on the 3D longitudinal image data. This results from the fact that the 3D reference tomographic image data or the 3D designated tomographic image data is present on the spatial coordinate system xyz. Accordingly, the area operation unit 83a can operate and output the area of the measurement range surrounded by the at least three measurement points using the vector components of the position vectors of the respective measurement points typically represented by Equation (4) and (5), and based on a well-known area operation method such as a formula and a cosine theorem for calculating the area of a triangle or the Heron's formula.

This area operation indication information is input by the operator's input operation, for example, when the operator operates the mouse or the like to move the cursor K to an icon "AREA" corresponding to the area operation indication, and click this icon "ARE", that is, selects the icon "AREA" as shown in FIG. 68. Likewise, the peripheral length operation indication information is input by the operator's input operation, for example, when the operator operates the mouse or the like to move the cursor K to the icon "PERIPHERAL LENGTH", and clicks, that is, selects this icon "PERIPHERAL LENGTH". If this peripheral length operation indication information is input, the controller 83 may perform the respective processings at step S1811 and the following.

If the operator then operates the input device 52 to input indication information for printing out an area measurement result onto a paper or the like, the controller 83 accepts a printout indication based on this indication information ("Yes" at step S2115). In addition, the controller 83 performs the same processing as that at step S1816 to control the printer 53 to output this area measurement result (at step S2116). On the other hand, if the operator does not the input device 52 to input this printout indication information, the controller 83 does not accept the printout indication ("No" at step S2115). In other words, the controller 83 completes the area measurement processing without controlling the printer 53 to print out the measurement result. If this area measurement processing is completed, the operator can, for example, approximate the area of the tumor tomographic image h located as the region of interest to that of a desired polygon and measure the area as shown in FIG. 68. The operator can thereby highly accurately estimate a cross-sectional area or the like of the affected site such as the tumor before a surgical operation.

Figure 69:
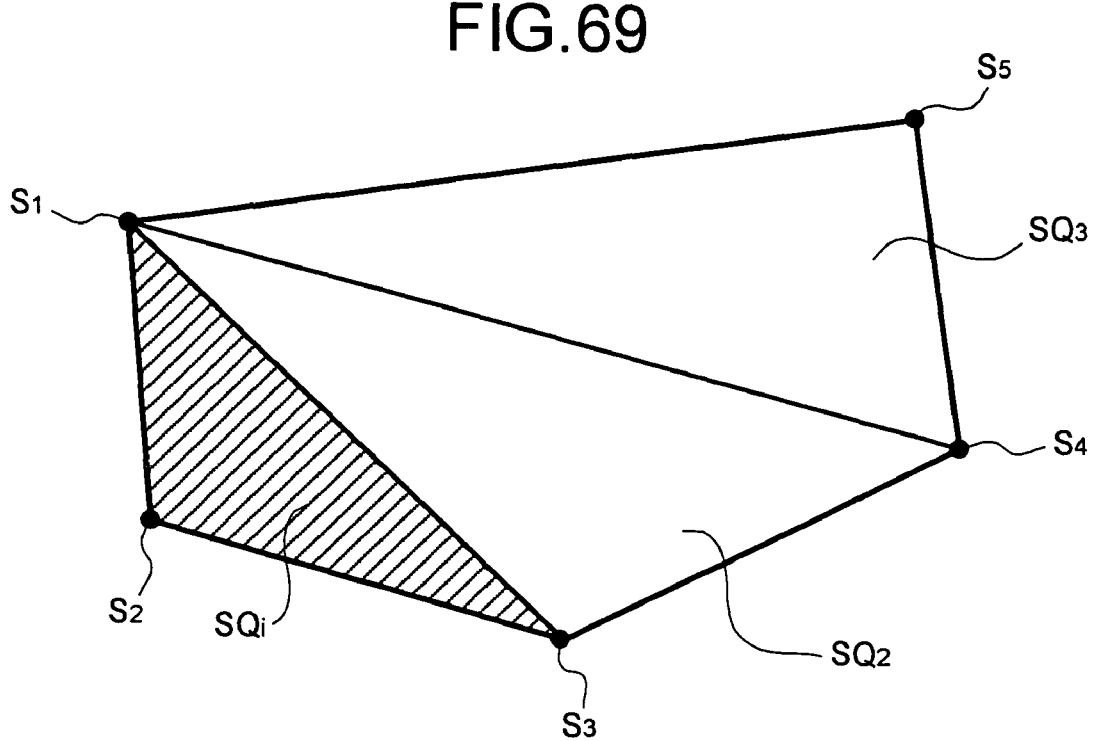
FIG. 69 is an explanatory view of a processing for dividing a convex polygon into a plurality of triangles.
Figure 70:
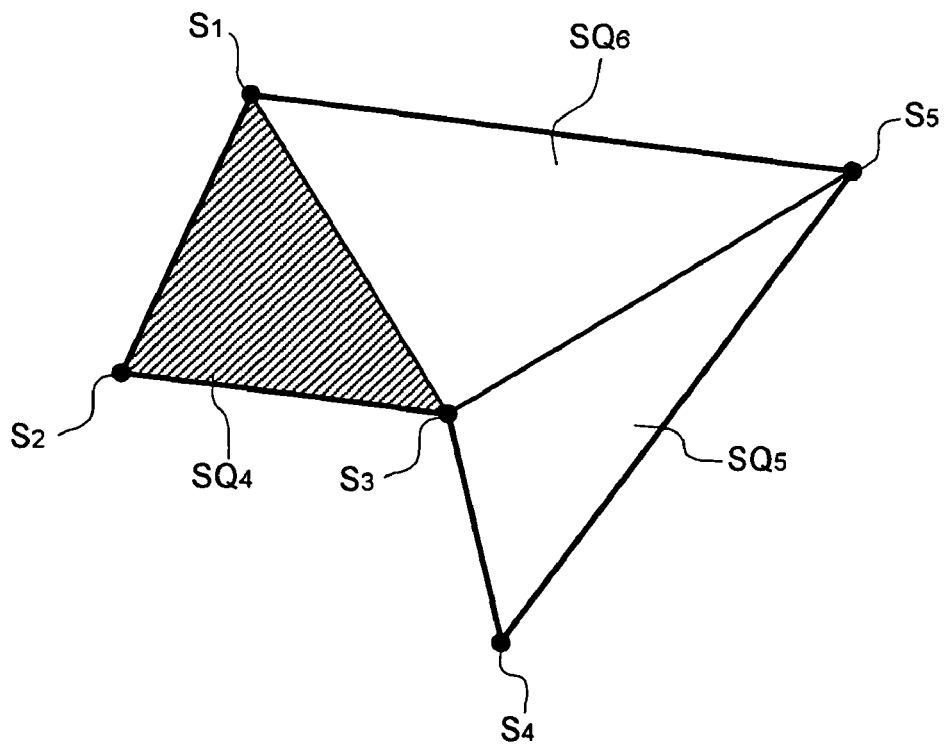
FIG. 70 is an explanatory view of a processing for dividing a concave polygon into a plurality of triangles.

The processing performed by the controller 83 for dividing the interior of the polygon, that is formed by at least four measurement points set on the 3D reference tomographic image data or the 3D designated tomographic image data, into a plurality of triangles will next be explained. FIG. 69 is an explanatory view of a state in which the controller 83 divides a convex polygon into a plurality of triangles if the controller 83 sets the five measurement points $S_1$ to $S_5$, and the polygon formed by the five measurement points $S_1$ to $S_5$ is the convex polygon. FIG. 70 is an explanatory view of a state in which the controller 83 divides polygon into a plurality of triangles if the controller 83 sets the five measurement points $S_1$ to $S_5$, and the polygon formed by the five measurement points $S_1$ to $S_5$ is not a convex polygon (but is a concave polygon).

If the controller 83 executes the respective processing steps S2101 to S2112 to operate and output the at least four measurement points and the segments that successively connect two of the four measurement points, a polygon having the at least four measurement points as vertexes and the segments as sides is formed. Thereafter, the controller 83 sets the initial measurement point set at step S2101 as a reference point, and successively selects two measurement points out of at least three measurement points set at steps S2105 to S2110 in an ascending order of setting time. The controller 83 successively generates triangles formed by this reference point and the two points, and divides the polygon into the triangles thus successively generated. In this example, the controller 83 constantly monitors whether an angle direction relative to the reference point of each of the triangles successively generated, e.g., the angle direction in which the segment that connects the reference point to the measurement point formed earlier in order is rotated around the reference point as the rotation center toward the segment that connects the reference point to the measurement point formed later in order is a predetermined direction (e.g., a positive direction). If the angle direction is the predetermined direction, then the controller 83 determines that this polygon is the convex polygon, and successively generates triangles into which the polygon is divided, with the initial measurement point set as each reference point.

As shown in FIG. 69, for example, if the controller 83 sets the measurement points $S_1$ to $S_5$, and operates and outputs the segments $(S_1S_2)$, $(S_2S_3)$, $(S_3S_4)$, and $(S_4S_5)$, and the start-to-end point segment $(S_1S_5)$, a pentagon having the measurement points $S_1$ to $S_5$ as vertexes is formed. In this example, the controller 83 generates triangles by the measurement points $S_1$ to $S_3$, with the measurement point $S_1$, which is the initial measurement point, set as the reference point of each triangle. In addition, the controller 83 monitors whether the angle direction relative to the measurement point $S_1$ is positive or negative.

If the angle direction in which the segment $(S_1S_2)$ is rotated around the measurement point $S_1$ as the rotation center through the interior of this polygon to the start-to-end point segment $(S_1S_5)$ is set as the positive direction, the controller 83 confirms that the angle direction relative to the measurement point $S_1$ of the triangle formed by the measurement points $S_1$ to $S_3$ is positive, and thereby determines that this polygon is a convex polygon. Based on the confirmation, the controller 83 sets a triangle $SQ_1$ formed by the measurement points $S_1$ to $S_3$ as one of the triangles into which the polygon is divided.

Thereafter, the controller 83 performs the same processings to a triangle formed by the measurement points $S_1$, $S_3$, and $S_4$ and a triangle formed by the measurement points $S_1$, $S_4$, and $S_5$ similarly to the triangle $SQ_1$, thereby setting a triangle $SQ_2$ formed by the measurement points $S_1$, $S_3$, and $S_4$ and a triangle $SQ_3$ formed by the measurement points $S_1$, $S_4$, and $S_5$. In this example, the controller 83 has set the triangle which includes the reference point and the measurement point last in the order, i.e., the measurement point $S_5$, so that the controller 83 completes a triangle setting processing for dividing the polygon into triangles. This polygon is thus divided into the triangles $SQ_1$, $SQ_2$, and $SQ_3$ set by the controller 83. Therefore, the area operation unit 83a operates and outputs the areas of the triangles $SQ_1$, $SQ_2$, and $SQ_3$ based on the vector components of the position vectors of the measurement points $S_1$ to $S_5$, respectively. In addition, the area operation unit 83a adds up all the obtained areas, thereby operating and outputting the area of this polygon.

On the other hand, if the angle direction relative to the reference position of the triangles into which the polygon is divided is not the predetermined direction, the controller 83 determines that this polygon is a concave polygon. In addition, the controller 83 updates the reference position to the measurement position earlier in order and forming the triangle based on which the controller 83 confirms that this angle direction is not the predetermined direction, as a new reference point. Thereafter, the controller 83 successively selects the two measurement points later in order than this new reference point, thereby successively forming triangles into which the polygon is divided. It is noted, however, that if the controller 83 updates the reference point once, the controller 83 repeatedly performs the triangle setting processing for dividing this polygon into triangles until generating the triangle which includes, as vertexes, the present reference point, the measurement point set as the reference point just before the present reference point, and the measurement point last in order. Further, if the controller 83 updates the reference point a plurality of times, the controller 83 repeatedly performs the triangle setting processing for dividing this polygon into triangles until generating the triangle which includes, as vertexes, the present reference point and the measurement point set as the reference point just before the present reference point, and which includes this measurement point as a measurement point later in order.

As shown in FIG. 70, for example, if the controller 83 sets the measurement points $S_1$ to $S_5$, and operates and outputs the segments $(S_1S_2)$, $(S_2S_3)$, $(S_3S_4)$, and $(S_4S_5)$, and the start-toend point segment ($S_1S_5$), a pentagon having the measurement points $S_1$ to $S_5$ as vertexes is formed. In this case, similarly to the convex polygon shown in FIG. 69, the controller 83 generates triangles by the measurement points $S_1$ to $S_3$, with the measurement point $S_1$, which is the initial measurement point, set as the reference point of each triangle. In addition, the controller 83 monitors whether the angle direction relative to the measurement point $S_1$ is positive or negative. In this case, the controller 83 determines that the angle direction relative to the measurement point $S_1$ of the triangle formed by the measurement points $S_1$ to $S_3$ is positive. Based on the determination, the controller 83 sets a triangle $SQ_4$ formed by the measurement points $S_1$ to $S_3$ as one of the triangles into which the polygon is divided.

The controller 83 then performs the same processing to a triangle formed by the measurement points $S_1$, $S_3$, and $S_4$ similarly to the triangle $SQ_1$. In this example, the controller 83 confirms that the angle direction relative to the measurement position $S_1$ of the triangle formed by the measurement points $S_1$, $S_3$, and $S_4$ is not the positive direction. Based on the confirmation, the controller 83 updates the reference point to the measurement point $S_3$ which is the measurement point earlier in order of this triangle as a new reference point. The controller 83 then generates a triangle formed by the measurement point $S_3$ as the reference point as well as the measurement points $S_4$ and $S_5$ which are later in order than the measurement point $S_3$. In addition, the controller 83 monitors whether the angle direction relative to the measurement point $S_3$ is the positive direction. In this example, the controller 83 confirms that the angle direction relative to the measurement point $S_3$ of the triangle formed by the measurement point $S_3$ to $S_5$ is the positive direction. Based on the confirmation, the controller 83 sets a triangle $SQ_5$ formed by the measurement points $S_3$ to $S_5$ as one of the triangles into which this polygon is divided.

Thereafter, the controller 83 performs the same processing to a triangle formed by the measurement points $S_3$, $S_5$, and $S_1$ similarly to the triangle $SQ_4$, thereby setting a triangle $SQ_6$ formed by the measurement points $S_3$, $S_5$, and $S_1$. In this example, the controller 83 has set the triangle which includes the measurement point $S_3$ that is the present reference point, the measurement point $S_1$ set as the reference point just before the present reference point, and the measurement point $S_5$ that is the last in the order, so that the controller 83 completes the triangle setting processing for dividing this polygon into triangles. This polygon is thus divided into the triangles $SQ_4$, $SQ_5$, and $SQ_6$ set by the controller 83. Therefore, the area operation unit 83a operates and outputs the areas of the triangles $SQ_4$, $SQ_5$, and $SQ_6$ based on the vector components of the position vectors of the measurement points $S_1$ to $S_5$, respectively. In addition, the area operation unit 83a adds up all the obtained areas, thereby operating and outputting the area of this polygon.

In the eighth embodiment of the present invention, the instance of performing the area measurement processing using coordinate information on a plurality of measurement points designated at the respective desired positions on the 3D designated tomographic image is explained. However, the present invention is not limited to this instance. The area measurement processing can be performed using coordinate information on a plurality of measurement points designated at the respective desired positions on the 3D reference tomographic image or the 2D ultrasonic tomographic image.

Figure 71:
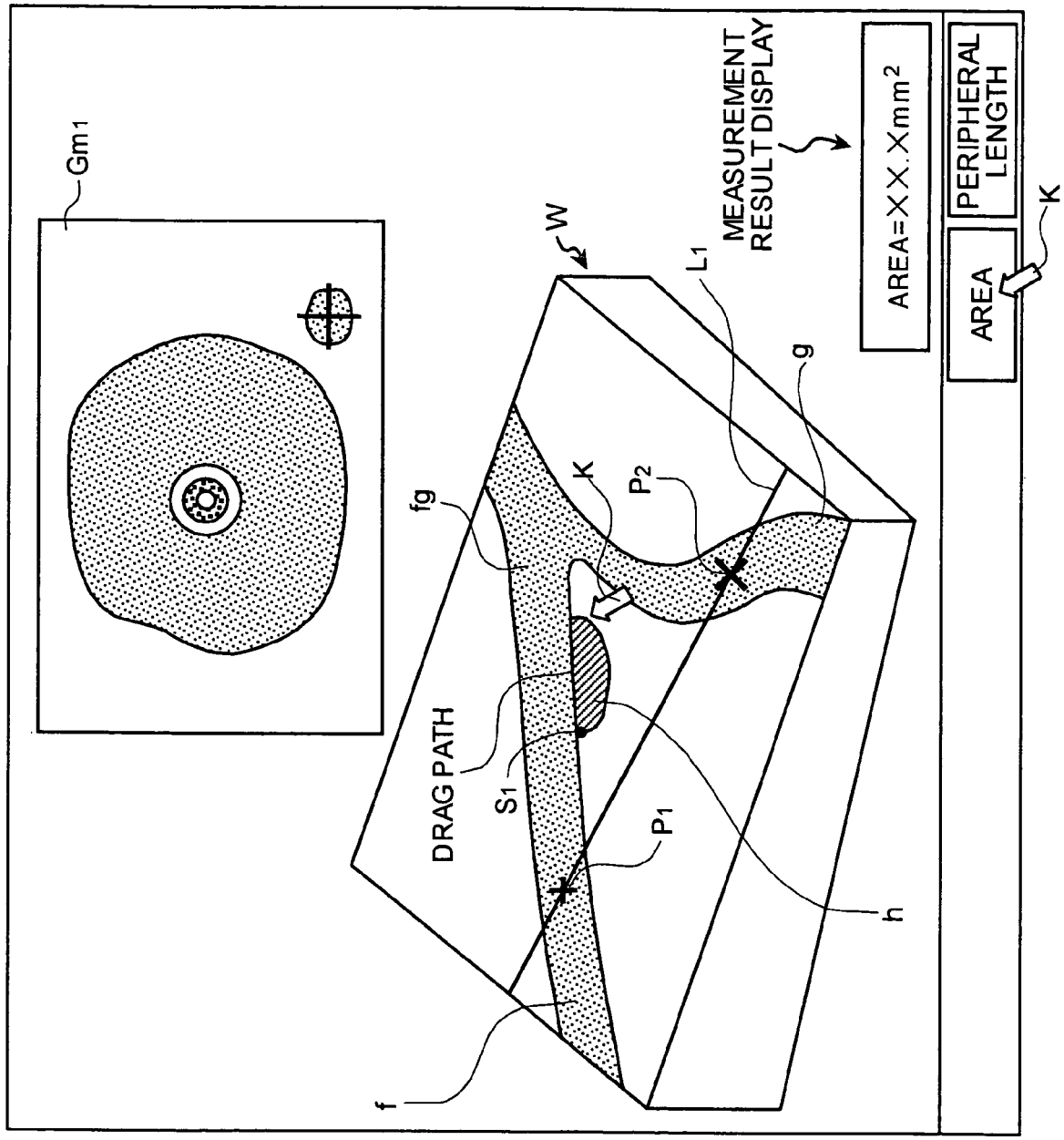
FIG. 71 is a typical view illustrating an operation for measuring the area of the measurement range surrounded by the drag path.
Figure 72:
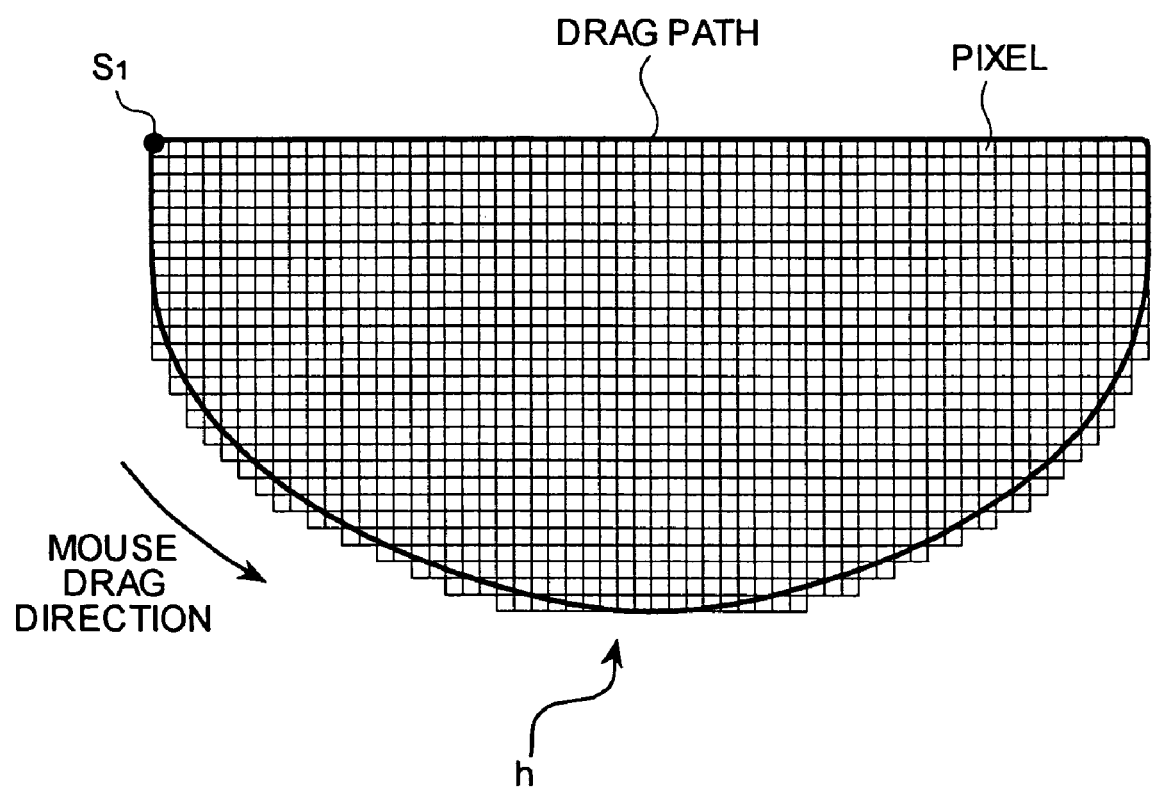
FIG. 72 is a typical view that depicts an example of a state in which the measurement range surrounded by the drag path is composed by a polygon formed by a plurality of pixels.

In the eighth embodiment, the operator uses the input device 52 to set a plurality of measurement points on the 3D designated tomographic image data, and measures the area of the measurement range surrounded by these measurement points based on the respective pieces of coordinate information on the measurement points. However, the present invention is not limited to this instance. The area of the measurement range surrounded by the drag path drawn by the drag operation using the input device 52 may be measured. FIG. 71 is a typical view illustrating an operation performed by the controller 83 for measuring the area of the measurement range surrounded by the drag path. FIG. 72 is a typical view illustrating an example of a state in which the measurement range surrounded by the drag path is composed by a polygon formed by a plurality of pixels.

As shown in FIG. 71, the operator first operates the input device 52, e.g., the mouse, to designate the first measurement point $S_1$ at the position near the boundary between the tumor tomographic image h and the pancreatic duct tomographic image f displayed on the screen of the monitor 9. The operator then performs a drag operation so as to surround the tumor tomographic image h. A radius from the designated measurement point $S_1$ is set to the controller 83 in advance. When the operator moves the cursor K within this radius and stops depressing the mouse button during this drag operation, the controller 83 connects this measurement point $S_1$ to a point at which the operator stops depressing the mouse button. In this example, the controller 83 automatically closes this drag path to form a closed curve. In addition, as shown in FIG. 72, based on position information on pixels of tomographic image data corresponding to this closed curve, the controller 83 generates a polygon composed by these pixels, and constitutes the measurement range surrounded by the closed curve. Thereafter, the controller 83 counts the total number of pixels present in the measurement range constituted by this polygon. The controller 83 multiplies the count value obtained by this counting processing by an actual area of the measurement range per pixel, thereby operating and outputting an area of the measurement range surrounded by the closed curve. The actual area of the measurement range per pixel can be obtained by a square of the actual size of the measurement range per pixel. Thereafter, similarly to the area measurement processing, the controller 83 converts the operated and output area into a value in a predetermined unit, and displays the resultant converted value on the monitor 9. At the same time, the controller 83 displays the measurement range surrounded by the closed curve on the monitor 9 while superimposing the measurement range on the 3D designated tomographic image W.

According to the eighth embodiment, the ultrasonic diagnostic apparatus is constituted as follows. The 3D reference tomographic image or the 3D designated tomographic image is displayed on the screen of the monitor 9 based on the 3D image data generated using a plurality of pieces of 2D image data associated with the pieces of position data on the moving path or moving direction of the probe 2 which performs the 3D scan. If at least three measurement points are designated at the respective desired positions on the 3D reference tomographic image or the 3D designated tomographic image, the area of the measurement range surrounded by the at least three measurement points is operated and output by approximating this area to that of a desired polygon based on the respective pieces of coordinate information corresponding to the desired positions. Therefore, the ultrasonic diagnostic apparatus which can easily display and output the tomographic images of the region of interest such as the characteristic site in the living body, e.g., the bile duct-to-pancreatic duct joint or the affected site, e.g. the tumor on one monitor screen, and which can highly accurately measure the area of this region of interest can be realized. If the operator uses this ultrasonic diagnostic apparatus, the operator can easily locate the tomographic image of this region of interest, highly accurately grasp the area of the region of interest thus located, and thereby highly accurately estimate the cross-sectional area or the like of the affected site, e.g., the tumor, before a surgical operation.

As a consequence, the operator can accurately grasp the magnitude of the affected site before the surgical operation. The ultrasonic diagnostic apparatus is therefore useful for determination of a surgical operation plan or a cutting range. Besides, the operator can determine more accurately and more objectively a treatment effect of an anticancer agent, radiation therapy, or the like on the affected site with the passage of time. If the magnitude of the affected site is estimated by measuring the area of the affected site, in particular, an estimation result obtained is objective irrespectively of the operator.

Moreover, since the area includes a dimension that is a square of the distance, the area tends to be influenced by a strain of the longitudinal image or tomographic image of the subject. Namely, if the distance has a strain of 10% vertically and horizontally as compared with the actual shape, the area eventually includes a strain of about 20%. It is, therefore, quite desirable to use the constitution of the ultrasonic diagnostic apparatus according to the eighth embodiment when the area is to be measured.

A ninth embodiment of the present invention is explained in detail. In the eighth embodiment, the ultrasonic diagnostic apparatus constituted as follows. If at least three measurement points are designated at the respective desired positions on the desired tomographic image, then the measurement points are set on the coordinates corresponding to the desired positions, respectively, and the area of the measurement range determined by the at least three measurement points is operated and output. In the ninth embodiment, an ultrasonic diagnostic apparatus is constituted as follows. A plurality of tomographic planes arranged in parallel at predetermined interval are set on 3D image data generated by interpolating respective adjacent pieces of 2D image data among a plurality of pieces of 2D image data arranged on the spatial coordinate system xyz. Thereafter, if at least three measurement points are designated at respective desired positions on tomographic images of the tomographic planes, a volume of a desired region of interest is operated and output based on respective pieces of coordinate information on the at least three measurement points and a distance between the tomographic images.

Figure 73:
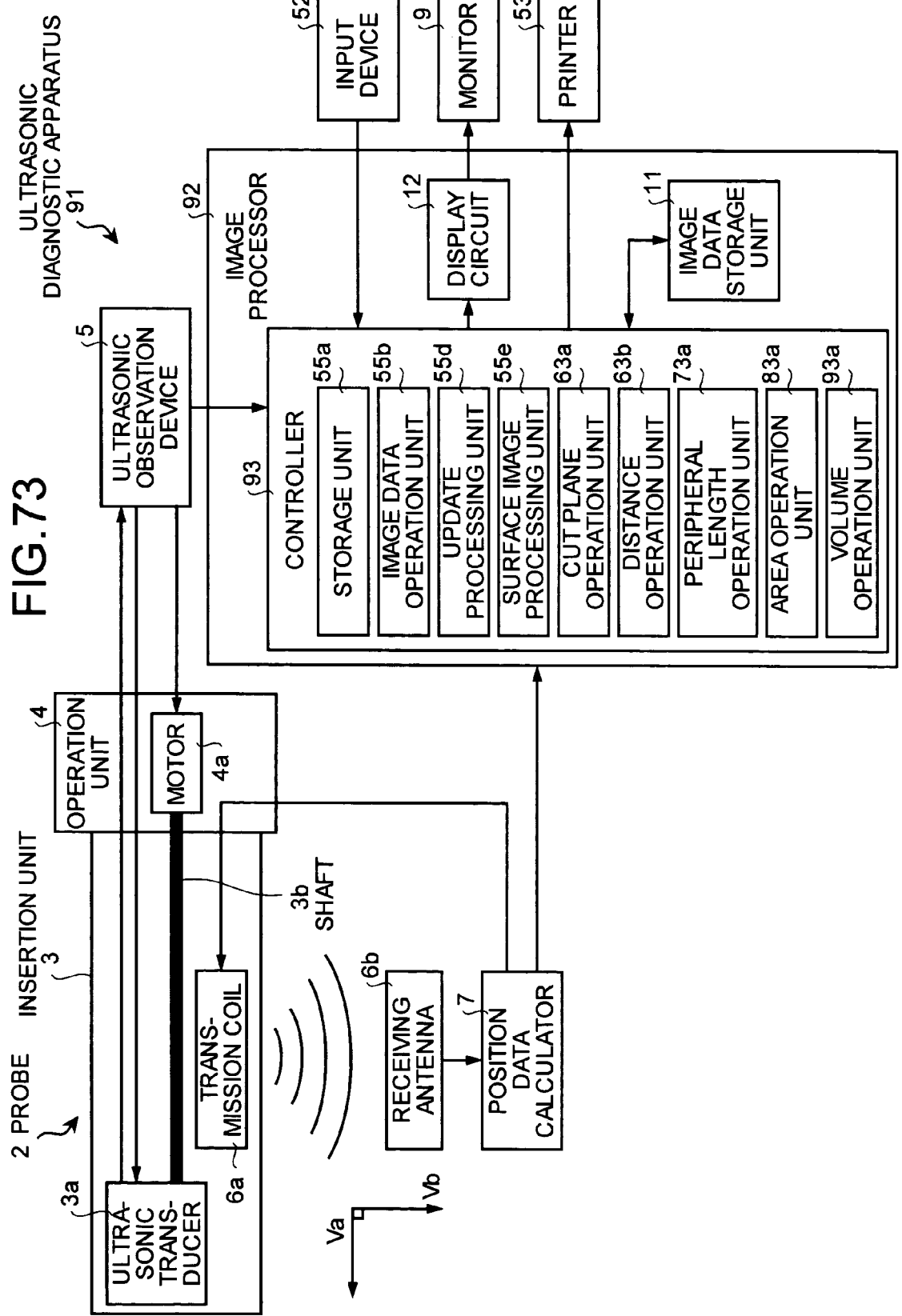
FIG. 73 is a block diagram that depicts schematic configuration of an ultrasonic diagnostic apparatus according to a ninth embodiment of the present invention.

FIG. 73 is a block diagram that depicts schematic configuration of the ultrasonic diagnostic apparatus according to the ninth embodiment of the present invention. This ultrasonic diagnostic apparatus 91 is constituted as follows, as compared with the ultrasonic diagnostic apparatus 81 according to the eighth embodiment. An image processor 92 is provided instead of the image processor 82. The image processor 92 includes a controller 93 instead of the controller 83. The controller 93 additionally includes a volume operation unit 93a. The controller 93 is realized by a ROM that stores various types of data such as a processing program, a RAM that stores each operation parameter, a CPU that executes the processing program stored in the ROM, and the like, substantially similarly to the controller 83. The other constituent elements of the ultrasonic diagnostic apparatus 91 are equal to those of the ultrasonic diagnostic apparatus 81 according to the eighth embodiment. Like constituent elements as those according to the eighth embodiment are denoted by like reference symbol, respectively.

Figure 74:
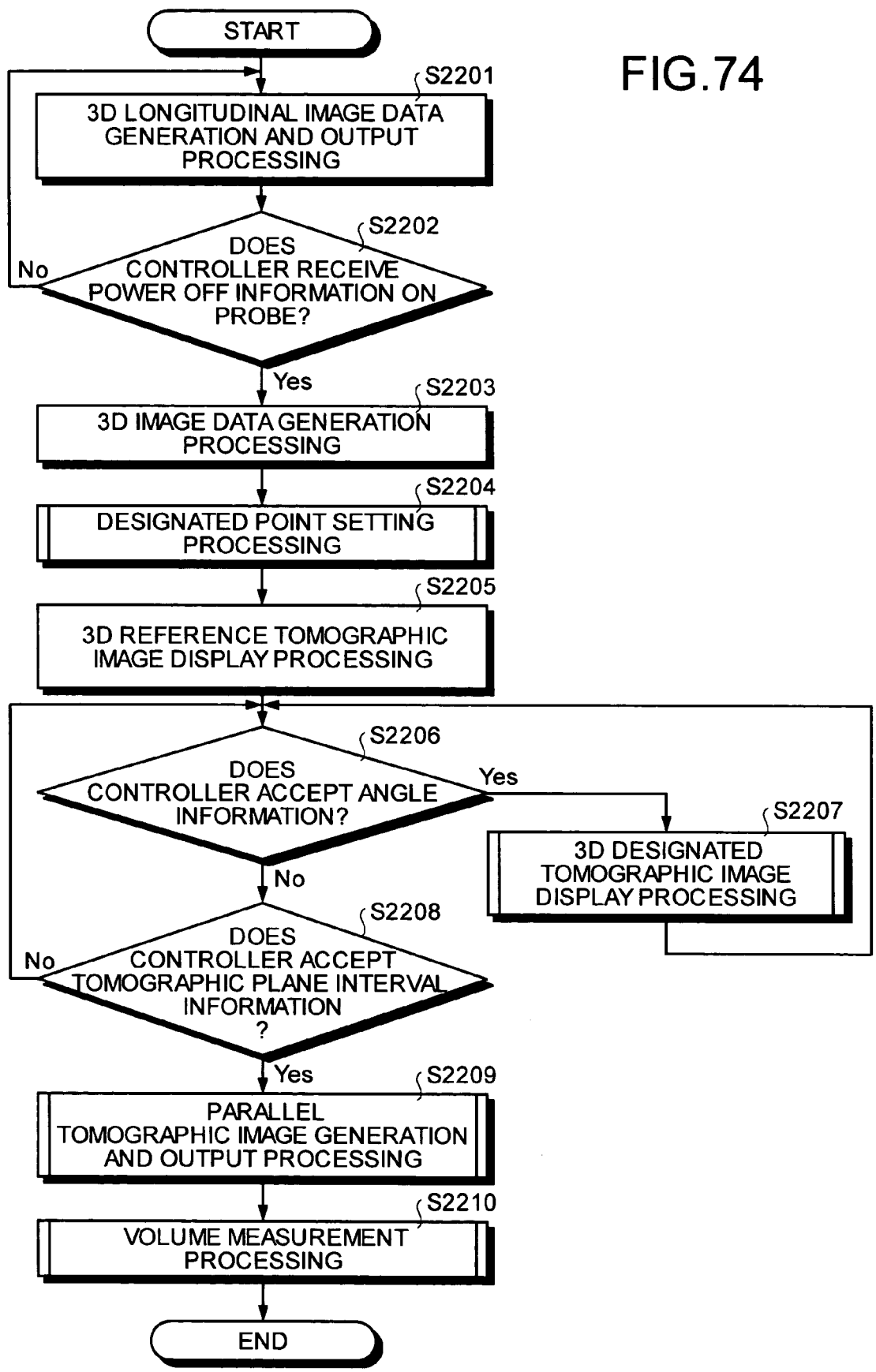
FIG. 74 is a flowchart showing respective processing steps executed until a volume of a measurement range set on a parallel tomographic image is measured.

FIG. 74 is a flowchart showing respective processing steps executed since the controller 93 displays a band-shaped or stereoscopic 3D longitudinal image on the monitor 9, generates 3D image data using n pieces of 2D image data on the spatial coordinate system xyz, then sets parallel tomographic planes parallel to one another at predetermined intervals, and displays parallel tomographic images of the respective parallel tomographic planes thus set on the 3D image data until measuring a volume of a measurement range determined by the at least three measurement points if at least three measurement points is designated on the displayed parallel tomographic planes. Referring to FIG. 74, if the ultrasonic observation device 5 generates 2D image data based on the echo signal and the position data calculator 7 calculates position data on a position at which this echo signal is obtained, the controller 93 executes respective processing steps S2201 to S2207 similarly to steps S2001 to S2007.

Thereafter, the operator observes the 3D reference tomographic image or the 3D designated tomographic image displayed on the screen of the monitor 9 and checks whether the desired region of interest is displayed on the screen of the monitor 9. If confirming that the desired region of interest is displayed on the screen of the monitor 9, the operator operates the input device 52 to perform an operation for inputting tomographic plane interval information on intervals of the respective parallel tomographic planes (tomographic plane interval) to the controller 93 without performing an operation for inputting the angle information to the controller 93. As for this tomographic plane information, the operator operates the input device 52 to input or select a numeric value corresponding to a desired tomographic plane interval, thereby inputting the tomographic plane interval information. In this case, the controller 93 does not accept the angle information ("No" at step S2206) but accepts the tomographic plane interval information ("Yes" at step S2208). The controller 93 then sets parallel tomographic planes at tomographic plane intervals corresponding to this tomographic plane interval information on the 3D image data. Further, the controller 93 generates parallel tomographic image data on the respective parallel tomographic planes thus set, and displays parallel tomographic images corresponding to the parallel tomographic image data on the monitor 9 (at step S2209).

The controller 93 then sets at least three measurement points on a desired parallel tomographic image using measurement point information input by operator's operating the input device 52. The controller 93 operates and outputs a volume of a measurement range surrounded by the at least three measurement points, and displays and outputs or prints out an obtained operation result as a measurement result of the volume (at step S2210). Details of a processing performed since the measurement points are set on the desired parallel tomographic image data until the measurement result of the volume is displayed and output or printed out (a volume measurement processing) is explained later.

If the operator does not operate the input device 52 to input the angle information and the tomographic plane interval information, then the controller 93 does not accept the angle information ("No" at step S2206), does not accept the tomographic plane interval information ("No" at step S2208), but repeatedly executes the processing step S2206 and the following. In this case, the controller 93 controls the monitor 9 to maintain a state in which the 3D reference tomographic image or 3D designated tomographic image is displayed on the monitor screen until the controller 93 accepts the angle information or the tomographic plane interval information input by the operator's input operation.

Figure 75:
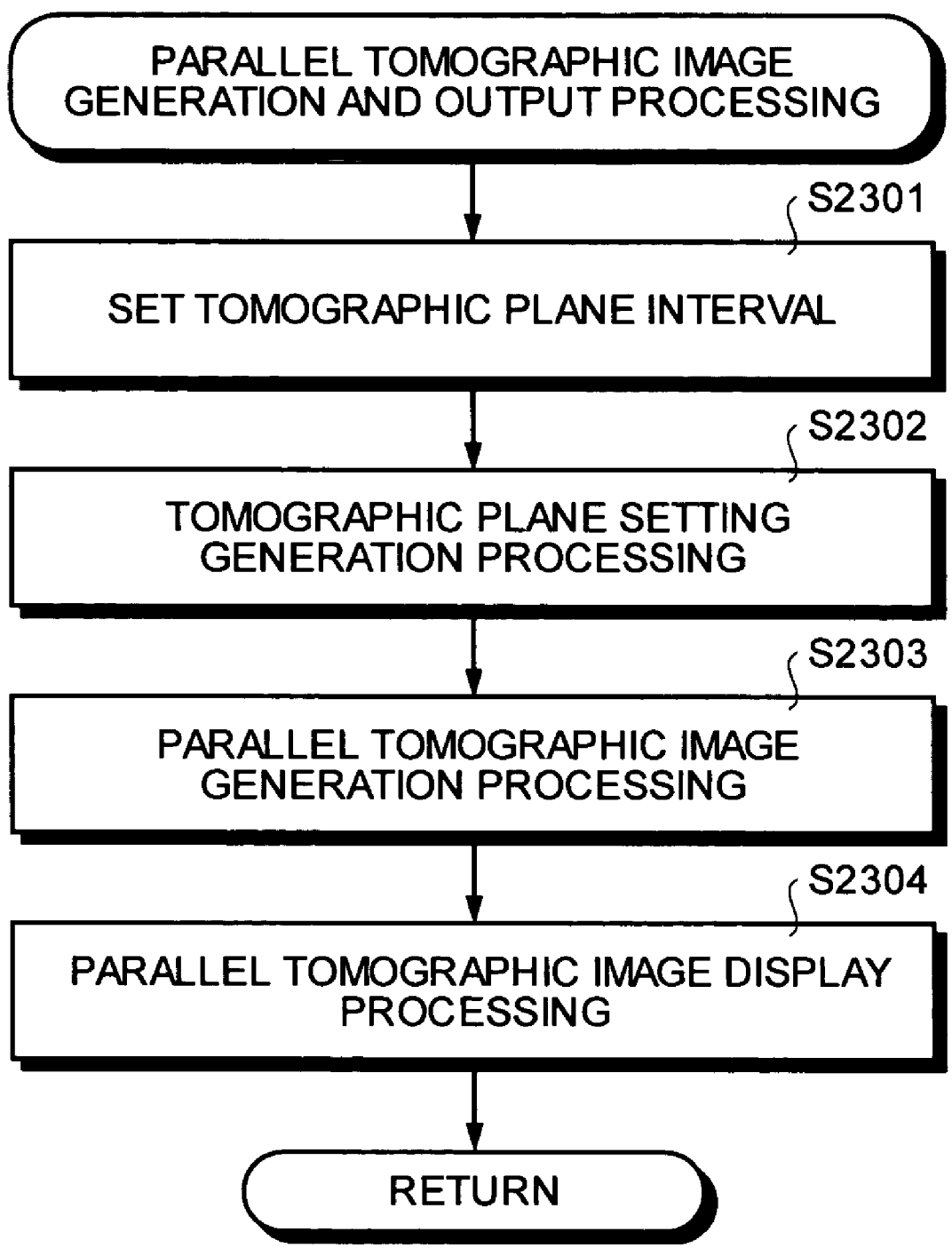
FIG. 75 is a flowchart showing respective processing steps executed until the a parallel tomographic image generation and output processing is completed in detail.

Respective processing steps executed until the controller 93 completes the processing at step S2209 for setting parallel tomographic planes at the tomographic plane intervals corresponding to the input tomographic plane interval information on the 3D image data, and generates parallel tomographic image data on the respective parallel tomographic planes thus set, until displaying a parallel tomographic image corresponding to the parallel tomographic image data (a parallel tomographic image generation and output processing) is explained in detail. FIG. 75 is a flowchart showing the respective processing steps executed until the controller 93 completes the parallel tomographic image generation and output processing in detail. FIG. 76 is an explanatory view of a processing for setting each parallel tomographic planes at the tomographic plane interval $\epsilon$ corresponding to the parallel tomographic plane interval information to 3D image data $VD_0$ arranged on the spatial coordinate system xyz until generating the parallel tomographic image data on the parallel tomographic planes thus set.

Referring to FIGS. 75 and 76, if the operator operates the input device 52 to input the tomographic plane interval information, then the controller 93 accepts this tomographic plane interval information, and sets the tomographic plane interval $\epsilon$ corresponding to this tomographic plane interval information as an interval between the two parallel tomographic planes set on the 3D image data (at step S2301). The controller 93 then reads 3D image data from the image data storage unit 11, and sets a parallel tomographic plane group for which the parallel tomographic planes are arranged at tomographic plane intervals $\epsilon$ on the 3D image data (at step S2302). Further, the controller 93 generates parallel tomographic image data for each parallel tomographic plane of the parallel tomographic plane group (at step S2303).

The 3D image data is stereoscopic image data generated by interpolating respective adjacent pieces of data of the n pieces of 2D image data obtained by the 3D scan. The 3D image data is composed by voxels corresponding to position data on this 3D scan, and having positions and luminances on the spatial coordinate system xyz. Therefore, if a desired parallel tomographic plane group is set on this 3D image data, the controller 93 can generate parallel tomographic image data on the respective parallel tomographic planes in this desired parallel tomographic plane group.

For example, if setting each parallel tomographic planes, which do not depend on an arrangement relationship of 2D image data $D_1, D_2, \ldots,$ and $D_n$ each including the position data on the 3D scan, for the 3D image data $VD_0$ on the spatial coordinate system xyz generated by the 2D image data $D_1, D_2, \ldots,$ and $D_n$ at the tomographic plane intervals $\epsilon$, the controller 93 can generate the parallel tomographic image data on each parallel tomographic pane. In this case, as shown in FIG. 76, the controller 93 can generate 3D image data VD including the parallel tomographic image data group in which the respective pieces of parallel tomographic image data are arranged at the tomographic plane intervals $\epsilon$, based on the 3D image data $VD_0$ on the spatial coordinate system xyz and the tomographic plane interval $\epsilon$.

Thereafter, the controller 93 stores the generated 3D image data VD including the parallel tomographic image data group in the image data storage unit 11. In addition, the controller 93 transmits one parallel tomographic image data in this parallel tomographic image data group to the monitor 9 through the display circuit 12, thereby displaying a parallel tomographic image corresponding to this parallel tomographic image data on the monitor 9 (at step S2304). Specifically, the controller 93 reads the parallel tomographic image data at a desired position in this parallel tomographic image data group, e.g., leading parallel tomographic image data. In addition, the controller 93 displays the parallel tomographic image corresponding to the parallel tomographic image data on the monitor 9, or successively reads one parallel tomographic image data from this parallel tomographic image data group based on indication information successively input by the operator's input operation and successively displays the parallel tomographic image corresponding to the parallel tomographic image data on the monitor 9.

Figure 77:
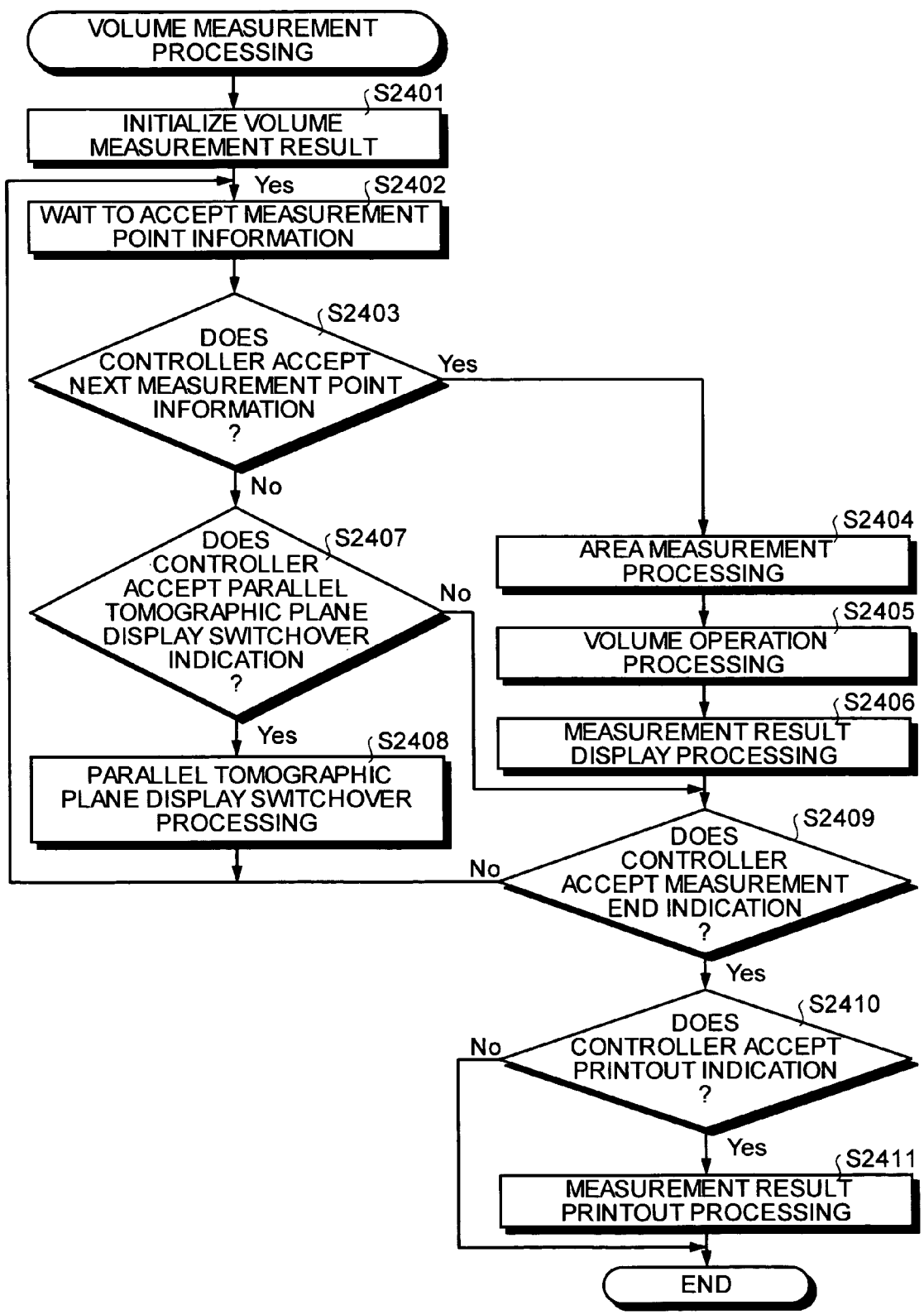
FIG. 77 is a flowchart showing respective processing steps executed until a volume measurement processing is completed in detail.
Figure 78:
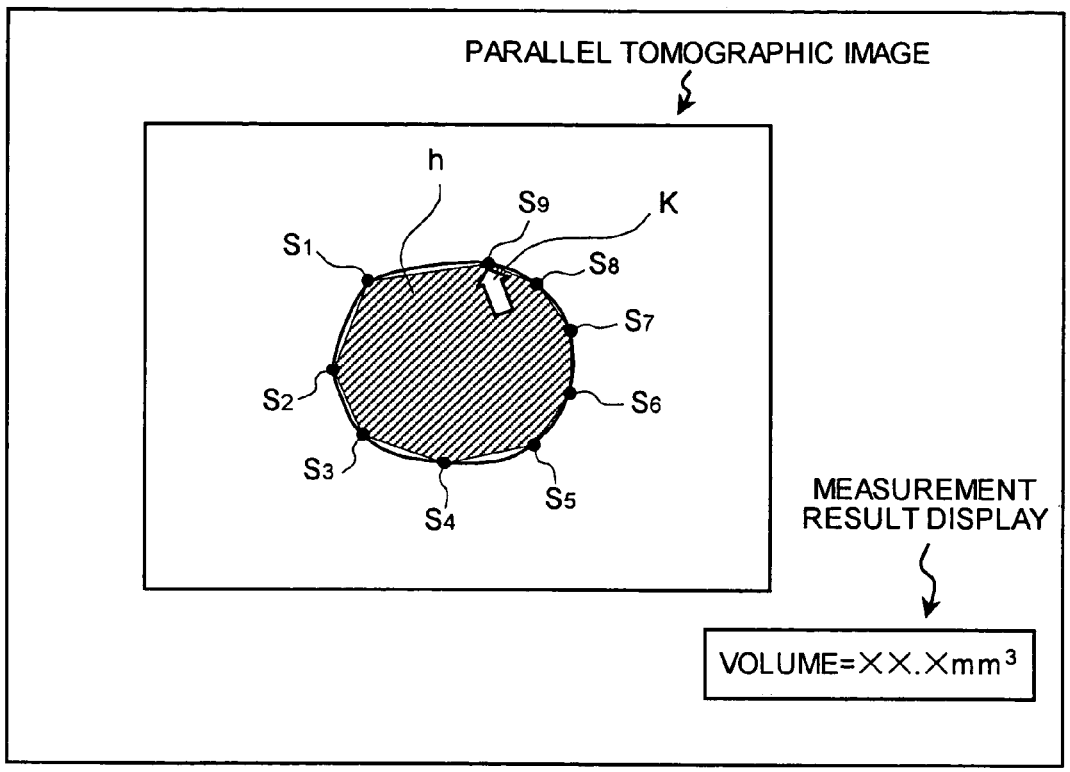
FIG. 78 depicts an example of display of the monitor if the volume of the measurement range set on the parallel tomographic image is measured.
Figure 79:
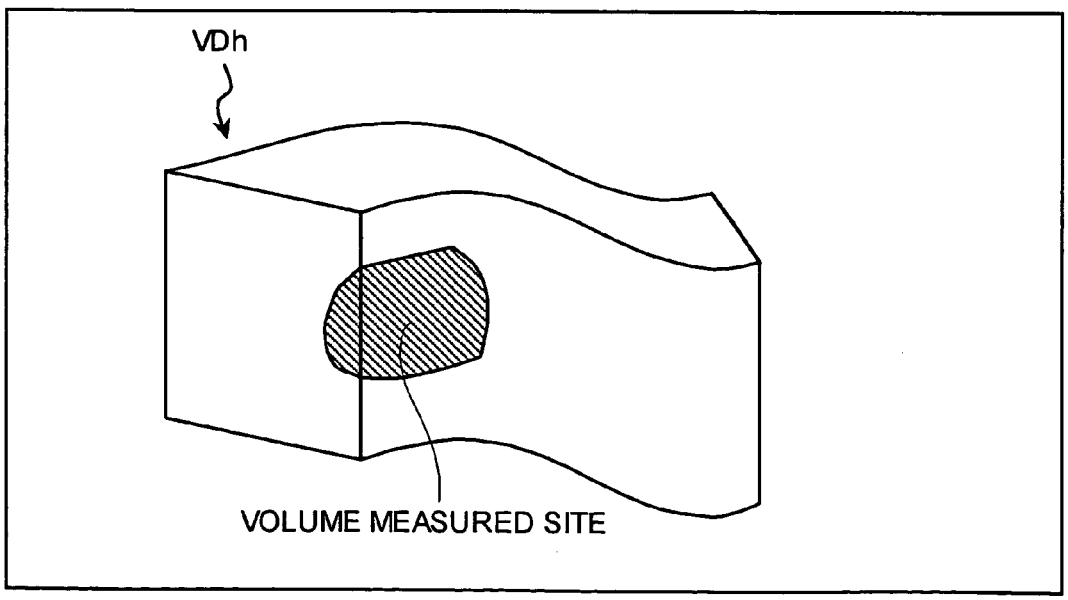
FIG. 79 depicts an example of display of the monitor if a progress of the volume operation processing is displayed on a 3D image of a region of interest as a volume measurement target.

Respective processing steps executed until the controller 93 completes the volume measurement processing at step S2210 will next be explained in detail. FIG. 77 is a flowchart showing the respective processing steps executed until the controller 93 completes the volume measurement processing on the measurement range designated on the parallel tomographic image in detail. FIG. 78 depicts an example of display of the monitor 9 if the controller 93 sets a desired number of, e.g., nine measurement points on the parallel tomographic image, on which the tumor tomographic image h that is the tomographic image of the region of interest is displayed, and measures the volume of the measurement range surrounded by the nine measurement points. FIG. 79 depicts an example of display of the monitor 9 if the controller 93 displays a progress of the volume operation processing on a 3D image of the region of interest that is a volume measurement target.

Referring to FIGS. 77 and 78, if the parallel tomographic image group is generated on the 3D image data, the controller 93 initializes the volume of the measurement range already stored in the storage unit 55*a*, i.e., sets the volume at zero (at step S2401), and turns into a standby state of waiting to accept the measurement information (at step S2402). If the operator then operates the input device 52, e.g., the mouse to move the cursor displayed on the screen of the monitor 9 to move to respective desired positions on the parallel tomographic image, to successively designate the respective desired positions, and to successively input measurement point information corresponding to the desired positions, the controller 93 performs a processing substantially equal to that at steps S2101 to S2113. Specifically, the controller 93 operates and outputs an area of a polygon formed by the designated measurement points (at step S2404). For example, the controller 93 operates and outputs the volume of a polygon formed by designated nine measurement points $S_1$ to $S_9$ as shown in FIG. 78.

The volume operation unit 93*a* performs a multiplication processing for multiplying the tomographic plane interval $\epsilon$ set at step S2209 by the area operated and output by the processing at step S2404. In addition, the volume operation unit 93*a* performs an addition processing for adding a value operated and output by the multiplication processing and the volume already stored in the storage unit 55*a* at this time together. Further, the volume operation unit 93*a* sets a value operated and output by the addition processing, that is, an accumulated volume at a present volume (at step S2405). In this case, the volume operation unit 93*a* operates and outputs a volume of a region having the measurement range formed by the measurement points designated on the parallel tomographic image set as a bottom, and having a thickness that is an integer multiple of the tomographic plane interval $\epsilon$ set at step S2209. For example, as shown in FIG. 78, the volume operation unit 93*a* operates and outputs the volume of the region having the tumor tomographic image h in a range surrounded by the measurement points $S_1$ to $S_9$ as a bottom, and having a thickness of the tomographic plane interval $\epsilon$.

Figure 80:
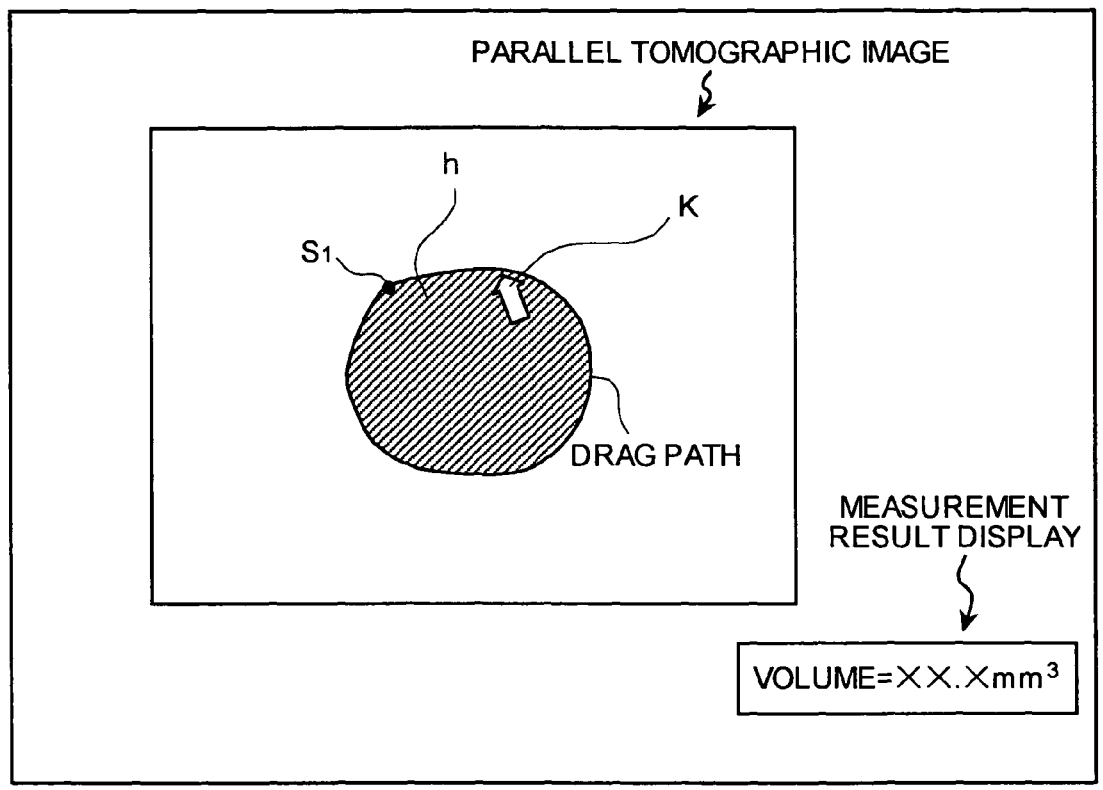
FIG. 80 is a typical view illustrating an operation for measuring the volume of the measurement range surrounded by the drag path.

Alternatively, the controller 93 may measure the area of the measurement range surrounded by a drag path by a drag operation using the input device 52, multiply the obtained area by the tomographic plane interval $\epsilon$, and thereby operate and output the volume of the region having this measurement range as the bottom, and having the thickness of the tomographic plane interval ε. FIG. 80 is a typical view illustrating an operation performed by the controller 93 for measuring the volume of the measurement range surrounded by the drag path.

As shown in FIG. 80, the operator first operates the input device 52, e.g., the mouse, to designate the first measurement point $S_1$ at the position near the boundary between the tumor tomographic image h and the pancreatic duct tomographic image f displayed on the screen of the monitor 9. The operator then performs the drag operation so as to surround the tumor tomographic image h. A radius from the designated measurement point $S_1$ is set to the controller 93 in advance. When the operator moves the cursor K within this radius and stops depressing the mouse button during this drag operation, the controller 93 connects this measurement point $S_1$ to a point at which the operator stops depressing the mouse button. In this case, the controller 93 automatically closes this drag path to form a closed curve. In addition, similarly to the measurement of the area, based on position information on pixels of tomographic image data corresponding to this closed curve, the controller 93 generates a polygon composed by these pixels, and constitutes the measurement range surrounded by the closed curve using the pixels. Thereafter, the controller 93 counts the total number of pixels present in the measurement range constituted by this polygon. The controller 93 multiplies the count value obtained by this count processing by an actual area of the measurement range per pixel, thereby operating and outputting an area of the measurement range surrounded by the closed curve. Thereafter, the controller 93 multiplies the area thus operated and output by the tomographic plane interval ε, thereby operating and outputting the volume of the measurement region having this measurement range as the bottom, and having the thickness of the tomographic plane interval ε.

If the volume operation unit 93 operates and outputs the present volume, the controller 93 stores this volume in the storage unit 55*a*. In addition, the controller 93 converts the volume thus operated and output into a value in a desired unit, to thereby display the resultant value on the monitor 9 as a measurement result of the volume of the measurement range formed by the measurement points designated on the parallel tomographic image (at step S2406). If the operator then does not operate the input device 52 to perform an input operation for inputting measurement end indication information on an end indication for this volume measurement processing, the controller 93 repeatedly executes the processing step S2402 and the following.

Alternatively, at this step S2406, the controller 93 can display this volume measurement result on the monitor 9, display the 3D image of the region of interest that is the volume measurement target on the same screen with the parallel tomographic image, and display a progress of the volume operation processing at step S2405 on this 3D image. A function carried out until this 3D image is displayed will now be explained.

The controller 93 locates the region of interest, e.g., the tumor tomographic image h whenever the volume measurement processing is performed at step S2404. The controller 93 then combines the region having the tumor tomographic image h as a bottom, and having a thickness of an integer multiple of the tomographic plane interval ε set at step S2209, with a region already extracted as a volume operation target region, and constructs a 3D tumor image $VD_h$ of the combined region. Further, as shown in FIG. 79, the controller 93 displays this 3D tumor image $VD_h$ as a site the volume of which is measured by the volume operation processing (a volume measured site). The controller 93 then repeatedly executes steps S2404 to S2406 as is explained later, and displays a new 3D tumor image $VD_h$ whenever the controller 93 locates the tumor tomographic image h. The controller 93 can thereby display the progress of the volume operation processing at step S2405. As a consequence, the operator can easily grasp a position at which the present volume operation processing is performed for the measurement target region of interest.

On the other hand, if the operator operates the input device 52 to input switchover indication information for switching display of the parallel tomographic image displayed on the screen without performing the measurement point information input operation, the controller 93 does not accept the measurement point information ("No" at step S2403) but accept a parallel tomographic image display switchover indication corresponding to this switchover indication information ("Yes" at step S2407). If so, the controller 93 reads parallel tomographic image data corresponding to the display switchover indication from the parallel tomographic image data group stored in the image data storage unit 11 in response to the display switchover indication. In addition, the controller 93 transmits the parallel tomographic image data thus read to the monitor 9 through the display circuit 12. In this case, the update processing unit 55*d* displays a parallel tomographic image corresponding to the parallel tomographic image data thus read in place of the parallel tomographic image already displayed on the screen of the monitor 9 (at step S2408). Thereafter, the controller 93 repeatedly executes step S2402 and the following.

If the operator does not operate the input device 52 to perform the input operation for inputting the measurement point information and to perform the input operation for inputting the indication information for switching the display of the parallel tomographic image on the monitor 9, then the controller 93 does not accept the measurement point information ("No" at step S2403) and does not accept the parallel tomographic image display switchover indication ("No" at step S2407). If so, the controller 93 repeatedly executes the processing step S2409 and the following.

On the other hand, if the operator operates the input device 52 to perform the input operation for inputting the measurement end indication information on an end indication of this volume measurement processing, the controller 93 accepts a measurement processing end indication corresponding to this measurement end indication information ("Yes" at step S2409). Thereafter, if the operator operates the input device 52 to input indication information for indicating that this volume measurement result is printed out onto a paper or the like, the controller 93 accepts a printout indication based on this indication information ("Yes" at step S2410). In addition, the controller 93 performs the same processing as that at step S2116 to control the printer 53 to output this volume measurement result (at step S2411). If the operator does not operate the input device 52 to input the indication information on the printout indication, the controller 93 does not accept the printout indication ("No" at step S2410). That is, the controller 93 completes this volume measurement processing without controlling the printer 53 to print out the measurement result. If this volume measurement processing is completed, the operator can highly accurately measure the volume of the desired region of interest. As shown in FIGS. 78 and 79, for example, the operator can measure the volume of the 3D tumor tomographic image $VD_h$ including the tumor tomographic image h located as the region of interest. As a result, the operator can accurately grasp the magnitude of the affected site before a surgical operation, which is useful for determination of an operation plan or a cutting range.

Besides, the operator can determine more accurately and more objectively a treatment effect of an anticancer agent, radiation therapy, or the like on the affected site with the passage of time. Since the volume is substantially proportional to the number of cells of the affected site such as the tumor, evaluation of the magnitude of the affected site by measuring the volume is desirable for evaluation of a force of a disease. If the magnitude of the affected site is estimated by measuring the volume of the affected site, an estimation result obtained is objective irrespectively of the operator.

Moreover, since the volume includes a dimension that is a cube of the distance, the volume tends to be influenced by a strain of the longitudinal image or tomographic image of the subject. Namely, if the distance has a strain of 10% vertically and horizontally as compared with the actual shape, the volume eventually includes a strain of about 30%. It is, therefore, quite desirable to use the constitution of the ultrasonic diagnostic apparatus according to the ninth embodiment when the volume is to be measured.

In the ninth embodiment, each parallel tomographic planes which do not depend on the arrangement relationship of a plurality of pieces of 2D image data associated with the respective pieces of position data by the 3D scan are set on the 3D image data on the spatial coordinate system xyz at the tomographic plane intervals. However, the present invention is not limited to this instance. The parallel tomographic planes parallel to desired 2D image data, 3D reference tomographic image data, or 3D designated tomographic image data may be set on this 3D image data at the tomographic plane intervals.

In the ninth embodiment, the ultrasonic diagnostic apparatus is constituted as follows. The parallel tomographic planes parallel to one another are set at predetermined tomographic plane intervals for the 3D image data generated using a plurality of pieces of 2D image data associated with the respective pieces of position data on the moving path or moving direction of the probe 2 which performs the 3D scan. The parallel tomographic images of the respective parallel tomographic planes are successively displayed on the screen of the monitor 9. If at least three measurement points are designated at the respective desired positions on the parallel tomographic image displayed on the screen of the monitor 9, the volume of the region having the measurement range surrounded by the at least three measurement points as the bottom, and having the thickness of the tomographic plane interval is operated and output based on the respective pieces of coordinate information corresponding to the desired positions and the tomographic plane interval. Therefore, the ultrasonic diagnostic apparatus which can highly accurately measure the volume of the desired range of the region of interest such as the characteristic site, e.g., the bile duct-to pancreatic duct joint or the affected site, e.g., the tumor in the living body can be realized. If the operator uses this ultrasonic diagnostic apparatus, the operator can highly accurately grasp the volume of this region of interest, easily grasp an occupation ratio of this region of interest to the entire 3D image displayed and output, and highly accurately grasp the volume of, or example, the affected site such as the tumor before a surgical operation.

As explained so far, according to the present invention, the tomographic image acquisition unit transmits and receives the ultrasonic wave by the ultrasonic transducer arranged on the tip end of the probe, and acquires a plurality of two-dimensional ultrasonic tomographic images for a subject in a living body, the detection unit detects information indicating the reference position of each of the two-dimensional ultrasonic tomographic images and the orientation of a tomographic plane of the each two-dimensional ultrasonic tomographic image, and the image generation unit generates the band-shaped longitudinal image including a curved plane along the moving path of the ultrasonic transducer, based on the reference position, the orientation of the tomographic plane, and the each two-dimensional ultrasonic tomographic image. Therefore, it is advantageously possible to realize the ultrasonic diagnostic apparatus constituted as follows. Even if the probe performs the 3D scan while being curved along the shape of the interior of the living body or performs the 3D scan while being twisted, depending on the operator's operation such as the insertion or guiding, then the tomographic image substantially equal in shape to the actual subject in the living body can be easily acquired, and the tomographic image that accurately grasps the shape and the like of the desired region of interest such as the characteristic site or the affected site, e.g., the tumor in the living body can be easily displayed and output.

According to the present invention, based on a plurality of pieces of 2D image data obtained by the 3D scan of the ultrasonic transducer arranged on the tip end of the flexible probe, and the position data corresponding to the moving path or moving direction of the probe during the 3D scan, the 3D image data that accurately traces the moving path is generated. Based on the 3D image data, the geometric value such as the length, the peripheral length, the area, or the volume of the desired measurement range is operated and output. Therefore, it is advantageously possible to realize the ultrasonic diagnostic apparatus constituted as follows. Even if the probe is guided along the shape of the living body, the longitudinal image or tomographic image substantially equal in shape to the actual subject in the living body can be easily displayed and output. In addition, the geometric value of the region of interest such as the characteristic site or the affected site displayed on this longitudinal image or tomographic image can be accurately measured. Accordingly, the operator can accurately grasp the shape, the size, or the position of the affected site before a surgical operation, which is useful for determination of a surgical operation plan or a cutting range. Besides, the operator can determine more accurately and more objectively a treatment effect of an anticancer agent, radiation therapy, or the like on the affected site with the passage of time.

Meanwhile, according to the conventional art disclosed in Japanese Patent Application Laid-Open No. 7-155328, the 3D scan is performed on the subject by moving forward or backward the small-diameter probe that is inserted into the forceps channel of the endoscope by the exclusive driving apparatus. Due to this, the opening of the ultrasonic transducer cannot be set larger than the inside diameter of the forceps channel. As a result, the output of the transmitted or received ultrasonic wave is restricted, and a penetration degree of the ultrasonic wave, by which the ultrasonic wave is penetrated toward a remote location, is lowered. An entire image of a large tumor is not in the obtained 2D image data. As a result, it is disadvantageously impossible to measure the geometric value of substantially a large tumor. According to the present invention, by contrast, the ultrasonic diagnostic apparatus is constituted so that a plurality of 2D ultrasonic tomographic images are acquired by the ultrasonic probe arranged on the tip end of the probe, and the three-dimensional geometric value is then operated based on the orientation information which indicates the reference position of each 2D ultrasonic tomographic image and the orientation of the tomographic plane of the each 2D ultrasonic tomographic image, and on each 2D ultrasonic tomographic image. It is, therefore, advantageously possible to employ the ultrasonic transducer having a large opening, and thereby acquire a 2D ultrasonic tomographic image having a high penetration degree. As a result, it is advantageously possible to measure the geometric value of substantially a large tumor.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. An ultrasonic diagnostic apparatus comprising:
    a tomographic image acquisition unit adapted to transmit and receive an ultrasonic wave by an ultrasonic transducer arranged on a tip end of a probe, and acquire a plurality of two-dimensional ultrasonic tomographic images of a subject in a living body;
    a detection unit adapted to detect information indicating a reference position of each of the two-dimensional ultrasonic tomographic images and an orientation of a tomographic plane of each of the two-dimensional ultrasonic tomographic images; and
    an image generation unit adapted to generate a band-shaped longitudinal image including a curved plane along a moving path of the ultrasonic transducer, based on the reference position, the orientation of the tomographic plane, and each of the two-dimensional ultrasonic tomographic images, and obtain relative coordinates of the two-dimensional ultrasonic tomographic images based on the reference position and the orientation of the tomographic planes, set straight lines that vertically cut the two-dimensional ultrasonic tomographic images so that the straight lines are equal on the relative coordinates, respectively, and generate a band-shaped longitudinal plane obtained by interpolating the respective straight lines as a band-shaped longitudinal image at an absolute coordinate.

2. The ultrasonic diagnostic apparatus according to claim 1, further comprising:
    a position designation unit adapted to designate positions of the straight lines each indicating a longitudinal plane position on the two-dimensional ultrasonic tomographic images, respectively.

3. The ultrasonic diagnostic apparatus according to claim 2, wherein
    the position designation unit is further adapted to designate the positions at any one of prior to acquisition of the two-dimensional ultrasonic tomographic images, during acquisition of the two-dimensional ultrasonic tomographic images, and after acquisition of the two-dimensional ultrasonic tomographic images.

4. The ultrasonic diagnostic apparatus according to claim 1, further comprising a three-dimensional longitudinal image generation unit adapted to generate a three-dimensional longitudinal image including, as one surface, the band-shaped longitudinal image.

5. The ultrasonic diagnostic apparatus according to claim 4, further comprising a display unit adapted to display at least one of each of the two-dimensional ultrasonic tomographic images, the band-shaped longitudinal image, and the three-dimensional longitudinal image.

6. The ultrasonic diagnostic apparatus according to claim 5, further comprising:
    a rotation indication unit adapted to transmit a rotation indication of at least one of the band-shaped longitudinal image and the three-dimensional longitudinal image displayed by the display unit; and
    a display processing unit adapted to perform a display processing for displaying the band-shaped longitudinal image and the three-dimensional longitudinal image corresponding to the rotation indication from the rotation indication unit.

7. The ultrasonic diagnostic apparatus according to claim 5, wherein
    the display unit simultaneously displays at least two of each of the two-dimensional ultrasonic tomographic images, the band-shaped longitudinal image, and the three-dimensional longitudinal image.

8. The ultrasonic diagnostic apparatus according to claim 5, wherein
    the display unit displays each of the two-dimensional ultrasonic tomographic images and the three-dimensional longitudinal image, and
    the image generation unit displays a straight line that indicates a position of each of the two-dimensional ultrasonic tomographic images on the three-dimensional longitudinal image, displays a cut line that corresponds to a position of a plane on which the band-shaped longitudinal image is formed, on each of the two-dimensional ultrasonic tomographic images, updates, if the cut line is rotated, the band-shaped longitudinal image and the three-dimensional longitudinal image including the band-shaped longitudinal image according to rotation of the cut line, and updates the straight line that indicates the position of each of the two-dimensional ultrasonic tomographic images to a straight line that corresponds to a position of a different one of the two-dimensional ultrasonic tomographic images on the three-dimensional longitudinal image if each of the two-dimensional ultrasonic tomographic image is switched to the different two-dimensional ultrasonic tomographic image.

9. The ultrasonic diagnostic apparatus according to claim 1, wherein
    the reference position is a position of the ultrasonic transducer, and the orientation of the tomographic plane is a plane formed by a vector in a predetermined direction on a tomographic plane of each of the two-dimensional ultrasonic tomographic images with the reference position set as a reference point, and by an outer product between the vector in the predetermined direction and a normal vector from the reference position set as the reference point.

10. The ultrasonic diagnostic apparatus according to claim 9, wherein
    each of the relative coordinates is a coordinate with the reference position set as an origin, the vector in the predetermined direction, the outer product, and the normal vector being set as three orthogonal axes of the each relative coordinate.

11. The ultrasonic diagnostic apparatus according to claim 1, wherein
    the detection unit detects the information indicating the reference position of each of the two-dimensional ultrasonic tomographic images and the orientation of the tomographic plane, based on a magnetic field generated from a magnetic field generation source provided near the tip end of the probe.

12. The ultrasonic diagnostic apparatus according to claim 1, wherein
    the tomographic image acquisition unit successively acquires the plurality of two-dimensional ultrasonic tomographic images as the ultrasonic transducer is guided along the moving path, and the image generation unit generates a band-shaped longitudinal image that is successively extended using the plurality of two-dimensional ultrasonic tomographic images input successively from the tomographic image acquisition unit.

13. An ultrasonic diagnostic apparatus comprising:
a tomographic image acquisition unit adapted to transmit and receive an ultrasonic wave by an ultrasonic transducer arranged on a tip end of a probe, and acquire a plurality of two-dimensional ultrasonic tomographic images of a subject in a living body;
a detection unit adapted to detect arrangement information indicating a reference position of each of the two-dimensional ultrasonic tomographic images and an orientation of a tomographic plane of each of the two-dimensional ultrasonic tomographic images;
an image generation unit adapted to
    generate a band-shaped longitudinal image including a curved plane along a moving path of the ultrasonic transducer, based on the reference position, the orientation of the tomographic plane, and each of the two-dimensional ultrasonic tomographic images,
    obtain relative coordinates of the two-dimensional ultrasonic tomographic images based on the reference position and the orientation of the tomographic planes,
    set straight lines that vertically cut the two-dimensional ultrasonic tomographic images so that the straight lines are equal on the relative coordinates, respectively, and
    generate a band-shaped longitudinal plane obtained by interpolating the respective straight lines as a band-shaped longitudinal image at an absolute coordinate; and
an operation unit adapted to determine a geometric value of the subject based on the arrangement information and the each two-dimensional ultrasonic tomographic image.

14. The ultrasonic diagnostic apparatus according to claim 13, further comprising:
an image data processing unit adapted to arrange the two-dimensional ultrasonic tomographic images at three-dimensional spatial coordinates corresponding to a moving path of the ultrasonic transducer, based on the arrangement information and the two-dimensional ultrasonic tomographic images, wherein
the operation unit determines a three-dimensional geometric value displayed on the three-dimensional spatial coordinates at which the two-dimensional ultrasonic tomographic images are arranged.

15. The ultrasonic diagnostic apparatus according to claim 14, wherein
the image data processing unit generates three-dimensional image data on which the plurality of two-dimensional ultrasonic tomographic images are arranged, based on the plurality of two-dimensional ultrasonic tomographic images arranged at the three-dimensional spatial coordinates, and
the operation unit operates and outputs the three-dimensional geometric value indicated by the three-dimensional image data.

16. The ultrasonic diagnostic apparatus according to claim 14, wherein
the image data processing unit generates a band-shaped longitudinal image including a curved plane along the moving path of the ultrasonic transducer, based on the reference position, the orientation of the tomographic plane, and the each two-dimensional ultrasonic tomographic image on the three-dimensional spatial coordinate system, and
the operation unit determines a geometric value on the band-shaped longitudinal image.

17. The ultrasonic diagnostic apparatus according to claim 16, wherein
the image data processing unit obtains relative coordinates of each two-dimensional ultrasonic tomographic image based on the reference position and the orientation of the tomographic plane, sets straight lines that vertically cut the two-dimensional ultrasonic tomographic images so that the straight lines are equal at the relative coordinates, respectively, and generate a band-shaped longitudinal plane obtained by interpolating the respective straight lines as a band-shaped longitudinal image at the three-dimensional spatial coordinate.

18. The ultrasonic diagnostic apparatus according to claim 16, further comprising:
a rotation indication unit adapted to transmit a rotation indication of the band-shaped longitudinal image; and
a display processing unit adapted to perform a display processing for displaying the band-shaped longitudinal image corresponding to the rotation indication from the rotation indication unit.

19. The ultrasonic diagnostic apparatus according to claim 16, further comprising a three-dimensional longitudinal image generation unit that generates a three-dimensional longitudinal image including, as one surface, the band-shaped longitudinal image.

20. The ultrasonic diagnostic apparatus according to claim 19, further comprising:
a rotation indication unit adapted to transmit a rotation indication to the three-dimensional longitudinal image, and
a display processing unit adapted to perform a display processing on the three-dimensional longitudinal image to correspond to the rotation indication of the rotation indication unit.

21. The ultrasonic diagnostic apparatus according to claim 19, further comprising:
a display unit adapted to simultaneously display at least two of the each two-dimensional ultrasonic tomographic image, the band-shaped longitudinal image, the three-dimensional longitudinal image, and the two-dimensional image of the cut plane.

22. The ultrasonic diagnostic apparatus according to claim 14, wherein
the image data processing unit generates a two-dimensional image of a cut plane having an indicated and input rotation angle with respect to a rotation reference plane which passes through a rotation axis, for the rotation reference plane, the rotation axis being a straight line that passes through at least two indicated and input points on the each two-dimensional ultrasonic tomographic image, and
the operation unit determines a geometric value on the two-dimensional image of the cut plane.

23. The ultrasonic diagnostic apparatus according to claim 22, wherein
a unit rotation angle for forming the cut plane is preset to the image data processing unit, and the image data processing unit generates the two-dimensional image on the cut plane for every unit rotation angle in a predetermined rotation direction from the rotation reference plane based on the each two-dimensional ultrasonic tomographic image.

24. The ultrasonic diagnostic apparatus according to claim 23, further comprising:
an input unit adapted to transmit an input indication for inputting the unit rotation angle.

25. The ultrasonic diagnostic apparatus according to claim 14, wherein
the image data processing unit generates a plurality of slice images sliced equidistantly based on the three-dimensional image data obtained by interpolating the plurality of two-dimensional ultrasonic tomographic images, and
the operation unit determines a value obtained by integrating areas surrounded by figures indicated and input on the plurality of slice images for the respective slice images, as a volume.

26. The ultrasonic diagnostic apparatus according to claim 13, wherein
the operation unit determines at least one of a distance between two indicated and input points, a path drawn by an indicated and input figure, a length of a periphery drawn by the indicated and input figure, an area surrounded by the indicated and input figure, and a volume surrounded by the indicated and input figure.

27. The ultrasonic diagnostic apparatus according to claim 26, wherein
the figure is a polygonal line, a polygon, or a stereoscopic figure having the polygon as a bottom, the polygonal line, the polygon, or the stereoscopic figure being formed by a plurality of indicated and input points.

28. The ultrasonic diagnostic apparatus according to claim 26, wherein
the operation unit determines a sum of areas of triangles formed by dividing the figure into the triangles, as the area of the figure.

29. The ultrasonic diagnostic apparatus according to claim 26, wherein
one of the figure operated by the operation unit and the two points is located on one of different band-shaped longitudinal images, two-dimensional images on different cut planes, and the different two-dimensional ultrasonic tomographic images.

30. The ultrasonic diagnostic apparatus according to claim 26, further comprising a display unit that displays various images generated by at least the image data processing unit, wherein
the display unit outputs at least the indicated and input two points or the indicated and input figure, and a target segment or a target region operated by the operation unit.

31. The ultrasonic diagnostic apparatus according to claim 13, further comprising a numeric value display unit that numerically displays the geometric value operated by the operation unit.

32. The ultrasonic diagnostic apparatus according to claim 13, further comprising a type indication unit adapted for indicating a type of an operation for determining the geometric value.

33. The ultrasonic diagnostic apparatus according to claim 13, wherein
the reference position is a position of the ultrasonic transducer, and the orientation of the tomographic plane is a plane formed by a vector in a predetermined direction on a tomographic plane of each of the two-dimensional ultrasonic tomographic image with the reference position set as a reference point, and by an outer product between the vector in the predetermined direction and a normal vector from the reference position set as the reference point.

34. The ultrasonic diagnostic apparatus according to claim 33, wherein
each of the relative coordinates is a coordinate with the reference position set as an origin, the vector in the predetermined direction, the outer product, and the normal vector being set as three orthogonal axes of the each relative coordinate.

35. The ultrasonic diagnostic apparatus according to claim 13, wherein the detection unit detects the information indicating the reference position of the each two-dimensional ultrasonic tomographic image and the orientation of the tomographic plane, based on a magnetic field generated from a magnetic field generation source provided near the tip end of the probe.

* * * * *